(12) United States Patent
Chen et al.

(10) Patent No.: US 9,586,956 B2
(45) Date of Patent: Mar. 7, 2017

(54) ISOQUINOLINE AND NAPHTHYRIDINE DERIVATIVES

(71) Applicant: Genentech, Inc., South San Francisco, CA (US)

(72) Inventors: Huifen Chen, South San Francisco, CA (US); Terry Crawford, South San Francisco, CA (US); Steven R. Magnuson, South San Francisco, CA (US); Chudi Ndubaku, South San Francisco, CA (US); Lan Wang, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/448,941

(22) Filed: Jul. 31, 2014

(65) Prior Publication Data

US 2014/0343036 A1 Nov. 20, 2014

Related U.S. Application Data

(63) Continuation of application No. PCT/EP2013/051613, filed on Jan. 29, 2013.

(60) Provisional application No. 61/592,443, filed on Jan. 30, 2012, provisional application No. 61/593,775, filed on Feb. 1, 2012, provisional application No. 61/701,916, filed on Sep. 17, 2012.

(51) Int. Cl.
| | | |
|---|---|---|
| *C07D 471/04* | (2006.01) | |
| *C07D 401/12* | (2006.01) | |
| *C07D 413/12* | (2006.01) | |
| *C07D 217/22* | (2006.01) | |
| *C07D 217/26* | (2006.01) | |
| *C07D 401/04* | (2006.01) | |
| *C07D 413/04* | (2006.01) | |

(52) U.S. Cl.
CPC ......... *C07D 471/04* (2013.01); *C07D 217/22* (2013.01); *C07D 217/26* (2013.01); *C07D 401/04* (2013.01); *C07D 401/12* (2013.01); *C07D 413/04* (2013.01); *C07D 413/12* (2013.01)

(58) Field of Classification Search
None
See application file for complete search history.

(56) References Cited

FOREIGN PATENT DOCUMENTS

| WO | 00/66583 | 9/2000 |
|---|---|---|
| WO | 2005/028444 | 3/2005 |
| WO | 2008/079906 | 7/2008 |
| WO | 2008/080001 | 7/2008 |

OTHER PUBLICATIONS

CAPLUS printout of "Pinto de Souza et al. A simple new method for the preparation of 1-aminoisoquinoline: synthesis and biological activity of pyrimido[2,1-a]isoquinolin-4-one and imidazo[2,1-a]isoquinolin-3-one. Indian Journal of Chemistry, Section B: Organic CHemistry Including Medicinal Chemistry, 1994, 33B, 795-798."*
Gamo et al., "Thousands of chemical starting points for antimalarial lead identification" Nature 465:305-314 (May 20, 2010).

* cited by examiner

*Primary Examiner* — Matthew Coughlin
*Assistant Examiner* — Po-Chih Chen

(57) ABSTRACT

The invention provides novel compounds having the general formula:

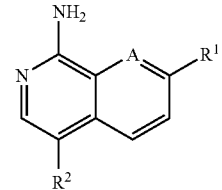

wherein A, $R^1$ and $R^2$ are as described herein, compositions including the compounds and methods of using the compounds.

32 Claims, No Drawings

ISOQUINOLINE AND NAPHTHYRIDINE DERIVATIVES

The present invention relates to organic compounds useful for therapy and/or prophylaxis in a mammal, and in particular to the inhibition of MAP4K4 useful for treating cancer.

Angiogenesis, the process by which new blood vessels develop from existing vasculature, is a critical step in the progression of solid tumors. In response to growth factors, a subset of endothelial cells is activated and migrate away from their parent vessels. Though many factors such as VEGF and FGF have been implicated in promoting the migration of endothelial cells, little is known about what molecules regulate and coordinate the migratory machinery in this cohort of highly motile cells.

Development of a vascular system is a fundamental requirement for many physiological and pathological processes. Active growth of embryos and tumors requires an adequate blood supply. Pro-angiogenic factors promote new blood vessel formation and maintenance via a process generally referred to as angiogenesis. Vascular formation is a complex but orderly biological event involving all or many of the following steps: a) endothelial cells (ECs) within existing vessels proliferate, or new ECs form via differentiation from progenitor cells; b) newly formed ECs migrate to target sites and coalesce to form cord-like structures; c) vascular cords then undergo tubulogenesis to form vessels with a central lumen d) existing cords or vessels send out sprouts to form secondary vessels; e) primitive vascular plexus undergo further remodeling and reshaping; and f) peri-endothelial cells are recruited to encase the endothelial tubes, providing maintenance and modulatory functions to the vessels; such cells including pericytes for small capillaries, smooth muscle cells for larger vessels, and myocardial cells in the heart (Hanahan, D. Science 277:48-50 (1997); Hogan, B. L. & Kolodziej, P. A. Nature Reviews Genetics. 3:513-23 (2002); Lubarsky, B. & Krasnow, M. A. Cell. 112:19-28 (2003)).

Angiogenesis is implicated in the pathogenesis of a variety of disorders. These include malignant tumor growth, atherosclerosis, retrolental fibroplasia, hemangiomas, chronic inflammation, intraocular neovascular diseases such as proliferative retinopathies, e.g., diabetic retinopathy, age-related neovascular macular degeneration (nvAMD), neovascular glaucoma, immune rejection of transplanted corneal tissue and other tissues, rheumatoid arthritis, and psoriasis (Folkman et al., J. Biol. Chem., 267:10931-10934 (1992); Klagsbrun et al., Annu. Rev. Physiol. 53:217-239 (1991); and Garner A., "Vascular diseases", In: Pathobiology of Ocular Disease. A Dynamic Approach, Garner A., Klintworth G K, eds., 2nd Edition (Marcel Dekker, NY, 1994), pp 1625-1710).

In the case of tumor growth, angiogenesis appears to be crucial for the transition from hyperplasia to neoplasia, and for providing nourishment for the growth and metastasis of the tumor (Folkman et al., Nature 339:58 (1989)). The neovascularization allows the tumor cells to acquire a growth advantage and proliferative autonomy compared to the normal cells. A tumor usually begins as a single aberrant cell, which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. Accordingly, a correlation has been observed between density of microvessels in tumor sections and patient survival in breast cancer as well as in several other tumors (Weidner et al., N. Engl. J. Med 324:1-6 (1991); Horak et al., Lancet 340:1120-1124 (1992); Macchiarini et al., Lancet 340:145-146 (1992)). The precise mechanisms that control the angiogenic switch is not well understood, but it is believed that neovascularization of tumor mass results from the net balance of a multitude of angiogenesis stimulators and inhibitors (Folkman, 1995, Nat Med 1(1):27-31). MAP4K4 may play a role in promoting tumor cell migration/invasion. MAP4K4 RNAi inhibited both migration and invasion of SKOV3 human ovarian cancer cells in vitro (Collins et al, 2006, PNAS 103:3775-3780). Analysis of human tumors, including pancreatic, hepatocellular and colorectal cancer, shows a link between high MAP4K4 expression and worse prognosis, with increased tumor size and increased metastasis (Liang et al, 2008, Clin Cancer Res 14:7043-7049, Liu et al, 2011, Clin Cancer Res 17:710-720, Hao et al, 2010, J Pathol 220:475-489).

The present invention provides a method for inhibiting angiogenesis in an animal, e.g., a mammal by inhibition of MAP4K4.

In one aspect the invention relates to compounds of Formula (I):

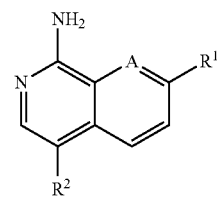

and stereoisomers, geometric isomers, tautomers, and pharmaceutically acceptable salts thereof, wherein A, $R^1$ and $R^2$ are as described therein. Compounds of Formula (I) can be useful as MAP4K4 inhibitors.

Another aspect of the invention provides a pharmaceutical composition comprising a Formula (I) compound and a pharmaceutically acceptable carrier, glidant, diluent, or excipient.

Another aspect of the invention provides the use of a Formula (I) compound in the manufacture of a medicament for treating cancer.

The invention also relates to methods of using the Formula (I) compounds for in vitro, in situ, and in vivo diagnosis or treatment of mammalian cells, organisms, or associated pathological conditions, such as cancer.

Another aspect of the invention provides a method of treating a disease or disorder which method comprises administering a Formula (I) compound to a patient with cancer.

The methods of treating cancer include where the cancer is breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic lymphoid leukemia, chronic myelogenous leukemia, lymphocytic leukemia, myeloid leukemia, oral cavity and pharynx, non-Hodgkin lymphoma, melanoma, or villous colon adenoma.

Another aspect of the invention provides a kit for treating a condition modulated by the inhibition MAP4K4, comprising a first pharmaceutical composition comprising a Formula (I) compound; and instructions for use.

Other aspects of the invention include: (i) method for preventing or treating conditions, disorders or diseases mediated by the activation of the MAP4K4 enzyme, in a subject in need of such treatment, which method comprises administering to said subject an effective amount of a compound of Formula (I) or a pharmaceutically acceptable salt thereof, in free form or in a pharmaceutically acceptable salt form as a pharmaceutical, in any of the methods as indicated herein; (ii) a compound of the Formula (I) in free form or in pharmaceutically acceptable salt form for use as a pharmaceutical in any of the methods described herein, in particular for the use in one or more MAP4K4 mediated diseases; (iii) the use of a compound of Formula (I) in free form or in pharmaceutically acceptable salt form in any of the methods as indicated herein, in particular for the treatment of one or more MAP4K4 mediated diseases; (iv) the use of a compound of Formula (I) in free form or in pharmaceutically acceptable salt form in any of the methods as indicated herein, in particular for the manufacture of a medicament for the treatment of one or more MAP4K4 mediated diseases.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

The term "$C_1$-$C_{12}$-alkoxy" means a $C_1$-$C_{12}$-alkyl group, wherein alkyl is as defined herein, that is linked to the rest of a molecule or to another group through an oxygen atom. Illustrative, non limiting examples of alkoxy include methoxy, ethoxy, n-propoxy, isopropoxy and the different butoxy isomers and $R^2$ groups as exemplified therein.

The term "alkyl" as used herein refers to a saturated linear or branched-chain monovalent hydrocarbon radical of one to twelve carbon atoms ($C_1$-$C_{12}$), wherein the alkyl radical is unsubstituted or substituted independently with one or more substituents described below. In one embodiment alkyl is unsubstituted. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and $R^2$ groups as exemplified therein.

The term "alkylene" or "alkylenyl" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and $R^2$ groups as exemplified therein.

"Aryl" means a monovalent aromatic hydrocarbon radical of 6-20 carbon atoms ($C_6$-$C_{20}$) or $C_6$-$C_{20}$-aryl, derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein. Further non limiting examples of aryl groups can be found in the definition of $R^1$ and $R^2$ herein.

The terms "carbocycle", "carbocyclyl", "carbocyclic ring" and "cycloalkyl" are used interchangeably herein and refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, adamantanyl, and $R^2$ groups as exemplified therein.

The term "halo" denotes chloro, iodo, fluoro and bromo, in one embodiment halo are fluoro, chloro and bromo, and yet in another embodiment fluoro and chloro.

The term "haloalkyl" denotes an alkyl group as defined above wherein at least one of the hydrogen atoms of the alkyl group is replaced by a halogen atom, selected from chloro, bromo, fluoro, iodo, for example fluoro or chloro, and in certain embodiments fluoro. Examples of haloalkyl include $C_1$-$C_{12}$-haloalkyl groups, but are not limited to, methyl, ethyl, propyl, isopropyl, isobutyl, sec-butyl, tert-butyl, pentyl or n-hexyl wherein one or more hydrogen atoms are replaced by Cl, F, Br or I atom(s), as well as those haloalkyl groups specifically illustrated by the examples herein below. Among the preferred haloalkyl groups are monofluoro-, difluoro- or trifluoro-methyl, -ethyl or -propyl, for example 3,3,3-trifluoropropyl, 2-fluoroethyl, 2,2,2-trifluoroethyl, fluoromethyl, trifluoromethyl. The term "$C_1$-$C_{12}$-haloalkyl" means a haloalkyl group having 1 to 12 carbon atoms, wherein the haloalkyl is as defined herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. Examples of heterocycly groups are $C_2$-$C_{12}$-heterocyclyl, i.e. heterocyclyl groups comprising 2 to 12 carbon atoms and 1 to 4 (1, 2, 3 or 4) heteroatoms selected from N, O, P, and S. Examples of $C_2$-$C_{12}$-heterocyclyl are $C_2$-$C_5$-heterocyclyl groups, i.e. heterocyclyl comprising 2 to 5 carbon atoms and 1 to 3 (1, 2 or 3) heteroatoms selected from N, O, P, and S. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2]octane, 3-oxa-8-azabicyclo[3.2.1]octane, 8-oxa-3-azabicyclo[3.2.1]octane, 6-oxa-3-azabicyclo[3.1.1]heptane, 2-oxa-5-azabicyclo[2.2.1]heptane, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituents described herein. In one embodiment, heterocyclic rings are selected from 5 or 6 membered heterocycles comprising 1, 2 or 3 heteroatom(s) selected from N, O or S which are unsubstituted or substituted as indicated herein.

The term "heteroaryl" refers to a monovalent aromatic radical of 5-, 6-, or 7-membered rings, and includes fused ring systems (at least one of which is aromatic) of 5-20 atoms containing one or more heteroatoms independently selected from nitrogen, oxygen, and sulfur. Examples of heteroaryl groups include $C_2$-$C_{12}$-heteroaryls which denotes monocyclic of bicyclic heteroaryl having 2 to 12 carbon atoms and one or more heteroatoms independently selected from nitrogen, oxygen, and sulfur, for example, 1, 2, 3 or 4 heteroatoms independently selected from nitrogen, oxygen, and sulfur. Examples of $C_2$-$C_{12}$-heteroaryls are $C_2$-$C_5$-heteroaryls, which denotes monocyclic of bicyclic heteroaryl having 2 to 5 carbon atoms and one or more heteroatoms independently selected from nitrogen, oxygen, and sulfur, for example, 1, 2, 3 or 4 heteroatoms independently selected from nitrogen, oxygen, and sulfur. Non limiting examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein, for example alkyl, alkoxy, cyano, halo, oxo, $NH_2$, OH, hydroxyalkyl, amido groups. Further examples of heteroaryl groups and of possible substituents can be found in the definition of $R^2$. In one embodiment, heteroaryls are selected from 5 or 6 membered heteroaryls comprising 1, 2 or 3 heteroatom(s) selected from N, O or S which are unsubstituted or substituted as indicated herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Ring nitrogen atoms of the heterocycle or heteroaryl groups may be bonded with oxygen to form N-oxides.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, benzimidazole, position 2 of a isoindole, or isoindoline, position 4 of a morpholine, and position 9 of a carbazole, or β-carboline.

The term "hydroxy" denotes a group of formula —OH.

The term "hydroxyalkyl" denotes an alkyl group as defined above wherein at least one of the hydrogen atoms of the alkyl group is replaced by a hydroxy group. Examples of hydroxyalkyl include, but are not limited to, methyl, ethyl, propyl, isopropyl, isobutyl, sec-butyl, tert-butyl, pentyl or n-hexyl wherein one or more hydrogen atoms are replaced by OH, as well as those hydroxyalkyl groups specifically illustrated by the examples herein below. The term "$C_1$-$C_{12}$-hydroxyalkyl" means a hydroxyalkyl group having 1 to 12 carbon atoms, wherein hydroxyalkyl is as defined herein.

Oxo denotes a group of formula =O.

The expression "one or more substituent" denotes a substitution by 1, 2, 3, 4, 5, 6, 7, 8, 9, 10, 11 or 12 substituent(s) that can be independently selected from the list following this expression. In one embodiment, one or more substituents denotes 1, 2, 3, 4 or 5 substituents. In one embodiment, one or more substituents denotes 1, 2 or 3 substituents.

The expression "substituted" denotes a substitution by "one or more substituent" as defined herein.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, multiple myeloma, acute myelogenous leukemia, chronic lymphoid leukemia, chronic myelogenous leukemia, lymphocytic leukemia, myeloid leukemia, oral cavity and pharynx, non-Hodgkin lymphoma, melanoma, and villous colon adenoma.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space. Stereoisomers include enantiomers and diastereomers.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography. Diastereomers include geometric isomers, cis/trans and E/Z isomers, and atropisomers.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this invention," and "compounds of the present invention" and "compounds of Formula (I)" include compounds of Formulas (I), (I-a), (I-b), (I-c), (I-d), specific compounds described herein and stereoisomers, tautomers, solvates, metabolites, and pharmaceutically acceptable salts and prodrugs thereof.

Any formula or structure given herein, including Formula (I) compounds, is also intended to represent hydrates, solvates, and polymorphs of such compounds, and mixtures thereof.

Any formula or structure given herein, including Formula (I) compounds, is also intended to represent isotopically labeled forms of the compounds as well as unlabeled forms. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

In one aspect, the invention relates to compounds of Formula (I):

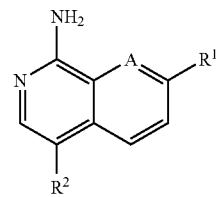

and stereoisomers, geometric isomers, tautomers, and pharmaceutically acceptable salts thereof, wherein:

A is CH or N;

$R^1$ and $R^2$ are independently selected from:

CN;

$C_1$-$C_{12}$-alkyl which is unsubstituted or substituted by one or more substituents selected from the group consisting of cyano, halo, hydroxy, $C_1$-$C_{12}$-alkoxy, $C_3$-$C_{12}$-cycloalkyl, —$NH_2$, —NH—$C_1$-$C_{12}$-alkyl, —NH—$C_2$-$C_{12}$-heteroaryl, —NHC(O)—$C_1$-$C_{12}$-alkyl, —NHC(O)—$C_3$-$C_{12}$-cycloalkyl, —NHC(O)—$C_6$-$C_{20}$-aryl, —NHC(O)—$C_2$-$C_{12}$-heteroaryl, —NHC(O)NH—$C_1$-

$C_{12}$-alkyl, —NHC(O)NH—$C_2$-$C_{12}$-heteroaryl, —NHS(O)$_2$—$C_1$-$C_{12}$-alkyl, and —NHS(O)$_2$—$C_3$-$C_{12}$-cycloalkyl;

$C_1$-$C_{12}$-alkoxy which is unsubstituted or substituted by halo;

$C_3$-$C_{12}$-cycloalkyl which is unsubstituted or substituted by one or more substituents selected from the group consisting of cyano, halo, hydroxy, —NH$_2$, $C_1$-$C_{12}$-alkyl, $C_1$-$C_{12}$-alkoxy, $C_3$-$C_{12}$-cycloalkyl, $C_2$-$C_{12}$-heterocyclyl, $C_6$-$C_{20}$-aryl, and $C_2$-$C_{12}$-heteroaryl, wherein said cycloalkyl, heterocyclyl, aryl, and heteroaryl can be unsubstituted or substituted by one or more substituents selected from the group consisting of: halo, OH, CN, NH$_2$, —NH($C_1$-$C_{12}$-alkyl), —N($C_1$-$C_{12}$-alkyl)$_2$, $C_1$-$C_{12}$-alkyl, $C_1$-$C_{12}$-alkoxy, $C_1$-$C_{12}$-haloalkyl, $C_1$-$C_{12}$-hydroxyalkyl, —C(O)$C_1$-$C_{12}$-alkyl, and —C(O)NH$C_1$-$C_{12}$-alkyl;

—NHR$^a$, wherein R$^a$ is selected from the group consisting of:
- $C_3$-$C_{12}$-cycloalkyl, which is unsubstituted or substituted by one or more $C_1$-$C_{12}$-alkyl;
- —$C_2$-$C_{12}$-heterocyclyl, which is unsubstituted or substituted by one or more substituents selected from the group consisting of: —C(O)—$C_1$-$C_{12}$-alkyl and —C(O)O—$C_1$-$C_{12}$-alkyl;
- —$C_1$-$C_{12}$-alkylenyl-$C_6$-$C_{20}$-aryl, wherein the aryl is unsubstituted or substituted by one or more substituents selected from the group consisting of: halo, $C_1$-$C_{12}$-alkyl and $C_2$-$C_{12}$-heterocyclyl;
- —$C_1$-$C_{12}$-alkylenyl-$C_1$-$C_{12}$-alkoxy-$C_6$-$C_{20}$-aryl, wherein the aryl is unsubstituted or substituted by halo; and
- —$C_1$-$C_{12}$-alkylenyl-$C_2$-$C_{12}$-heteroaryl, wherein the heteroaryl is unsubstituted or substituted by $C_1$-$C_{12}$-alkyl;

—C(O)—$C_2$-$C_{12}$-heterocyclyl, which is unsubstituted or substituted by one or more substituents selected from the group consisting of: $C_1$-$C_{12}$-alkyl, —$C_1$-$C_{12}$-hydroxyalkyl, —C(O)—NH$_2$, —C(O)—N(H)($C_1$-$C_{12}$-alkyl), —C(O)—N($C_1$-$C_{12}$-alkyl)$_2$, —$C_1$-$C_{12}$-alkylenyl-C(O)—N($C_1$-$C_{12}$-alkyl)$_2$-NH—C(O)—$C_1$-$C_{12}$-alkyl, —NH—C(O)—$C_3$-$C_{12}$-cycloalkyl, and —N(C(O)—$C_3$-$C_{12}$-cycloalkyl)$_2$;

—C(O)OH;

—C(O)—$C_1$-$C_{12}$-alkoxy;

—C(O)NR$^b$R$^c$, wherein R$^b$ and R$^c$ are independently selected from the group consisting of:
H;
- —$C_1$-$C_{12}$-alkyl, which is unsubstituted or substituted by one or more substituent selected from the group consisting of:
  OH, CN, NH$_2$, —$C_3$-$C_{12}$-cycloalkyl, —C(O)—NH$_2$, —C(O)—$C_2$-$C_{12}$-heterocyclyl, —N(H)(C(O)—$C_1$-$C_{12}$-alkyl), —N(H)($C_1$-$C_{12}$-alkyl), —N($C_1$-$C_{12}$-alkyl)$_2$, —NHC(O)—NH($C_3$-$C_{12}$-cycloalkyl), —NHC(O)—NH($C_1$-$C_{12}$-alkyl);
- $C_2$-$C_{12}$-heterocyclyl, wherein the heterocyclyl is unsubstituted or substituted by one or more substituents selected from the group consisting of oxo, hydroxy and $C_1$-$C_{12}$-alkyl;
- —C(O)—$C_2$-$C_{12}$-heterocyclyl, wherein the heterocyclyl is unsubstituted or substituted by one or more substituents selected from the group consisting of oxo, hydroxy and $C_1$-$C_{12}$-alkyl;
- —SO$_2$—$C_2$-$C_{12}$-heterocyclyl;
- aryl, which is unsubstituted or substituted by one or more substituents selected from the group consisting of $C_1$-$C_{12}$-alkyl, $C_1$-$C_{12}$-alkoxy, —$C_1$-$C_{12}$-hydroxyalkyl, $C_1$-$C_{12}$-alkylenyl-$C_1$-$C_{12}$-alkoxy; $C_1$-$C_{12}$-alkylenyl-NH$_2$, and —O—$C_2$-$C_{12}$-heterocyclyl, which heterocyclyl is unsubstituted or substituted by $C_1$-$C_{12}$-alkyl; and
- $C_2$-$C_{12}$-heteroaryl, which is unsubstituted or substituted by one or more substituents selected from the group consisting of $C_1$-$C_{12}$-alkyl, $C_1$-$C_{12}$-alkoxy, —C(O)—NH$_2$, —C(O)—N(H)($C_1$-$C_{12}$-alkyl), —C(O)—N($C_1$-$C_{12}$-alkyl)$_2$, and —$C_1$-$C_{12}$-alkylenyl-C(O)—N($C_1$-$C_{12}$-alkyl)$_2$;

—$C_3$-$C_{12}$-cycloalkyl, which is unsubstituted or substituted by one or more hydroxy;

—$C_2$-$C_{12}$-heterocyclyl, which is unsubstituted or substituted by one or more substituents selected from the group consisting of: $C_1$-$C_{12}$-alkyl, —SO$_2$—$C_1$-$C_{12}$-alkyl, —C(O)—$C_1$-$C_{12}$-alkyl, —C(O)—NH$_2$, —C(O)—N(H)($C_1$-$C_{12}$-alkyl), —C(O)—N($C_1$-$C_{12}$-alkyl)$_2$, —C(O)—$C_1$-$C_{12}$-alkylenyl-$C_1$-$C_{12}$-alkoxy, —$C_1$-$C_{12}$-alkylenyl-C(O)—N($C_1$-$C_{12}$-alkyl)$_2$, —C(O)—$C_3$-$C_{12}$-cycloalkyl, and —C(O)NH—$C_3$-$C_{12}$-cycloalkyl;

$C_6$-$C_{20}$-aryl, which is unsubstituted or substituted by one or more substituents selected from the group consisting of $C_1$-$C_{12}$-alkyl, $C_1$-$C_{12}$-alkoxy, —$C_1$-$C_{12}$-hydroxyalkyl, $C_1$-$C_{12}$-alkylenyl-$C_1$-$C_{12}$-alkoxy; $C_1$-$C_{12}$-alkylenyl-NH$_2$, and —O—$C_2$-$C_{12}$-heterocyclyl, which heterocyclyl is unsubstituted or substituted by $C_1$-$C_{12}$-alkyl;

$C_6$-$C_{20}$-heteroaryl, which is unsubstituted or substituted by one or more substituents selected from the group consisting of $C_1$-$C_{12}$-alkyl, $C_1$-$C_{12}$-hydroxyalkyl, and —O—$C_2$-$C_{12}$-heterocyclyl which heterocyclyl is unsubstituted or substituted by $C_1$-$C_{12}$-alkyl;

—O—$C_3$-$C_{12}$-cycloalkyl, —O—$C_2$-$C_{12}$-heterocyclyl, —O—$C_6$-$C_{20}$-aryl and —O—$C_6$-$C_{20}$-heteroaryl, wherein the cycloalkyl, heterocyclyl, aryl and heteroaryl is unsubstituted or substituted by one or more substitutent(s) selected from the group consisting of: halo, cyano, $C_1$-$C_{12}$-alkyl, $C_1$-$C_{12}$-alkoxy and —C(O)NH$_2$;

$C_2$-$C_{12}$-heterocyclyl, which is unsubstituted or substituted by one or more substituents selected from the group consisting of:
halo,
oxo,
—NH$_2$,
$C_1$-$C_{12}$-alkyl, which is unsubstituted or substituted by one or more substituents selected from the group consisting of: OH, halo, $C_1$-$C_{12}$-alkoxy, —C(O)—NH—$C_1$-$C_{12}$-alkyl, and $C_2$-$C_{12}$-heteroaryl, which heteroaryl is unsubstituted or substituted by one or more substituents selected from the group consisting of: $C_1$-$C_{12}$-alkyl, $C_1$-$C_{12}$-alkylenyl-$C_1$-$C_{12}$-alkoxy and —N($C_1$-$C_{12}$-alkyl)$_2$,
$C_1$-$C_{12}$-alkoxy,
—C(O)—R$^d$, wherein R$^d$ is selected from the group consisting of $C_1$-$C_{12}$-alkyl, —$C_2$-$C_{12}$-heterocyclyl, —NH$_2$, —NH—$C_3$-$C_{12}$-cycloalkyl, and —O—$C_1$-$C_{12}$-alkyl,
—N($C_1$-$C_{12}$-alkyl)$_2$,
—N($C_1$-$C_{12}$-alkyl)C(O)—$C_1$-$C_{12}$-alkyl,
—NH(CO)—$C_1$-$C_{12}$-alkylenyl-N($C_1$-$C_{12}$-alkyl)$_2$,
—NH(CO)—$C_1$-$C_{12}$-alkylenyl-$C_1$-$C_{12}$-alkoxy,
—NH(CO)O—$C_1$-$C_{12}$-alkyl, —NH(CO)—$C_1$-$C_{12}$-alkylenyl-N($C_1$-$C_{12}$-alkyl)-C(O)—$C_1$-$C_{12}$-alkyl, —NH(CO)—$C_2$-$C_{12}$-heterocyclyl, wherein the heterocyclyl is unsubstituted or substituted by one or more substituents selected from the group consisting of: oxo, $C_1$-$C_{12}$-alkyl, —C(O)—$C_1$-$C_{12}$-alkyl and —S(O)$_2$—$C_1$-$C_{12}$-alkyl, —NH(CO)—$C_1$-$C_{12}$-alkylenyl-$C_2$-$C_{12}$-heterocyclyl, wherein the heterocyclyl is unsubstituted or substituted by one or more substituents selected from the group consisting of oxo, $C_1$-$C_{12}$-alkyl and —C(O)—$C_1$-$C_{12}$-alkyl, —NH(CO)—$C_1$-$C_{12}$-alkylenyl-$C_2$-$C_{12}$-heteroaryl, wherein the heteroaryl is unsubstituted or substituted by $C_1$-$C_{12}$-alkyl, and $C_3$-$C_{12}$-cycloalkyl, $C_2$-$C_{12}$-heterocyclyl, $C_6$-$C_{20}$-aryl or $C_2$-$C_{12}$-heteroaryl which cycloalkyl, heterocloalkyl, aryl or heteroaryl is unsubstituted or substituted by one or more substituents selected from the group consisting of: OH, $C_1$-$C_{12}$-alkyl, $C_1$-$C_{12}$-haloalkyl, $C_1$-$C_{12}$-hydroxyalkyl, $C_1$-$C_{12}$-alkylenyl-$C_1$-$C_{12}$-alkoxy, —NH—$C_1$-$C_{12}$-alkyl, —N($C_1$-$C_{12}$-alkyl)$_2$, —C(O)NH$_2$, —C(O)NH—$C_1$-$C_{12}$-alkyl, —C(O)N($C_1$-$C_{12}$-alkyl)$_2$ and —S(O)$_2$—$C_1$-$C_{12}$-alkyl;

$C_6$-$C_{20}$-aryl which is unsubstituted or substituted by one or more substituents selected from the group consisting of:

halo;
CN;
OH;
—NH$_2$;
$C_1$-$C_{12}$-alkyl, which is unsubstituted or substituted by one or more substituents selected from the group consisting of:
halo;
OH;
NH($C_1$-$C_{12}$-alkyl), wherein the alkyl is unsubstituted or substituted by OH, —N($C_1$-$C_{12}$-alkyl)$_2$, —C(O)N($C_1$-$C_{12}$-alkyl)$_2$, $C_3$-$C_{12}$-cycloalkyl, or $C_2$-$C_{12}$-heterocyclyl, which cycloalkyl or heterocyclyl is unsubstituted or substituted by $C_1$-$C_{12}$-alkyl;
—NH($C_2$-$C_{12}$-heterocyclyl) which heterocyclyl is unsubstituted or substituted by one or more substituents selected from the group consisting of: oxo and $C_1$-$C_{12}$-alkyl;
—N($C_1$-$C_{12}$-alkyl)($C_2$-$C_{12}$-heterocyclyl) which heterocyclyl is unsubstituted or substituted by one or more substituents selected from the group consisting of: oxo and $C_1$-$C_{12}$-alkyl;
—N($C_1$-$C_{12}$-alkyl)($C_1$-$C_{12}$-alkylenyl-$C_1$-$C_{12}$-alkoxy);
—N($C_1$-$C_{12}$-alkyl)-C(O)—$C_2$-$C_{12}$-heterocyclyl;
—NH($C_3$-$C_{12}$-cycloalkyl), wherein the cycloalkyl is unsubstituted or substituted by halo, or $C_1$-$C_{12}$-hydroxyalkyl;
$C_2$-$C_{12}$-heterocyclyl which is unsubstituted or substituted by one or more substituents selected from the group consisting of:
halo, oxo, OH, $C_1$-$C_{12}$-alkyl, $C_1$-$C_{12}$ hydroxyalkyl, $C_1$-$C_{12}$alkoxy, $C_1$-$C_{12}$-alkylenyl-C(O)—$C_1$-$C_{12}$-alkyl, $C_1$-$C_{12}$-alkylenyl-C(O)N($C_1$-$C_{12}$-alkyl)$_2$, —N($C_1$-$C_{12}$-alkyl)$_2$, —N($C_1$-$C_{12}$-alkyl)-C(O)—$C_1$-$C_{12}$-alkyl, —C(O)—$C_1$-$C_{12}$-alkyl, —C(O)NH$_2$, —C(O)NH($C_1$-$C_{12}$-alkyl), —C(O)NH($C_1$-$C_{12}$-haloalkyl), —C(O)NH($C_1$-$C_{12}$-hydroxyalkyl), —S(O)$_2$—$C_1$-$C_{12}$-alkyl, —S(O)$_2$—N($C_1$-$C_{12}$-alkyl)$_2$, —C(O)NH($C_2$-$C_{12}$-heterocyclyl), —C(O)N($C_1$-$C_{12}$-alkyl)$_2$, and —C(O)—$C_2$-$C_{12}$-heterocyclyl, which heterocyclyl is unsubstituted or substituted by $C_1$-$C_{12}$-alkyl, —C(O)OH, —S(O)$_2$—$C_1$-$C_{12}$-alkyl, —S(O)$_2$—N($C_1$-$C_{12}$-alkyl)$_2$, or $C_2$-$C_{12}$-heterocyclyl;

$C_1$-$C_{12}$-alkoxy which is unsubstituted or substituted by one or more substituents selected from the group consisting of: halo and $C_2$-$C_{12}$-heterocyclyl;

$C_1$-$C_{12}$-alkoxy which is unsubstituted or substituted by $C_2$-$C_{12}$-heterocyclyl;

$C_1$-$C_{12}$-haloalkoxy;
—NH—$C_1$-$C_{12}$-alkylenyl-N($C_1$-$C_{12}$-alkyl)$_2$;
—NH—$C_1$-$C_{12}$-alkylenyl-$C_2$-$C_{12}$-heterocyclyl;
—NH—$C_1$-$C_{12}$-alkylenyl-$C_6$-$C_{20}$-aryl, wherein the $C_6$-$C_{20}$-aryl is unsubstituted or substituted by halo;
—NH—$C_2$-$C_{12}$-heterocyclyl-$C_1$-$C_{12}$-alkylenyl-$C_2$-$C_{12}$-heterocyclyl;
—NHC(O)—$C_1$-$C_{12}$-alkyl, wherein the $C_1$-$C_{12}$-alkyl group is unsubstituted or substituted by one or more substituents selected from the group consisting of: halo, $C_1$-$C_{12}$-alkoxy, —N($C_1$-$C_{12}$-alkyl)$_2$, —$C_3$-$C_{12}$-cycloalkyl, and —$C_2$-$C_{12}$-heterocyclyl, wherein the $C_2$-$C_{12}$-heterocyclyl is unsubstituted or substituted by oxo;
—NHC(O)—$C_1$-$C_{12}$-alkoxy;
—NHC(O)—$C_3$-$C_{12}$-cycloalkyl, wherein the cycloalkyl is unsubstituted or substituted by halo;
—NHC(O)—$C_2$-$C_{12}$-heterocyclyl, wherein the $C_2$-$C_{12}$-heterocyclyl is unsubstituted or substituted by one or more substituents selected from the group consisting of: $C_1$-$C_{12}$-alkyl and —C(O)—$C_1$-$C_{12}$-alkyl;
—NHC(O)NH—$C_3$-$C_{12}$-cycloalkyl, wherein the cycloalkyl is unsubstituted or substituted by OH;
—NH(SO$_2$)—$C_1$-$C_{12}$-alkylenyl-$C_2$-$C_{12}$-heterocyclyl, wherein the heterocyclyl is unsubstituted or substituted by $C_1$-$C_{12}$-alkyl;
—NH(SO$_2$)—$C_2$-$C_{12}$-heterocyclyl;
—C(O)NH$_2$;
—C(O)NH—$C_1$-$C_{12}$-alkyl;
—C(O)NH—$C_1$-$C_{12}$-alkylenyl-N($C_1$-$C_{12}$-alkyl)$_2$;
—C(O)NH—$C_1$-$C_{12}$-alkylenyl-$C_2$-$C_{12}$-heterocyclyl, wherein the heterocyclyl is unsubstituted or substituted by one or more substituents selected from the group consisting of $C_1$-$C_{12}$-alkyl, —C(O)NH—$C_1$-$C_{12}$-hydroxyalkyl, and —C(O)NH—$C_3$-$C_{12}$-cycloalkyl; and $C_3$-$C_{12}$-cycloalkyl, $C_2$-$C_{12}$-heterocyclyl, $C_6$-$C_{20}$-aryl; $C_2$-$C_{12}$-heteroaryl; and —O—$C_2$-$C_{12}$-heteroaryl wherein said cycloalkyl, heterocyclyl, aryl, and heteroaryl can be unsubstituted or substituted by one or more substituents selected from the group consisting of: halo, oxo, OH, CN, NH$_2$, —NH($C_1$-$C_{12}$-alkyl), —N($C_1$-$C_{12}$-alkyl)$_2$, $C_1$-$C_{12}$-alkyl, $C_1$-$C_{12}$-alkoxy, $C_1$-$C_{12}$-haloalkyl, $C_1$-$C_{12}$-hydroxyalkyl, —C(O)$C_1$-$C_{12}$-alkyl, and —C(O)NH$C_1$-$C_{12}$-alkyl;

$C_2$-$C_{12}$-heteroaryl which is unsubstituted or substituted by one or more substituents selected from the group consisting of:
oxo,
halo,
—CN,
—NH$_2$, —NH—C$_1$-C$_{12}$-alkylenyl-N(C$_1$-C$_{12}$-alkylenyl)$_2$,
—NH—C$_1$-C$_{12}$-alkylenyl-C$_2$-C$_{12}$-heterocyclyl;
C$_1$-C$_{12}$-alkyl, which is unsubstituted or substituted by one or more substituents selected from the group consisting of halo, —C(O)—N(C$_1$-C$_{12}$-alkyl)$_2$, and —C$_2$-C$_{12}$-heterocyclyl, wherein the C$_2$-C$_{12}$-heterocyclyl is unsubstituted or substituted by C$_1$-C$_{12}$-alkyl;
—C(O)—NH$_2$,
—C(O)—N(H)(C$_1$-C$_{12}$-alkyl),
—C(O)—N(C$_1$-C$_{12}$-alkyl)$_2$, and
C$_3$-C$_{12}$-cycloalkyl, C$_2$-C$_{12}$-heterocyclyl, C$_6$-C$_{20}$-aryl, C$_2$-C$_{12}$-heteroaryl wherein said cycloalkyl, heterocyclyl, aryl, and heteroaryl can be unsubstituted or substituted by one or more substituents selected from the group consisting of: halo, OH, CN, NH$_2$, —NH(C$_1$-C$_{12}$-alkyl), —N(C$_1$-C$_{12}$-alkyl)$_2$, C$_1$-C$_{12}$-alkyl, C$_1$-C$_{12}$-alkoxy, C$_1$-C$_{12}$-haloalkyl, C$_1$-C$_{12}$-hydroxyalkyl, —C(O)C$_1$-C$_{12}$-alkyl, and —C(O)NHC$_1$-C$_{12}$-alkyl;
with the proviso that when A is CH, R$^1$ is selected from phenyl that is unsubstituted or substituted by halo.

In one embodiment, the invention relates to compounds of Formula (I) and stereoisomers, geometric isomers, tautomers, and pharmaceutically acceptable salts thereof, wherein:
A is CH or N;
R$^1$ is
C$_6$-C$_{20}$-aryl, which is unsubstituted or substituted by one or more halo, CN, or C$_1$-C$_{12}$-alkyl, which is unsubstituted or substituted by one or more halo; or
C$_2$-C$_{12}$-heteroaryl which is unsubstituted or substituted by one or more substituents selected from the group consisting of halo and C$_1$-C$_{12}$-alkyl;
R$^2$ is independently selected from:
CN;
C$_1$-C$_{12}$-alkyl which is unsubstituted or substituted by one or more substituents selected from the group consisting of cyano, halo, hydroxy, C$_1$-C$_{12}$-alkoxy, C$_3$-C$_{12}$-cycloalkyl, —NH$_2$, —NH—C$_1$-C$_{12}$-alkyl, —NH—C$_2$-C$_{12}$-heteroaryl, —NHC(O)—C$_1$-C$_{12}$-alkyl, —NHC(O)—C$_3$-C$_{12}$-cycloalkyl, —NHC(O)—C$_6$-C$_{20}$-aryl, —NHC(O)—C$_2$-C$_{12}$-heteroaryl, —NHC(O)NH—C$_1$-C$_{12}$-alkyl, —NHC(O)NH—C$_2$-C$_{12}$-heteroaryl, —NHS(O)$_2$—C$_1$-C$_{12}$-alkyl, and —NHS(O)$_2$—C$_3$-C$_{12}$-cycloalkyl;
—C(O)—C$_2$-C$_{12}$-heterocyclyl, which is unsubstituted or substituted by one or more substituents selected from the group consisting of: C$_1$-C$_{12}$-alkyl, —C$_1$-C$_{12}$-hydroxyalkyl, —C(O)—NH$_2$, —C(O)—N(H)(C$_1$-C$_{12}$-alkyl), —C(O)—N(C$_1$-C$_{12}$-alkyl)$_2$, —C$_1$-C$_{12}$-alkylenyl-C(O)—N(C$_1$-C$_{12}$-alkyl)$_2$-NH—C(O)—C$_1$-C$_{12}$-alkyl, —NH—C(O)—C$_3$-C$_{12}$-cycloalkyl, and —N(C(O)—C$_3$-C$_{12}$-cycloalkyl)$_2$;
—C(O)OH;
—C(O)—C$_1$-C$_{12}$-alkoxy;
—C(O)NR$^b$R$^c$, wherein R$^b$ and R$^c$ are independently selected from the group consisting of:
H;
—C$_1$-C$_{12}$-alkyl, which is unsubstituted or substituted by one or more substituent selected from the group consisting of:
OH, CN, NH$_2$, —C$_3$-C$_{12}$-cycloalkyl, —C(O)—NH$_2$, —C(O)—C$_2$-C$_{12}$-heterocyclyl, —N(H)C(O)—C$_1$-C$_{12}$-alkyl), —N(H)(C$_1$-C$_{12}$-alkyl), —N(C$_1$-C$_{12}$-alkyl)$_2$, —NHC(O)—NH(C$_3$-C$_{12}$-cycloalkyl), —NHC(O)—NH(C$_1$-C$_{12}$-alkyl);

C$_2$-C$_{12}$-heterocyclyl, wherein the heterocyclyl is unsubstituted or substituted by one or more substituents selected from the group consisting of oxo, hydroxy and C$_1$-C$_{12}$-alkyl;
—C(O)—C$_2$-C$_{12}$-heterocyclyl, wherein the heterocyclyl is unsubstituted or substituted by one or more substituents selected from the group consisting of oxo, hydroxy and C$_1$-C$_{12}$-alkyl;
—SO$_2$—C$_2$-C$_{12}$-heterocyclyl;
aryl, which is unsubstituted or substituted by one or more substituents selected from the group consisting of C$_1$-C$_{12}$-alkyl, C$_1$-C$_{12}$-alkoxy, —C$_1$-C$_{12}$-hydroxyalkyl, C$_1$-C$_{12}$-alkylenyl-C$_1$-C$_{12}$-alkoxy; C$_1$-C$_{12}$-alkylenyl-NH$_2$, and —O—C$_2$-C$_{12}$-heterocyclyl, which heterocyclyl is unsubstituted or substituted by C$_1$-C$_{12}$-alkyl; and
C$_2$-C$_{12}$-heteroaryl, which is unsubstituted or substituted by one or more substituents selected from the group consisting of C$_1$-C$_{12}$-alkyl, C$_1$-C$_{12}$-alkoxy, —C(O)—NH$_2$, —C(O)—N(H)(C$_1$-C$_{12}$-alkyl), —C(O)—N(C$_1$-C$_{12}$-alkyl)$_2$, and —C$_1$-C$_{12}$-alkylenyl-C(O)—N(C$_1$-C$_{12}$-alkyl)$_2$;
—C$_3$-C$_{12}$-cycloalkyl, which is unsubstituted or substituted by one or more hydroxy;
—C$_2$-C$_{12}$-heterocyclyl, which is unsubstituted or substituted by one or more substituents selected from the group consisting of: C$_1$-C$_{12}$-alkyl, —SO$_2$—C$_1$-C$_{12}$-alkyl, —C(O)—C$_1$-C$_{12}$-alkyl, —C(O)—NH$_2$, —C(O)—N(H)(C$_1$-C$_{12}$-alkyl), —C(O)—N(C$_1$-C$_{12}$-alkyl)$_2$, —C(O)—C$_1$-C$_{12}$-alkylenyl-C$_1$-C$_{12}$-alkoxy, —C$_1$-C$_{12}$-alkylenyl-C(O)—N(C$_1$-C$_{12}$-alkyl)$_2$, —C(O)—C$_3$-C$_{12}$-cycloalkyl, and —C(O)NH—C$_3$-C$_{12}$-cycloalkyl;
C$_6$-C$_{20}$-aryl, which is unsubstituted or substituted by one or more substituents selected from the group consisting of C$_1$-C$_{12}$-alkyl, C$_1$-C$_{12}$-alkoxy, —C$_1$-C$_{12}$-hydroxyalkyl, C$_1$-C$_{12}$-alkylenyl-C$_1$-C$_{12}$-alkoxy; C$_1$-C$_{12}$-alkylenyl-NH$_2$, and —O—C$_2$-C$_{12}$-heterocyclyl, which heterocyclyl is unsubstituted or substituted by C$_1$-C$_{12}$-alkyl;
C$_6$-C$_{20}$-heteroaryl, which is unsubstituted or substituted by one or more substituents selected from the group consisting of C$_1$-C$_{12}$-alkyl, C$_1$-C$_{12}$-hydroxyalkyl, and —O—C$_2$-C$_{12}$-heterocyclyl which heterocyclyl is unsubstituted or substituted by C$_1$-C$_{12}$-alkyl;
C$_2$-C$_{12}$-heteroaryl which is unsubstituted or substituted by C$_1$-C$_{12}$-alkyl, which alkyl is unsubstituted or substituted by one or more substituents selected from the group consisting of halo, —C(O)—N(C$_1$-C$_{12}$-alkyl)$_2$, and —C$_2$-C$_{12}$-heterocyclyl, wherein the C$_2$-C$_{12}$-heterocyclyl is unsubstituted or substituted by C$_1$-C$_{12}$-alkyl.

In one embodiment, the compounds of the invention are compounds of Formula (I), wherein:
A is CH or N;
R$^1$ is C$_6$-C$_{20}$-aryl substituted by one two or three halo;
R$^2$ is:
CN;
C$_1$-C$_{12}$-alkyl which is unsubstituted or substituted by one or more substituents selected from the group consisting of —NH$_2$, —NH—C$_1$-C$_{12}$-alkyl, —NHC(O)—C$_3$-C$_{12}$-cycloalkyl, —NHC(O)—C$_6$-C$_{20}$-aryl, and —NHS(O)$_2$—C$_3$-C$_{12}$-cycloalkyl;
—C(O)—C$_2$-C$_{12}$-heterocyclyl, which is unsubstituted or substituted by one or more substituents selected from the group consisting of: —C$_1$-C$_{12}$-hydroxyalkyl, —C$_1$-

$C_{12}$-alkylenyl—C(O)—N($C_1$-$C_{12}$-alkyl)$_2$, —NH—C(O)—$C_1$-$C_{12}$-alkyl, —NH—C(O)—$C_3$-$C_{12}$-cycloalkyl, and —N(C(O)—$C_3$-$C_{12}$-cycloalkyl)$_2$;

—C(O)OH;

—C(O)—$C_1$-$C_{12}$-alkoxy;

—C(O)NR$^b$R$^c$, wherein R$^b$ and R$^c$ are independently selected from the group consisting of:

H;

—$C_1$-$C_{12}$-alkyl, which is unsubstituted or substituted by one or more substituent selected from the group consisting of:

OH, CN, NH$_2$, —$C_3$-$C_{12}$-cycloalkyl, —C(O)—NH$_2$, —C(O)—$C_2$-$C_{12}$-heterocyclyl, —N(H)(C(O)—$C_1$-$C_{12}$-alkyl), —N(H)($C_1$-$C_{12}$alkyl), —N($C_1$-$C_{12}$-alkyl)$_2$, —NHC(O)—NH($C_3$-$C_{12}$-cycloalkyl), —NHC(O)—NH($C_1$-$C_{12}$-alkyl);

$C_2$-$C_{12}$-heterocyclyl, wherein the heterocyclyl is unsubstituted or substituted by one or more substituents selected from the group consisting of oxo, hydroxy and $C_1$-$C_{12}$-alkyl;

—C(O)—$C_2$-$C_{12}$-heterocyclyl;

—SO$_2$—$C_2$-$C_{12}$-heterocyclyl;

$C_6$-$C_{20}$-aryl, which is unsubstituted or substituted by $C_1$-$C_{12}$alkoxy; and $C_2$-$C_{12}$-heteroaryl, which is unsubstituted or substituted by one or more substituents selected from the group consisting of $C_1$-$C_{12}$-alkyl, —C(O)—NH$_2$, —C(O)—N(H)($C_1$-$C_{12}$-alkyl), and —C(O)—N($C_1$-$C_{12}$-alkyl)$_2$;

—$C_3$-$C_{12}$-cycloalkyl, which is unsubstituted or substituted by one or more hydroxy;

—$C_2$-$C_{12}$-heterocyclyl, which is unsubstituted or substituted by one or more substituents selected from the group consisting of: $C_1$-$C_{12}$-alkyl, —SO$_2$—$C_1$-$C_{12}$-alkyl, —C(O)—$C_1$-$C_{12}$-alkyl, —C(O)—NH$_2$, —C(O)—N(H)($C_1$-$C_{12}$-alkyl), —C(O)—N($C_1$-$C_{12}$-alkyl)$_2$, —C(O)—$C_1$-$C_{12}$-alkylenyl-$C_1$-$C_{12}$-alkoxy, —$C_1$-$C_{12}$-alkylenyl-C(O)—N($C_1$-$C_{12}$-alkyl)$_2$, —C(O)—$C_3$-$C_{12}$-cycloalkyl, and —C(O)NH—$C_3$-$C_{12}$-cycloalkyl;

$C_6$-$C_{20}$-aryl, which is unsubstituted or substituted by one or more substituents selected from the group consisting of $C_1$-$C_{12}$-alkyl, $C_1$-$C_{12}$-alkoxy, —$C_1$-$C_{12}$-hydroxyalkyl, $C_1$-$C_{12}$-alkylenyl-$C_1$-$C_{12}$-alkoxy; $C_1$-$C_{12}$-alkylenyl-NH$_2$, and —O—$C_2$-$C_{12}$-heterocyclyl, which heterocyclyl is unsubstituted or substituted by $C_1$-$C_{12}$-alkyl;

$C_6$-$C_{20}$-heteroaryl, which is unsubstituted or substituted by one or more substituents selected from the group consisting of $C_1$-$C_{12}$-alkyl, which is unsubstituted or substituted by $C_2$-$C_{12}$-heterocyclyl, $C_1$-$C_{12}$-hydroxyalkyl, and —O—$C_2$-$C_{12}$-heterocyclyl which is unsubstituted or substituted by $C_1$-$C_{12}$-alkyl;

$C_2$-$C_{12}$-heteroaryl which is unsubstituted or substituted by $C_1$-$C_{12}$-alkyl, which alkyl is unsubstituted or substituted by one or more substituents selected from the group consisting of halo, —C(O)—N($C_1$-$C_{12}$-alkyl)$_2$, and —$C_2$-$C_{12}$-heterocyclyl, wherein the heterocyclyl is unsubstituted or substituted by $C_1$-$C_{12}$-alkyl.

In one embodiment, the compounds of the invention are compounds of Formula (I), wherein A is CH.

In one embodiment, the compounds of the invention are compounds of Formula (I), wherein R$^2$ is CN, for example, the following compound:

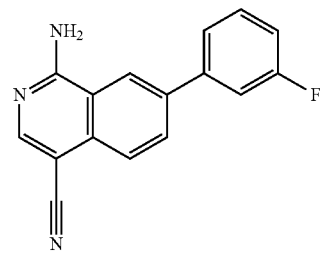 [SMILES: N#Cc1cnc(N)c2cc(-c3cccc(F)c3)ccc12]

In one embodiment, the compounds of the invention are compounds of Formula (I), wherein R$^2$ is $C_1$-$C_{12}$-alkyl which is unsubstituted or substituted by one or more substituents selected from the group consisting of —NH$_2$, —NH—$C_1$-$C_{12}$-alkyl, —NHC(O)—$C_3$-$C_{12}$-cycloalkyl, —NHC(O)—$C_6$-$C_{20}$-aryl, and —NHS(O)$_2$—$C_3$-$C_{12}$-cycloalkyl, for example the following compounds:

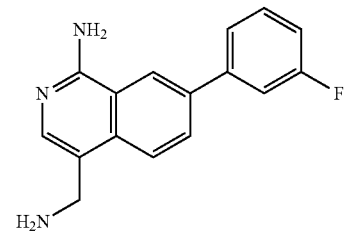

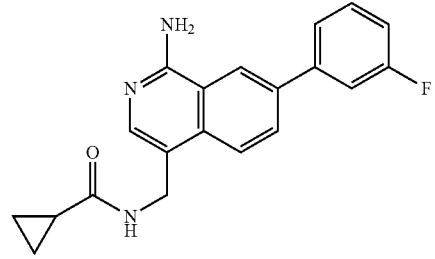

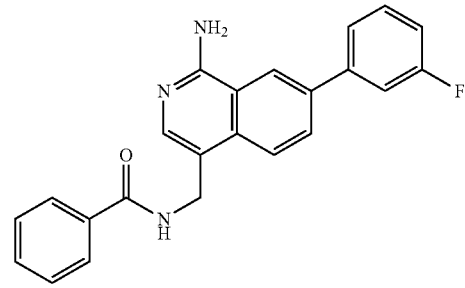

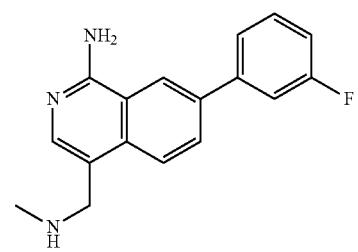

-continued

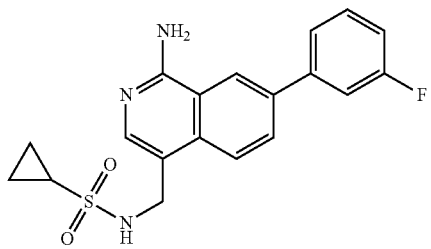

In one embodiment, the compounds of the invention are compounds of Formula (I), wherein $R^2$ is —C(O)—$C_2$-$C_{12}$-heterocyclyl, which is unsubstituted or substituted by one or more substituents selected from the group consisting of: —$C_1$-$C_{12}$-hydroxyalkyl and —$C_1$-$C_{12}$-alkylenyl-C(O)—N($C_1$-$C_{12}$-alkyl)$_2$, for example the following compounds:

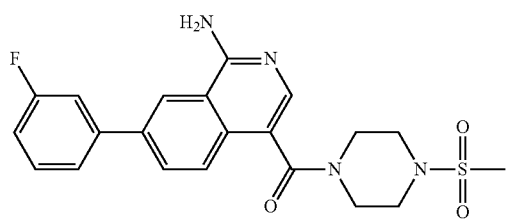

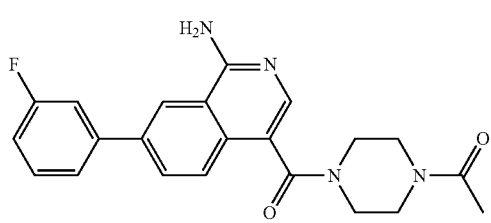

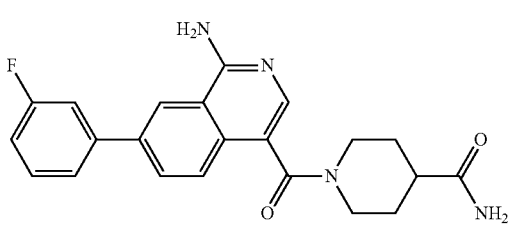

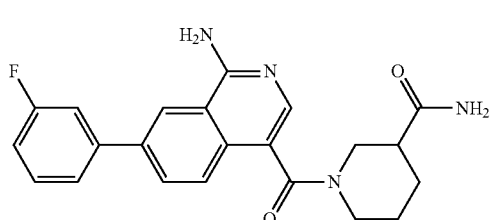

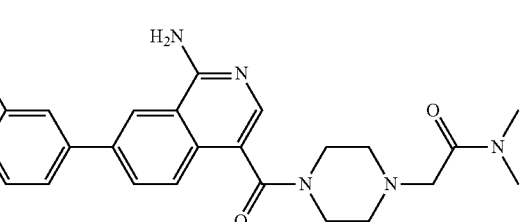

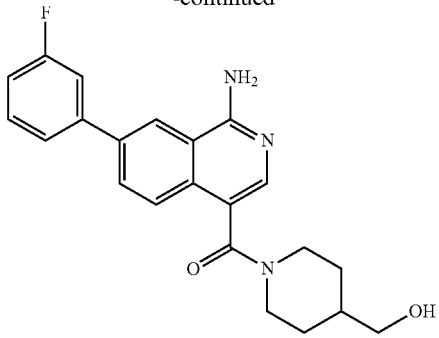

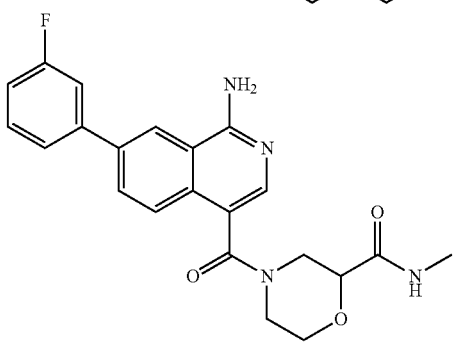

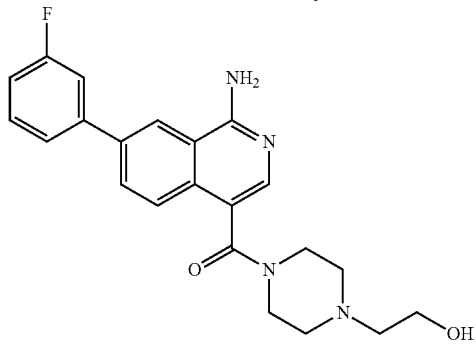

In one embodiment, the compounds of the invention are compounds of Formula (I), wherein $R^2$ is —C(O)OH, for example the following compound:

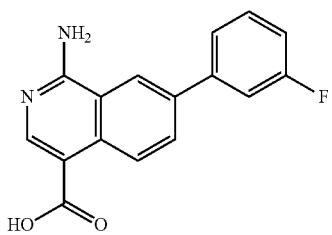 [SMILES: Nc1ncc(C(=O)O)c2ccc(-c3cccc(F)c3)cc12]

In one embodiment, the compounds of the invention are compounds of Formula (I), wherein $R^2$ is —C(O)NR$^b$R$^c$, wherein R$^b$ and R$^c$ are independently selected from the group consisting of:
H;
—$C_1$-$C_{12}$-alkyl, which is unsubstituted or substituted by one or more substituent selected from the group consisting of:
OH, CN, NH$_2$, —$C_3$-$C_{12}$-cycloalkyl, —C(O)—NH$_2$, —C(O)—$C_2$-$C_{12}$-heterocyclyl, —N(H)(C(O)—$C_1$-$C_{12}$-alkyl), —N(H)($C_1$-$C_{12}$-alkyl), —N($C_1$-$C_{12}$- alkyl)$_2$, —NHC(O)—NH(C$_3$-C$_{12}$-cycloalkyl), —NHC(O)—NH(C$_1$-C$_{12}$-alkyl);

C$_2$-C$_{12}$-heterocyclyl, wherein the heterocyclyl is unsubstituted or substituted by one or more substituents selected from the group consisting of oxo, hydroxy and C$_1$-C$_{12}$-alkyl;

—C(O)—C$_2$-C$_{12}$-heterocyclyl;

—SO$_2$—C$_2$-C$_{12}$-heterocyclyl;

C$_6$-C$_{20}$-aryl, which is unsubstituted or substituted by C$_1$-C$_{12}$-alkoxy; and C$_2$-C$_{12}$-heteroaryl, which is unsubstituted or substituted by one or more substituents selected from the group consisting of C$_1$-C$_{12}$-alkyl, —C(O)—NH$_2$, —C(O)—N(H)(C$_1$-C$_{12}$-alkyl), and —C(O)—N(C$_1$-C$_{12}$-alkyl)$_2$;

—C$_3$-C$_{12}$-cycloalkyl, which is unsubstituted or substituted by one or more hydroxy;

—C$_2$-C$_{12}$-heterocyclyl, which is unsubstituted or substituted by one or more substituents selected from the group consisting of: oxo, hydroxy, C$_1$-C$_{12}$-alkyl, —SO$_2$—C$_1$-C$_{12}$-alkyl, —C(O)—C$_1$-C$_{12}$-alkyl, —C(O)—NH$_2$, —C(O)—N(H)(C$_1$-C$_{12}$-alkyl), —C(O)—N(C$_1$-C$_{12}$-alkyl)$_2$, —C(O)—C$_1$-C$_{12}$-alkylenyl-C$_1$-C$_{12}$-alkoxy, —C$_1$-C$_{12}$-alkylenyl-C(O)—N(C$_1$-C$_{12}$-alkyl)$_2$, and —C(O)—C$_3$-C$_{12}$-cycloalkyl, —C(O)NH—C$_3$-C$_{12}$-cycloalkyl;

C$_6$-C$_{20}$-aryl, which is unsubstituted or substituted by one or more substituents selected from the group consisting of C$_1$-C$_{12}$-alkyl, C$_1$-C$_{12}$-alkoxy, —C$_1$-C$_{12}$-hydroxyalkyl, C$_1$-C$_{12}$-alkylenyl-C$_1$-C$_{12}$-alkoxy; C$_1$-C$_{12}$-alkylenyl-NH$_2$, and —O—C$_2$-C$_{12}$-heterocyclyl, which heterocyclyl is unsubstituted or substituted by C$_1$-C$_{12}$-alkyl; and C$_6$-C$_{20}$-heteroaryl, which is unsubstituted or substituted by one or more substituents selected from the group consisting of C$_1$-C$_{12}$-alkyl, which is unsubstituted or substituted by C$_2$-C$_{12}$-heterocyclyl, C$_1$-C$_{12}$-hydroxyalkyl, and —O—C$_2$-C$_{12}$-heterocyclyl which is unsubstituted or substituted by C$_1$-C$_{12}$-alkyl, for example the following compounds:

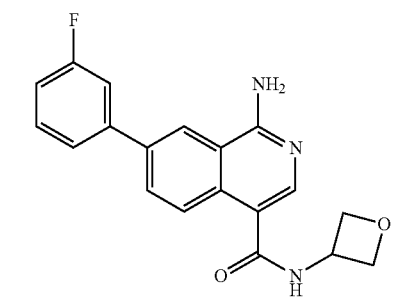

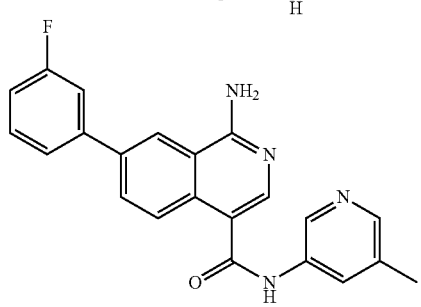

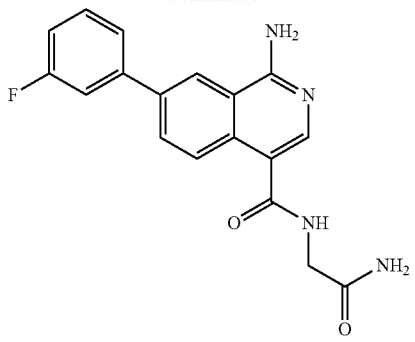

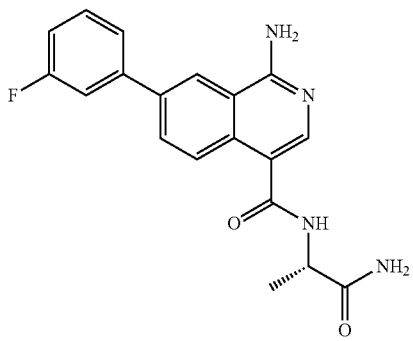

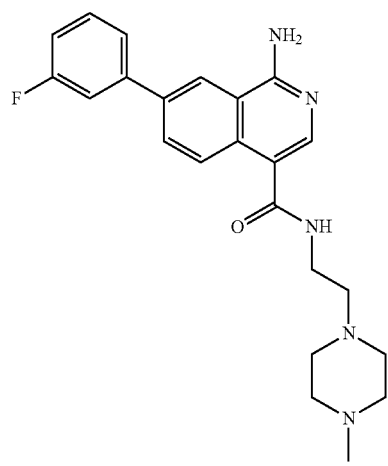

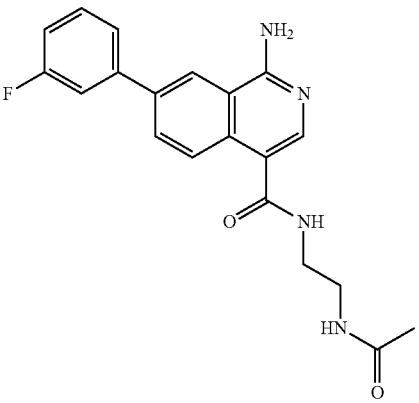

23
-continued
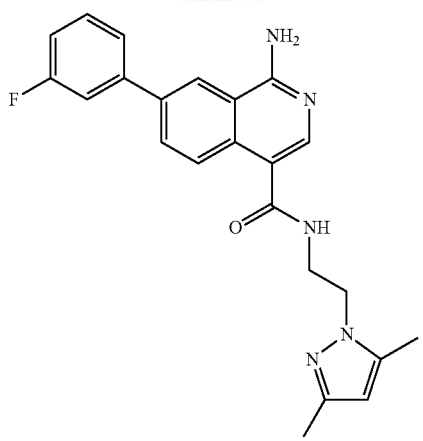
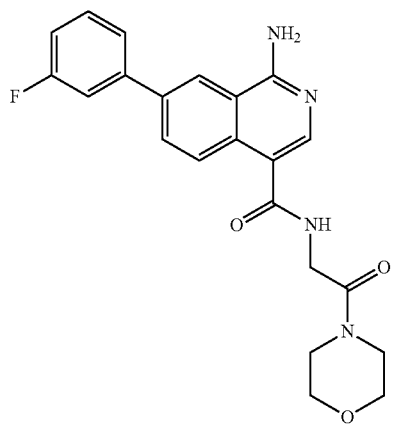
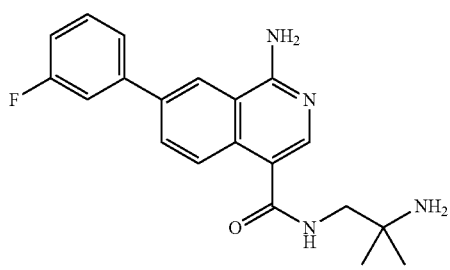
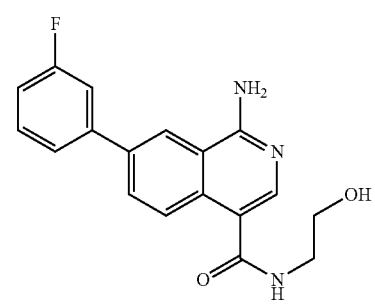
24
-continued
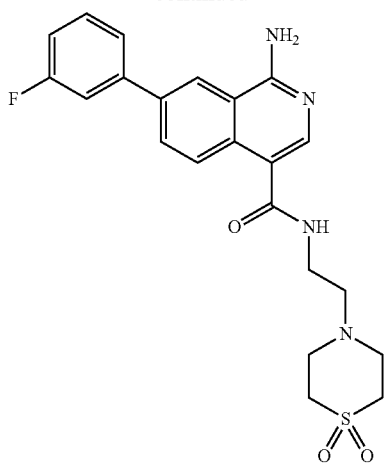
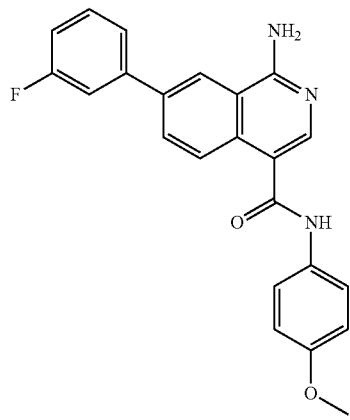
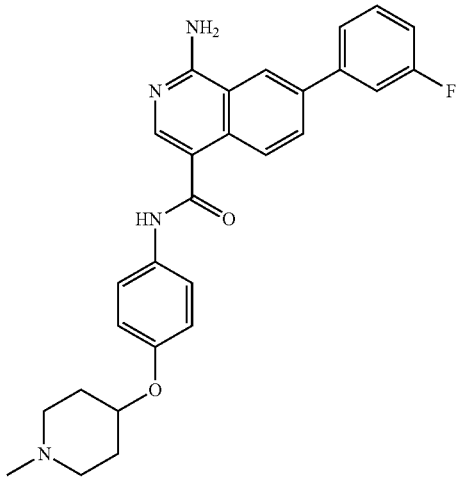

25
-continued
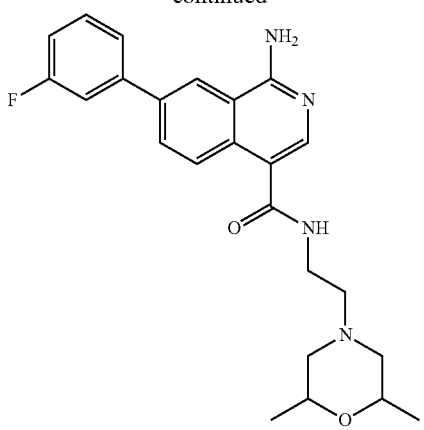
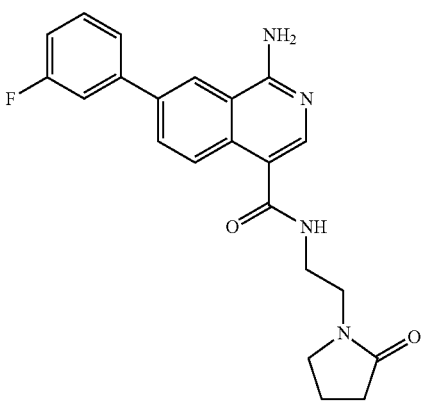
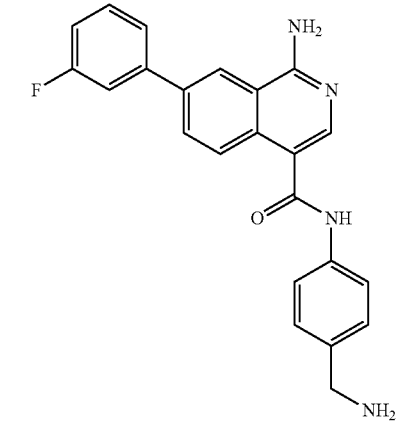
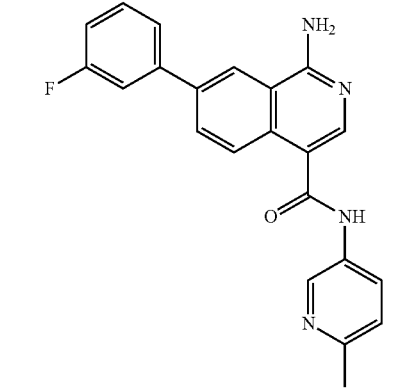
26
-continued
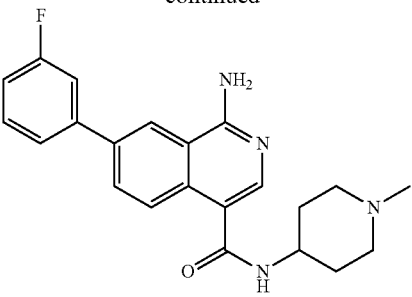
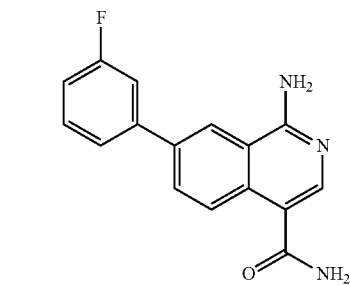
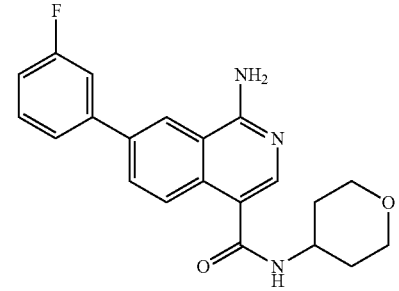
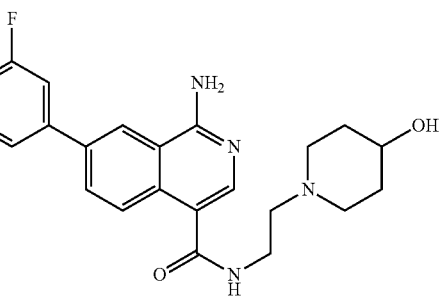
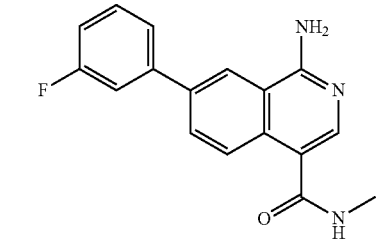

27
-continued
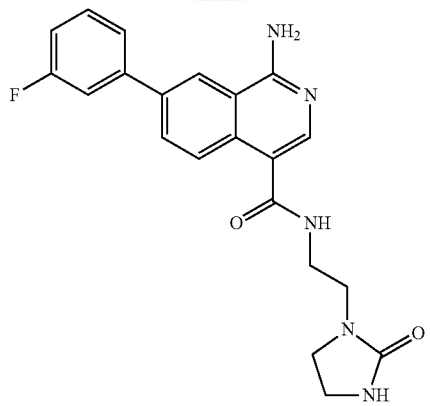
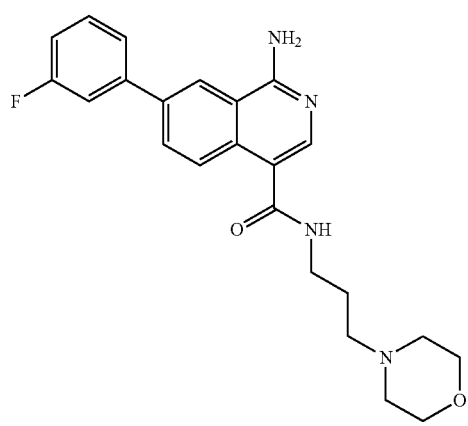
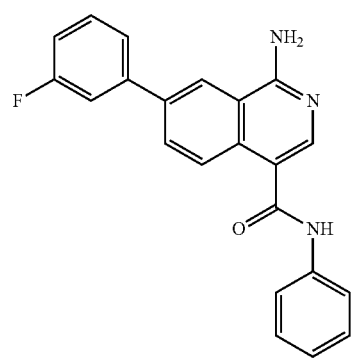
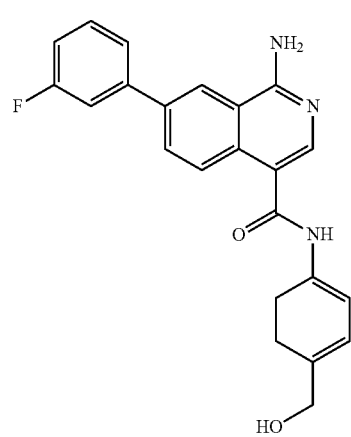
28
-continued
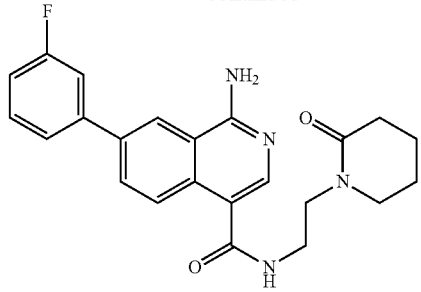
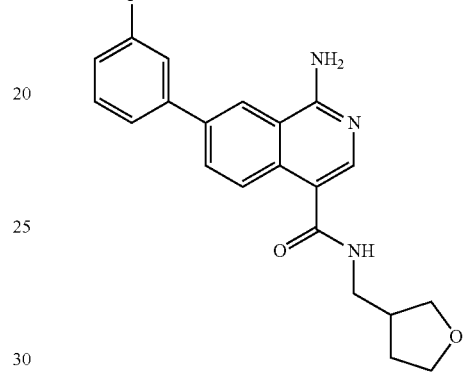
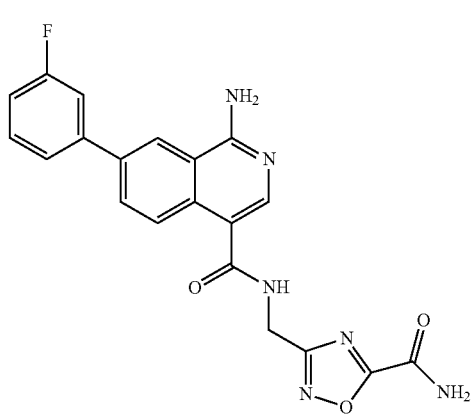
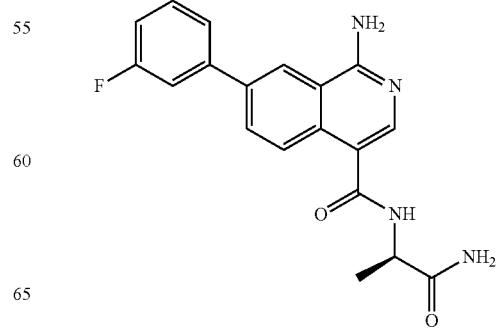

29
-continued
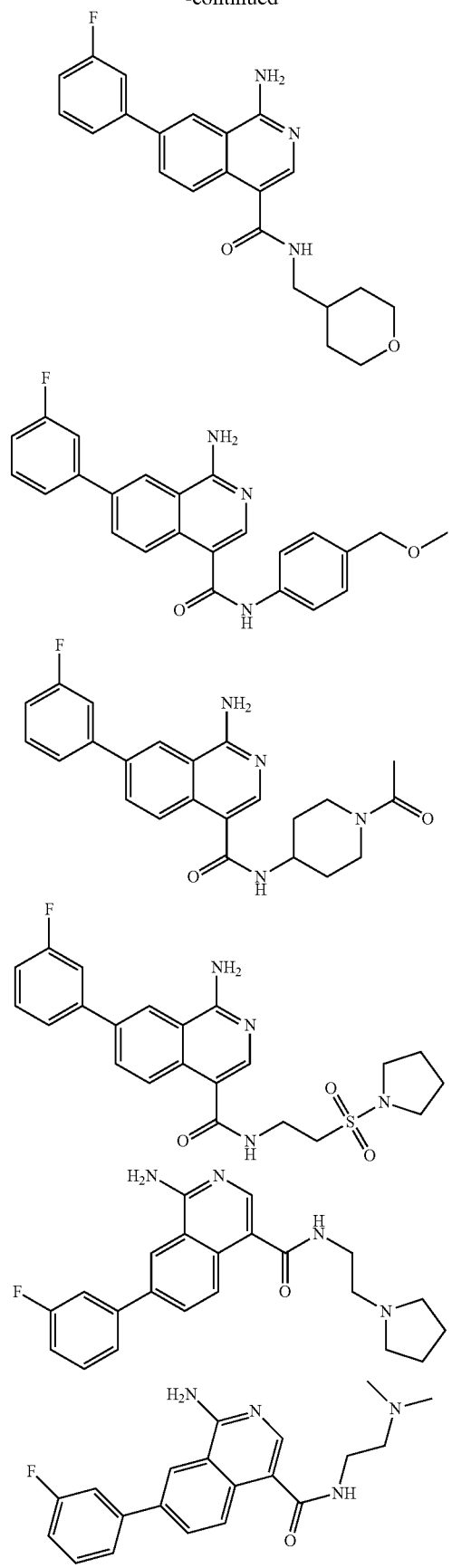
30
-continued
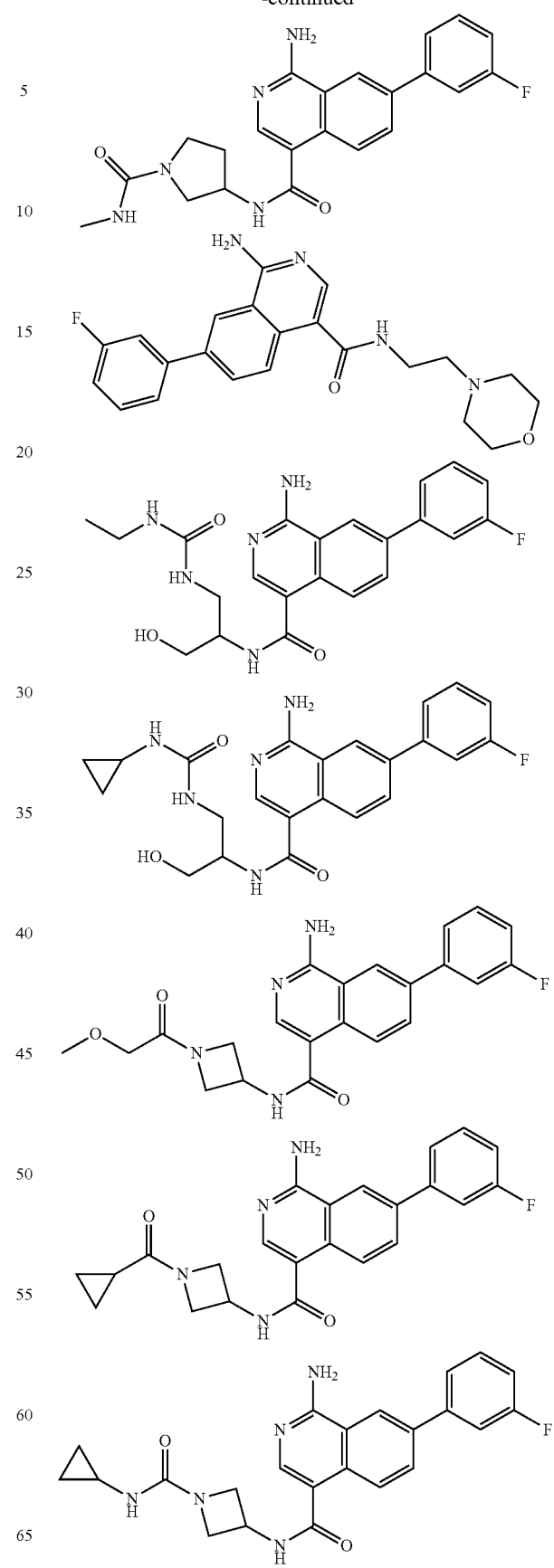

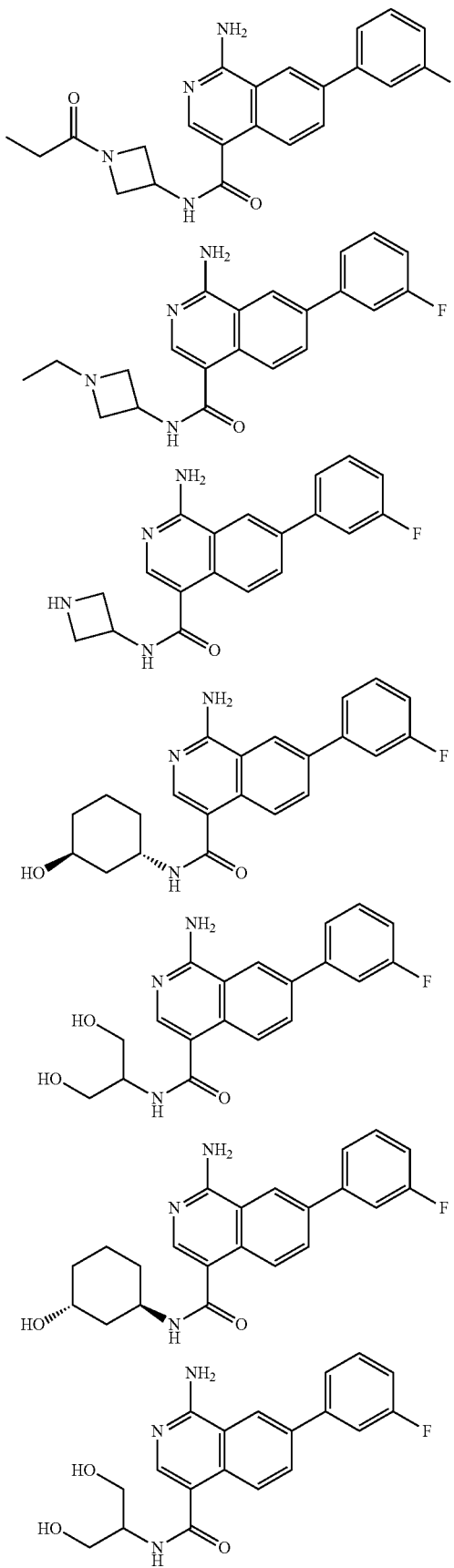
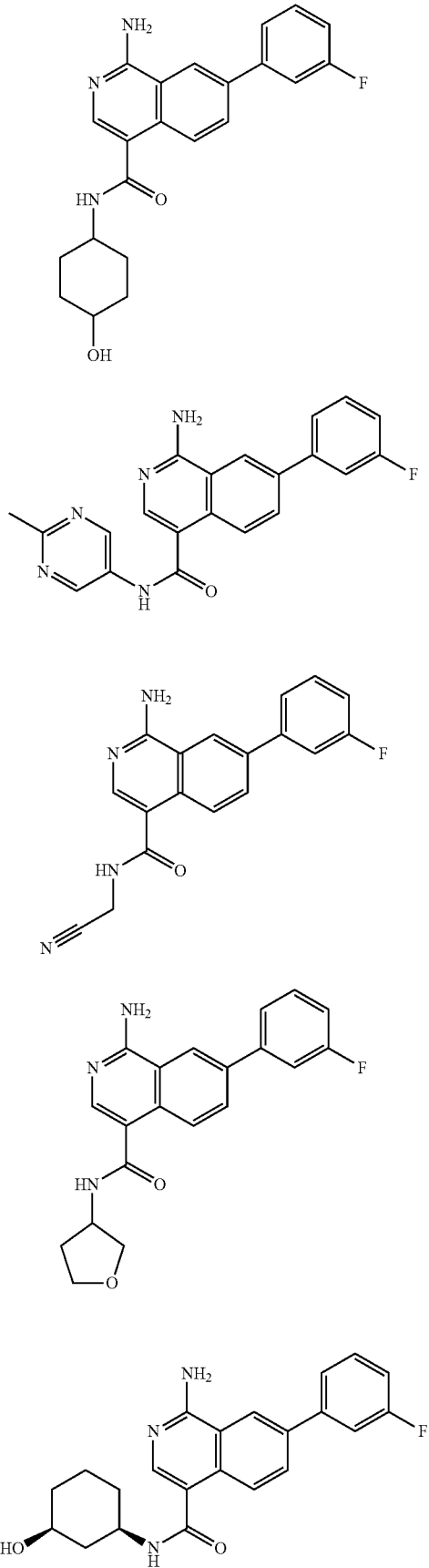

33
-continued
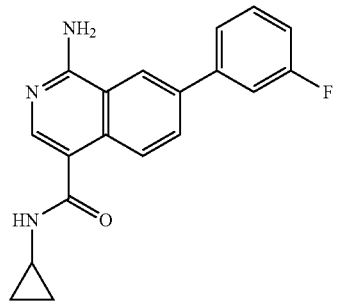
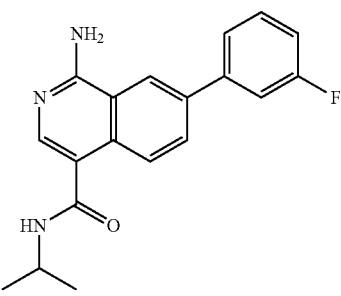
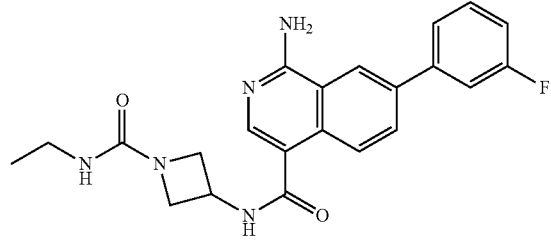
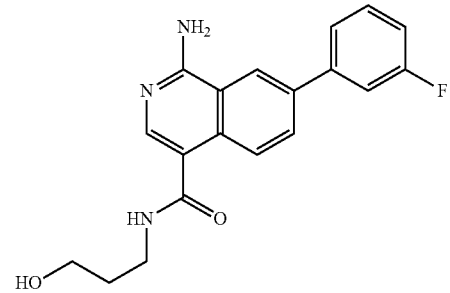
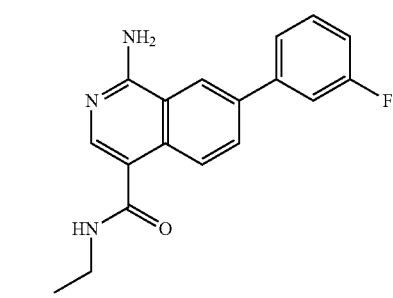
34
-continued
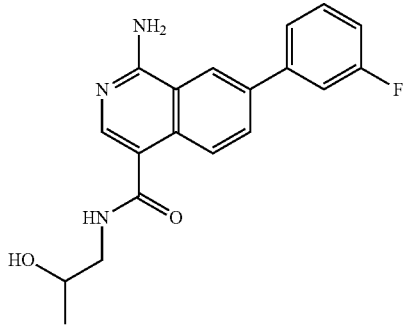
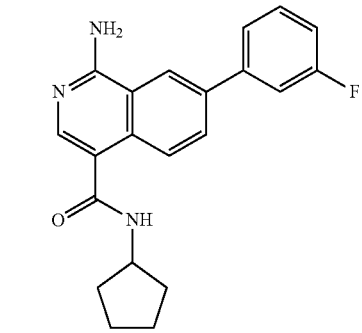
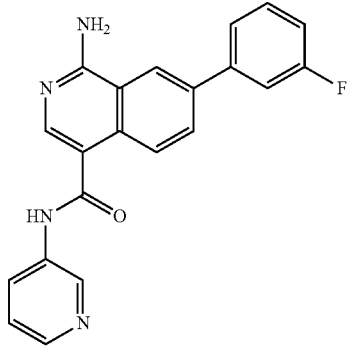
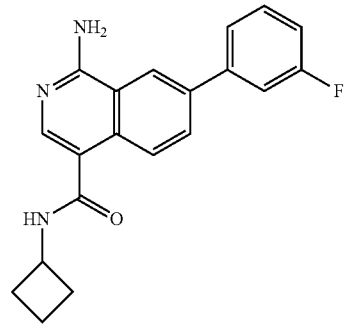
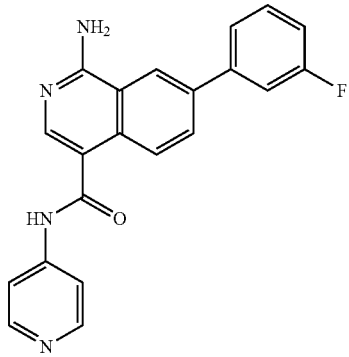

35
-continued
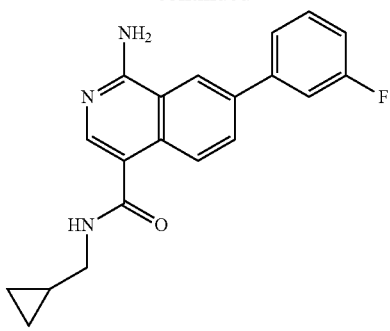
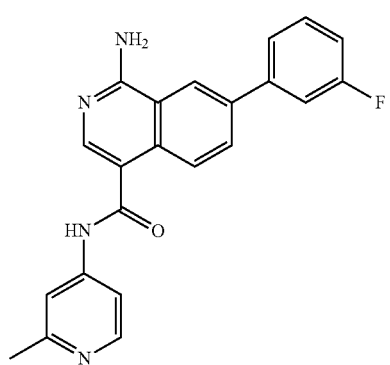
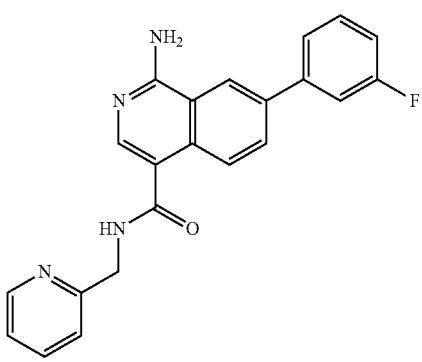
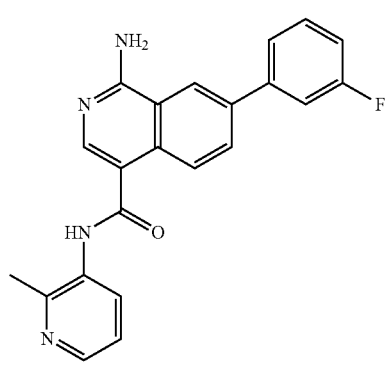
36
-continued
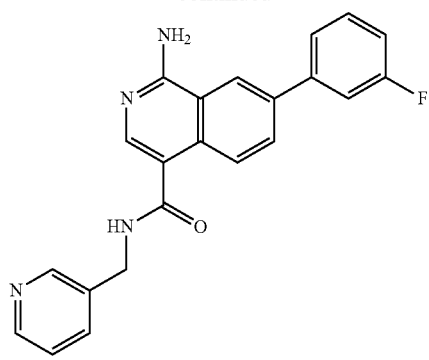
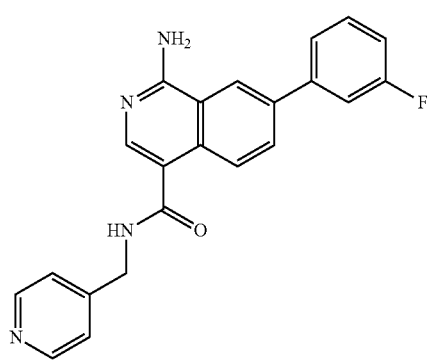
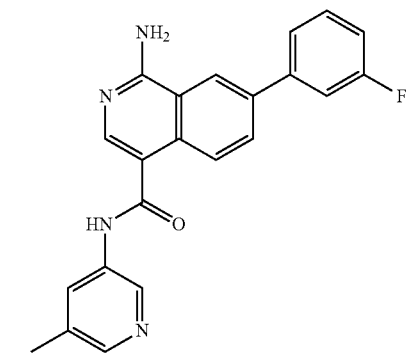
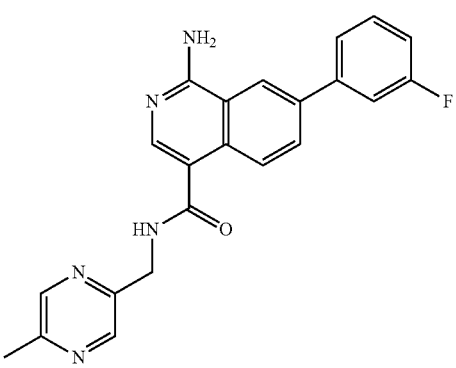

37
-continued
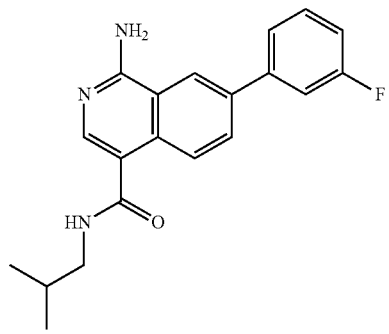
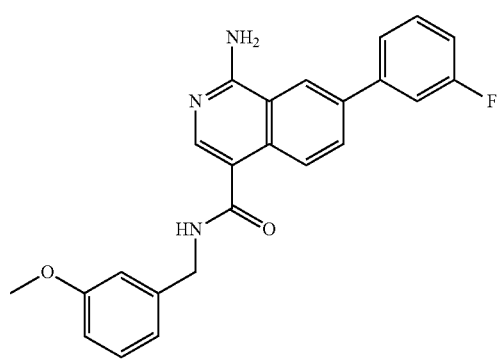
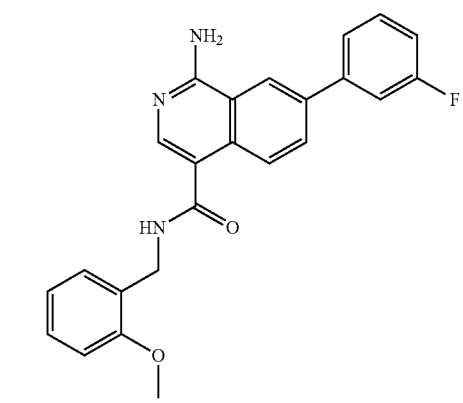
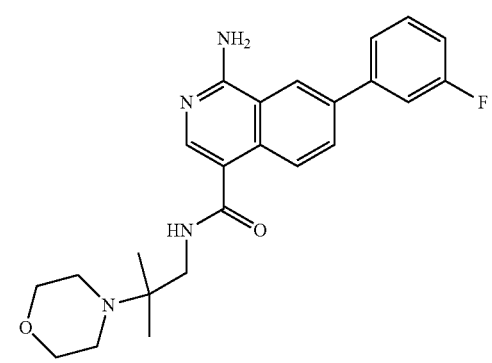
38
-continued
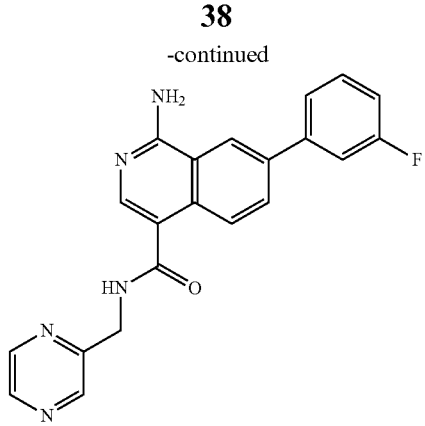
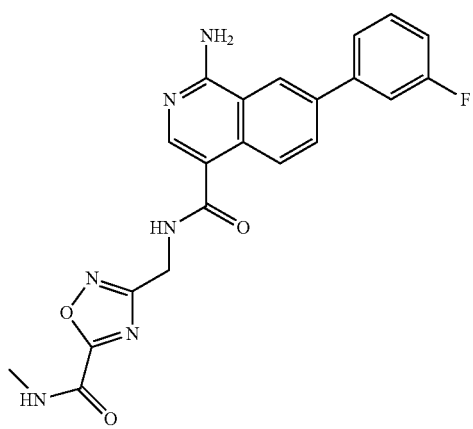
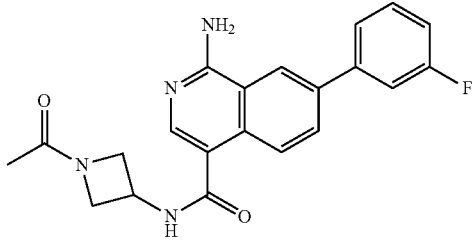
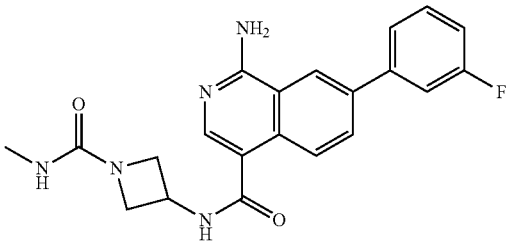

-continued

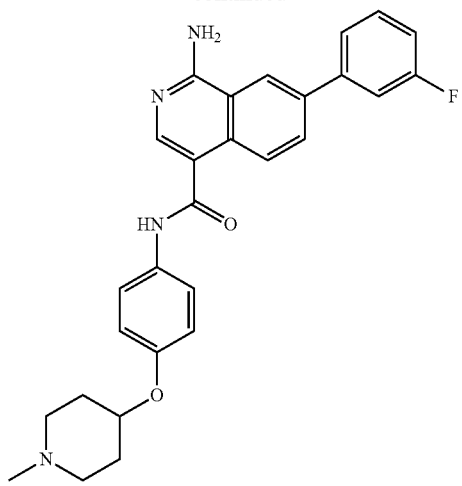

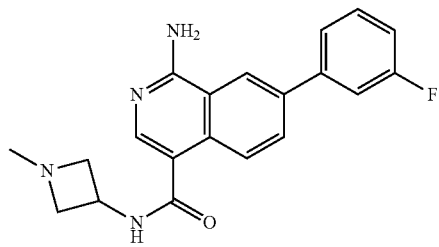

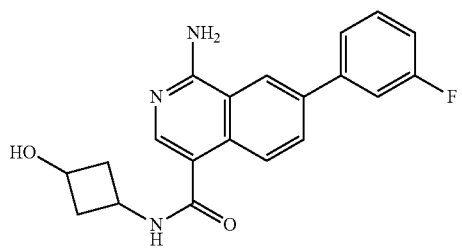

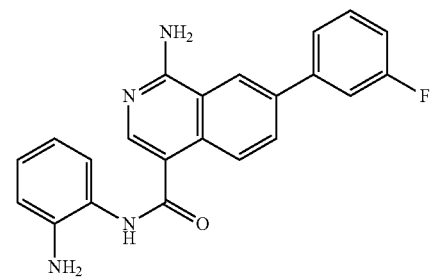

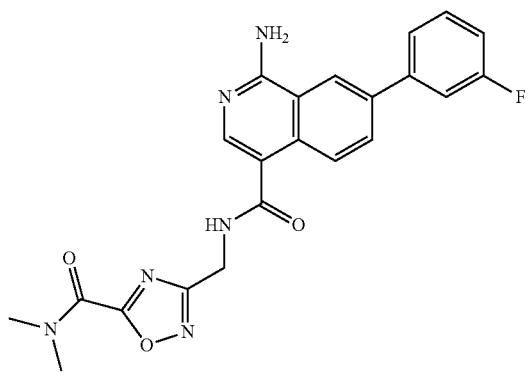

-continued

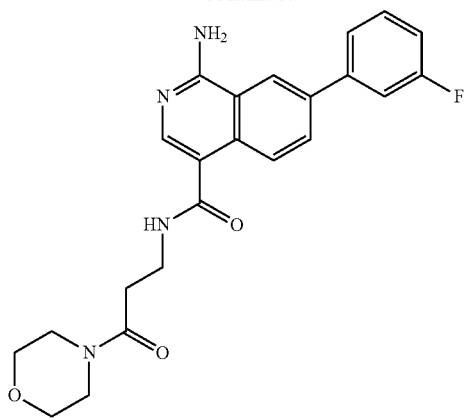

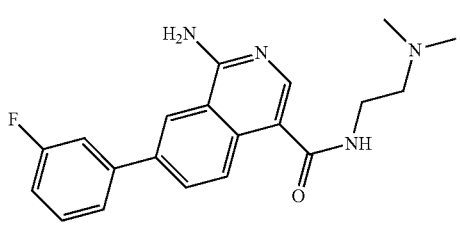

In one embodiment, the compounds of the invention are compounds of Formula (I), wherein $R^2$ is —$C_2$-$C_{12}$-heteroaryl which is unsubstituted or substituted by $C_1$-$C_{12}$-alkyl, which alkyl is unsubstituted or substituted by one or more substituents selected from the group consisting of halo, —C(O)—N($C_1$-$C_{12}$-alkyl)$_2$, and —$C_2$-$C_{12}$-heterocyclyl, wherein the heterocyclyl is unsubstituted or substituted by $C_1$-$C_{12}$-alkyl, for example the following compounds:

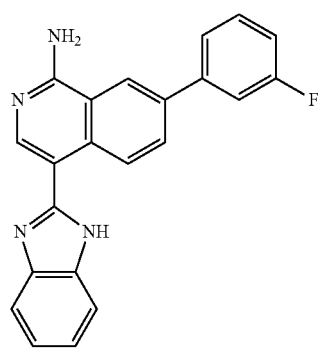

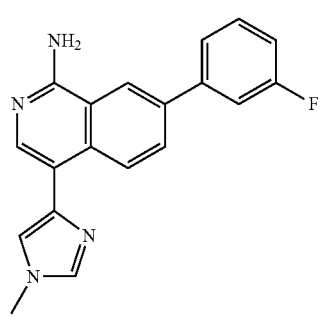

-continued

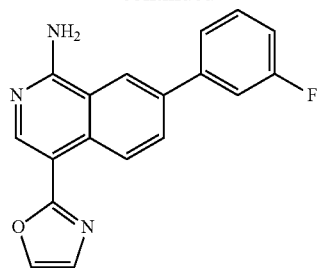

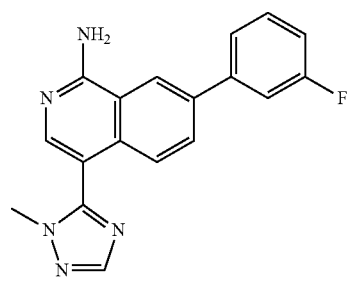

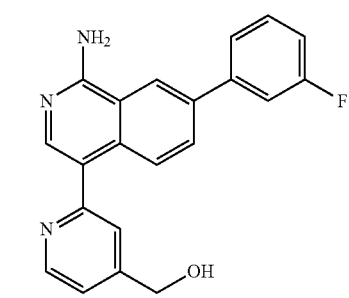

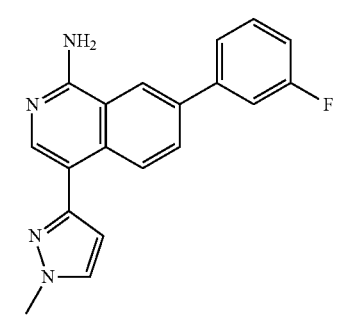 [SMILES: Cn1ccc(-c2cnc(N)c3cc(-c4cccc(F)c4)ccc23)n1]

In one embodiment, the compounds of the invention are compounds of Formula (I), wherein A is N.

In one embodiment, the compounds of the invention are compounds of Formula (I), wherein $R^2$ is $C_6$-$C_{20}$-heteroaryl, which is unsubstituted or substituted by one or more substituents selected from the group consisting of $C_1$-$C_{12}$-alkyl, which is unsubstituted or substituted by $C_2$-$C_{12}$-heterocyclyl;

$C_1$-$C_{12}$-hydroxyalkyl; and

—O—$C_2$-$C_{12}$-heterocyclyl which is unsubstituted or substituted by $C_1$-$C_{12}$-alkyl, for example the following compounds:

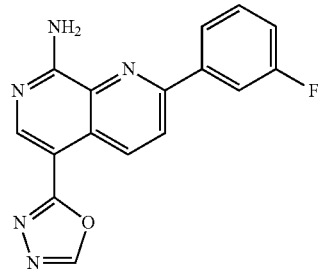

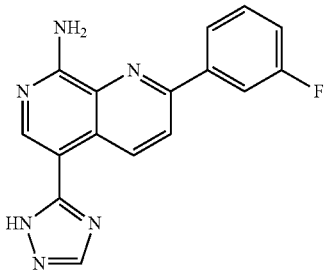

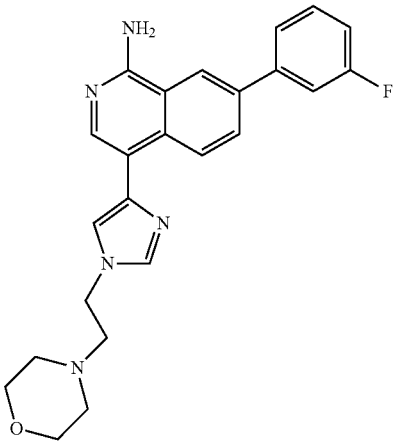

In one embodiment, the compounds of the invention are compounds of Formula (I), wherein $R^2$ is —C(O)—$C_1$-$C_{12}$-alkoxy, for example the following compound:

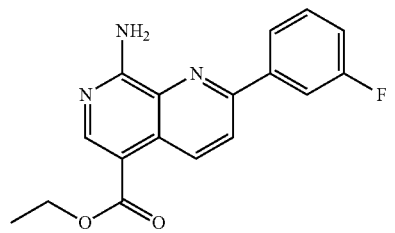

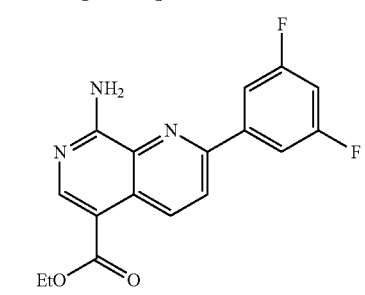

-continued
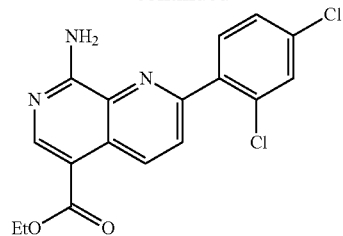
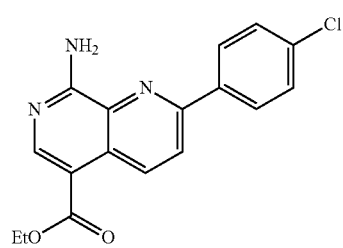
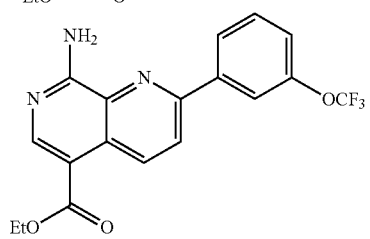
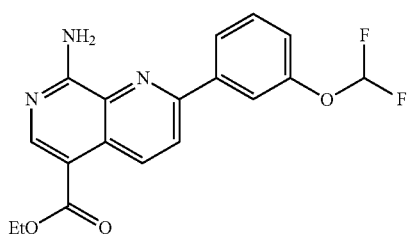
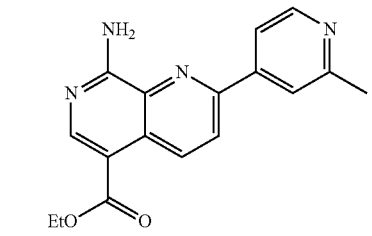
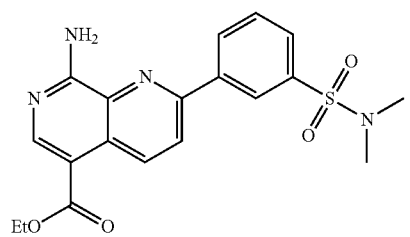
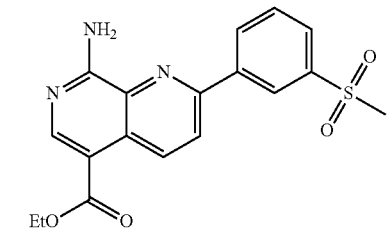
-continued
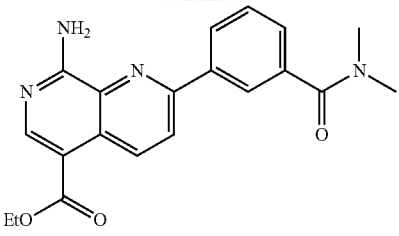
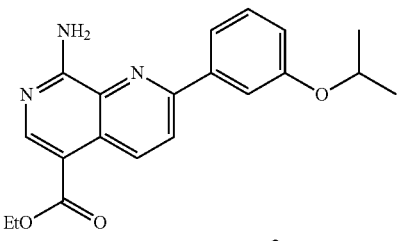
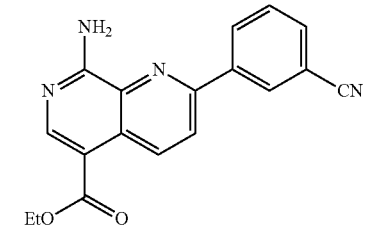
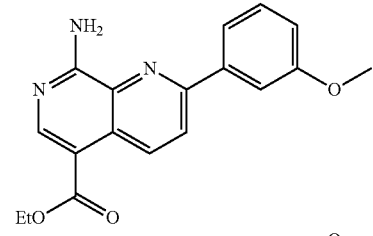
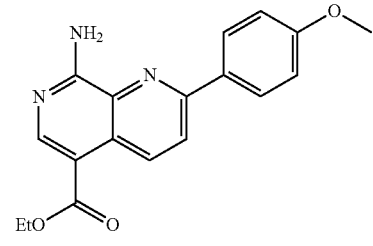
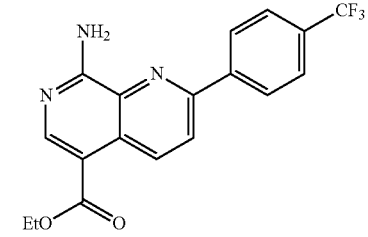
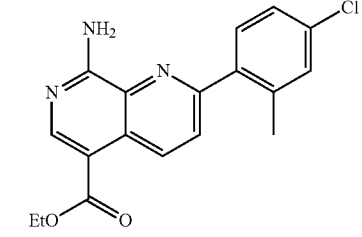

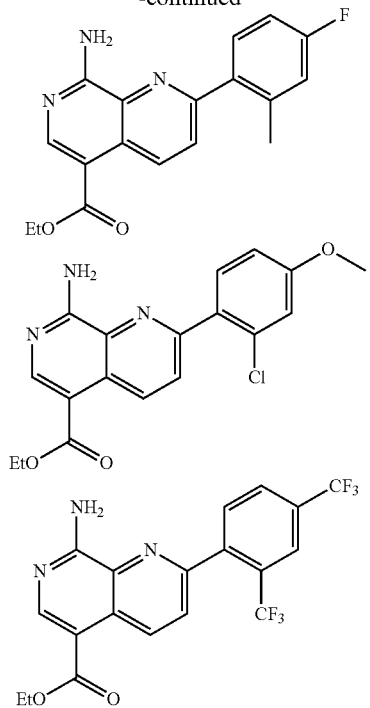

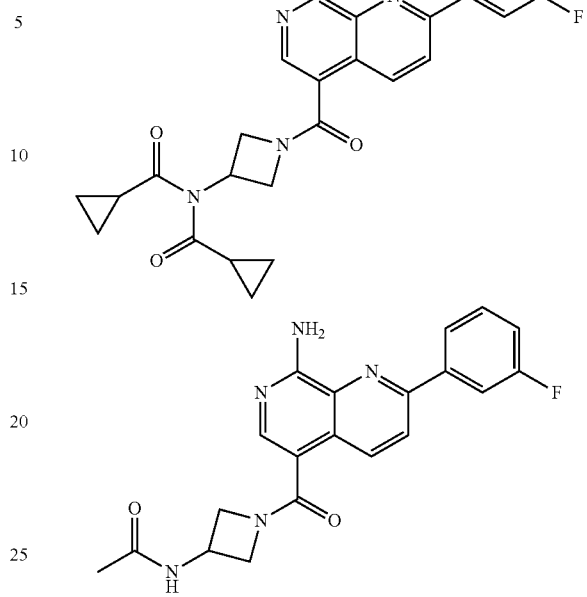

In one embodiment, the compounds of the invention are compounds of Formula (I), wherein $R^1$ is phenyl substituted by halo.

In one embodiment, the compounds of the invention are compounds of Formula (I), wherein $R^2$ is —C(O)—$C_2$-$C_{12}$-heterocyclyl, which is unsubstituted or substituted by one or more substituents selected from the group consisting of: $C_1$-$C_{12}$-alkyl, —$C_1$-$C_{12}$-hydroxyalkyl, —C(O)—$NH_2$, —C(O)—N(H)($C_1$-$C_{12}$-alkyl), —C(O)—N($C_1$-$C_{12}$-alkyl)$_2$, —$C_1$-$C_{12}$-alkylenyl-C(O)—N($C_1$-$C_{12}$-alkyl)$_2$, —NH—C(O)—$C_1$-$C_{12}$-alkyl, —NH—C(O)—$C_3$-$C_{12}$-cycloalkyl, and —N(C(O)—$C_3$-$C_{12}$-cycloalkyl)$_2$, for example the following compounds:

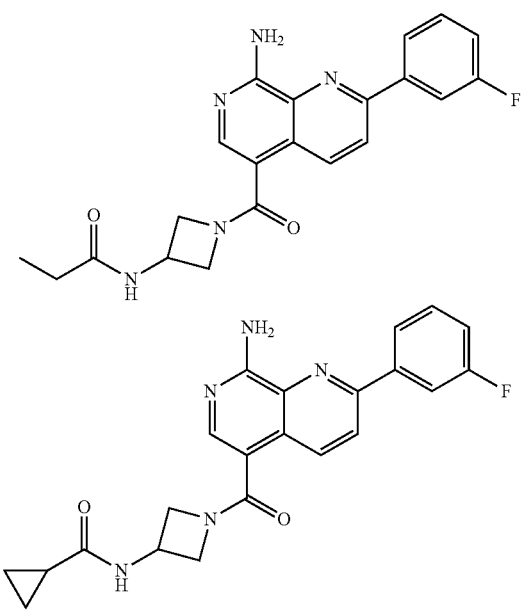

In one embodiment, the compounds of the invention are compounds of Formula (I), wherein wherein $R^2$ is —C(O)NR$^b$R$^c$, wherein R$^b$ and R$^c$ are independently selected from the group consisting of:

H;
$C_1$-$C_{12}$-alkyl;
—$C_3$-$C_{12}$-cycloalkyl, which is unsubstituted or substituted by one or more hydroxy, —$C_2$-$C_{12}$-heterocyclyl, which is unsubstituted or substituted by:
  $C_1$-$C_{12}$-alkyl which is unsubstituted or substituted by halo;
  —(CO)—$C_1$-$C_{12}$-alkyl, which alkyl is unsubstituted or substituted by hydroxy, $C_1$-$C_{12}$-alkoxy or $C_2$-$C_{12}$-heterocyclyl;
  —(CO)—$C_3$-$C_{12}$-cycloalkyl;
  —S(O)$_2$—$C_1$-$C_{12}$-alkyl, which alkyl is unsubstituted or substituted by halo;
  —S(O)$_2$—$NH_2$;
  —S(O)$_2$—NH($C_1$-$C_{12}$-alkyl);
  —S(O)$_2$—N($C_1$-$C_{12}$-alkyl)$_2$;
  —C(O)—$C_2$-$C_{12}$-heterocyclyl which heterocyclyl is unsubstituted or substituted by oxo, for example the following compounds:

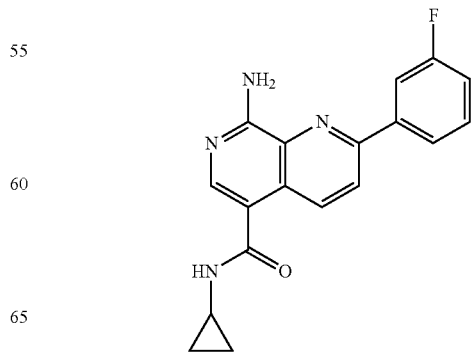

47
-continued
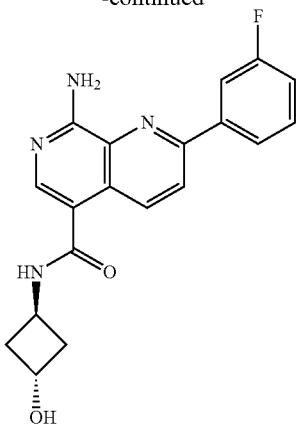
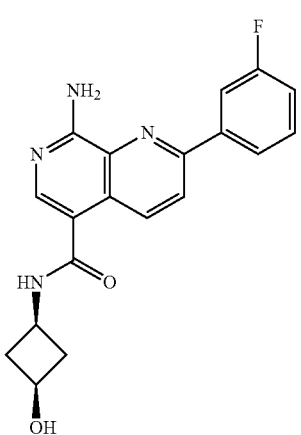
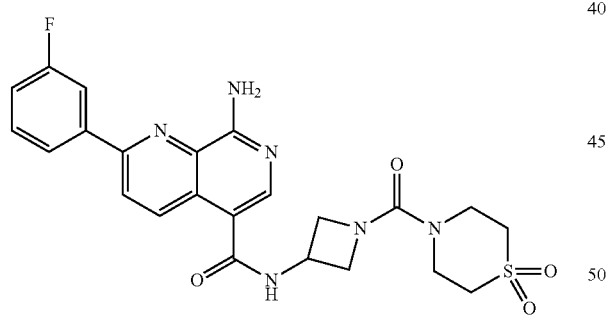
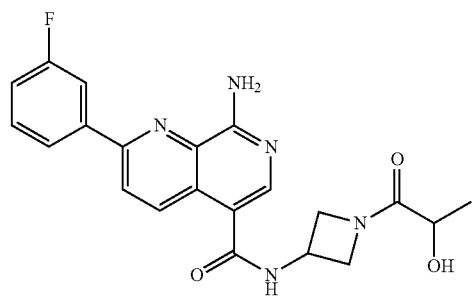
48
-continued
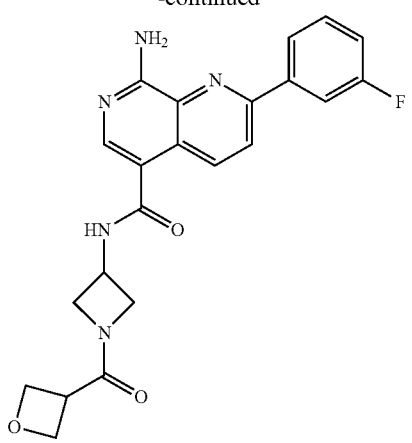
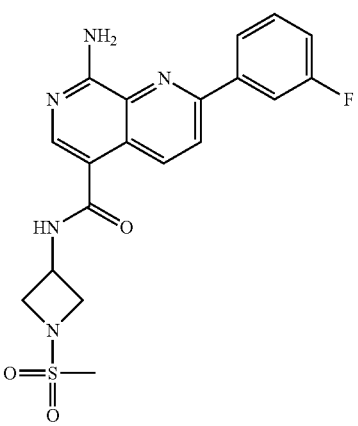
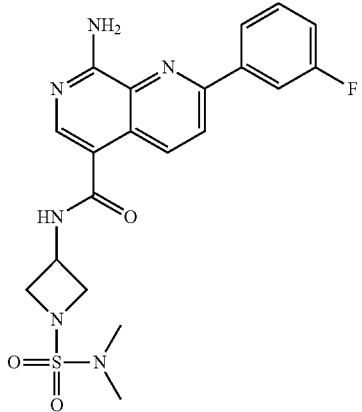

49
-continued
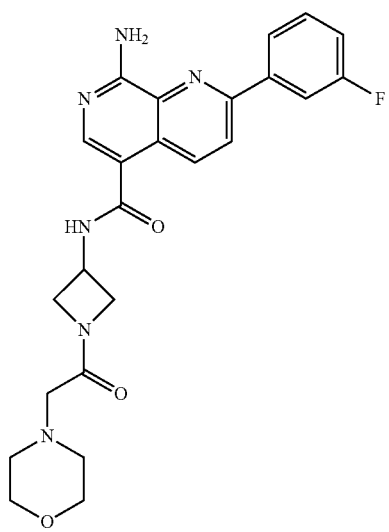
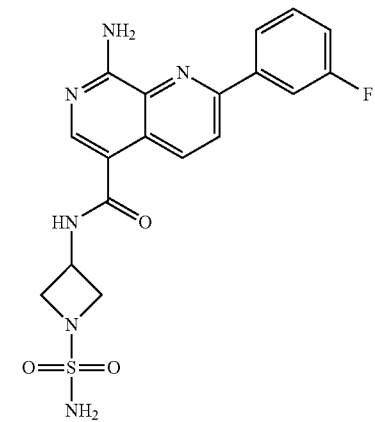
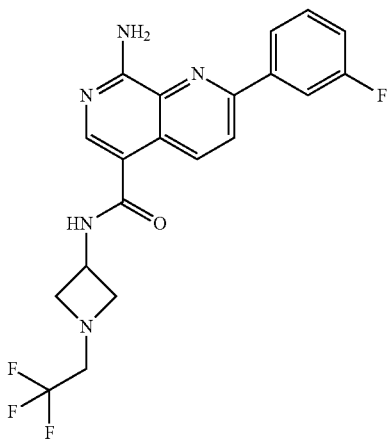
50
-continued
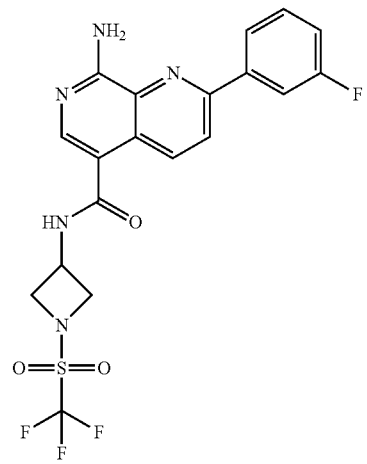
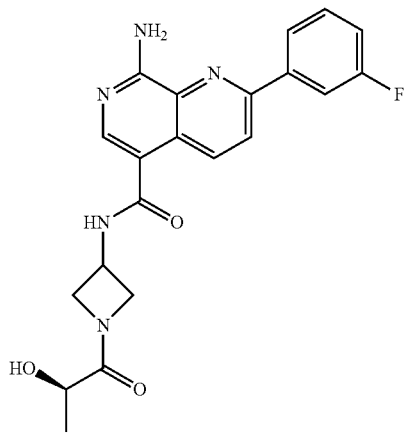
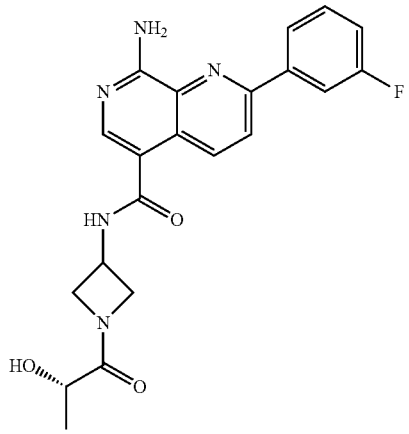
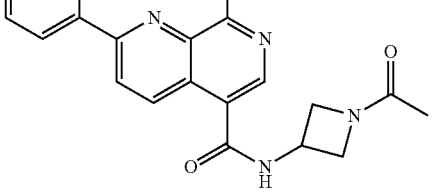

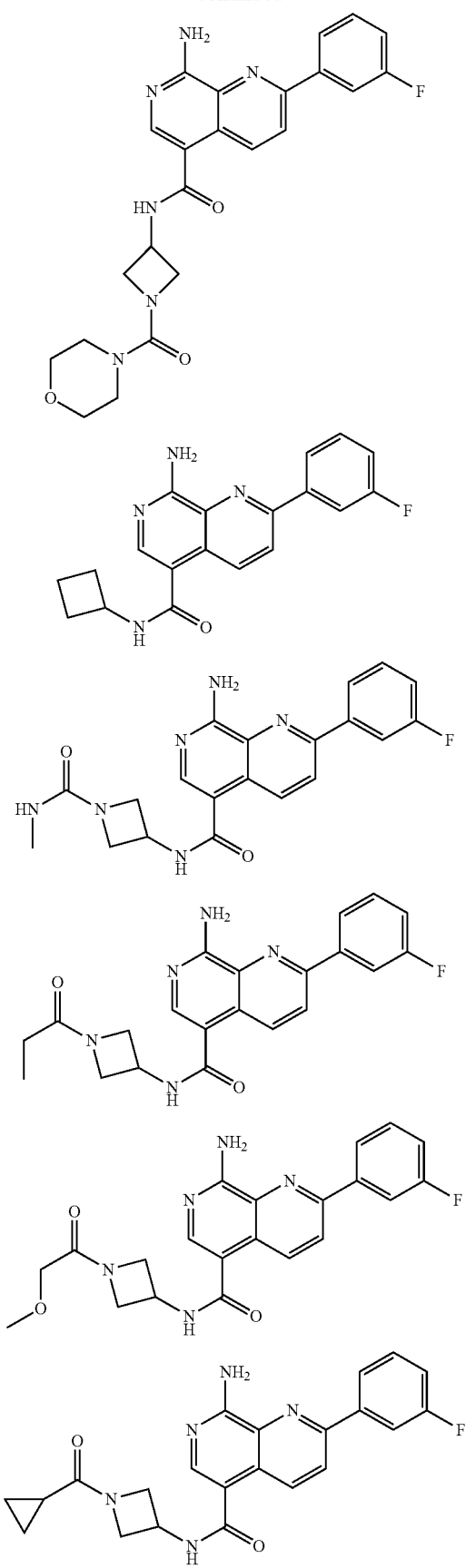

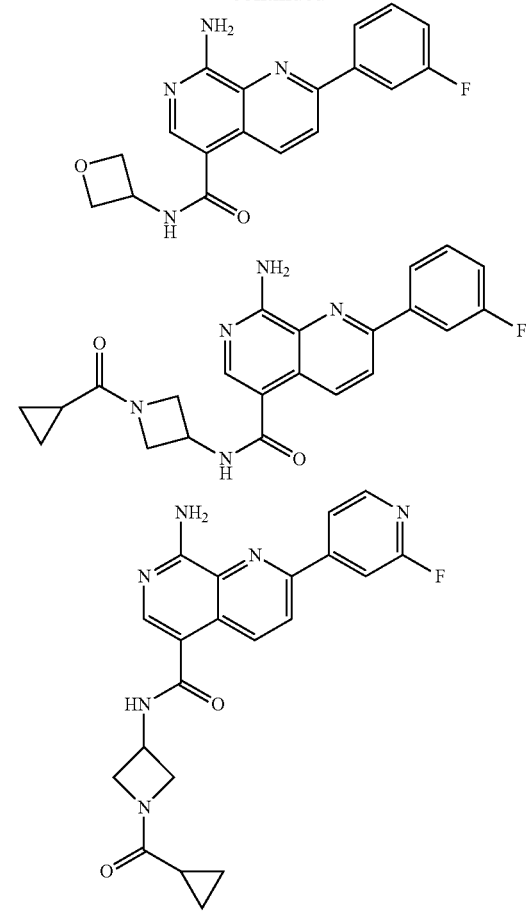

In one embodiment, the compounds of the invention are compounds of Formula (I), wherein R¹ is phenyl meta-substituted by halo.

In one embodiment, the compounds of the invention are compounds of Formula (I), wherein R¹ is halo and halo is F.

In one embodiment, the compounds of the invention are compounds of Formula (I-a):

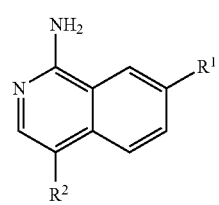

I-a and stereoisomers, geometric isomers, tautomers, and pharmaceutically acceptable salts thereof, wherein R¹ and R² is as defined herein.

In one embodiment, the compounds of the invention are compounds of Formula (I-b):

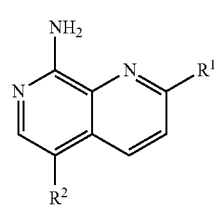

I-b and stereoisomers, geometric isomers, tautomers, and pharmaceutically acceptable salts thereof, wherein $R^1$ and $R^2$ is as defined herein.

In one embodiment, the compounds of the invention are compounds of Formula (I-c):

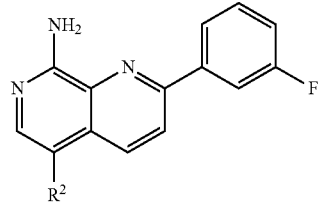

I-c and stereoisomers, geometric isomers, tautomers, and pharmaceutically acceptable salts thereof, wherein $R^2$ is as defined herein.

In one embodiment, the compounds of the invention are compounds of Formula (I-d):

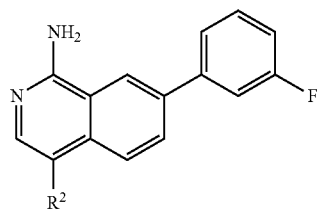

I-d and stereoisomers, geometric isomers, tautomers, and pharmaceutically acceptable salts thereof, wherein $R^2$ is as defined herein.

In one embodiment of the present invention, $R^2$ can be chosen from:

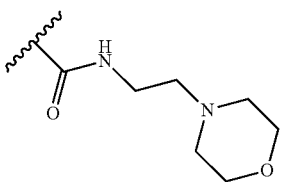

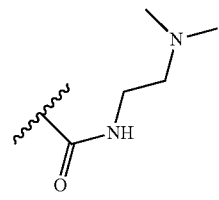

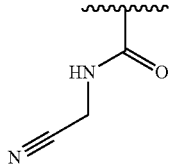

-continued

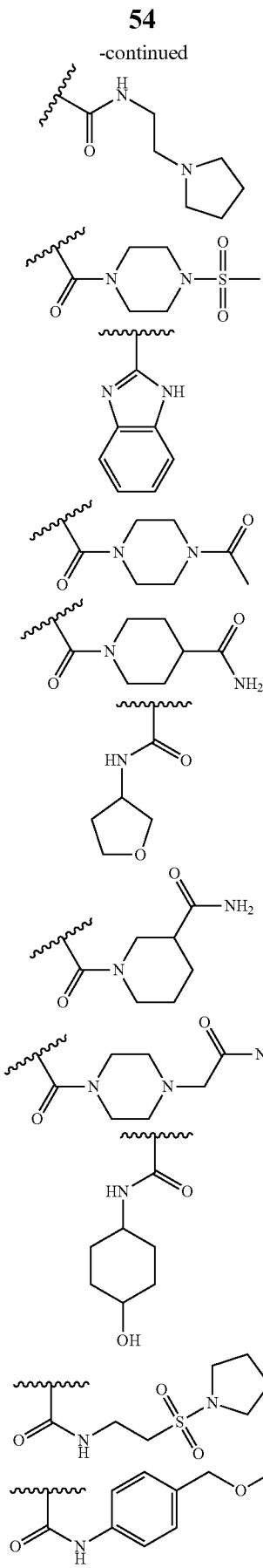

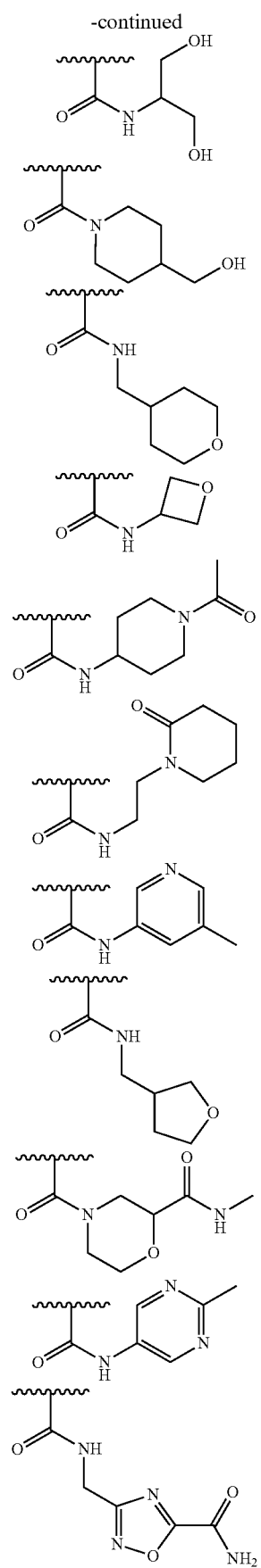
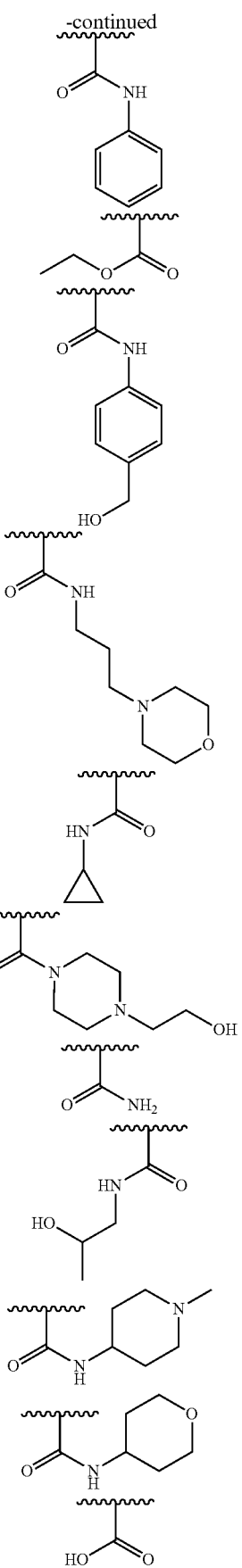

57
-continued
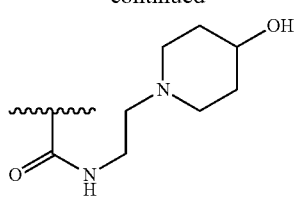
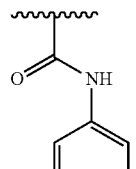
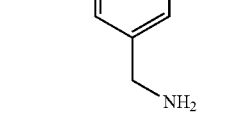
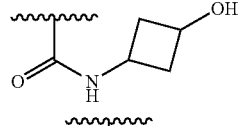
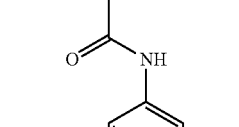
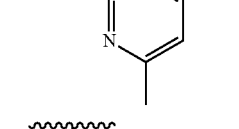
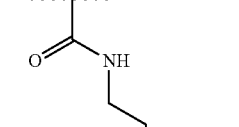
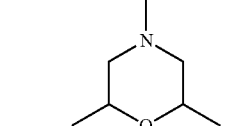
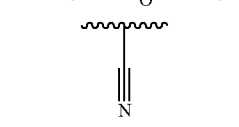
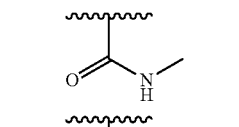
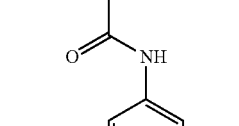
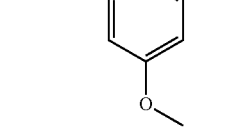
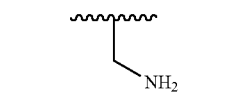
58
-continued
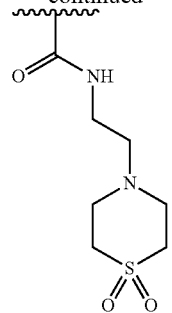
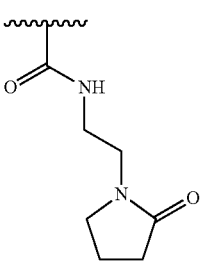
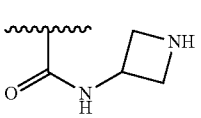
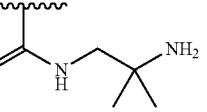
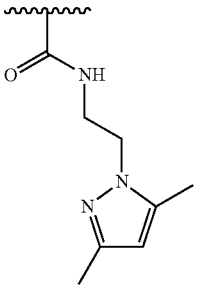
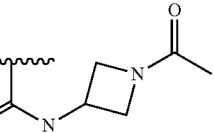
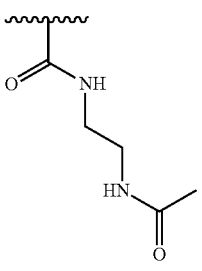

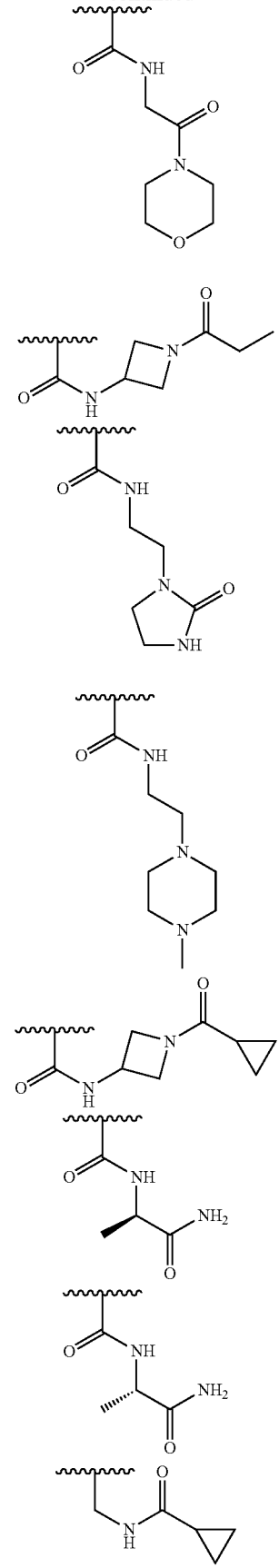
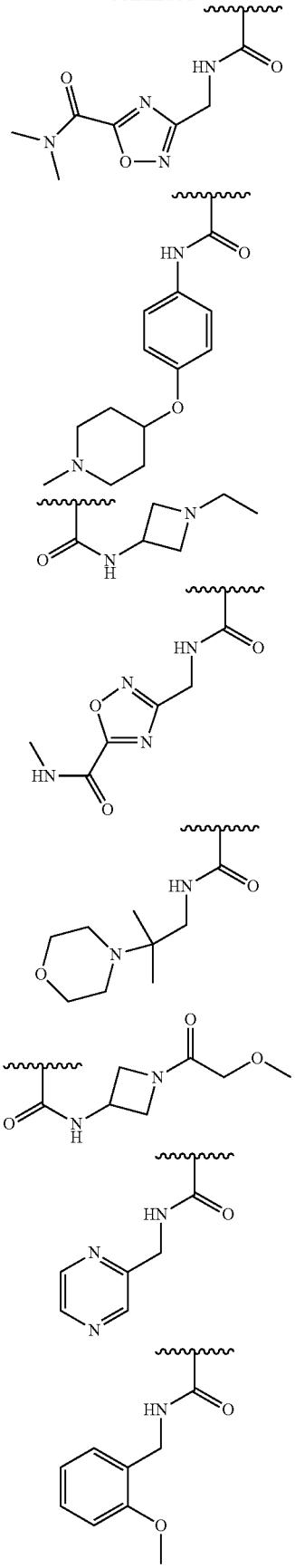

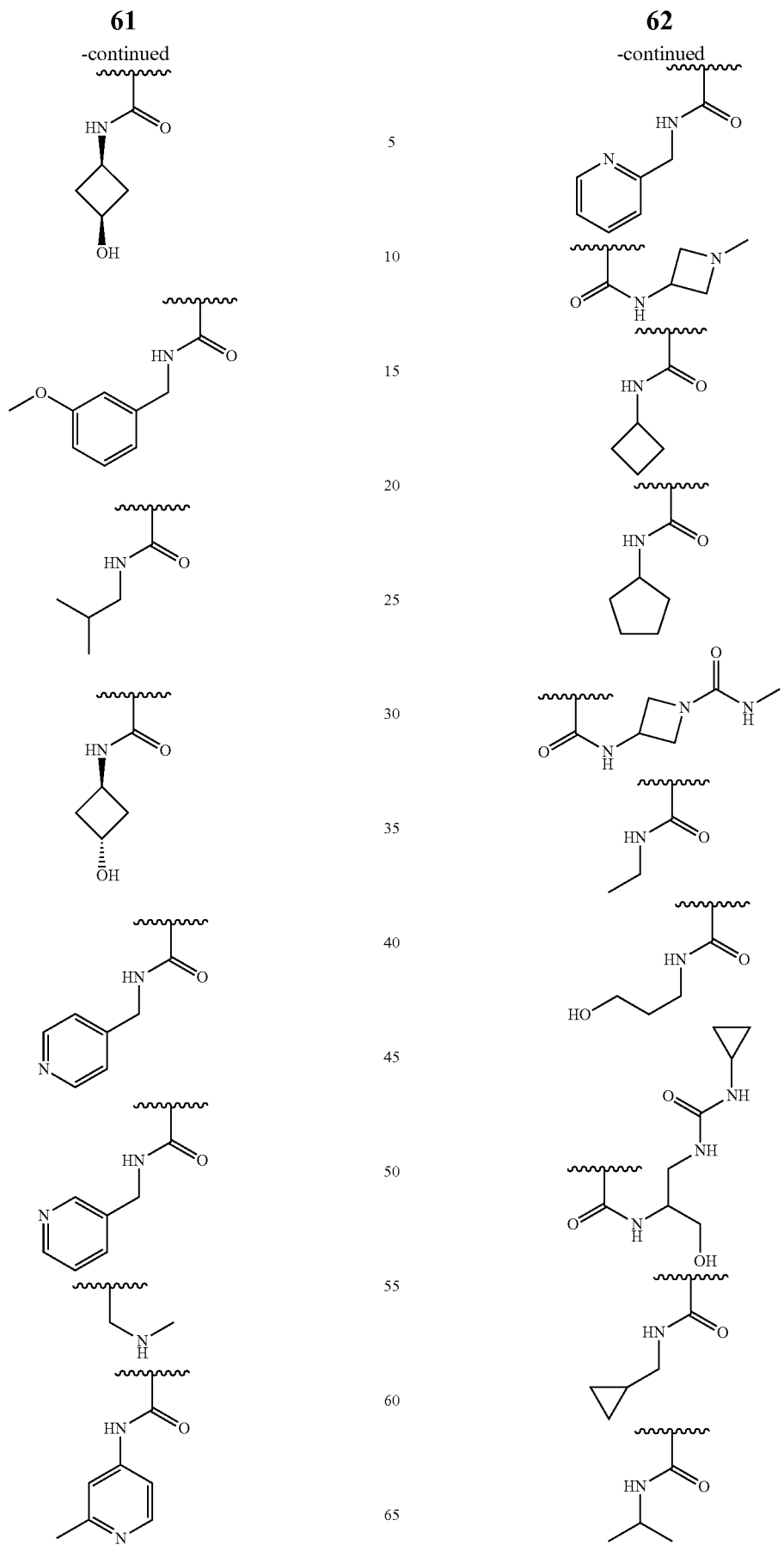

63
-continued
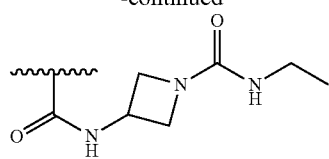
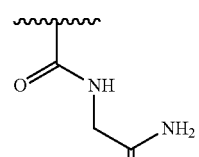
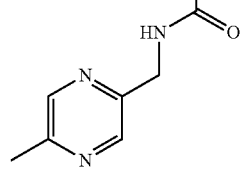
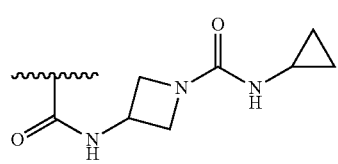
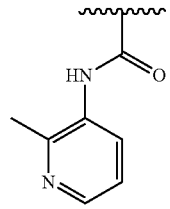
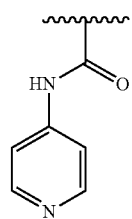
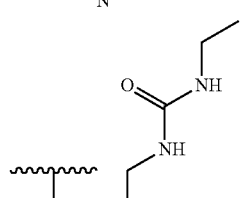
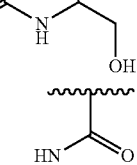
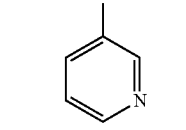
64
-continued
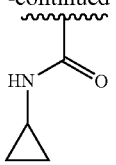
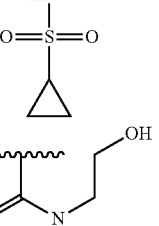
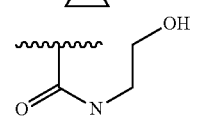
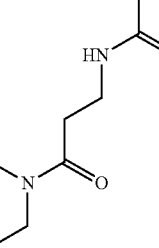
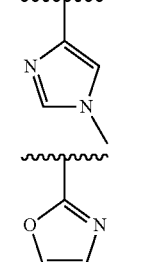
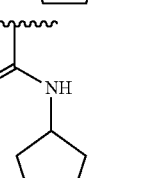
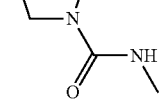
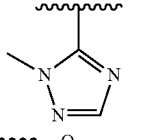
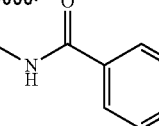
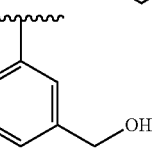

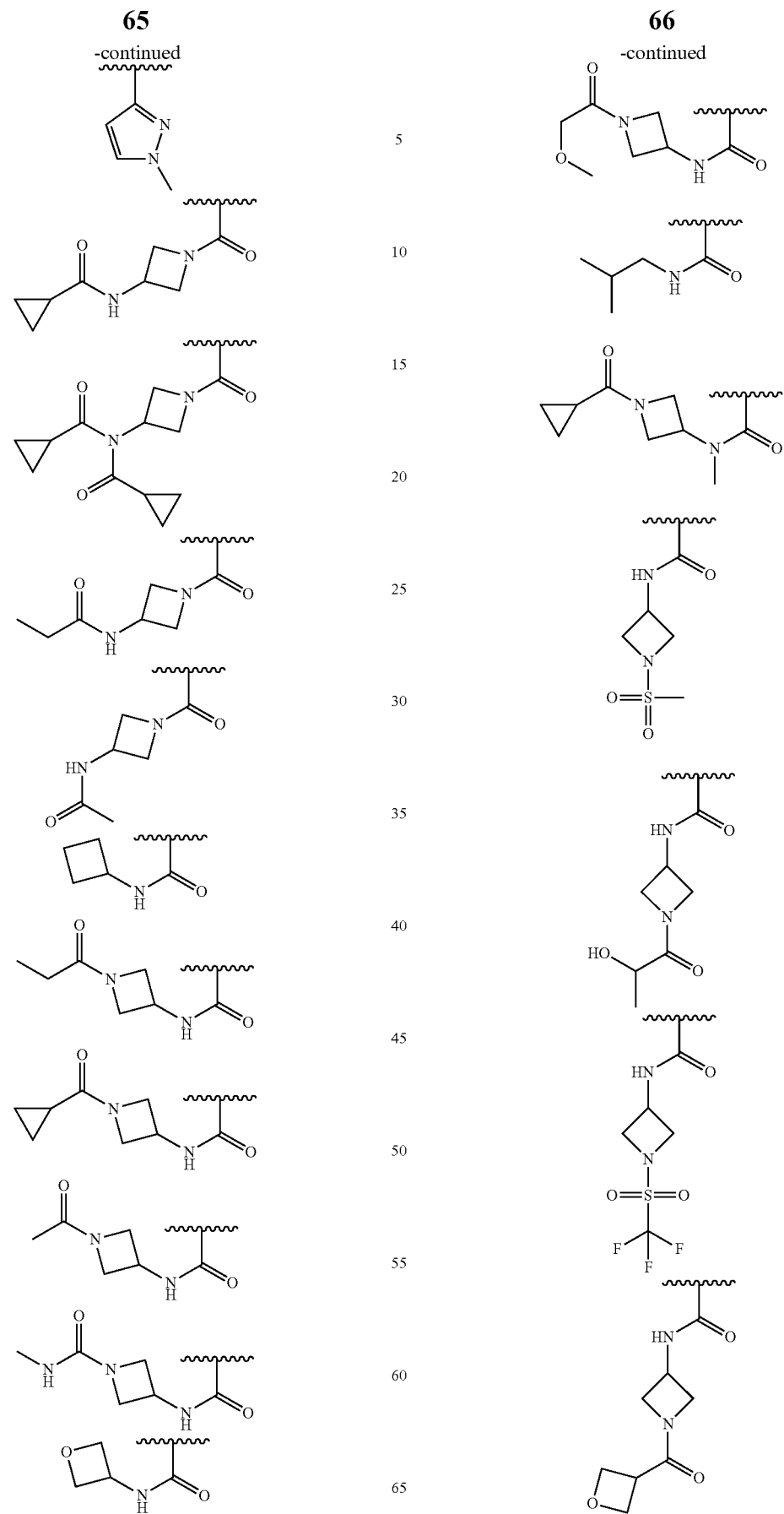

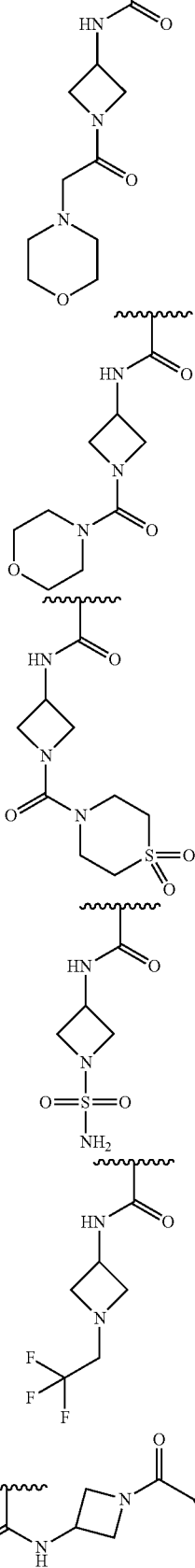

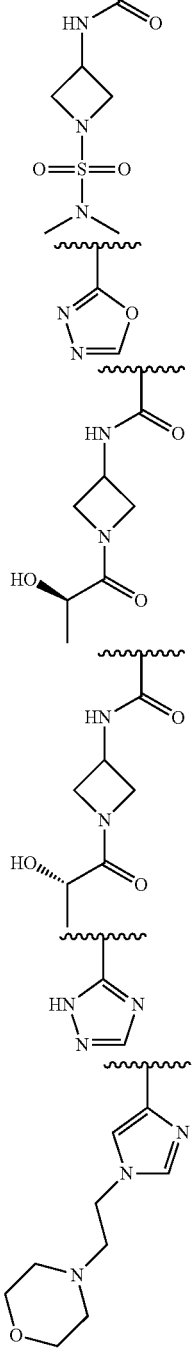

wherein ⁓ indicates the position at which $R^2$ binds to the rest of compound of Formula (I).

In one embodiment, the invention relates to a compound according to the invention for use as therapeutically active substance.

In one embodiment, the invention relates to a pharmaceutical composition comprising a compound according to the invention and a therapeutically inert carrier.

In one embodiment, the invention relates to a compound according to the invention for use in the inhibition of cell migration.

In one embodiment, the invention relates to a compound according to the invention for use in the inhibitiong of cell proliferation.

In one embodiment, the invention relates to a compound according to the invention for use in the inhibitiong of cell survival.

In one embodiment, in the aforementioned use according of the invention, the cells are endothelial cells.

In one embodiment, the invention relates to a compound according to the invention for use in the inhibitiong of angiogenesis.

In one embodiment, the invention relates to a compound according to the invention for the treatment or prophylaxis of cancer.

In one embodiment, the invention relates to the use of a compound according to the invention for the preparation of a medicament for the treatment or prophylaxis of cancer.

In one embodiment, the invention relates to a compound according to the invention for the treatment or prophylaxis of cancer.

In one embodiment, the invention relates to a method for the treatment or prophylaxis of cancer which method comprises administering an effective amount of a compound according to the invention.

In one embodiment, the invention cancer is selected from the groups consisting of the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic lymphoid leukemia, chronic myelogenous leukemia, lymphocytic leukemia, myeloid leukemia, oral cavity and pharynx, non-Hodgkin lymphoma, melanoma, or villous colon adenoma.

In order to use a Formula (I) compound for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula (I) having the desired degree of purity may optionally be mixed with pharmaceutically acceptable diluents, carriers, excipients or stabilizers (Remington's Pharmaceutical Sciences (1980) $16^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16$^{th}$ edition, Osol, A. Ed. (1980).

Sustained-release preparations of compounds of Formula (I) may be prepared. Suitable examples of sustained-release preparations include semipermeable matrices of solid hydrophobic polymers containing a compound of Formula (I), which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula (I) suitable for oral administration may be prepared as discrete units such as pills, capsules, cachets or tablets each containing a predetermined amount of a compound of Formula (I). Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula (I) intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxy groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner, including a mixture of at least one emulsifier with a fat or an oil, or with both a fat and an oil. A hydrophilic emulsifier included together with a lipophilic emulsifier acts as a stabilizer. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween®

60, Span® 80, cetostearyl alcohol, benzyl alcohol, myristyl alcohol, glyceryl mono-stearate and sodium lauryl sulfate.

Aqueous suspensions of Formula (I) compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula (I) may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and *acacia*; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

The compounds of Formula (I) may be employed alone or in combination with other therapeutic agents for the treatment of a disease or disorder described herein, such as inflammation or a hyperproliferative disorder (e.g., cancer). In certain embodiments, a compound of Formula (I) is combined in a pharmaceutical combination formulation, or dosing regimen as combination therapy, with a second therapeutic compound that has anti-inflammatory or anti-hyperproliferative properties or that is useful for treating an inflammation, immune-response disorder, or hyperproliferative disorder (e.g., cancer). The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula (I) such that they do not adversely affect each other. Such compounds are suitably present in combination in amounts that are effective for the purpose intended. In one embodiment, a composition of this invention comprises a compound of Formula (I), or a stereoisomer, tautomer, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula (I), or a stereoisomer, tautomer, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula (I), or a stereoisomer, tautomer, or pharmaceutically acceptable salt or prodrug thereof, and the use of at least one other cancer treatment method. The amounts of the compound(s) of Formula (I) and the other pharmaceutically active chemotherapeutic agent(s) and the relative timings of administration will be selected in order to achieve the desired combined therapeutic effect.

Also falling within the scope of this invention are the in vivo metabolic products of Formula (I) described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula (I), including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

In another embodiment of the invention, an article of manufacture, or "kit", containing materials useful for the treatment of the diseases and disorders described above is provided. In one embodiment, the kit comprises a container comprising a compound of Formula (I). The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula (I) or a formulation thereof which is effective for treating the condition and may have a sterile access port (for example, the container may be an intravenous solution bag or a vial having a stopper pierceable by a hypodermic injection needle). At least one active agent in the composition is a compound of Formula (I). The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula (I) can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula (I) and, if present, the second pharmaceutical formulation. For example, if the kit comprises a first composition comprising a compound of Formula (I) and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula (I), such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula (I) contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula (I) and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Within the scope of the present invention the inventors have identified MAP4K4 as a key regulator of endothelial membrane dynamics during migration. Loss of MAP4K4 expression or MAP4K4 kinase activity in vitro reduces retraction of subcellular membrane protrusions, leading to the lengthening of these protrusions and persistent subcellular membrane branching, which ultimately impairs cell motility. The inventors have discovered that vascular-specific MAP4K4 knockout in mice results in severe hemorrhage and edema by E14.5 that culminates in embryonic lethality at ~E16.5. Embryonic endothelial cells have long aberrant protrusions, increased subcellular membrane branches, and delayed migration, with decreased vascular coverage in multiple organs.

The inventors have discovered that MAP4K4 in endothelial cells regulates the endothelial cell membrane dynamics during sprouting angiogenesis. The inventors discovered that inhibition of MAP4K4 kinase activity with small molecule inhibitors reduced cancer cell migration without affecting their proliferation or survival. Inhibition of MAP4K4 can therefore be useful for treating cancer by both reducing the tumor blood supply to decrease tumor growth, and by decreasing invasion/metastasis—the main cause of cancer fatality. The inventors have developed MAP4K4 antagonists that can be useful for the treatment of angiogenesis and cancer.

The relative efficacies of Formula (I) compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Accordingly, a "selective MAP4K4 inhibitor" can be understood to refer to a compound that exhibits a 50% inhibitory concentration ($IC_{50}$) with respect to MAP4K4 that is at least at least 10-fold lower than the $IC_{50}$ value with respect to any or all of the other MAP4K4 family members.

Determination of the activity of MAP4K4 kinase activity of Formula (I) compounds is possible by a number of direct and indirect detection methods. The range of IC50 values for inhibition of MAP4K4 was less than 1 nM (nanomolar) to about 10 μM (micromolar). Certain exemplary compounds of the invention had MAP4K4 inhibitory $IC_{50}$ values less than 10 nM. Certain Formula (I) compounds may have antiangiogenesis activity to treat hyperproliferative disorders such as cancer. The Formula (I) compounds may inhibit angiogenesis in mammals and may be useful for treating human cancer patients.

The Example section of this patent application herein shows Formula (I) compounds that were made, characterized, and tested for inhibition of MAP4K4 and selectivity according to the methods of this invention, and have the corresponding structures and names (ChemBioDraw Ultra, Version 11.0, CambridgeSoft Corp., Cambridge Mass.).

The compounds of Formula (I) may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula (I) compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{th}$ Ed., John Wiley and Sons (1999); and L. Paquette, ed., Encyclopedia of Reagents for Organic Synthesis, John Wiley and Sons (1995) and subsequent editions thereof.

Compounds of Formula (I) may be prepared singly or as compound libraries comprising at least 2, for example 5 to 1,000 compounds, or 10 to 100 compounds. Libraries of compounds of Formula (I) may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, —New York, 1991.

For illustrative purposes, the following schemes show general methods for preparing compounds of Formula (I) according to the invention, as well as key intermediates. For a more detailed description of the individual reaction steps, see the Examples sections. Those skilled in the art will appreciate that other synthetic routes may be used to synthesize the inventive compounds. Although specific starting materials and reagents are depicted and discussed in the General Procedures, Examples, and schemes, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

SYNTHESIS

General Method A:

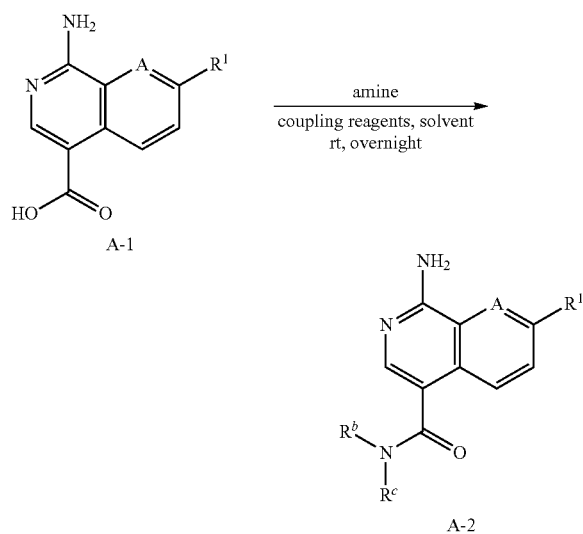

To a solution of compound A-1 in a solvent, e.g. anhydrous THF, is added coupling reagents, e.g. HATU/DIPEA, and an amine of formula HNR$^b$R$^c$ or an unsubstituted or substituted N-containing heterocyclyl. The mixture is stirred at room temperature overnight. Water is added and the mixture is extracted with EtOAc. The combined organic layer is washed with brine, concentrated, and purified by prep-HPLC to give the desired product A-2, wherein R$^1$, R$^b$ and R$^c$ are as defined herein. Compound A-1 can be prepared as described in example A. Compounds wherein R$^2$—C(O)—C$_2$-C$_{12}$-heterocyclyl, which is unsubstituted or substituted as described herein can also be made by this general method.

General Method B:

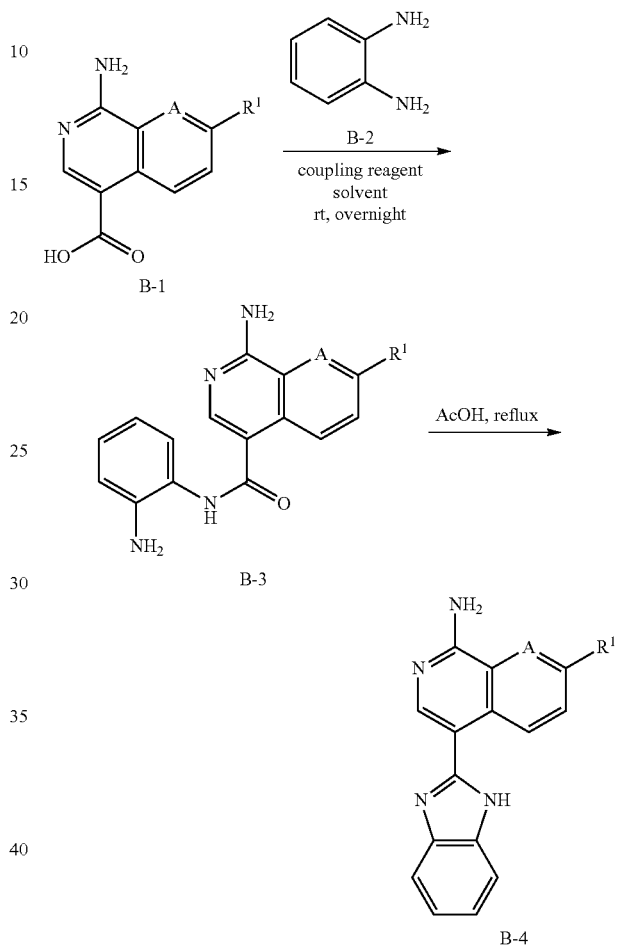

To a solution of Compound B-1 in a solvent, e.g. anhydrous DMF, is added coupling reagents, e.g. HATU, DIPEA, and Compound B-2. The mixture is stirred at room temperature overnight. Water is added and the mixture is extracted with e.g. EtOAc. The combined organic layer is washed with brine, dried over Na$_2$SO$_4$, concentrated and used in next step without further purification. A solution of Compound B-3 in HOAc is heated at reflux for 2 h. HOAc is removed under reduced pressure and the residue is purified by prep-HPLC to give the desired product B-4. In this General Method, A and R$^1$ are as defined herein.

General Method C:

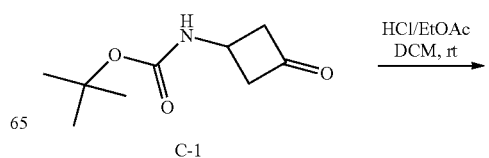

-continued

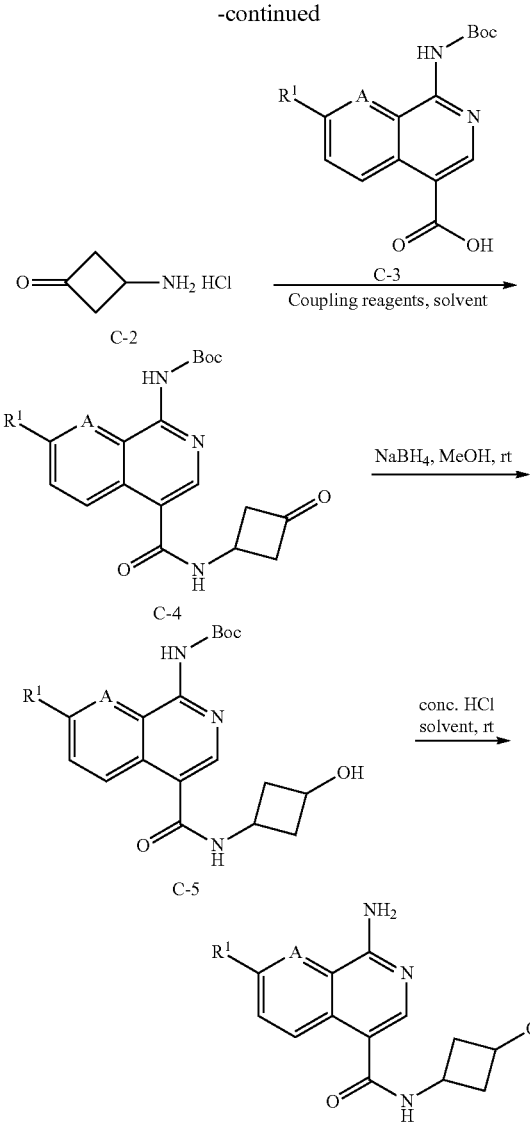

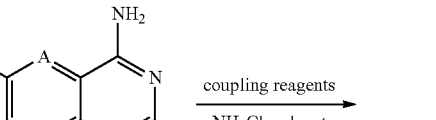

Step 1: Preparation of Compound C-2

To a solution of Compound C-1 in DCM, is added EtOAc/HCl, and it is stirred at room temperature for 30 min. The solution is concentrated to give the Compound C-2.

Step 2: Preparation of Compound C-4

To a solution of Compound C-2 in a solvent, e.g. THF, is added coupling agents, e.g. DIPEA/HATU, and Compound C-3. The mixture is stirred at room temperature overnight and poured into water. The resulting mixture is extracted with EtOAc, and concentrated to give the crude compound C-5.

Step 3: Preparation of Compound C-5

To a solution of Compound C-4 in MeOH, is added NaBH$_4$. The mixture is stirred at r.t. for 1 h, and poured into water. The mixture is extracted with EtOAc, and washed with NaCl, dried over Na$_2$SO$_4$, and concentrated to give the crude product C-5.

Step 4: Preparation of Compound C-6

To a solution of Compound C-5 in a solvent, e.g. THF, is added conc. HCl. After it is stirred at r.t. for about 5 h, organic solvent is removed and the residue is poured into water, and pH is adjusted to about 8-9 with sat NaHCO$_3$. It is extracted with EtOAc. The combined organic layers is washed with sat NaCl, dried over Na$_2$SO$_4$, concentrated, and purified by prep-HPLC to give product C-6, wherein R$^1$ is as defined herein.

General Method D:

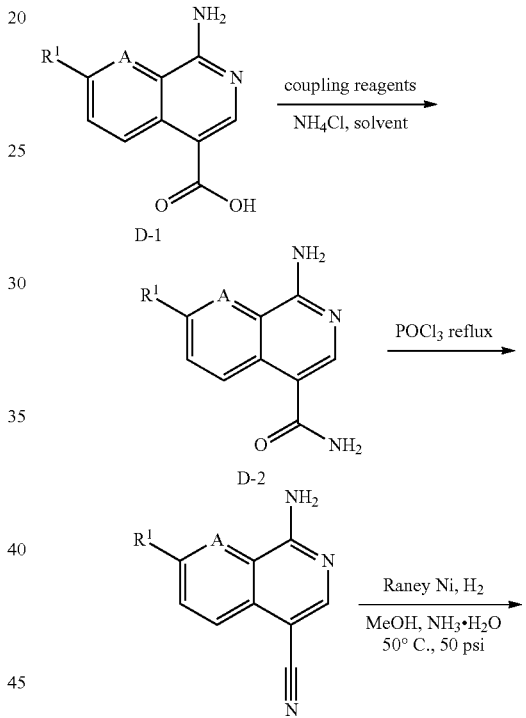

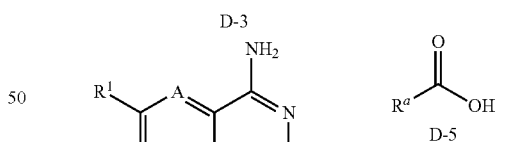

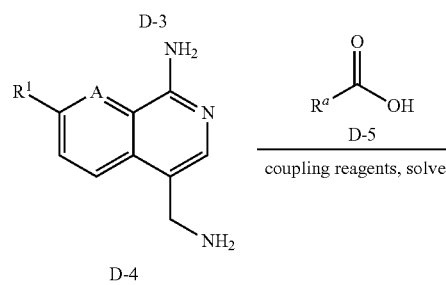

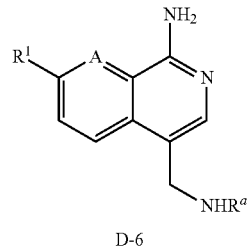

Step 1: Preparation of Compound D-2

To a solution of Compound D-1 in a solvent, e.g DMF, is added coupling reagents, e.g. DIPEA, HATU, and NH$_4$Cl. After the mixture can be stirred at about 40-50° C. for about 4 h, it is poured into water. The resulting mixture is filtered and concentrated to give the product D-2.

Step 2: Preparation of Compound D-3

A solution of Compound D-2 in POCl$_3$ is heated at reflux overnight. Organic solvent is poured into ice-water, and pH is adjusted to about 8-9 with sat NaHCO$_3$. It is extracted with EtOAc and the combined organic layers is washed with sat NaCl, dried over Na$_2$SO$_4$, and concentrated to give the product.

Step 3: Preparation of Compound D-4

To a solution of Compound D-3 in MeOH and NH$_3$.H$_2$O, is added Raney Ni, and the mixture is stirred at about 50° C. overnight under H$_2$ at about 50 psi. The resulting mixture is filtered and concentrated to give the product.

Step 4: Preparation of Compound of Compound D-6

To a solution of Compound D-4 in a solvent, e.g. DMF, is added DIPEA, HATU, and Compound D-5, wherein R$^a$ is as defined herein. Then the mixture is stirred at r.t. for about 30 min, and poured into water. The resulting mixture is extracted with EtOAc (30 mL×2), concentrated and purified by prep-HPLC to give the product. In scheme D, A, R$^1$ and R$^a$ are as defined herein.

General Method E:

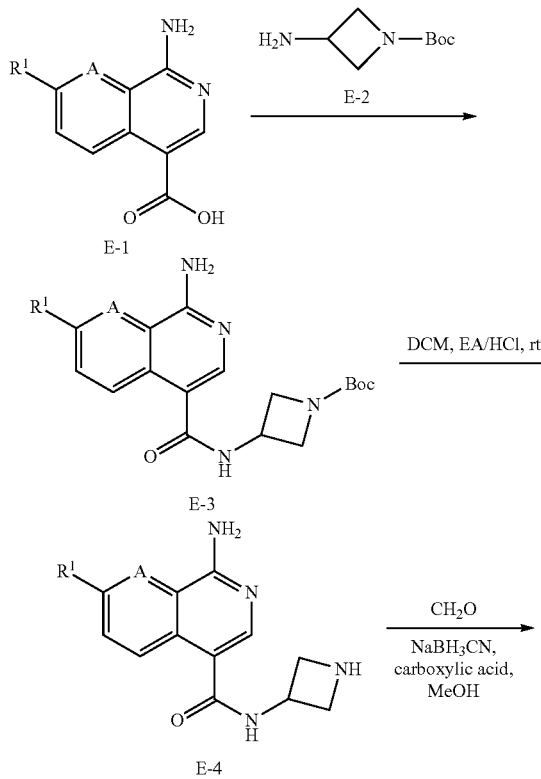

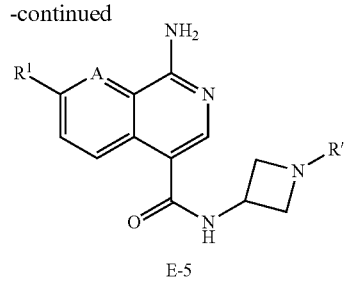

Step 1: Preparation of Compound E-3

To a solution of Compound E-1 in a solvent, e.g. DMF, is added HATU, DIPEA, and Compound E-2. After the mixture is stirred at about 40-50° C. for about 3 h, it is cooled to r.t. and water is added. The mixture is extracted with EtOAc and it is washed with H$_2$O, sat. NaCl, concentrated and purified by column (PE:EtOAc=1:3) to give the Compound E-3, wherein A and R$^1$ are as defined herein and R' is H or C$_{1-12}$-alkyl.

Step 2: Preparation of Compound E-4

To a solution of Compound E-3 in DCM, is added EtOAc/HCl, and the mixture is stirred at r.t. for about 2 h. The mixture is concentrated to give the crude Compound E-4.

Step 3: Preparation of Compound E-5

To a solution of Compound E-4 in a solvent, e.g. MeOH, is added HOAc, formaldehyde solution, and the mixture is stirred at r.t. for about 30 min. NaBH$_3$CN is added, and the mixture is stirred at r.t. for about 2 h. It is poured into water. The mixture is extracted with EtOAc and the organic layer is concentrated and purified by prep HPLC to give Compound E-5 wherein A and R$^1$ are as defined herein and R' is H or C$_{1-12}$-alkyl.

General Method F:

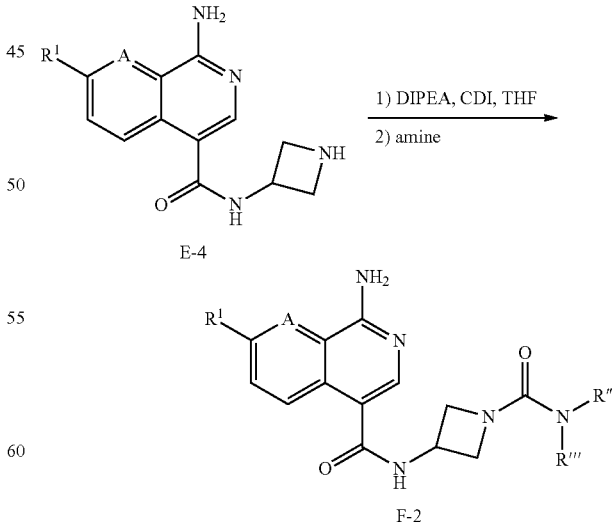

To a solution of Compound E-4 in a solvent, e.g. THF, is added DIPEA, CDI. After the mixture is stirred at r.t. for 1 h, an amine is added, and the mixture is stirred at r.t. for 2 h, and purified by (basic) prep-HPLC to give Compound F-2, wherein A and $R^1$ are as defined herein and R''' and R'''' are chosen from H, $C_1$-$C_{12}$-alkyl and $C_3$-$C_{12}$-cycloalkyl.

General Method G:

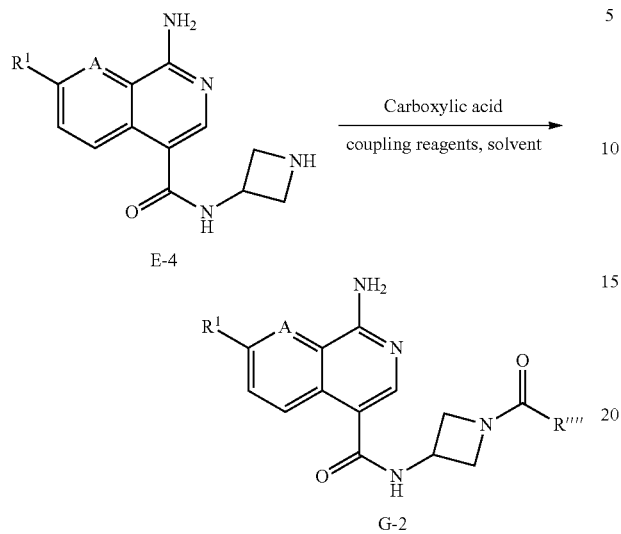

To a solution of Compound E-4 in a solvent, e.g. THF is added coupling reagents, e.g. DIPEA, HATU, and a carboxylic acid. After the mixture is stirred at r.t for 3 h, it is poured into water, extracted with EtOAc, concentrated and purified by prep HPLC to give the product, wherein A and $R^1$ are as defined herein and R'''' is chosen from $C_1$-$C_{12}$-alkyl, —$C_1$-$C_{12}$-alkylenyl-$C_1$-$C_{12}$-alkoxy, and —$C_3$-$C_{12}$-cycloalkyl.

General Method H:

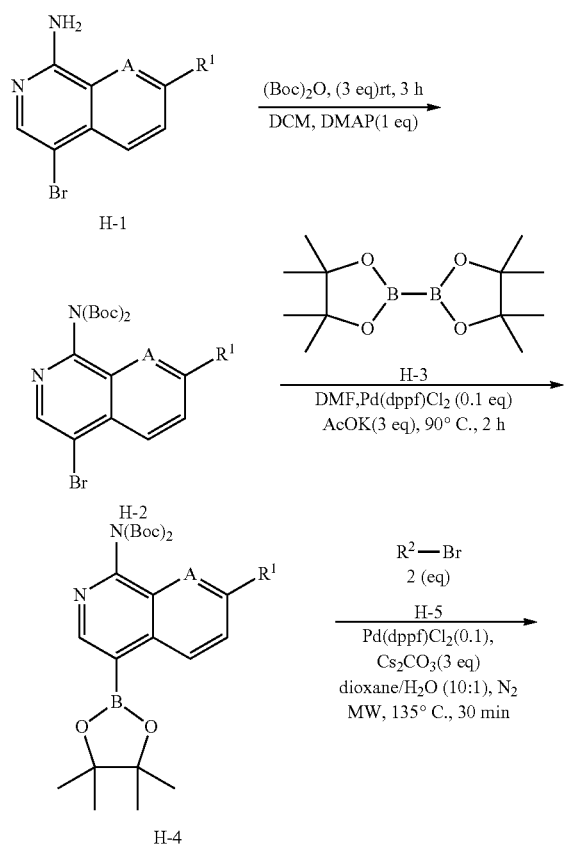

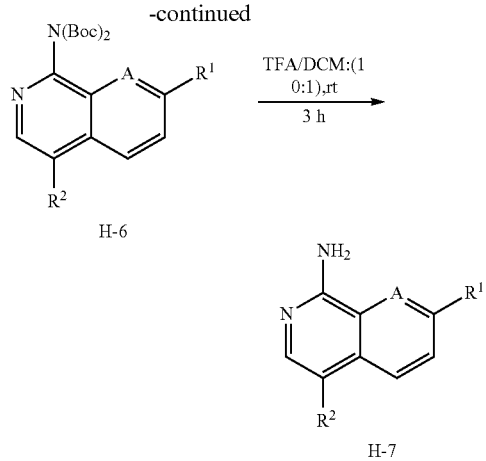

Step 1: Preparation of Compound H-2

To a solution of Compound H-1 in DCM, DMAP and $Boc_2O$ are added in DCM. After the mixture is stirred at r.t. for 6 h, DCM is removed, and water is added. The resulting mixture is extracted with EtOAc, concentrated and purified by column (PE:EtOAc=5:1 to 3:1) to give the product.

Step 2: Preparation of Compound H-4

A suspension of Compound H-2, Compound H-3, KOAc, and a Pd catalyst such as Pd(dppf)$Cl_2$ in anhydrous DMF is degassed for 3 times and heated at 90° C. for 2 h under $N_2$. It is poured into water and extracted with EtOAc and the combined organic layers is washed with sat NaCl, dried over $Na_2SO_4$ and concentrated in vacuum to give the crude product.

Step 3: Preparation of Compound H-6

A solution of Compound H-4 in a mixture of dioane-$H_2O$, is added Compound H-5 (wherein $R^2$ is a $C_2$-$C_{12}$-heteroaryl which is unsubstituted or substituted by $C_1$-$C_{12}$-alkyl, which alkyl is unsubstituted or substituted by one or more substituents selected from the group consisting of halo, —C(O)—N($C_1$-$C_{12}$-alkyl)$_2$, and —$C_2$-$C_{12}$-heterocyclyl, wherein the heterocyclyl is unsubstituted or substituted by $C_1$-$C_{12}$-alkyl), $Cs_2CO_3$ and a Pd catalyst, such as Pd(dppf)$Cl_2$ and heated under irradiation of MW at 130° C. for 30 min under $N_2$. Catalyst is filtered through diatomite and concentrated in vacuum to give the crude product.

Step 4: Preparation of Compound H-7

A solution of Compound H-6 in a mixture of DCM:TFA (10:1), is stirred at rt for 3 h. The resulting mixture is concentrated, and purified by prep-HPLC to give the product, wherein A and $R^1$ are as defined herein and $R^2$ is chosen from $C_2$-$C_{12}$-heteroaryl which is unsubstituted or substituted by $C_1$-$C_{12}$-alkyl, which alkyl is unsubstituted or substituted by one or more substituents selected from the group consisting of halo, —C(O)—N($C_1$-$C_{12}$-alkyl)$_2$, and —$C_2$-$C_{12}$-heterocyclyl, wherein the $C_2$-$C_{12}$-heterocyclyl is unsubstituted or substituted by $C_1$-$C_{12}$-alkyl.

General Method I:

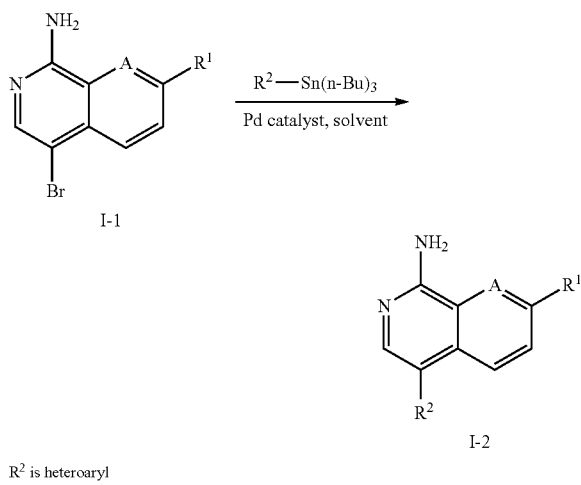

R² is heteroaryl

Compound I-2 can be prepared by heating a suspension of Compound I-1, 2-(tributylstannyl)R², wherein R² is heteroaryl and a palladium catalyst such as Pd(PPh₃)₄ in a solvent, e.g. toluene overnight. The solution was quenched with saturated aqueous CsF solution and extracted with EtOAc (100 mL). The organic layer can be washed with brine, concentrated and purified by prep-HPLC to give the desire product, wherein a and R¹ are as defined herein.

General Method J:

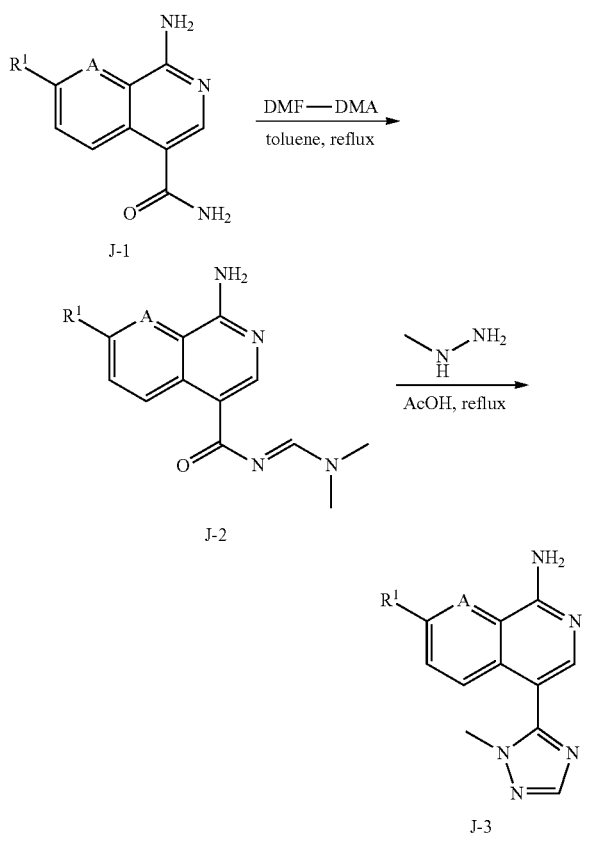

Step 1: Preparation of Compound J-2

Compound J-2 can be obtained by heating at reflux a solution of Compound J-1 and DMF-DMA in a solvent, e.g. toluene for about 3 h. Solvent can be removed and the crude product can be used in next step without further purification.

Step 2: Preparation of Compound J-3

Compound J-3 can be prepared by heating a Compound J-2 and methylhydrazine in HOAc at reflux overnight. Solvent can be removed and the residue can be purified by prep-HPLC to give desired product. In this method, A and R¹ are as defined herein.

General Method K:

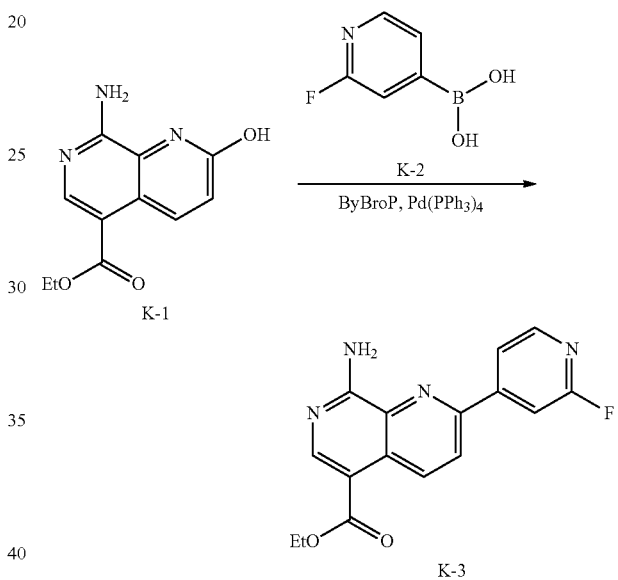

Compound K-3 can be prepared as following: to a solution of K-1 (150 mg, 0.65 mmol) in dioxane (20 mL), was added TEA (300 mg, 3.0 mol), and PyBroP (400 mg, 1.0 mmol). After the mixture was stirred at r.t. for 1 h, Pd(PPh₃)₄ (80 mg, 0.07 mmol), boronic acid K-2 (180 mg, 1.3 mmol), K₂CO₃ (200 mg, 1.3 mmol), and H₂O (5 mL) was added. After the mixture was stirred at 90° C. for 3 h under N₂, it was extracted with EtOAc (50 mL×2), washed with sat NaCl (50 mL), dry over Na₂SO₄, and concentrated to give the crude product as brown solid. The solid was washed with EtOH (10 mL) to give the yellow solid as product (100 mg, yield 50%).

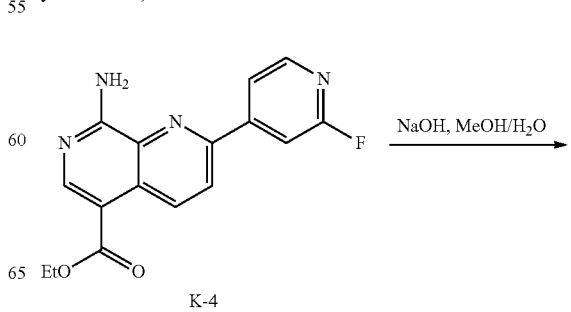

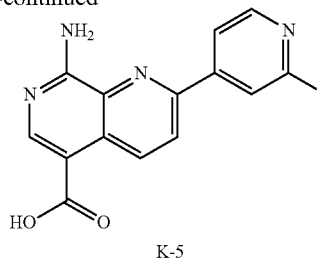
K-5

Compound K-5 can be prepared as following: to a solution of K-4 (100 mg, 0.3 mmol) in a mixture of MeOH/H$_2$O (30 mL/10 mL) was added NaOH (120 mg, 3.0 mol). The mixture was stirred at r.t. o.n., adjust pH was adjust to 5-6 with HCl (aq). It was extracted with EtOAc (50 mL×2), washed with sat NaCl (50 mL), and concentrated to give the product as yellow solid (60 mg, 60%).

Compounds K-7 can be prepared as following: to a solution of K-5 (e.g. 60 mg, 0.2 mmol), K-6 (e.g. 60 mg, 0.4 mmol) in solvent, e.g. DMF (10 mL) was added coupling reagents, e.g. HATU (e.g. 100 mg, 0.3 mmol), and DIPEA (e.g. 130 mg, 1.0 mmol). After the mixture was stirred at r.t. for 3 h, water (e.g. 30 mL) was added, and it was extracted with EtOAc (e.g. 50 mL×2), washed with sat NaCl (e.g. 50 mL), concentrated and purified by prep HPLC to give the product. Compounds according to the invention wherein R$^1$ is C$_2$-C$_{12}$-heteroaryl or aryl unsubstituted or substituted as described herein can also be made according to this general method by replacing compound K-2 by the appropriate C$_2$-C$_{12}$-heteroaryl or aryl boronic acid derivative.

EXAMPLES

The invention will be more fully understood by reference to the following examples. They should not, however, be construed as limiting the scope of the invention.

The chemical reactions described in the Examples may be readily adapted to prepare a number of other MAP4K4 inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting reactive functional groups, by utilizing other suitable reagents known in the art other than those described, and/or by making routine modifications of reaction conditions. Alternatively, other reactions disclosed herein or known in the art will be recognized as having applicability for preparing other compounds of the invention.

$^1$H NMR spectra were recorded at ambient temperature using an NMR spectrometer, including a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography/Mass Spectrometry (LCMS) experiments to determine retention times (R$_T$) and associated mass ions may be performed. The spectrometers may have an electrospray source operating in positive and negative ion mode. Additional detection is achieved using a evaporative light scattering detector.

Unless otherwise stated, all reactions were performed under an inert, i.e. argon or nitrogen, atmosphere.

Abbreviations

AcOH: Acetic acid; BOC: Di-tert-butyl dicarbonate; DCM: Dichloromethane; DIPEA: Diisopropylethylamine; DMAP: 4-Dimethylaminopyridine; EtOAc: Ethyl acetate; HATU: (2-(7-Aza-1H-benzotriazole-1-yl)-1,1,3,3-tetramethyluronium hexafluorophosphate); HCl: Hydrochloric acid; MeOH: Methanol; NaBH$_4$: Sodium borohydride, NBS: N-Bromosuccinimide; NH$_4$Cl: Ammonium chloride; NMR: Nuclear magnetic resonance; Pd(dppf)Cl$_2$: [1,1'-Bis(diphenylphosphino)ferrocene]dichloropalladium(II), complex with dichloromethane; RT: Room temperature; TFA: Trifluoroacetic acid; THF: Tetrahydrofuran.

PREPARATIVE EXAMPLES

Intermediate A

Preparation of the Intermediates of Formula A

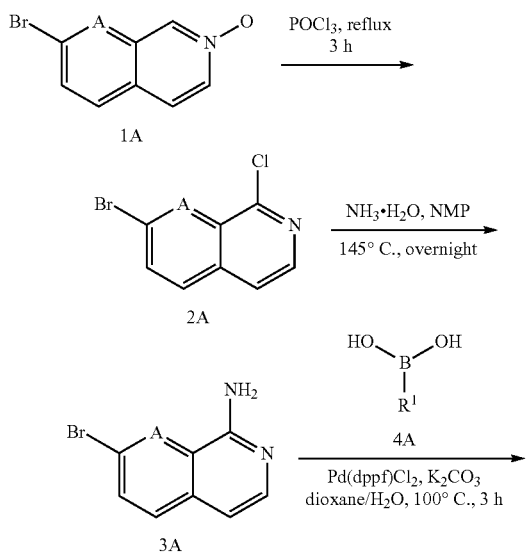

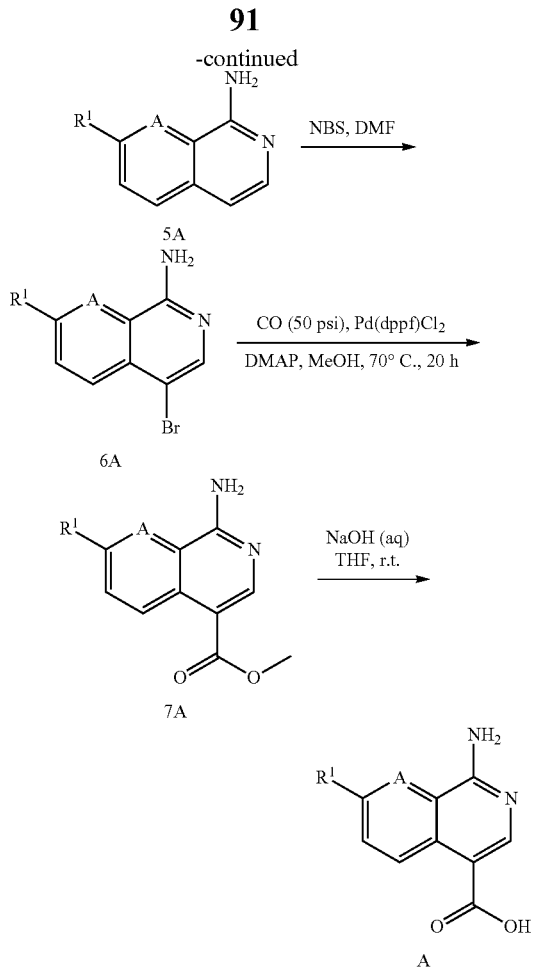

Step 1: Preparation of Compound 2A

Compound 1A (50 g, 0.22 mol) was added slowly in small portions to POCl$_3$ (200 mL) and the temperature was controlled below 30° C. After the mixture was stirred at 90° C. for 3 h, POCl$_3$ was removed under reduced pressure at 50-60° C., and cooled to room temperature. The resulting mixture was pour into water (200 mL), and pH was adjusted to 8-9 with sat. NaHCO$_3$. It was extracted with EtOAc (500 mL×3) and the combined organic layers was washed with sat NaCl (300 mL), dried over Na$_2$SO$_4$ and concentrated in vacuum to give the crude product 2A (45 g, yield 87%). In this step, A is as defined herein.

Step 2: Preparation of Compound 3A

To a solution of compound 2A (45 g, 0.18 mol) in NMP (150 mL), was added NH$_3$.H$_2$O (170 mL) slowly, and the mixture was stirred at 145-150° C. overnight. After the mixture was cooled to r.t., it was poured into water (200 mL), and extracted with EtOAc (500 mL×4). The combined organic layers was washed with sat NaCl (300 mL), dried over Na$_2$SO$_4$, concentrated and purified by column (PE:EtOAc=1:1 to 1:3) to give the product (37 g, yield 83%). In this step, A is as defined herein.

Step 3: Preparation of Compound 5A

To a solution of compound 3A (37 g, 0.16 mol) in dioxane/H$_2$O (300 mL/50 mL), was added compound 4A (28 g, 0.2 mol), K$_2$CO$_3$ (45 g, 0.32 mol), and Pd(dppf)Cl$_2$ (11 g, 0.016 mol). The mixture was stirred at 80-90° C. for 3 h, and poured into water (200 mL). It was extracted with EtOAc (500 mL×2) and the combined organic layers was washed with sat NaCl (300 mL), and dried over Na$_2$SO$_4$, concentrated and purified by column (PE:EtOAc=1:2 to 1:4) to give the product (32 g, yield 83%). In this step, A is as defined herein, for example CH and R$^1$ is as defined herein, for example fluoro-phenyl.

Step 4: Preparation of Compound 6A

To a solution of compound 5A (34 g, 0.14 mol) in DMF (200 mL), was added dropwise NBS (25.5 g, 0.14 mol) in DMF (30 mL) at r.t. and the mixture was stirred at r.t. for 1 h. It was poured into water (500 mL) and extracted with EtOAc (500 mL×3). The combined organic layers was washed with sat NaHCO$_3$ (100 mL), sat NaCl (300 mL), dried over Na$_2$SO$_4$, concentrated and purified by column to give the product (28 g, yield 65%). In this step, A is as defined herein, for example CH and R$^1$ is as defined herein, for example fluoro-phenyl.

Step 5: Preparation of Compound 7A

To a solution of compound 6A (15 g, 0.047 mol) in MeOH (200 mL), was added DMAP (12 g, 0.094 mol), and Pd(dppf)Cl$_2$ (3.7 g, 0.005 mol). The mixture was stirred at 75-80° C. under CO (50 psi) overnight, and poured into water (400 mL). The resulting mixture was extracted with EtOAc (500 mL×3). The combined organic layers was washed with sat NaCl (300 mL), dried over Na$_2$SO$_4$, concentrated and purified by column (PE:EtOAc=1:1 to 1:3) to give the product (11 g, yield 80%). In this step, A is as defined herein, for example CH and R$^1$ is as defined herein, for example fluoro-phenyl.

Step 6: Preparation of Intermediate A

To a solution of compound 7A (10 g, 0.034 mol) in MeOH-THF-H$_2$O (100 mL, 2:1:1), was added NaOH (5.2 g, 0.13 mol). The mixture was stirred at 40-50° C. overnight. The organic solvent was removed under reduced pressure and poured into water (100 mL). HCl (5 M) was added to adjust pH to 6-7. The resulting precipitate was filtered and concentrated to give the product as white solid (8.5 g, yield 91%). In this step, A is as defined herein, for example CH and R$^1$ is as defined herein, for example fluoro-phenyl.

Intermediate B 1-amino-N-(2-aminophenyl)-7-(3-fluorophenyl)isoquinoline-4-carboxamide

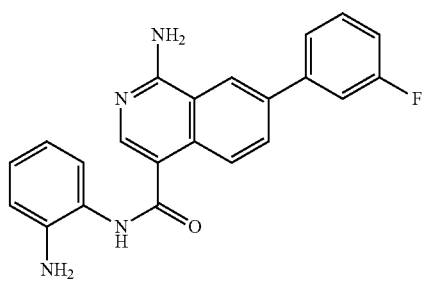 [SMILES: Nc1ccccc1NC(=O)c1cnc(N)c2cc(-c3cccc(F)c3)ccc12]

To a solution of compound 1B (corresponds to Intermediate of Formula A wherein A is CH and R¹ is 3-fluorophenyl) (280 mg, 1.0 mmol) in anhydrous DMF (10 mL), was added HATU (460 mg, 1.2 mmol), DIPEA (260 mg, 2.0 mmol), and 2B (160 mg, 1.5 mmol). The mixture was stirred at room temperature overnight. Water (10 mL) was added and the mixture was extracted with EtOAc (10 mL×3). The combined organic layer was washed with brine (10 mL×3), dried over Na₂SO₄, concentrated and used in next step without further purification.

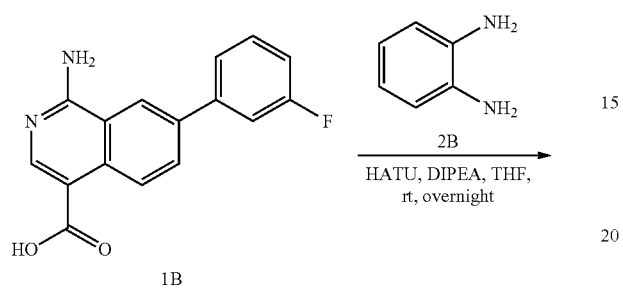

Intermediate C 8-amino-N-(azetidin-3-yl)-2-(3-fluorophenyl)-1,7-naphthyridine-5-carboxamide

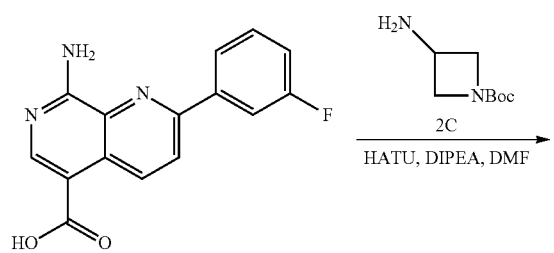

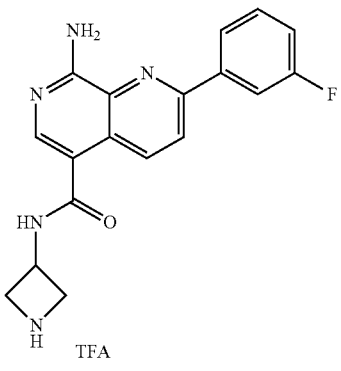

Step 1: Preparation of C-3

After a mixture of C-1 (300 mg, 1 mmol), C-2 (218 mg, 1.2 mmol), HATU (600 mg, 1.6 mmol), and DIPEA (270 mg, 2.1 mmol) in DMF (20 mL) was stirred at r.t. for 3 h, water (30 mL) was added. It was filtered and filtrate was concentrated to give the crude product (378 mg 85%)

Step 2: Preparation of C

To a solution of C-3 (378 mg, 0.85 mmol) in DCM (12 mL) was added TFA (3 mL) at r.t. After the mixture was stirred o.n., it was concentrated to give the crude product, which was used directly (300 mg, 85%).

Intermediate D ethyl 8-amino-2-hydroxy-1,7-naphthyridine-5-carboxylate

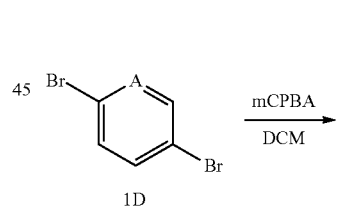

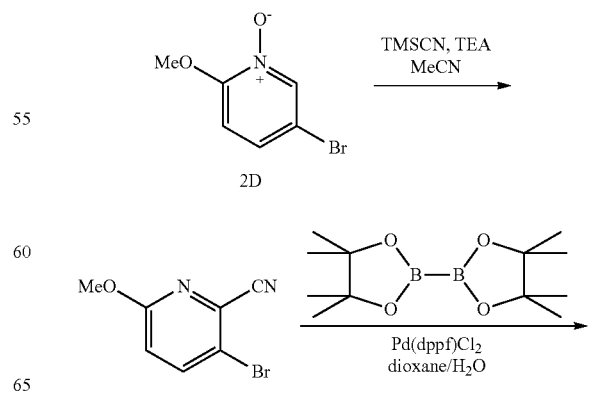

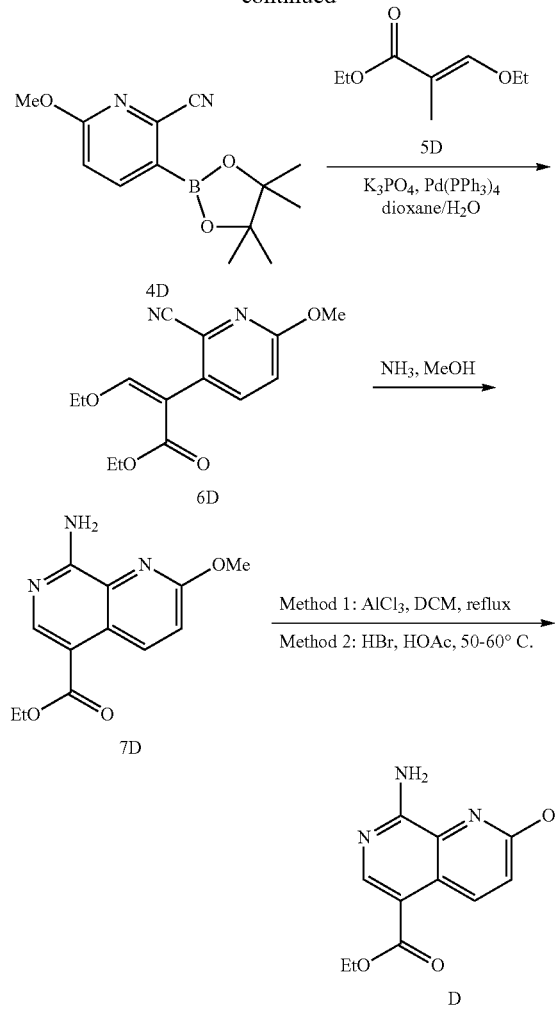

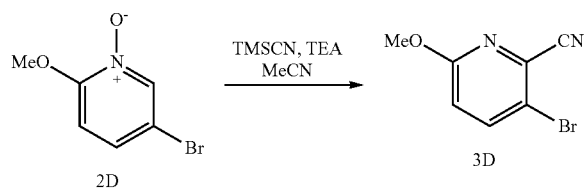

Step 1: Preparation of 5-Bromo-2-methoxypyridine 1-oxide (2D)

To a stirred solution of 5-bromo-2-methoxypyridine 1D (22.6 g, 120.2 mmol) in DCM (120 mL) was added m-CPBA (82.7 g, 480.8 mmol) in two portions. The reaction mixture was stirred at 40° C. for 16 h. After the mixture was cooled to rt, and the precipitate was filtered. The filtrate was washed with aqueous $Na_2S_2O_3$, followed by aqueous $Na_2CO_3$. The organic layer was concentrated and purified directly by column chromatography (MeOH: DCM=10:1) to give the product as white solid (14 g, 57.1%).

Step 2: Preparation of 3-Bromo-6-methoxypicolinonitrile (3D)

To a stirred solution of 2D (28 g, 137.9 mmol) in MeCN (60 ml) was added TMSCN (54.6 g, 551.6 mmol) and TEA (41.8 g, 413.7). The mixture was stirred at 80° C. for 15 h under $N_2$. After the reaction mixture was concentrated and water (60 mL) was added, it was extracted with EtOAc (80 mL×2), dried over $Na_2SO_4$, concentrated and purified by column (PE:EtOAc=3:1) to give the product as white solid (24.4 g, 82.7%). $^1$H NMR (400 MHz, CDCl3) δ8.16 (d, J=9.2 Hz, 1H), 7.15 (d, J=8.8 Hz, 1H), 3.86 (s, 3H).

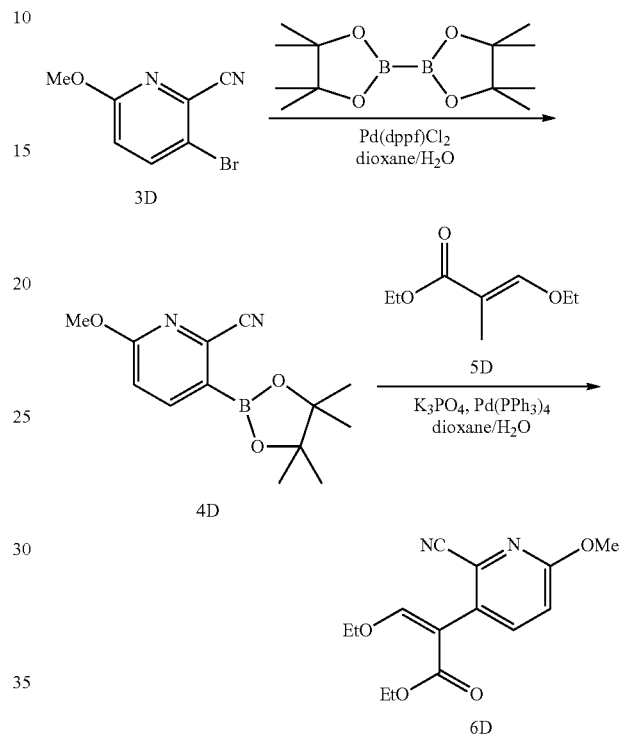

Steps 3 and 4: Preparation of ethyl 2-(2-cyano-6-methoxypyridin-3-yl)-3-ethoxyacrylate (6D)

A mixture of 3D (1.0 g, 4.7 mmol), bis(pinacolato) diboron (1.7 g, 7.0 mmol), $Pd(dppf)Cl_2$ (360 mg, 0.5 mmol), and KOAc (1.0 g, 10.0 mmol) in dioxane (50 mL) was degassed and stirred at 80° C. for 2 h under $N_2$. After the mixture was cooled to r.t. and compound 5D (1.30 g, 4.8 mmol), $Pd(PPh_3)_4$ (550 mg, 0.5 mmol), $K_2CO_3$ (1.4 g, 10.0 mmol), and $H_2O$ (10 mL) was added, and the mixture was stirred at 90° C. for 3 h under $N_2$. The mixture was extracted with EtOAc (200 mL×2), washed with sat NaCl (100 mL), dried over $Na_2SO_4$, concentrated and purified by column (PE:EtOAc=3:1) to give the product as white solid (600 mg, 48%).

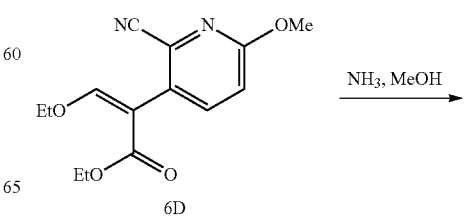

-continued

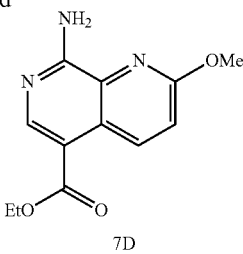

7D

Step 5: Preparation of ethyl 8-amino-2-methoxy-1,7-naphthyridine-5-carboxylate (7D)

To a solution of 6D (600 mg, 2.2 mmol) in EtOH (30 mL), was added NH$_3$H$_2$O (10 mL), and the mixture was stirred at r.t. overnight. After no STM was left as checked by TLC, and it was concentrated to give the crude product as white solid (400 mg, yield 80%).

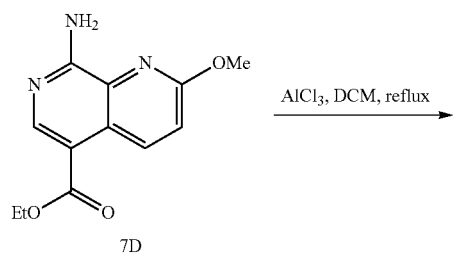

7D

AlCl$_3$, DCM, reflux →

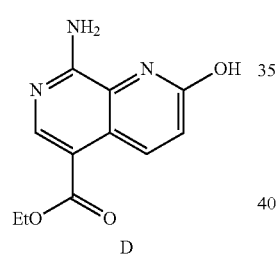

D

Step 5: Preparation of ethyl 8-amino-2-hydroxy-1,7-naphthyridine-5-carboxylate (D), Method 1

To a solution of 7D (400 mg, 1.6 mmol) in DCM (50 mL), was added AlCl$_3$ (1.5 g), and the mixture was heated at reflux overnight. After there was no starting material left as checked by TLC, it was cooled to r.t. Water (30 mL) was added and it was adjust to pH=5-6 with NaHCO$_3$. It was extracted DCM (100 mL×5), dry over Na$_2$SO$_4$, and concentrated to give the product as white solid (200 mg, 55%).

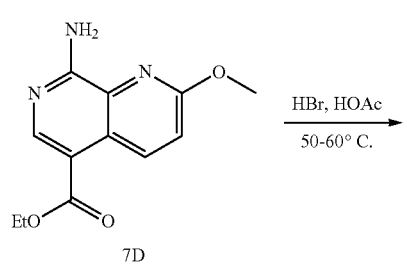

7D

HBr, HOAc
50-60° C. →

-continued

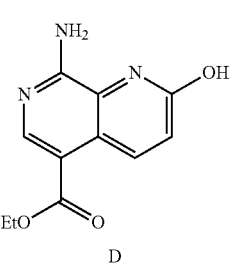

D

Step 5: Preparation of Ethyl 8-amino-2-hydroxy-1,7-naphthyridine-5-carboxylate (8), Method 2

A mixture of 7 (600 mg, 2.43 mmol) in HBr-HOAc (10 mL) was heated to 60-70° C. for 3 h. After the mixture was cooled to r.t., MTBE (30 mL) was added. The precipitate was collected to give the desired product (500 mg, 88%). LCMS: (5-95, AB, 1.5 min), 0.627 min, MS=233.9 [M+1], $^1$H NMR (400 MHz, DMSO-d6) δ8.95 (m, 2H), 8.25 (s, 1H), 7.24 (br, 1H), 4.32 (q, 2H), 1.31 (t, J=7.2 Hz, 1H).

Example 1

3-[[[1-amino-7-(3-fluorophenyl)isoquinoline-4-carbonyl]amino]methyl]-N,N-dimethyl-1,2,4-oxadiazole-5-carboxamide

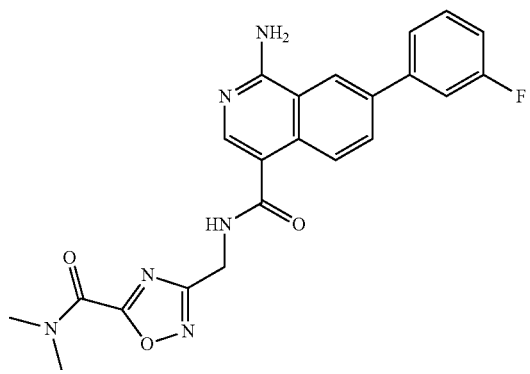

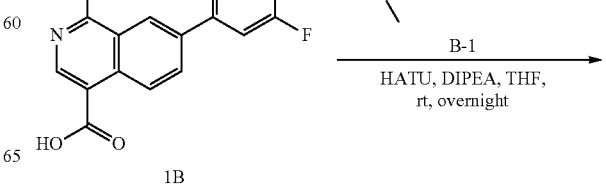

1B

B-1
HATU, DIPEA, THF,
rt, overnight →

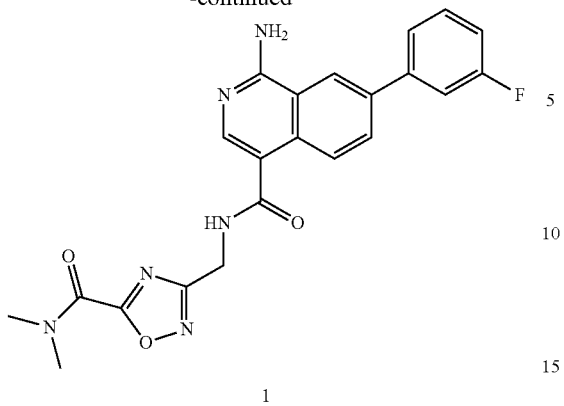

1

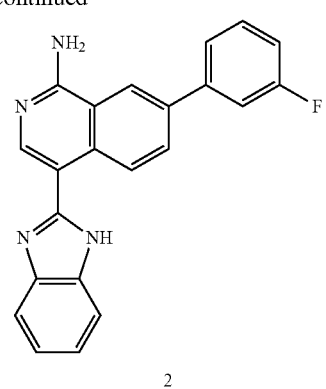

2

To a solution of compound 1B (corresponds to Intermediate of Formula A wherein A is CH and R[1] is 3-fluorophenyl) (140 mg, 0.5 mmol) in anhydrous THF (10 mL), was added HATU (230 mg, 0.6 mmol), DIPEA (130 mg, 1.0 mmol), and compound B-1 (128 mg, 0.75 mmol). The mixture was stirred at room temperature overnight. Water (50 mL) was added and the mixture was extracted with EtOAc (30 mL×3). The combined organic layer was washed with brine (30 mL), concentrated, and purified by prep-HPLC to give the desired product as a white solid (61.2 mg yield: 28%). LCMS: (0-60), A 1.132 434.9 0-60 $^1$H NMR (400 MHz, Methanol-d4) δ: 8.84 (s, 1H), 8.52 (d, J=8.8 Hz, 1H), 8.38 (d, J=8.8 Hz, 1H), 7.92 (s, 1H), 7.71-7.57 (m, 3H), 7.25 (t, J=8.8 Hz, 1H), 3.29 (s, 3H), 3.18 (s, 3H).

A solution of Compound B in HOAc was heated at reflux for 2 h. HOAc was removed under reduced pressure and the residue was purified by prep-HPLC to give the desired producted as a white solid (45 mg, 13%). $^1$H NMR (400 MHz, MeOH-d4) δ: 9.03 (s, 1H), 8.49 (dd, J=8.8 1.6 Hz, 1H), 8.34 (s, 1H), 8.25 (d, J=8.8 Hz, 1H), 7.98-7.96 (m, 2H), 7.77-7.65 (m, 4H), 7.64-7.61 (m, 1H), 7.28-7.27 (m, 1H).

Example 3

1-amino-7-(3-fluorophenyl)-N-(3-hydroxycyclobutyl)isoquinoline-4-carboxamide

Example 2

4-(1H-benzimidazol-2-yl)-7-(3-fluorophenyl)isoquinolin-1-amine

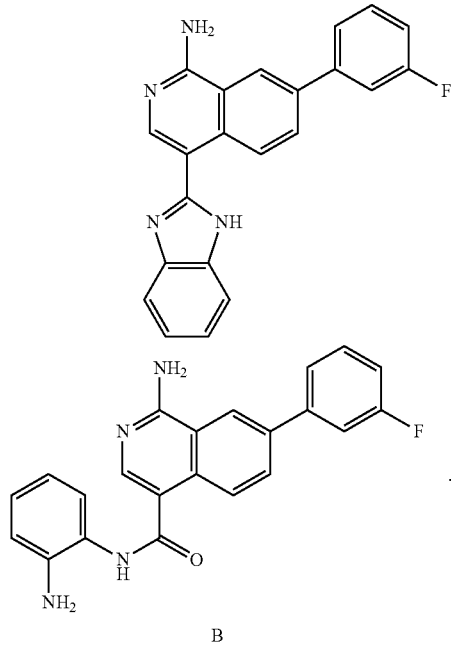

B

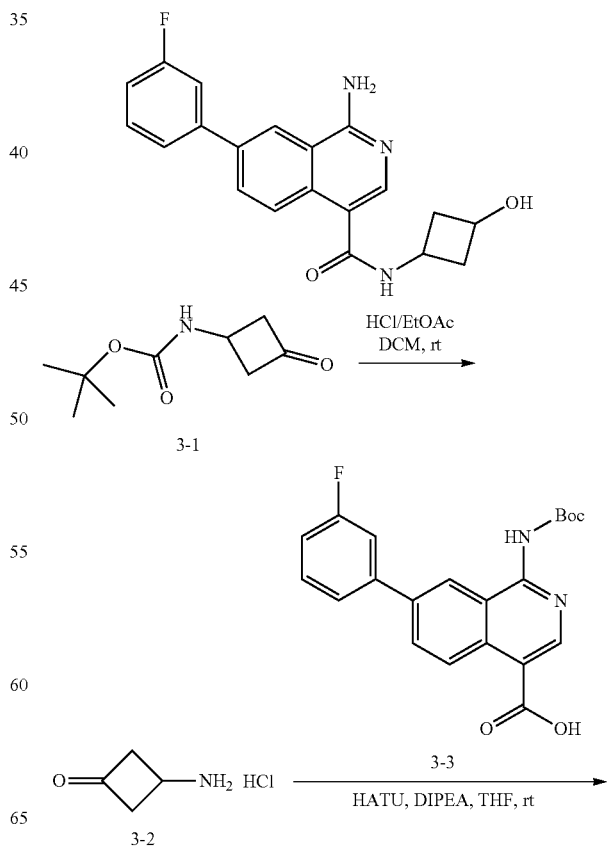

-continued

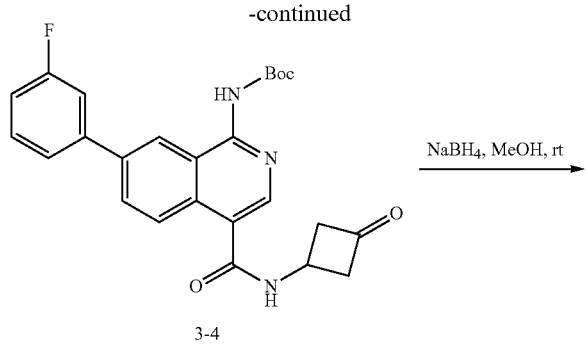

3-4

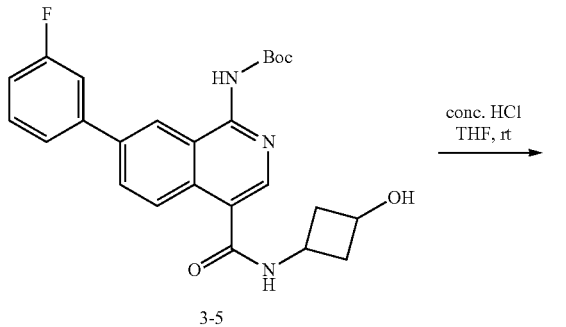

3-5

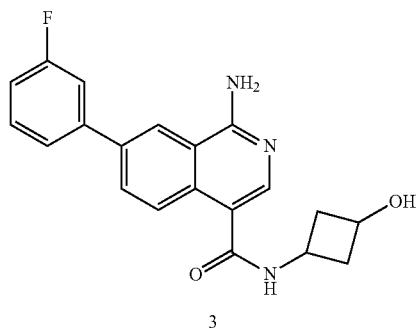 [SMILES: Nc1ncc(C(=O)NC2CC(O)C2)c2ccc(-c3cccc(F)c3)cc12]

3

General Procedure for Preparation of Compound 3-2

To a solution of Compound 3-1 (300 mg, 1.76 mmol) in DCM (10 mL), was added EtOAc/HCl (2.0 mL, 4 M), and it was stirred at room temperature for 30 min. The solution was concentrated to give the Compound 3-2 (250 mg).

General Procedure for Preparation of Compound 3-3

To a solution of Compound 3-2 (200 mg, 0.5 mmol) in THF (10 mL), was added DIPEA (528.9 mg, 2.6 mmol), HATU (290 mg, 0.75 mmol), and compound 3-3 (140 mg, 1.0 mmol). The mixture was stirred at room temperature overnight and poured into water (20 mL). The resulting mixture was extracted with EtOAc (30 mL×2), and concentrated to give the crude compound 3-4 (250 mg, crude).

General Procedure for Preparation of Compound 3-5

To a solution of Compound 3-4 (250 mg, 0.5 mmol) in MeOH (10 mL), was added NaBH$_4$ (77.8 mg, 2.0 mmol). The mixture was stirred at r.t. for 1 h, and poured into water (30 mL). The mixture was extracted with EtOAc (30 mL×2), and washed with NaCl (20 mL), dried over Na$_2$SO$_4$, and concentrated to give the crude product (200 mg).

General Procedure for Preparation of Compound 3

To a solution of Compound 3-5 (200 mg, crude) in THF (10 mL), was added conc. HCl (2 mL). After it was stirred at r.t. for 5 h, organic solvent was removed and the residue was poured into water (20 mL), and pH was adjusted to 8-9 with sat NaHCO$_3$. It was extracted with EtOAc (20 mL×3). The combined organic layers was washed with sat NaCl (30 mL), dried over Na$_2$SO$_4$, concentrated, and purified by prep-HPLC to give product. $^1$H NMR (400 MHz, DMSO-d6) δ: 8.64 (s, 1H), 8.51 (d, J=7.2 Hz, 1H), 8.40 (d, J=9.2 Hz 1H), 8.11-8.04 (m, 2H), 7.77-7.72 (m, 4H), 7.57-7.54 (m, 1H), 7.25-7.21 (m, 1H), 5.08 (bs, 1H), 3.93-3.82 (m, 2H), 2.57-2.55 (m, 2H), 1.91-1.84 (m, 2H).

Example 4

1-amino-7-(3-fluorophenyl)isoquinoline-4-carbonitrile

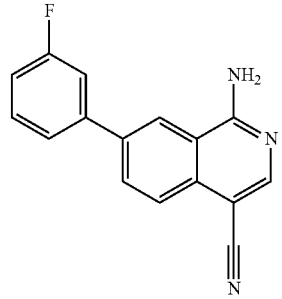

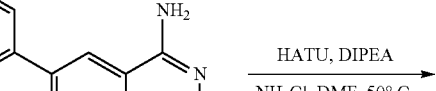

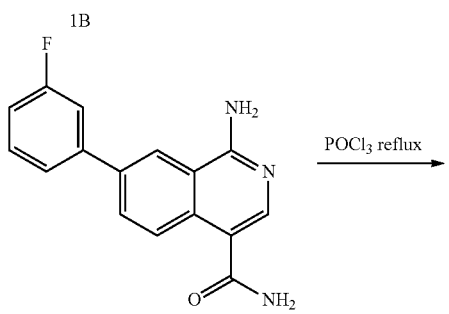

1B

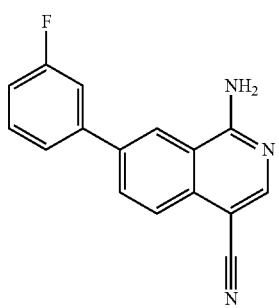

4

Step 1: Preparation of Compound 4-1

To a solution of Compound 1B (5 g, 0.017 mol) in DMF (50 mL), was added DIPEA (11 g, 0.085 mol), HATU (8.4 g, 0.022 mol), and NH$_4$Cl (3.6 g, 0.068 mol). After the mixture was stirred at 40-50° C. for 4 h, it was poured into water (500 mL). The resulting mixture was filtered and concentrated to give the product (4.0 g, yield 80%).

Step 2: Preparation of Compound 4

A solution of Compound 4-1 (4.0 g, 0.014 mol) in POCl$_3$ (20 mL) was heated at reflux overnight. Organic solvent was poured into ice-water (100 mL), and pH was adjusted to 8-9 with sat NaHCO$_3$. It was extracted with EtOAc (200 mL×3) and the combined organic layers was washed with sat NaCl (300 mL), dried over Na$_2$SO$_4$, and concentrated to give the product (3.2 g, yield 72%). $^1$H NMR (400 MHz, DMSO-d6) δ: 8.74 (s, 1H), 8.38 (s, 1H), 8.28-8.16 (m, 3H), 7.86 (d, J=8.8 Hz, 1H), 7.77-7.72 (m, 2H), 7.60-7.54 (m, 1H), 7.28-7.22 (m, 1H).

Example 5

4-(aminomethyl)-7-(3-fluorophenyl)isoquinolin-1-amine

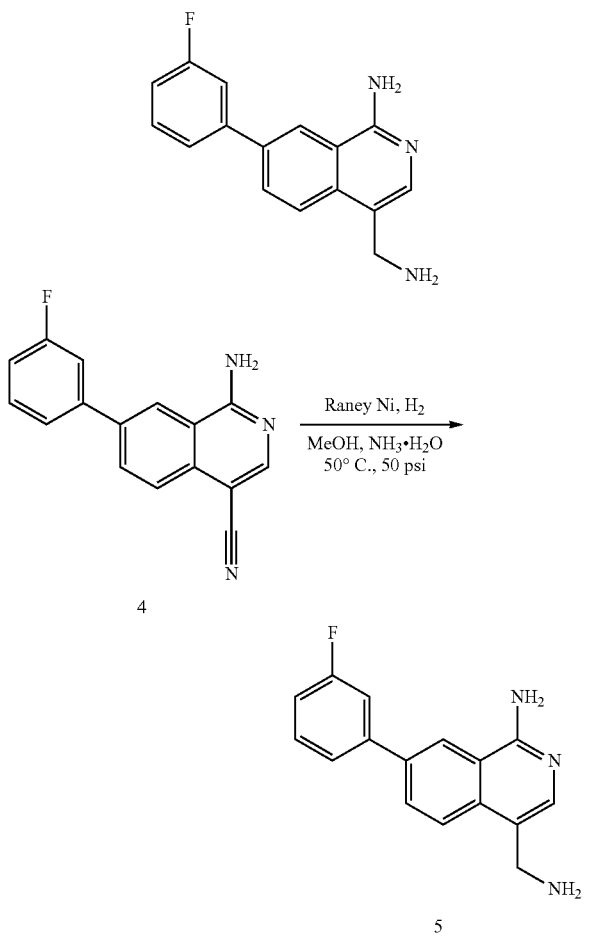

To a solution of Compound 4 (2.0 g, 7.0 mmol) in MeOH (100 mL) and NH$_3$·H$_2$O (10 mL), was added Raney Ni (2.0 g), and the mixture was stirred at 50° C. overnight under H$_2$ at 50 psi. The resulting mixture was filtered and concentrated to give the product (1.6 g, yield 80%). $^1$H NMR (400 MHz, MeOH-d4) δ: 8.91 (s, 1H), 8.46 (dd, J=8.8 1.6 Hz, 1H), 8.27 (d, J=8.8 Hz, 1H), 7.84 (s, 1H), 7.73-7.58 (m, 3H), 7.28-7.24 (m, 1H), 4.54 (s, 2H).

Example 6

N-[[1-amino-7-(3-fluorophenyl)-4-isoquinolyl]methyl]cyclopropanecarboxamide

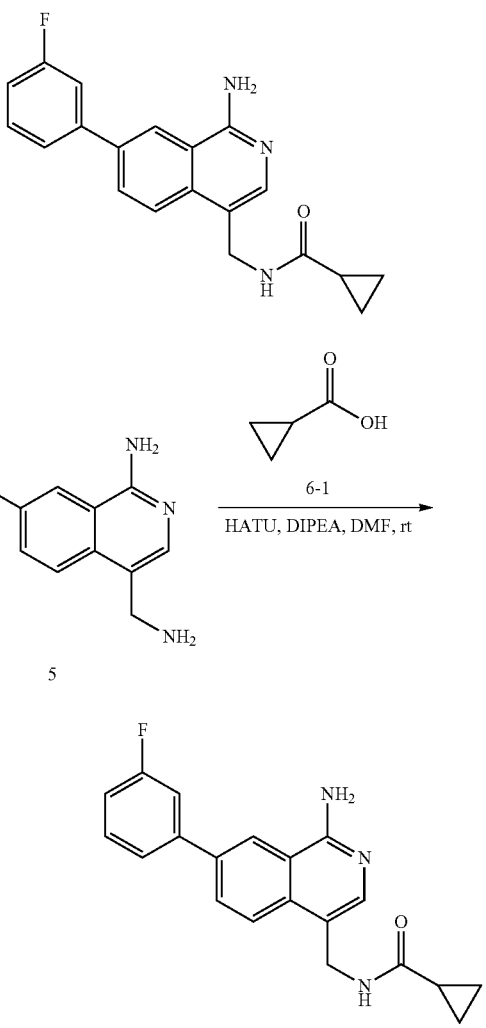

To a solution of Compound 5 (100 mg, 0.37 mmol) in DMF (10 mL), was added DIPEA (190 mg, 1.5 mmol), HATU (200 mg, 0.52 mol), and compound 6-1 (0.55 mmol, 1.5 eq). Then the mixture was stirred at r.t. for 30 min, and poured into water (20 mL). The resulting mixture was extracted with EtOAc (30 mL×2), concentrated and purified by prep-HPLC to give the product. $^1$H NMR (400 MHz, MeOH-d4) δ: 8.84 (s, 1H), 8.38 (dd, J=8.8 1.6 Hz, 1H), 8.22 (d, J=8.8 Hz, 1H), 7.78-7.55 (m, 3H), 7.48-7.38 (m, 1H), 7.26-7.21 (m, 1H), 4.69 (s, 2H), 1.65-1.59 (m, 1H), 0.94-0.87 (m, 2H), 0.84-0.79 (m, 2H).

Example 7

1-amino-7-(3-fluorophenyl)-N-(1-methylazetidin-3-yl)isoquinoline-4-carboxamide

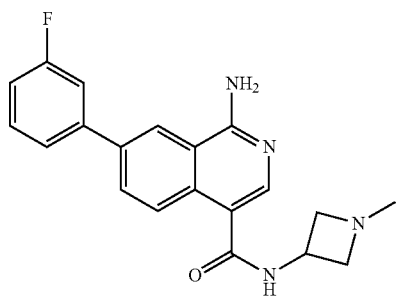

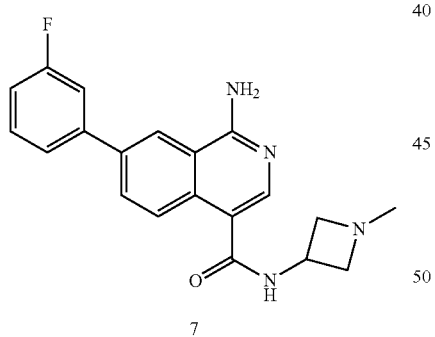

Example 8

1-amino-7-(3-fluorophenyl)-N-[1-(methylcarbamoyl)azetidin-3-yl]isoquinoline-4-carboxamide

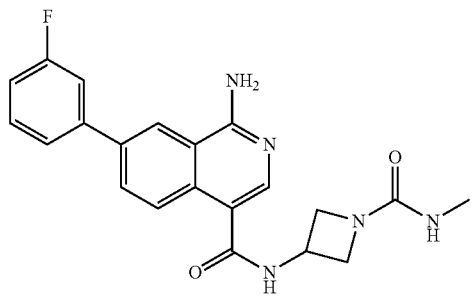

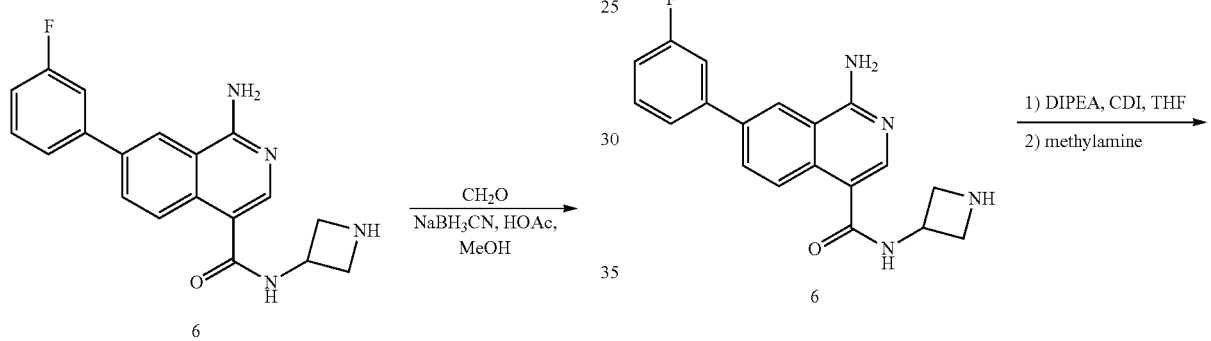

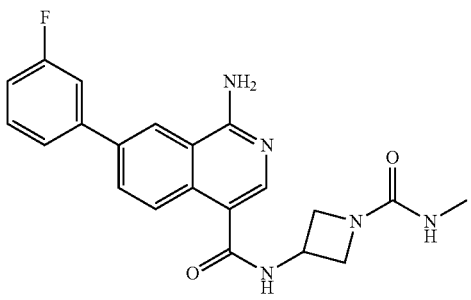

To a solution of Compound 6 (120 mg, 0.36 mmol) in MeOH (10 mL), was added HOAc (0.3 mL), formaldehyde solution (15 mg, 1.2 eq), and the mixture was stirred at r.t. for 30 min. NaBH$_3$CN (50 mg, 0.72 mmol) was added, and the mixture was stirred at r.t. for 2 h. It was poured into water (10 mL). The mixture was extracted with EtOAc (20 mL×2) and the organic layer was concentrated and purified by prep HPLC to give product. $^1$H NMR (400 MHz, MeOH-d4) δ: 8.55-8.52 (m, 2H), 8.39 (bs, 2H), 8.15 (bs, 1H), 8.09 (d, J=8.8 Hz, 1H), 7.66-7.51 (m, 3H), 7.17 (t, J=8.4 Hz, 1H), 4.71-4.69 (m, 1H), 4.57-4.52 (m, 2H), 4.43-4.39 (m, 2H), 3.04 (s, 3H).

To a solution of Compound 6 (150 mg, 0.47 mmol) in THF (10 mL), was added DIPEA (290 mg, 2.2 mmol), CDI (100 mg, 0.61 mmol). After the mixture was stirred at r.t. for 1 h, methylamine (150 mg, 47 mmol) was added, and the mixture was stirred at r.t. for 2 h, and purified by (basic) prep-HPLC to give the product. $^1$H NMR (400 MHz, DMSO-d6) δ: 8.84 (d, J=7.2 Hz, 1H), 8.61 (s, 1H), 8.47 (d, J=8.8 Hz, 1H), 8.18 (s, 2H), 8.08 (dd, J=8.8 2.0 Hz, 1H), 7.78-7.74 (m, 2H), 7.59-7.53 (m, 1H), 7.47 (bs, 2H), 7.26-7.21 (m, 1H), 6.28-6.27 (m, 1H), 4.66-4.64 (m, 1H), 4.08-4.06 (m, 2H), 3.82-3.79 (m, 2H), 2.55 (d, J=4.8 Hz, 3H).

Example 9

N-(1-acetylazetidin-3-yl)-1-amino-7-(3-fluorophenyl)isoquinoline-4-carboxamide

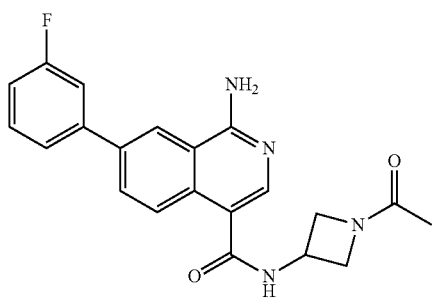

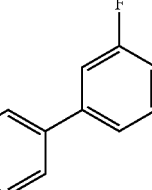

Example 10

7-(3-fluorophenyl)-4-(1-methylimidazol-4-yl)isoquinolin-1-amine

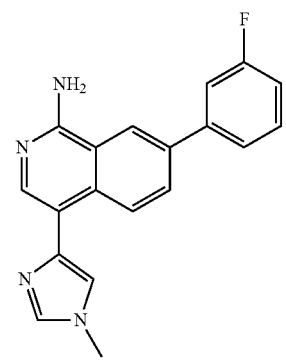

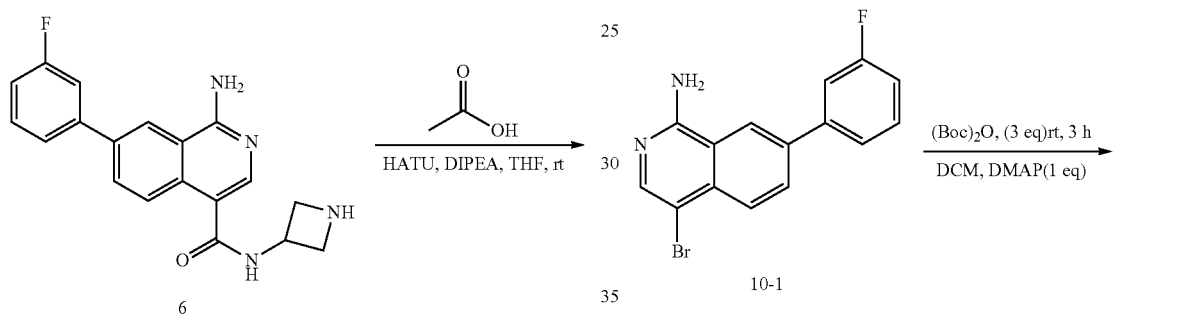

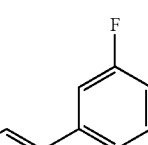

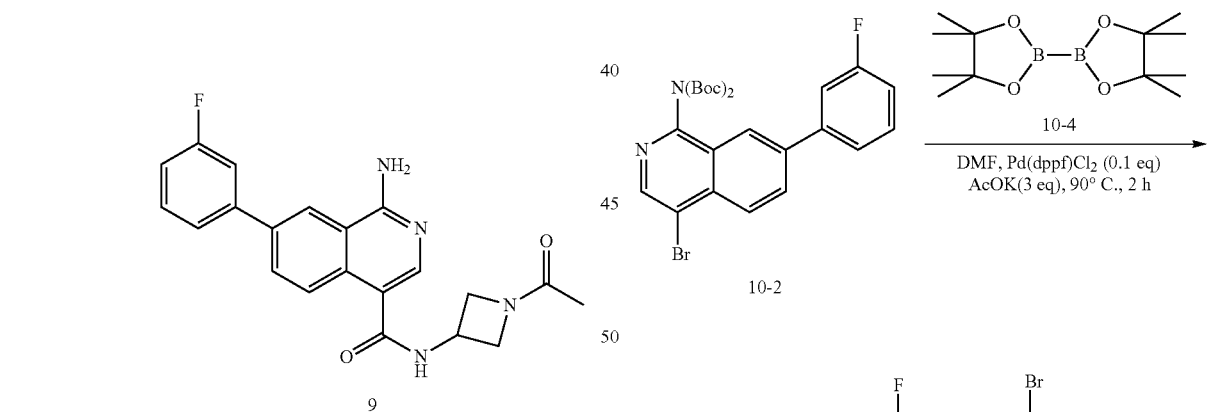

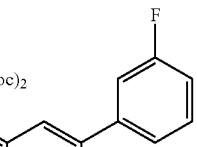

To a solution of Compound 6 (80 mg, 0.24 mmol) in THF (10 mL), was added DIPEA (180 mg, 1.5 mmol), HATU (136.8 mg, 0.36 mmol), and acetic acid (0.36 mmol, 1.5 eq). After the mixture was stirred at r.t for 3 h, it was poured into water (20 mL), extracted with EtOAc (30 mL×2), concentrated and purified by prep HPLC to give the product. $^1$H NMR (400 MHz, DMSO-d6) δ: 8.59 (s, 1H), 8.45 (d, J=8.8 Hz, 1H), 8.14 (dd, J=8.8 2.0 Hz, 1H), 8.09 (s, 1H), 7.68-7.52 (m, 3H), 7.20-7.15 (m, 1H), 4.85-4.84 (m, 1H), 4.63 (t, J=8.8 Hz, 1H), 4.40 (t, J=8.8 Hz, 1H), 4.27-4.23 (m, 1H), 4.06-4.02 (m, 1H), 1.93 (s, 3H).

-continued

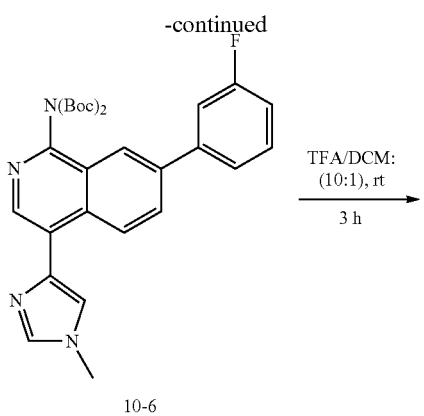

10-6

General Procedure for Preparation of Compound 10-2

To a solution of Compound 10-1 (1.9 g, 6 mmol) in DCM (50 mL), was added DMAP (73.3 mg, 0.6 mmol), and BoC$_2$O (3.98 g, 18 mmol) in DCM (10 mL). After the mixture was stirred at r.t. for 6 h, DCM was removed, and water (100 mL) was added. The resulting mixture was extracted with EtOAc (200 mL×2), concentrated and purified by column (PE:EtOAc=5:1 to 3:1) to give the product (1.8 g, yield 58%).

General Procedure for Preparation of Compound 10-3

A suspension of Compound 10-2 (1.5 g, 3 mmol), Compound 10-4 (1.52 g, 6 mmol), KOAc (882 mg, 9.0 mmol), and Pd(dppf)Cl$_2$ (219.6 mg, 0.5 mmol) in anhydrous DMF (20 mL) was degassed for 3 times and heated at 90° C. for 2 h under N$_2$. It was poured into water (50 mL), and extract with EtOAc (100 mL×2) and the combined organic layers was washed with sat NaCl (50 mL), dried over Na$_2$SO$_4$ and concentrated in vacuum to give the crude product (800 mg, yield 47.3%).

General Procedure for Preparation of Compound 10-6

A solution of Compound 10-3 (169 mg, 0.3 mmol) in a mixture of dioane (10 mL)-H$_2$O (1 mL), was added Compound 10-5 (55.8 mg, 0.3 mmol), Cs$_2$CO$_3$ (195 mg, 0.6 mmol) and Pd(dppf)Cl$_2$ (22 mg, 0.03 mmol) and heated under irradiation of MW at 130° C. for 30 min under N$_2$.

Catalyst was filtered through diatomite and concentrated in vacuum to give the crude product (100 mg, yield 61.3%).

General Procedure for Preparation of Compound 10

A solution of Compound 10-6 (100 mg, crude) in a mixture of DCM:TFA (10:1, 20 mL), was stirred at rt for 3 h. The resulting mixture was concentrated, and purified by prep-HPLC to give the product (20.9 mg. yield 20.9%). $^1$H NMR (400 MHz, DMSO-d6) δ: 9.10 (bs, 1H), 8.96 (s, 1H), 8.51 (s, 1H), 8.38 (s, 2H), 7.87 (s, 1H), 7.83-7.79 (m, 3H), 7.66-7.60 (m, 1H), 7.35-7.30 (m, 1H), 3.86 (s, 3H).

Example 11

7-(3-fluorophenyl)-4-oxazol-2-yl-isoquinolin-1-amine

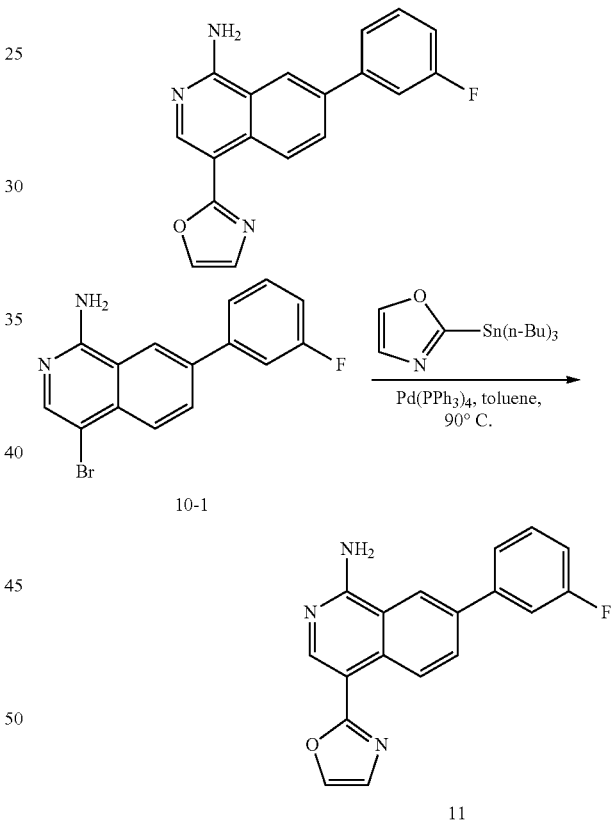

11

A suspension of Compound 10-1 (96 mg, 0.3 mmol), 2-(tributylstannyl)oxazole (360 mg, 1.0 mmol) and Pd(PPh$_3$)$_4$ (30 mg) in toluene (1.0 mL) was heated to 90° C. overnight. The solution was quenched with saturated aqueous CsF solution and extracted with EtOAc (100 mL). The organic layer was washed with brine, concentrated and purified by prep-HPLC to give the desire product. $^1$H NMR (400 MHz, DMSO-d6) δ: 9.32 (d, J=8.8 Hz, 1H), 9.11 (s, 1H), 8.52 (dd, J=8.8 1.6 Hz, 1H), 8.36 (d, J=6.4 Hz, 2H), 7.89-7.84 (m, 2H), 7.65-7.60 (m, 1H), 7.54 (s, 1H), 7.35-7.30 (m, 1H).

Example 12

7-(3-fluorophenyl)-4-(2-methyl-1,2,4-triazol-3-yl)isoquinolin-1-amine

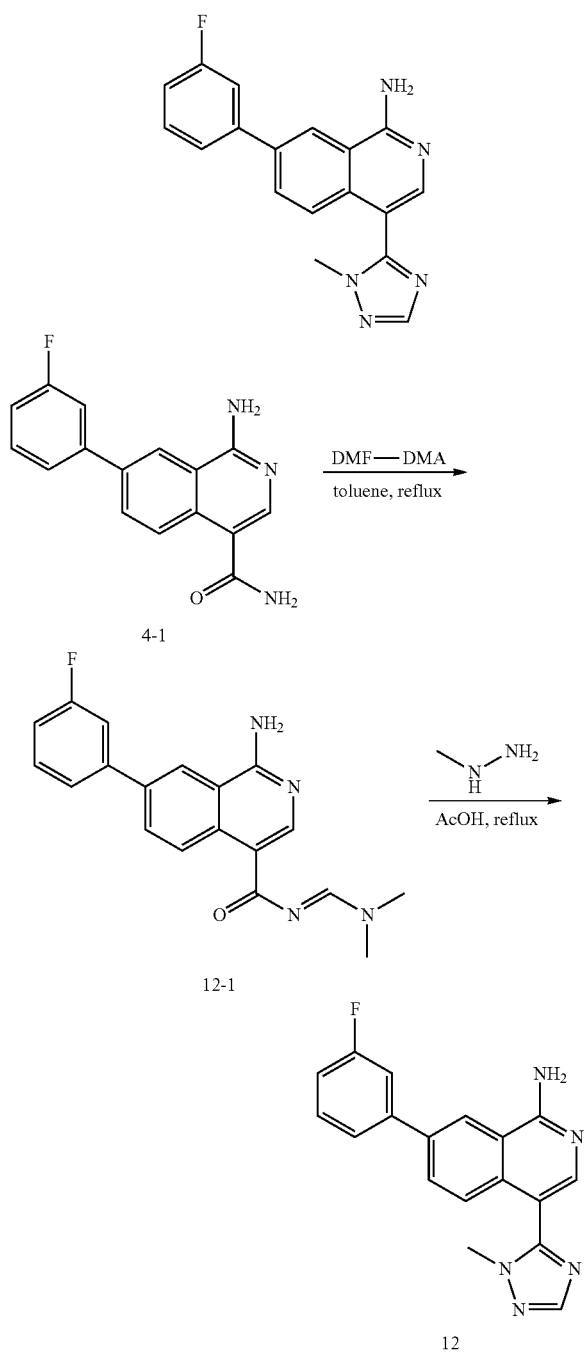

Step 1: Preparation of Compound 12-1

A solution of compound 4-1 (280 mg, 1 mmol) and DMF-DMA (2 mL) in toluene (10 mL) was heated at reflux for 3 h. Solvent was removed and the crude product was used in next step without further purification.

Step 2: Preparation of Compound 12

A solution of compound S (300 mg, crude) and methylhydrazine (100 mg, 2 mmol) in HOAc (10 mL) was heated at reflux overnight. Solvent was removed and the residue was purified by prep-HPLC to give desired product. $^1$H NMR (400 MHz, DMSO-d6) δ: 9.11 (s, 1H), 8.40 (dd, J=8.8 2.0 Hz, 1H), 8.23 (s, 1H), 8.10 (s, 1H), 7.86-7.80 (m, 3H), 7.64-7.62 (m, 1H), 7.34-7.33 (m, 1H), 3.87 (s, 3H).

Example 13

8-amino-N-cyclopropyl-2-(3-fluorophenyl)-1,7-naphthyridine-5-carboxamide

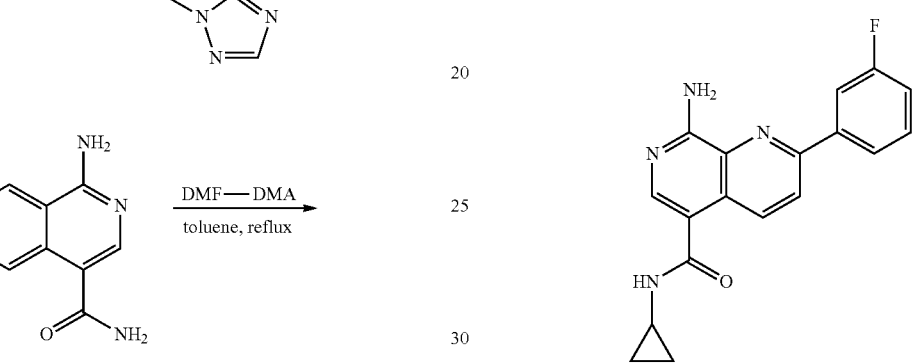

Step 1: Preparation of 5-bromo-7-(2-trimethylsilylethoxymethyl)-1,7-naphthyridin-8-one 13-1

To a RBF was added 5-bromo-7H-1,7-naphthyridin-8-one (7.350 g, 32.66 mmol) followed by THF (200 mL). The reaction was cooled to 0° C., then 1,8-diazabicyclo[5.4.0]undec-7-ene (DBU); 3 equiv., 97.98 mmol, 14.80 mL) and 2-(chloromethoxy)ethyl-trimethyl-silane (2 equiv., 65.32 mmol, 11.6 mL) were added. The reaction was stirred at 0° C. for 3 h, then room temperature overnight. LCMS showed ~65% conversion. An additional equivalent of base and chloride were added, and the reaction was stirred for 4 h. LCMS showed full conversion. The reaction was diluted with ethyl acetate, then washed with water. Aqueous was extracted 2× with ethyl acetate. Organics were combined, dried over magnesium sulfate, filtered, and concentrated. Crude was purified by flash chomatography, (2-5% MeOH: DCM), then again with (25-100% ethyl acetate: heptanes), yielding 7.58 g of 8-oxo-7-(2-trimethylsilylethoxymethyl)-1,7-naphthyridine-5-carboxylate as a white semi-solid, clean by H NMR and LCMS. $^1$H NMR (400 MHz, DMSO) δ 8.96-8.84 (dd, J=4.4, 1.5 Hz, 1H), 8.25-8.16 (dd, J=8.3, 1.5 Hz, 1H), 8.09-8.02 (s, 1H), 7.96-7.86 (dd, J=8.3, 4.4 Hz, 1H), 5.49-5.40 (s, 2H), 3.71-3.60 (m, 2H), 0.97-0.86 (m, 2H), 0.01--0.02 (s, 9H). LCMS M/Z (M+H)=357

Step 2: Preparation of ethyl 8-oxo-7-(2-trimethylsilylethoxymethyl)-1,7-naphthyridine-5-carboxylate 13-2

To a RBF was added 5-bromo-7-(2-trimethylsilylethoxymethyl)-1,7-naphthyridin-8-one (14.5 g, 40.8 mmol) followed by palladium (II) acetate (0.1 equiv., 4.08 mmol, 964 mg), Bis(dicyclohexyl-phosphino)propane (0.1 equiv., 4.08 mmol, 2580 mg), potassium carbonate (1.5 equiv., 61.2 mmol, 8460 mg), dimethylformamide (40 equiv., 1630 mmol, 128 mL), and ethanol (10 equiv. 408 mmol, 24.8 mL). The reaction was placed under CO(g) balloon, and vacuum purged/backfilled 3×. The reaction mix was then heated to 85° C., and purged/back-filled 3 additional times. The reaction was then stirred under CO atmosphere for 3 h. The reaction was concentrated, then taken up in dichloromethane. The solids were removed via filtration. The filtrate was concentrated, then purified by flash chromatography (25-75% EA:Heptane), yielding 11.4 g of ethyl 8-oxo-7-(2-trimethylsilylethoxymethyl)-1,7-naphthyridine-5-carboxylate as a white semi-solid. $^1$H NMR (400 MHz, DMSO) δ 9.20-9.07 (dd, J=8.5, 1.5 Hz, 1H), 8.95-8.85 (dd, J=4.3, 1.5 Hz, 1H), 8.52-8.45 (s, 1H), 7.90-7.80 (dd, J=8.5, 4.3 Hz, 1H), 5.56-5.46 (s, 2H), 4.46-4.28 (q, J=7.1 Hz, 2H), 3.72-3.62 (m, 2H), 1.42-1.33 (t, J=7.1 Hz, 3H), 0.98-0.90 (m, 2H), 0.01--0.03 (s, 9H). LCMS M/Z (M+H)=349.

Step 3: Preparation of ethyl 1-oxido-8-oxo-7-(2-trimethylsilylethoxymethyl)-1,7-naphthyridin-1-ium-5-carboxylate 13-3

To a round bottom flask was added ethyl 8-oxo-7-(2-trimethylsilylethoxymethyl)-1,7-naphthyridine-5-carboxylate (5.84 g, 16.8 mmol) followed by dichloromethane (150 mL) and hydrogen peroxide-urea adduct (3.0 equiv., 50.3 mmol, 4.88 g). The mixture was stirred at room temperature for 5 minutes. Trifluoroacetic anhydride (4 equiv., 67.0 mmol, 9.42 mL) was then added dropwise at room temperature, then stirred for 30 minutes. The reaction was then washed with sat. sodium thiosulfate, and the aqueous further extracted 2× with DCM. Combined organics were dried over mag sulfate, filtered, and concentrated. Crude was purified by flash column, (2-5% methanol: dichloromethane), yielding 3.77 g of ethyl 1-oxido-8-oxo-7-(2-trimethylsilylethoxymethyl)-1,7-naphthyridin-1-ium-5-carboxylate as a brown foam. $^1$H NMR (400 MHz, DMSO) δ 8.54-8.50 (d, J=8.6 Hz, 1H), 8.48-8.45 (s, 1H), 8.40-8.33 (d, J=6.3 Hz, 1H), 7.72-7.62 (dd, J=8.5, 6.5 Hz, 1H), 5.45-5.37 (s, 2H), 4.40-4.28 (q, J=7.1 Hz, 2H), 3.70-3.63 (t, J=7.5 Hz, 2H), 1.41-1.30 (t, J=7.1 Hz, 3H), 0.96-0.88 (t, J=8.0 Hz, 2H), 0.04--0.02 (s, 9H). LCMS M/Z (M+H)=365.

Step 4: Preparation of ethyl 2-chloro-8-oxo-7-(2-trimethylsilylethoxymethyl)-1,7-naphthyridine-5-carboxylate 13-4

To a round bottom flask was added ethyl 1-oxido-8-oxo-7-(2-trimethylsilylethoxymethyl)-1,7-naphthyridin-1-ium-5-carboxylate (3.77 g, 10.3 mmol, 3770 mg) followed by dichloromethane (100 mL). Oxalyl chloride (1.3 equiv., 13.4 mmol, 1.30 mL) was then added dropwise. The reaction was stirred at room temperature for 30 minutes. The reaction was washed with water. The aqueous was back-extracted 2× with DCM, then the combined organics were dried over magnesium sulfate, filtered, and concentrated, yielding 3.60 g of ethyl 2-chloro-8-oxo-7-(2-trimethylsilylethoxymethyl)-1,7-naphthyridine-5-carboxylate as a white semi-solid. $^1$H NMR (400 MHz, DMSO) δ 9.20-9.14 (d, J=8.8 Hz, 1H), 8.56-8.50 (s, 1H), 7.99-7.92 (d, J=8.8 Hz, 1H), 5.56-5.48 (s, 2H), 4.42-4.34 (q, J=7.1 Hz, 2H), 3.72-3.64 (m, 2H), 1.42-1.35 (t, J=7.1 Hz, 3H), 0.97-0.90 (t, J=8.0 Hz, 2H), 0.04--0.01 (s, 11H). LCMS M/Z (M+H)=383.

Step 5: Preparation of 2-(3-fluorophenyl)-8-oxo-7-(2-trimethylsilylethoxymethyl)-1,7-naphthyridine-5-carboxylate 13-5

To a round bottom flask was added ethyl 2-chloro-8-oxo-7-(2-trimethylsilylethoxymethyl)-1,7-naphthyridine-5-carboxylate (4.78 g, 12.5 mmol), (3-fluorophenyl)boronic acid (1.5 equiv., 18.7 mmol, 2.62 g), Bis(di-tert-butyl(4-dimethylaminophenyl)phosphine)dichloropalladium(II) (0.05 equiv., 0.62 mmol, 442 mg), potassium phosphate tribasic (2M in water, 3 equiv., 27.5 mmol, 18.7 mL), and 35 mL of dioxane. The mixture was stirred at 100° C. for 2 h. The reaction was then cooled to room temperature, and the organic phase extracted. The aqueous was further extracted 2× with ethyl acetate. Combined organics were dried over sodium sulfate, filtered, and concentrated. Crude was purified by flash chromatography (50-100% ethyl acetate: heptanes) yielding 4.55 g of 2-(3-fluorophenyl)-8-oxo-7-(2-trimethylsilylethoxymethyl)-1,7-naphthyridine-5-carboxylate. $^1$H NMR (400 MHz, DMSO) δ 9.27-9.13 (d, J=8.8 Hz, 1H), 8.56-8.44 (t, J=4.4 Hz, 2H), 8.19-7.99 (m, 2H), 7.70-7.57 (m, 1H), 7.43-7.32 (m, 1H), 4.46-4.29 (q, J=7.1 Hz, 2H), 3.76-3.62 (t, J=8.0 Hz, 2H), 1.45-1.32 (t, J=7.1 Hz, 3H), 0.99-0.86 (t, J=8.0 Hz, 2H), 0.06--0.04 (s, 9H). LCMS M/Z (M+H)=443.

Step 6: Preparation of ethyl 2-(3-fluorophenyl)-8-oxo-7H-1,7-naphthyridine-5-carboxylate 13-6

To a 40 mL screw-cap vial was added ethyl 2-(3-fluorophenyl)-8-oxo-7-(2-trimethylsilylethoxymethyl)-1,7-naphthyridine-5-carboxylate (2.300 g, 5.197 mmol) followed by TBAF, (1.0 mol/L in THF, 5 equiv., 26 mmol, 26 mL). The reaction was capped and shaken at room temperature for 2 h. The reaction was diluted with 30 mL water. The resulting precipitate was collected by filtration, washed with water, and then dried overnight under high vac. Product from 71605-015 was added to the precip, yielding 1.7 g of ethyl 2-(3-fluorophenyl)-8-oxo-7H-1,7-naphthyridine-5-carboxylate, 85% pure. The product was too insoluble to purify, and was carried directly on to the chlorination step. $^1$H NMR (400 MHz, DMSO) δ 9.25-9.21 (d, J=8.9 Hz, 1H), 8.48-8.43 (d, J=8.9 Hz, 1H), 8.20-8.17 (s, 1H), 8.15-8.11 (d, J=7.8 Hz, 1H), 8.11-8.05 (d, J=10.5 Hz, 1H), 7.67-7.59 (m, 1H), 7.40-7.33 (t, J=8.5 Hz, 1H), 4.38-4.30 (q, J=7.1 Hz, 2H), 1.40-1.34 (t, J=7.2 Hz, 3H). LCMS M/Z (M+H)=313.

Step 7: Preparation of ethyl 8-chloro-2-(3-fluorophenyl)-1,7-naphthyridine-5-carboxylate 13-7

To an 40 mL screw-cap vial was added ethyl 2-(3-fluorophenyl)-8-oxo-7H-1,7-naphthyridine-5-carboxylate (1.705 g, 5.459 mmol) followed by phosphorus(V) trichloride oxide (6 mL, 63.73 mmol).

The reaction was capped and shaken at 100° C. for 3 h. The reaction was carefully quenched in iced sat. sodium bicarbonate, then extracted 3× with DCM. Combined organics were dried over sodium sulfate, filtered, and concentrated. Crude was triturated with iPrOH at room temperature yielding 1.23 g of ethyl 8-chloro-2-(3-fluorophenyl)-1,7-naphthyridine-5-carboxylate. LCMS M/Z (M+H)=331.

Step 8: Preparation of ethyl 2-(3-fluorophenyl)-8-oxo-7H-1,7-naphthyridine-5-carboxylate 13-8

Isopropanol was saturated with bubbling NH$_3$ gas for 20 minutes, then 15 mL was added to ethyl 8-chloro-2-(3-fluorophenyl)-1,7-naphthyridine-5-carboxylate (1230 mg, 3.719 mmol). The reaction was capped and stirred under microwave irradiation for 80 min at 140° C. The reaction was concentrated, then partitioned with dichloromethane: water. Organic was extracted, and aqueous was further extracted 3× with DCM. Combined organics were dried over sodium sulfate, filtered, and concentrated. Crude was purified by flash column (25-100% ethyl acetate: heptanes), yielding 860 mg of clean desired ethyl 2-(3-fluorophenyl)-8-oxo-7H-1,7-naphthyridine-5-carboxylate. $^1$H NMR (400 MHz, DMSO) δ 9.29-9.23 (d, J=9.0 Hz, 1H), 8.69-8.64 (s, 1H), 8.52-8.39 (m, 2H), 8.31-8.14 (m, 2H), 8.14-7.96 (bs, 1H), 7.64-7.52 (m, 1H), 7.38-7.28 (m, 1H), 4.40-4.28 (q, J=7.1 Hz, 2H), 1.40-1.33 (t, J=7.1 Hz, 3H). LCMS M/Z (M+H)=312.

Step 9: Preparation of 8-amino-2-(3-fluorophenyl)-1,7-naphthyridine-5-carboxylic acid 13-9

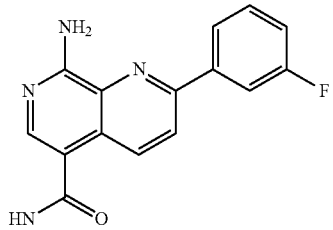

13-9

To ethyl 8-amino-2-(3-fluorophenyl)-1,7-naphthyridine-5-carboxylate (860 mg, 2.76 mmol) was added 2.5 mL methanol, 5.5 mL THF, and sodium hydroxide (1 mol/L in H2O, 1 equiv., 2.76 mmol, 2.763 mL). The reaction was capped and shaken at 50° C. for 2 h. The organics were concentrated, and the aqueous was then acidified to pH 3 with 1 N HCl. Resultant precipitate was collected via filtration, and then dried under high vacuum to afford 784 mg of 8-amino-2-(3-fluorophenyl)-1,7-naphthyridine-5-carboxylic acid as a white solid. 1H NMR (400 MHz, DMSO) δ 9.38-9.31 (d, J=9.0 Hz, 1H), 8.67-8.60 (s, 1H), 8.52-8.40 (m, 2H), 8.39-8.29 (bs, 1H), 8.27-8.22 (d, J=7.8 Hz, 1H), 8.18-8.04 (s, 1H), 7.65-7.51 (m, 1H), 7.39-7.28 (t, J=8.4 Hz, 1H). LCMS M/Z (M+H)=284.

Step 10: Preparation of 8-amino-N-cyclopropyl-2-(3-fluorophenyl)-1,7-naphthyridine-5-carboxamide 13

To an 8 mL screw-cap vial was added 8-amino-2-(3-fluorophenyl)-1,7-naphthyridine-5-carboxylic acid (230 mg, 0.81 mmol), followed by dimethylformamide (3 mL), HATU (1.5 equiv., 1.218 mmol, 467.7 mg), triethylamine (4 equiv., 3.25 mmol, 0.46 mL), and cyclopropanamine (2 equiv., 1.6 mmol, 92.70 mg). The reaction was capped and shaken at room temperature for 3 h. The reaction was diluted with 5 mL ethyl acetate, and 3 mL water. The resulting precipitate was collected by filtration, and washed with ethyl acetate, yielding 150 of 8-amino-N-cyclopropyl-2-(3-fluorophenyl)-1,7-naphthyridine-5-carboxamide. $^1$H NMR (400 MHz, DMSO) δ 9.00-8.92 (d, J=9.0 Hz, 1H), 8.42-8.36 (d, J=9.1 Hz, 2H), 8.36-8.32 (d, J=3.9 Hz, 1H), 8.25-8.21 (d, J=7.7 Hz, 1H), 8.19-8.16 (s, 1H), 7.71-7.53 (m, 3H), 7.36-7.29 (t, J=8.4 Hz, 1H), 2.92-2.83 (m, 1H), 0.74-0.67 (m, 2H), 0.61-0.56 (m, 2H). LCMS M/Z (M+H)=323.

Examples 14a and 14b 8-amino-2-(3-fluorophenyl)-N-(trans-3-hydroxycyclobutyl)-1,7-naphthyridine-5-carboxamide

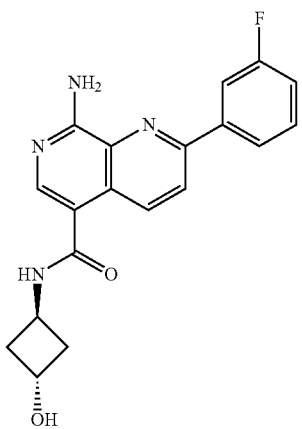

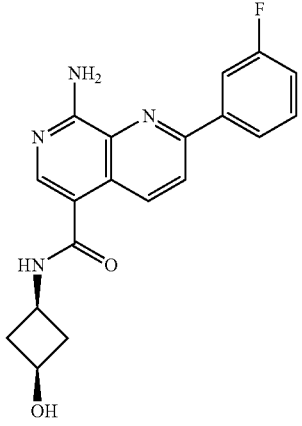

To an 8 mL screw-cap vial was added 8-amino-2-(3-fluorophenyl)-1,7-naphthyridine-5-carboxylic acid (50 mg, 0.18 mmol), followed by dimethylformamide (0.5 mL), HATU (1.2 equiv., 0.21 mmol, 81.34 mg), triethylamine (4 equiv. 0.71 mmol, 72 mg; 0.099 mL), and 3-aminocyclobutanol hydrochloride (2 equiv., 0.35 mmol, 44 mg). The reaction was capped and shaken at room temperature for 3 h. The reaction was diluted with 3 mL dichloromethane, and 1 mL water. A precipitate formed, and was collected via filtration, yielding 25 mg of product. The filtrate was then partitioned, and the aqueous extracted 3× with dichloromethane. Combined organics were combined with the precipitate and concentrated. Crude was purified by chiral SCF chromatography, yielding 5 mg of the cis, and 5 mg of the trans isomers. Cis (example 2A): $^1$H NMR (400 MHz, DMSO) δ 8.95-8.90 (d, J=9.0 Hz, 1H), 8.50-8.46 (d, J=7.3 Hz, 1H), 8.42-8.36 (m, 2H), 8.25-8.21 (m, 2H), 7.73-7.53 (m, 3H), 7.35-7.29 (dd, J=9.7, 7.3 Hz, 1H), 5.09-5.05 (d, J=5.6 Hz, 1H), 3.98-3.80 (m, 2H), 2.64-2.54 (m, 2H), 1.97-1.84 (m, 2H). LCMS M/Z (M+H)=353. Trans (Example 2B): $^1$H NMR (400 MHz, DMSO) δ 8.94-8.89 (d, J=9.0 Hz, 1H), 8.56-8.51 (d, J=6.9 Hz, 1H), 8.42-8.36 (m, 2H), 8.25-8.20 (m, 2H), 7.71-7.53 (m, 3H), 7.36-7.29 (t, J=8.5 Hz, 1H), 5.02-4.98 (d, J=5.4 Hz, 1H), 4.50-4.39 (m, 1H), 4.39-4.29 (m, 1H), 2.34-2.23 (m, 2H), 2.23-2.13 (m, 2H). LCMS M/Z (M+H)=353.

Example 15

8-amino-N-(1-(1,1-dioxidothiomorpholine-4-carbonyl)azetidin-3-yl)-2-(3-fluorophenyl)-1,7-naphthyridine-5-carboxamide

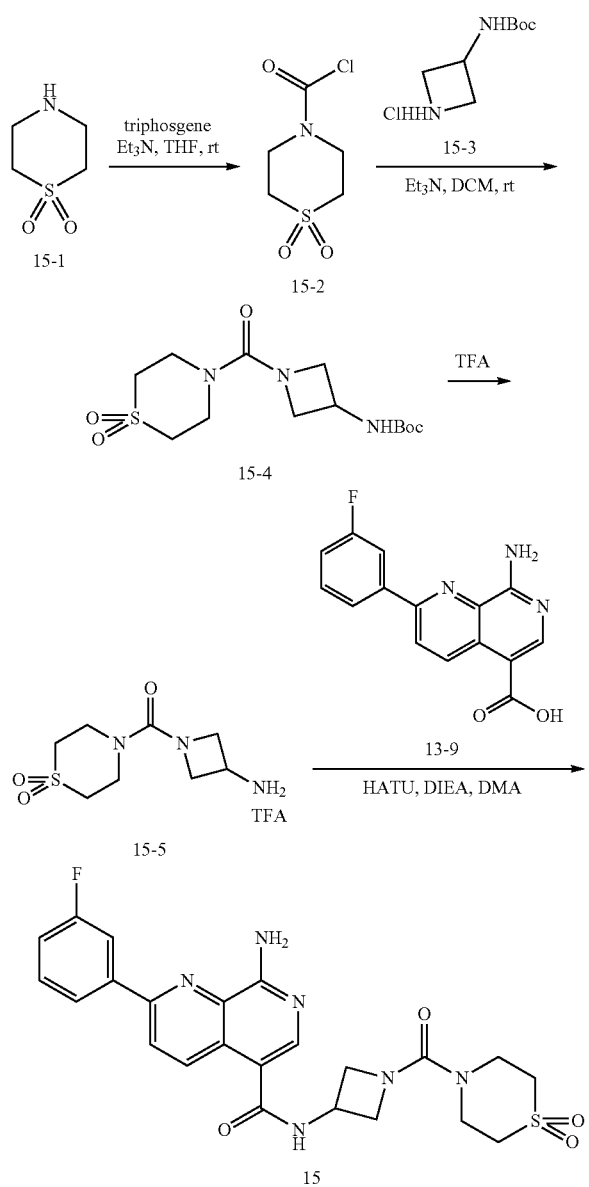

Step 1: Preparation of Compound 15-2

To a solution of compound 15-1 (541 mg, 4.0 mmol) and Et₃N (1.21 g, 12.0 mmol) in THF (20.0 mL), a solution of triphosgene (1.42 g, 4.8 mmol) in THF (5.0 mL) was added dropwise. After the mixture was stirred at rt o.n., water was added and it was extracted with EtOAc. The organic layer was combined and washed with brine, dried over Na₂SO₄, filtered. Solvent was removed and the residue was purified by column chromatography to give a white solid (760 mg, yield: 96%).

¹H NMR (400 MHz, DMSO-d6) δ4.23 (m, 2H), 4.08-4.14 (m, 2H), 3.39-3.48 (m, 1H), 3.13-3.15 (m, 4H), 1.18-1.27 (m, 2H).

Step 2: Preparation of Compound 15-4

To a mixture of compound 15-2 (210 mg, 1.06 mmol) and Et₃N (310 mg, 3.0 mmol) in DCM (5 mL), compound 15-3 (200 mg, 0.958 mmol) was added at r.t. After the mixture was stirred at r.t. o.n., water was added to the mixture and it was extracted with DCM. Organic layer was combined and washed with brine. After solvent was removed, the residue was purified by column chromatography to give a white solid (280 mg, 84%).

Step 3: Preparation of Compound 15-5

To a solution of compound 15-4 (85 mg, 0.256 mmol) in DCM (2 mL) was added TFA (0.5 mL) at rt. After the mixture was stirred o.n., it was concentrated to give the crude product, which was used directly (86 mg, 98%).

Step 4: Preparation of Compound 15

To a solution of 13-9 (70 mg, 0.25 mmol) in DMF (3 mL) was added DIPEA (64 mg, 0.494 mmol), HATU (113 mg, 0.297 mmol), and 2 (86 mg, 0.247 mmol). After the mixture was stirred at r.t. o.n., it was poured into water (5 mL) and extracted with DCM (10 mL×3), concentrated and purified by prep-HPLC to give the product (40 mg, 33%). LCMS: (0-60AB, 2 min) 1.011 min, 499.2 [M+1] ¹H NMR (400 MHz, DMSO-d6) δ 9.40 (d, J=9.2 Hz, 1H), 8.89 (d, J=6.4 Hz, 1H), 8.37 (m, 1H), 8.30 (s, 1H), 8.21 (m, 1H), 7.51-7.88 (br, 2H), 7.54 (m, 1H), 7.30 (m, 1H), 4.63 (m, 1H), 4.22 (m, 2H), 3.96 (m, 2H), 3.63 (m, 4H), 3.09 (m, 2H).

Example 16

8-amino-2-(3-fluorophenyl)-N-(1-(2-hydroxypropanoyl)azetidin-3-yl)-1,7-naphthyridine-5-carboxamide

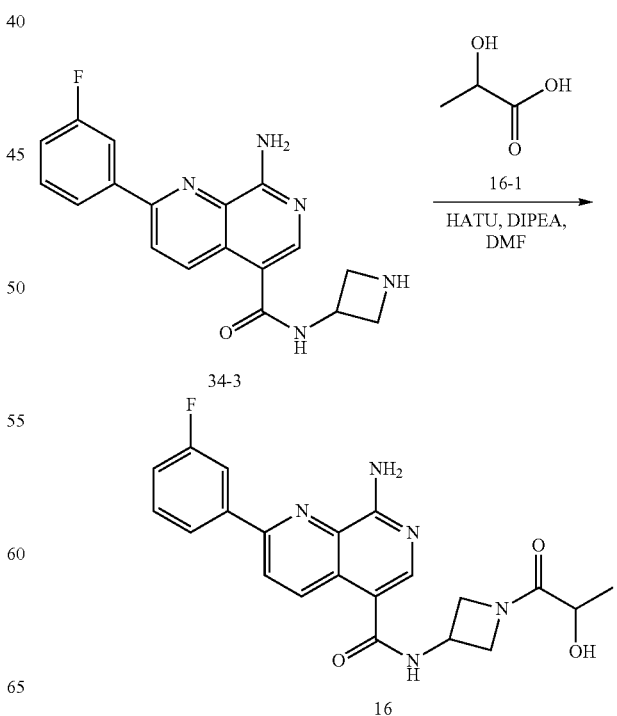

To a solution of compound 34-3 (100 mg, 0.222 mmol), which can be prepared as described below in step 2 of example 34, in DMF (2 mL) was added DIPEA (116 mg, 0.887 mmol) and compound 16-1 (48 mg, 0.532 mmol), and HATU (202 mg, 0.54 mmol). After the mixture was stirred o.n., it was concentrated and purified by prep-TLC to give the desired product 16 (20 mg, 22%). LCMS: (10-80AB, 2 min) 0.904 min, 409.9 [M+1]; $^1$H NMR (400 MHz, DMSO-$d_6$) δ 8.87 (d, J=9.2 Hz, 1H), 8.70 (d, J=9.2 Hz, 1H), 8.21 (s, 1H), 8.06 (m, 2H), 7.54 (m, 1H), 7.23 (m, 1H), 4.73 (m, 2H), 4.38 (m, 2H), 4.28 (m, 1H), 4.05 (m, 2H), 1.33 (d, J=6.80 Hz, 1H).

Example 17

8-amino-2-(3-fluorophenyl)-N-(1-(oxetane-3-carbonyl)azetidin-3-yl)-1,7-naphthyridine-5-carboxamide

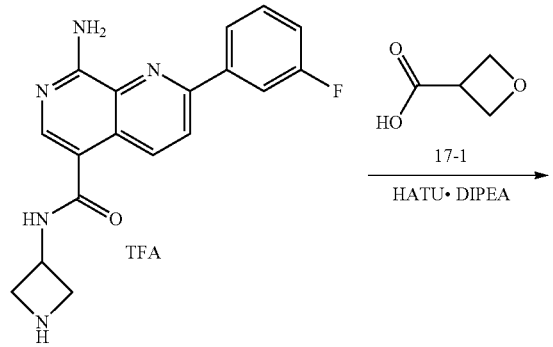

A solution of 34-3 (74 mg, 0.164 mmol), 17-2 (22.6 mg, 0.22 mmol), HATU (126 mg, 0.33 mmol) and DIPEA (115 mg, 0.89 mmol) in DMF (10 mL) was stirred at r.t. for 3 h. It was concentrated and the crude product was purified by prep-HPLC to give the pure product as yellow solid (9.0 mg, yield 10%). LCMS: (0-60AB, 2 min), 0.973 min, Ms=422.1 (M+1); $^1$H NMR (400 MHz, MeOH-d4) δ 8.88 (d, J=8.8 Hz, 1H), 8.28-8.26 (m, 1H), 8.20 (s, 1H), 8.09 (d, J=8.8 Hz, 1H), 8.12-8.06 (m, 1H), 7.57-7.52 (m, 1H), 7.24-7.21 (m, 1H), 4.80-4.78 (m, 5H), 4.50-4.46 (m, 1H), 4.41-4.36 (m, 1H), 4.12-3.92 (m, 3H).

Example 18

8-amino-2-(3-fluorophenyl)-N-(1-(methylsulfonyl)azetidin-3-yl)-1,7-naphthyridine-5-carboxamide

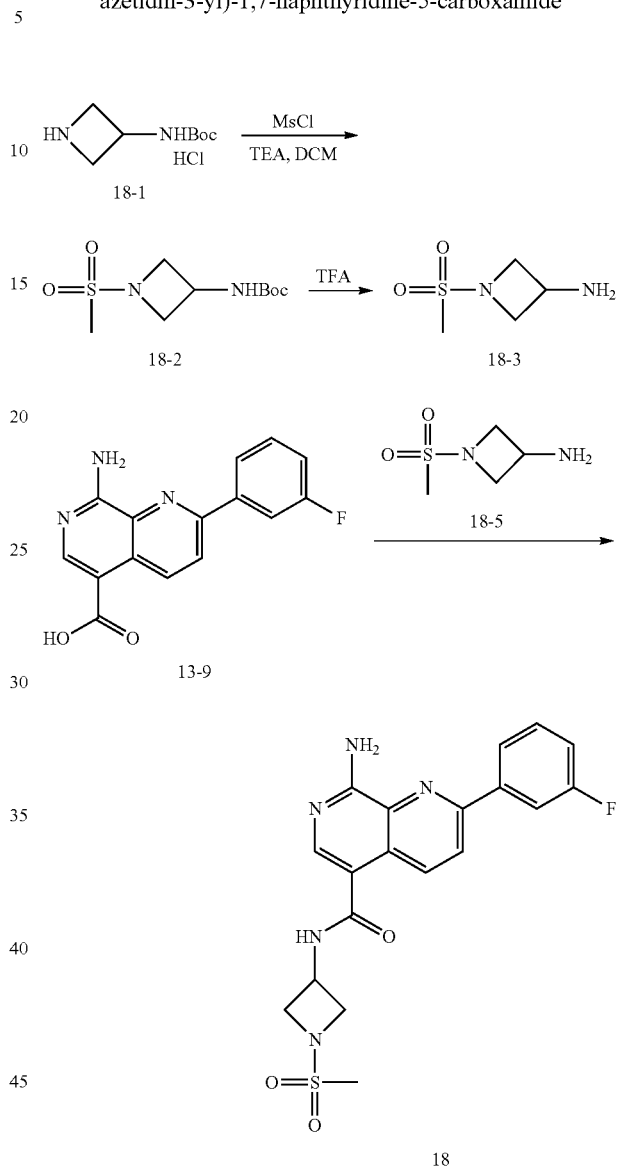

Step 1: Preparation of Compound 18-2

To a solution of compound 1 (500 mg, 2.4 mmol) in DCM (2 mL) and TEA (900 mg, 8.72 mmol) was added MsCl (500 mg, 4.36 mmol) dropwise at 0° C. After the mixture was stirred at r.t. for 2 h, it was concentrated to give the crude product, which was used directly (550 mg, 92%).

Step 2: Preparation of Compound 18-3

To a solution of compound 18-2 (550 mg, 2.2 mmol) in DCM (10 mL) was added TFA (4 mL) at rt. The formed mixture was stirred overnight. The mixture was concentrated to give the crude product, which was used for the next directly (300 mg, 91%).

Step 3: Preparation of Compound 18

To a solution of 13-9 (100 mg, 0.35 mmol) in THF (3 mL) was added DIPEA (230 mg, 1.77 mmol), HATU (200 mg, 0.53 mmol), and compound 3 (106 mg, 0.7 mmol). After the mixture was stirred at r.t. o.n., it was poured into water (5 mL) and extracted with DCM (10 mL×3), concentrated and purified by prep-HPLC to give the product (3 mg, 3%). LCMS: (0-60AB, 2 min), 1.029 min, Ms=416.1 (M+1); $^1$H NMR (400 MHz, DMSO-d6) δ 9.56-9.52 (m, 1H), 8.42 (m, 3H), 8.23 (m, 1H), 7.58-7.53 (m, 1H), 7.33-7.29 (m, 1H), 7.21 (m, 1H), 4.42-4.33 (m, 3H), 4.17-4.13 (m, 2H), 2.91 (s, 3H).

Example 19

8-amino-N-(1-(N,N-dimethylsulfamoyl)azetidin-3-yl)-2-(3-fluorophenyl)-1,7-naphthyridine-5-carboxamide

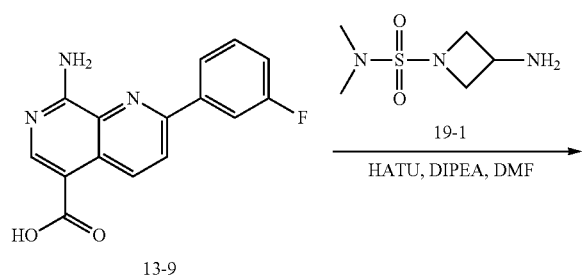

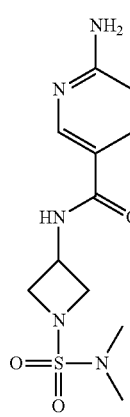

19

To a solution of compound 13-9 (150 mg, 0.53 mmol) in DMF (5 mL), DIPEA (684 mg, 5.3 mmol) and compound 19-1 (284 mg, 1.59 mmol), was added HATU (300 mg, 0.8 mmol). After the mixture was stirred o.n. at rt, it was concentrated and purified by prep-HPLC to give the product (7.8 mg, 3.5%). LCMS: (5-95AB, 2 min), 0.771 min, Ms=444.9 [M+1]; $^1$H NMR (400 MHz, DMSO-d$_6$) δ 9.05-8.93 (m, 2H), 8.42-8.38 (m, 2H), 8.32 (s, 1H), 8.23 (d, J=8.0 Hz, 1H), 7.85-7.73 (m, 2H), 7.60-7.54 (m, 1H), 7.35-7.30 (m, 1H), 4.74-4.67 (m, 1H), 4.06-4.02 (t, J=8.0 Hz, 2H), 3.95-3.92 (t, J=7.4 Hz, 2H), 2.76 (s, 6H).

Example 20

8-amino-2-(3-fluorophenyl)-N-(1-(2-morpholinoacetyl)azetidin-3-yl)-1,7-naphthyridine-5-carboxamide

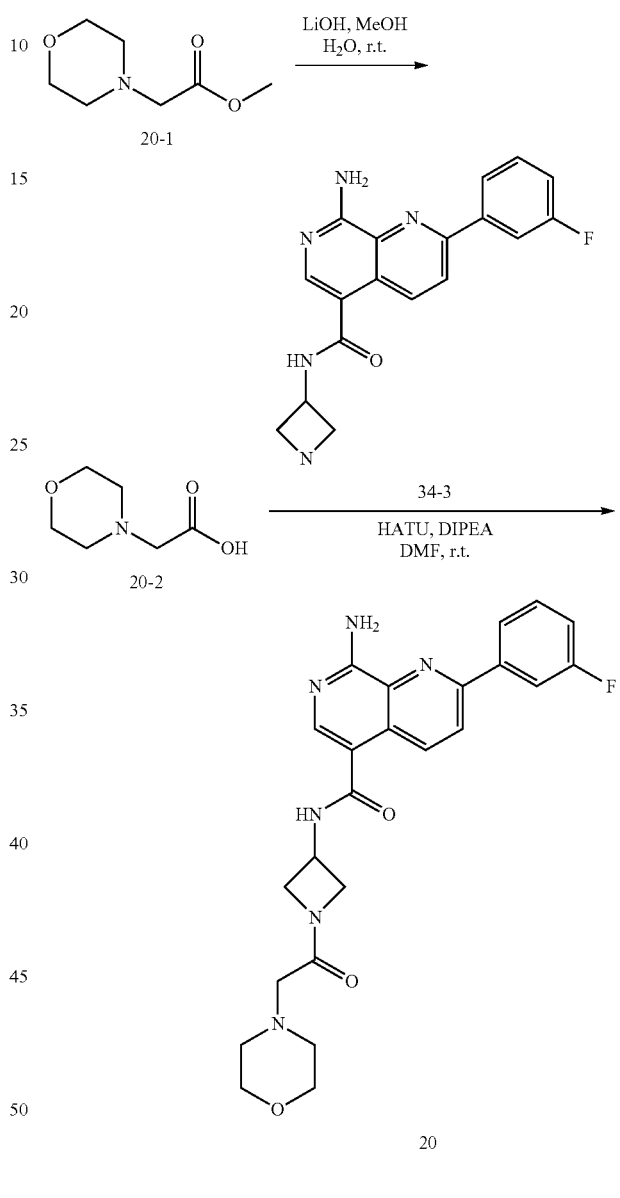

Step 1: Preparation of Compound 20-2

To a solution of 20-1 (50 mg, 0.3 mmol) in MeOH (8 mL) was added LiOH (14.4 mg, 0.6 mmol), H$_2$O (1 mL). After the mixture was stirred at r.t. for 3 h, it was concentrated to give the crude product, which was used for the next directly. (32 mg, yield 100%).

Step 2: Preparation of Compound 20

To a solution of 20-2 (32 mg, 0.22 mmol) in DMF (5 mL), was added DIPEA (142 mg, 1.1 mmol), HATU (125 mg, 0.33 mmol), and 34-3 (75 mg, 0.22 mmol). After the mixture was stirred at r.t for 3 h, it was extracted with EtOAc (30 mL×2), concentrated and purified by prep-HPLC to give the product (10 mg, 10%). LCMS: (0-60AB, 2 min), 1.040 min, MS=465.0 (M+1); $^1$H NMR (400 MHz, DMSO-d6) δ8.95-8.90 (m, 2H), 8.40-8.36 (m, 2H), 8.29 (s, 1H), 8.21 (d, J=8.4 Hz, 1H), 7.77-7.70 (m, 2H), 7.57-7.51 (m, 1H), 7.32-7.27 (m, 1H), 4.71-4.64 (m, 1H), 4.57-4.48 (m, 1H), 4.17-4.13 (m, 2H), 3.89-3.85 (m, 1H), 3.56-3.53 (t, 4H), 2.95 (d, J=3.6 Hz, 2H), 2.39-2.37 (t, 4H).

Example 21

8-amino-2-(3-fluorophenyl)-N-(1-sulfamoylazetidin-3-yl)-1,7-naphthyridine-5-carboxamide

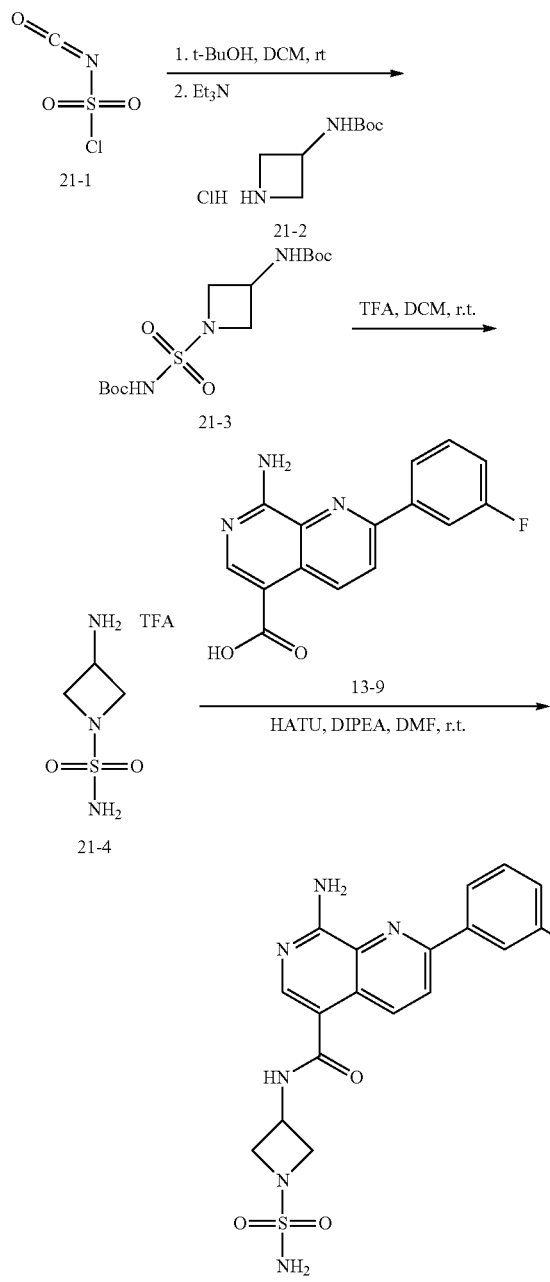

Step 1: Preparation of Compound 21-3

Compound 21-1 (425 mg, 3.0 mmol) was added dropwise to the solution of t-BuOH (222 mg, 3.0 mmol) in DCM (5.0 mL) at 0° C. After the mixture was stirred at 0° C. for 30 mins, a solution of compound 21-2 (689 mg, 3.3 mmol) and Et$_3$N (708 mg, 7.0 mmol) in DCM (3.0 mL) was added dropwise at 0° C. The mixture was warmed to rt and stirred at r.t. for another hour. Water was added to the mixture and it was extracted with DCM, the organic layer was combined and washed with brine, dried over Na$_2$SO$_4$, filtered.

Solvent was evaporated to give an off-white solid (480 mg, 46%). $^1$H NMR (400 MHz, CDCl$_3$) δ4.41 (br, 1H), 4.28 (m, 2H), 3.99 (m, 2H), 1.49 (s, 9H), 1.42 (s, 9H).

Step 2: Preparation of Compound 21-4

To a solution of compound 21-3 (400 mg, 1.14 mmol) in DCM (20 mL) was added TFA (2 mL) at rt. The formed mixture was stirred overnight. The mixture was concentrated to give the crude product, which was used for the next directly (410 mg, 90%).

Step 3: Preparation of Compound 21

To a solution of 21-4 (150 mg, 0.53 mmol) in DMF (3 mL), DIPEA (341.85 mg, 2.65 mmol), HATU (302.1 mg, 0.795 mmol), was added 13-9 (240 mg, 0.904 mmol). After the mixture was stirred at r.t. for 2 h, it was poured into water (5 mL) and extracted with DCM (10 mL×3), concentrated and purified by prep-HPLC to give the product (43 mg, 20%).

LCMS: (0-60AB, 2 min), 1.104 min, 416.8 [M+1]. $^1$H NMR (400 MHz, DMSO-d6) δ 8.94-8.89 (m, 2H), 8.40-8.35 (m, 2H), 8.29 (s, 1H), 8.21-8.19 (t, 1H), 7.81-7.70 (m, 2H), 7.57-7.51 (m, 1H), 7.32-7.27 (m, 1H), 6.93 (s, 2H), 4.57-4.52 (m, 1H), 3.97-3.93 (m, 2H), 3.76-3.72 (m, 2H), 3.63 (m, 4H), 3.09 (m, 2H).

Example 22

8-amino-2-(3-fluorophenyl)-N-(1-(2,2,2-trifluoroethyl)azetidin-3-yl)-1,7-naphthyridine-5-carboxamide

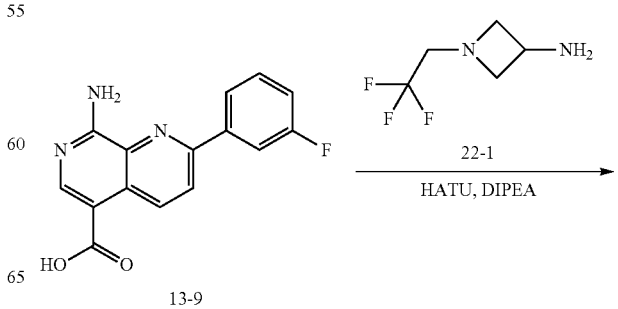

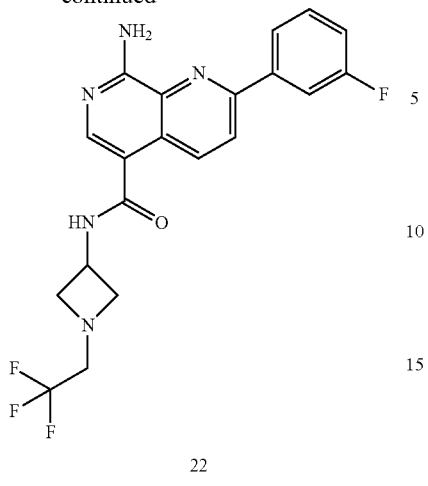

22

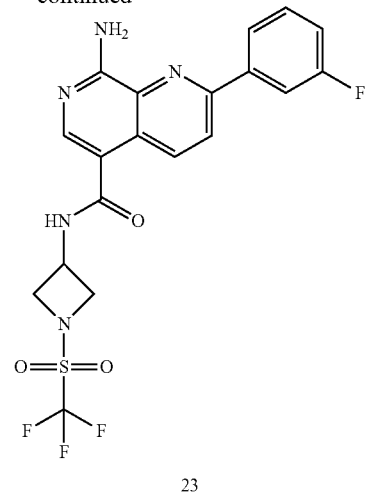

23

A mixture of 13-9 (200 mg, 0.71 mmol), 2 (217 mg, 1.42 mmol), HATU (537 mg, 1.41 mmol) and DIPEA (456 mg, 3.53 mmol) in DMF (10 mL) was stirred at r.t. for 3 h. It was concentrated and the crude product was purified by prep-HPLC to give the pure product as yellow solid (11.1 mg, 4%). LCMS: (0-60, AB, 2 min), 0.980 min, MS=420.0 (M+1); $^1$H NMR (400 MHz, DMSO-d6) δ: 8.90 (d, J=8.8 Hz, 1H), 8.75-8.73 (m, 1H), 8.39-8.35 (m, 2H), 8.26 (s, 1H), 8.19 (d, J=8.8 Hz, 1H), 7.72 (br, 2H), 7.57-7.51 (m, 1H), 7.32-7.27 (m, 1H), 4.56-4.50 (m, 1H), 3.74-3.70 (m, 2H), 3.27-3.17 (m, 1H).

Example 23

8-amino-2-(3-fluorophenyl)-N-(1-((trifluoromethyl)sulfonyl)azetidin-3-yl)-1,7-naphthyridine-5-Carboxamide

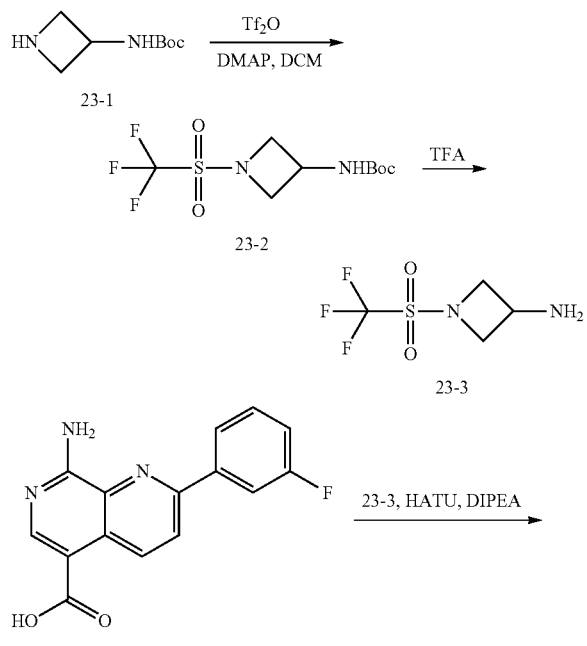

Step 1: Preparation of Compound 23-2

To a solution of compound 23-1 (500 mg, 2.4 mmol) in DCM (10 mL) was added DMAP (426 mg, 3.49 mmol) and Tf$_2$O (985 mg, 3.49 mmol) dropwise at 0° C. After the mixture was stirred at rt for 2 h, it was concentrated to give the crude product, which was used for the next directly (560 mg, 77%).

Step 2: Preparation of Compound 23-3

To a solution of compound 23-2 (560 mg, 1.8 mmol) in DCM (10 mL) was added TFA (4 mL) at rt. After the mixture was stirred o.n., it was concentrated to give the crude product, which was used for the next directly (310 mg, 82%).

Step 3: Preparation of Compound 23

To a solution of 4 (100 mg, 0.35 mmol) in THF (3 mL) was added DIPEA (230 mg, 1.77 mmol), HATU (200 mg, 0.53 mmol), and compound 3 (145 mg, 0.7 mmol). After the mixture was stirred at r.t. o.n., it was poured into water (5 mL), extracted with DCM (10 mL×3), concentrated and purified by prep-HPLC to give the product (33 mg, 20%). LCMS: (0-60AB, 2 min), 1.317 min, MS=469.9 (M+1). $^1$H NMR (400 MHz, DMSO-d6) δ 9.12 (m, 1H), 8.94 (m, 1H), 8.45-8.40 (m, 2H), 8.24 (m, 1H), 8.21 (m, 1H), 7.59-7.53 (m, 1H), 7.34-7.29 (m, 1H), 4.93-4.84 (m, 1H), 4.50 (m, 2H), 4.34 (m, 2H).

Example 24

(R)-8-amino-2-(3-fluorophenyl)-N-(1-(2-hydroxypropanoyl)azetidin-3-yl)-1,7-naphthyridine-5-carboxamide

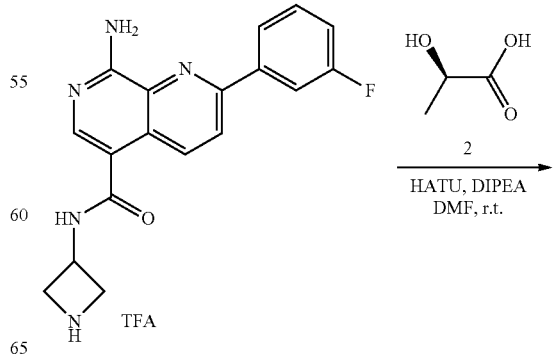

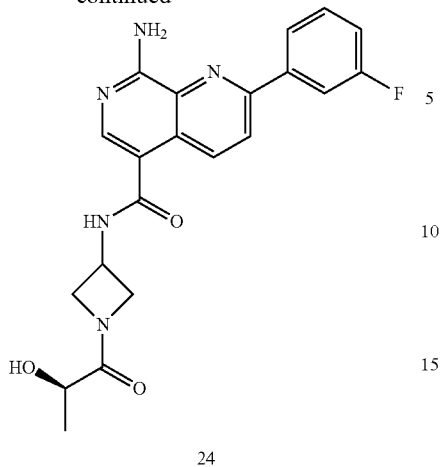

24

To a solution of compound 34-3 (100 mg, 0.222 mmol) in DMF (2 mL) was added DIPEA (116 mg, 0.887 mmol) and compound 2 (48 mg, 0.54 mmol), followed by HATU (202 mg, 0.54 mmol). After the mixture was stirred o.n. at rt, it was concentrated and purified by prep-TLC to give the desired product (12 mg, 13%). LCMS: (5-95AB, 2 min), 0.729 min, MS=410.0 (M+1); $^1$H NMR (400 MHz, Methanol-d4) δ 8.87 (d, J=9.2 Hz, 1H), 8.27 (d, J=8.0 Hz, 1H), 8.21 (s, 1H), 8.12-8.07 (m, 2H), 7.56-7.51 (m, 1H), 7.23-7.18 (m, 1H), 4.75-4.71 (m, 1H), 4.43-4.36 (m, 2H), 4.34-4.25 (m, 1H), 4.08-4.01 (m, 1H), 3.34-3.24 (m, 1H), 1.33 (d, J=6.8 Hz, 3H).

Example 25
(S)-8-amino-2-(3-fluorophenyl)-N-(1-(2-hydroxypropanoyl)azetidin-3-yl)-1,7-naphthyridine-5-carboxamide

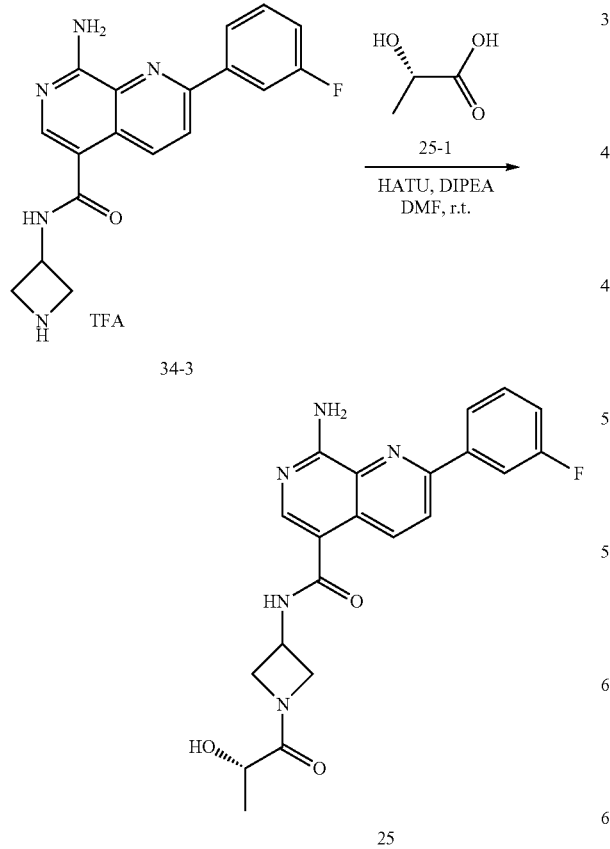

To a solution of compound 34-3 (100 mg, 0.222 mmol) in DMF (2 mL) was added DIPEA (116 mg, 0.887 mmol) and compound 25-1 (48 mg, 0.54 mmol), followed by HATU (202 mg, 0.54 mmol). After the mixture was stirred o.n. at rt, it was concentrated and purified by preparative TLC to give the desired product 25 (12 mg, 13%). LCMS: (5-95AB, 2 min), 0.729 min, MS=410.0 (M+1) $^1$H NMR (400 MHz, DMSO-d4) δ 8.97 (d, J=8.8 Hz, 2H), 8.43-8.39 (m, 2H), 8.33 (s, 1H), 8.24 (d, J=8 Hz, 1H), 7.85-7.71 (m, 2H), 7.60-7.55 (m, 1H), 7.35-7.30 (m, 1H), 5.11-5.06 (m, 1H), 4.75-4.53 (m, 2H), 4.26-4.09 (m, 3H), 3.94-3.87 (m, 1H), 1.19 (d, J=6.8 Hz, 3H).

Example 26
N-(1-acetylazetidin-3-yl)-8-amino-2-(3-fluorophenyl)-1,7-naphthyridine-5-carboxamide

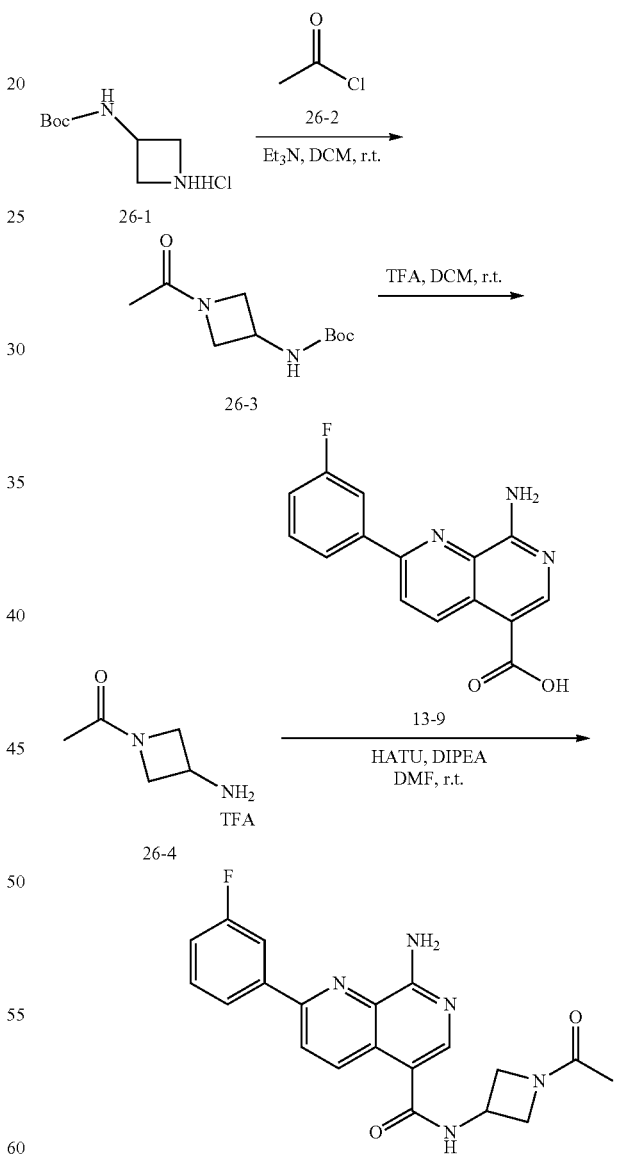

Step 1: Preparation of Compound 26-2

To a solution of compound 1 (2 g, 9.6 mmol) in DCM (30 mL) and Et$_3$N (3.53 g, 28.8 mmol) at rt was added 2 dropwise at r.t. After the mixture was stirred at r.t. for 1 h, it was concentrated to give the crude product, which was used directly (2 g, 97%).

Step 2: Preparation of Compound 26-4

To a solution of compound 3 (2 g, 9.3 mmol) in DCM (20 mL) was added TFA (4 mL) at rt. After the mixture was stirred o.n., it was concentrated to give the crude product, which was used directly (2.2 g, 98%).

Step 3: Preparation of Compound 26

To a solution of 5 (400 mg, 1.41 mmol) in DMF (5 mL) was added DIPEA (1.83 g, 14.12 mmol), HATU (805.41 mg, 2.12 mmol), and 4 (966.62 mg, 4324 mmol). After the mixture was stirred at r.t. for 2 h, it was poured into water (8 mL) and extracted with DCM (10 mL×3), concentrated and purified by prep-HPLC to give the product (217.2 mg, 40%).

LCMS: (5-95AB, 2 min), 0.738 min, MS=379.9 (M+1)
$^1$H NMR (400 MHz, DMSO-d6) δ 8.95-8.89 (m, 2H), 8.40-8.36 (m, 2H), 8.29 (s, 1H), 8.20 (d, J=8.0 Hz, 1H), 7.85-7.64 (m, 2H), 7.57-7.51 (m, 1H), 7.31-7.27 (m, 1H), 7.30 (m, 1H), 4.69-4.61 (m, 1H), 4.42-4.40 (t, 1H), 4.13-4.04 (m, 2H), 3.85-3.81 (m, 1H), 1.74 (s, 3H).

Example 27

8-amino-2-(3-fluorophenyl)-N-(1-(morpholine-4-carbonyl)azetidin-3-yl)-1,7-naphthyridine-5-carboxamide

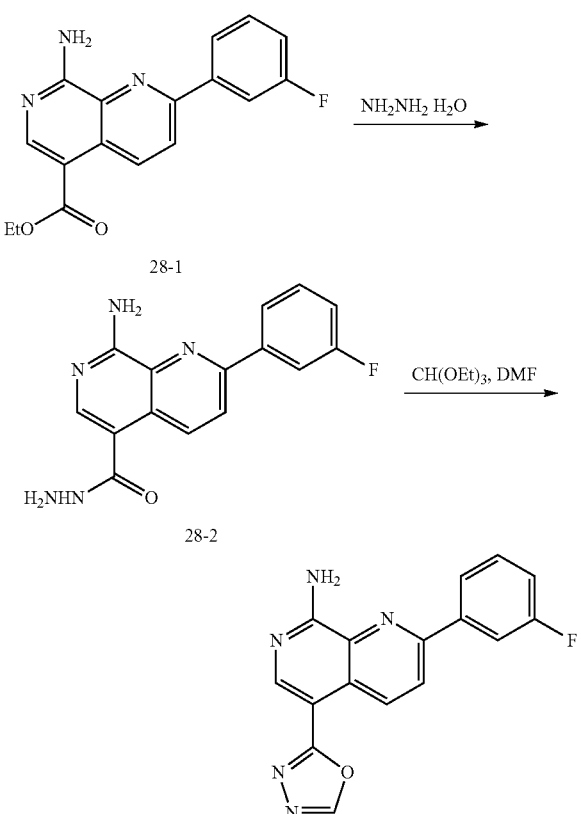

To a solution of 34-3 (100 mg, 0.221 mmol) in DCM (5 mL) was added Et$_3$N (90 mg, 0.887 mmol) and 2 (33 mg, 0.221 mmol). After the mixture was stirred o.n. at r.t., it was concentrated and purified by prep-HPLC to give the product (17 mg, 17%). LCMS: (10-80AB, 2 min), 0.938 min, MS=450.9 (M+1). $^1$H NMR (400 MHz, DMSO-d$_6$) δ 8.94 (d, J=8.8 Hz, 1H), 8.88 (d, J=6.4 Hz, 1H), 8.40-8.36 (m, 2H), 8.29 (s, 1H), 8.20 (d, J=4 Hz, 1H), 7.81-7.72 (m, 2H), 7.57-7.52 (m, 1H), 7.32-7.27 (m, 1H), 4.66-4.61 (m, 1H), 4.20-4.16 (t, J=8 Hz, 2H), 3.93-3.89 (m, 2H), 3.52-3.50 (t, J=4.8 Hz, 4H), 3.21-3.19 (t, J=4.8 Hz, 4H).

Example 28

2-(3-fluorophenyl)-5-(1,3,4-oxadiazol-2-yl)-1,7-naphthyridin-8-amine

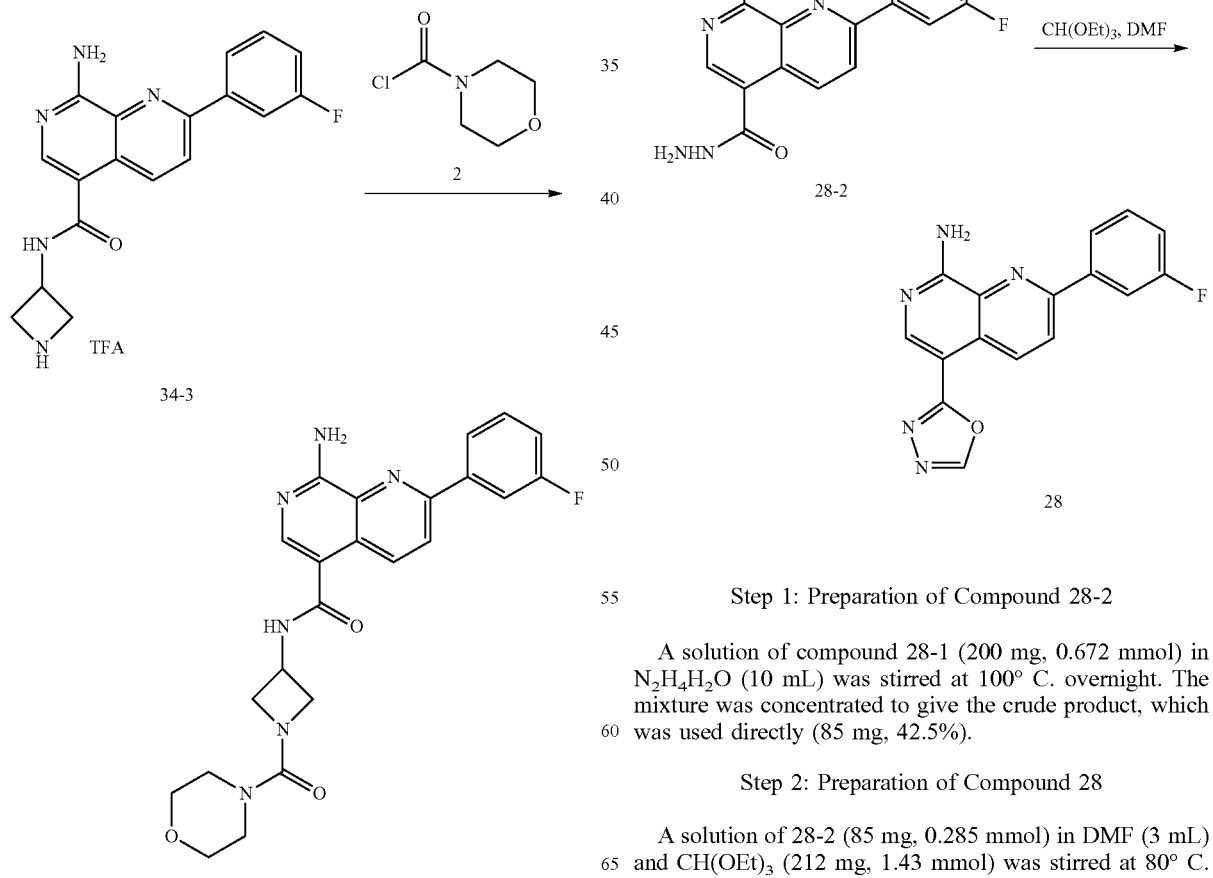

Step 1: Preparation of Compound 28-2

A solution of compound 28-1 (200 mg, 0.672 mmol) in N$_2$H$_4$H$_2$O (10 mL) was stirred at 100° C. overnight. The mixture was concentrated to give the crude product, which was used directly (85 mg, 42.5%).

Step 2: Preparation of Compound 28

A solution of 28-2 (85 mg, 0.285 mmol) in DMF (3 mL) and CH(OEt)$_3$ (212 mg, 1.43 mmol) was stirred at 80° C. overnight. The mixture was poured into water (5 mL) and extracted with EtOAc (10 mL×3), concentrated and purified by prep-HPLC to give the product (12.8 mg, 15%). LCMS: (5-95AB, 2 min), 0.792 min, MS=307.8 (M+1). $^1$H NMR (400 MHz, DMSO-d6) δ9.37 (d, J=8.8 Hz, 1H), 9.31 (s, 1H), 8.59-8.57 (t, J=6.6 Hz, 2H), 8.47 (d, J=10 Hz, 1H), 8.29 (d, J=8 Hz, 1H), 8.09-7.99 (m, 2H), 7.63-7.57 (m, 1H), 7.37-7.33 (m, 1H).

Example 29

N-(1-(8-amino-2-(3-fluorophenyl)-1,7-naphthyridine-5-carbonyl)azetidin-3-yl)propionamide

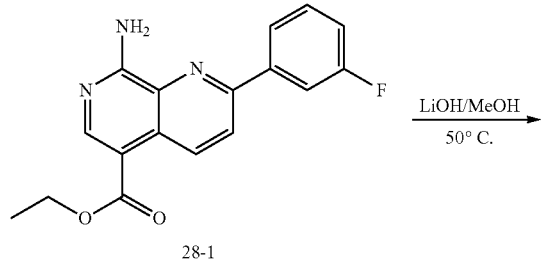

28-1

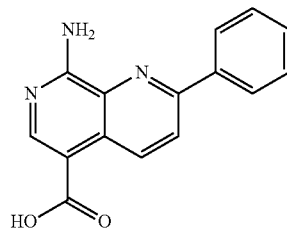

13-9

Step 1: Preparation of Compound 13-9

Ethyl 8-amino-2-(3-fluorophenyl)-1,7-naphthyridine-5-carboxylate 28-1 (500 mg) in methanol (20 mL) was treated with 8 mL of lithium hydroxide monohydrate (1 mol/L) in H$_2$O (1 mol/L). The reaction mixture was heated to 50° C. and stirred for 2 hours or longer until the reaction was completed. The crude was acidified with 10% citric acid, solid was crashed out, filtered off and washed with EtOAc to obtain pure product 13-9. LC/MS (ESI+): m/z 284.3 (M+H).

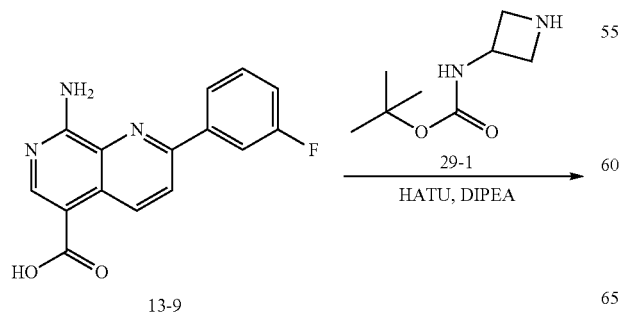

13-9

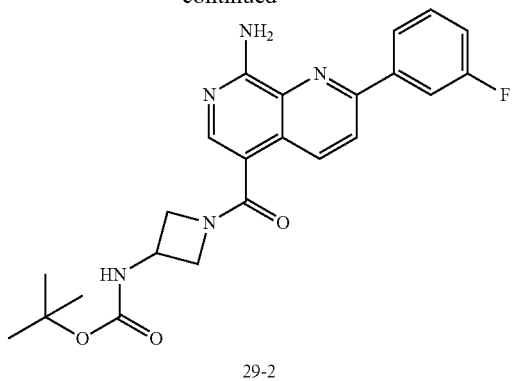

29-2

Step 2: Preparation of Compound 29-2

8-amino-2-(3-fluorophenyl)-1,7-naphthyridine-5-carboxylic acid 13-9 (0.45 g, 1.59 mmol) in DMF (3 mL) was treated with DIPEA (1.39 mL, 7.94 mmol) followed by HATU (1.25 g, 3.18 mmol). The mixture was stirred at room temperature for 15 minutes, tert-butyl N-(azetidin-3-yl) carbamate 29-1 (0.55 g, 3.18 mmol) was then added, continue stirred at room temperature for 1 hours until the reaction went to completion. Diluted with EtOAc, Solid was crashed out and the filtered solid is the pure product 29-2 (63%). LC/MS (ESI+): m/z 438.4 (M+H).

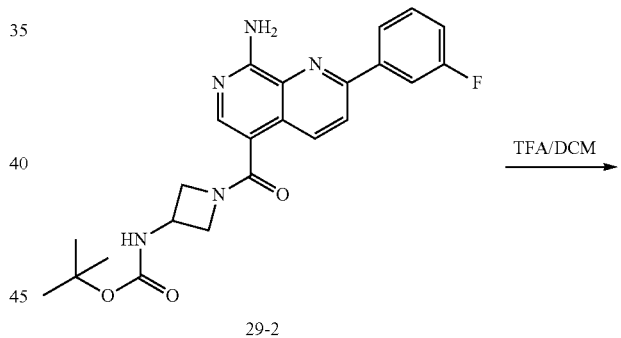

29-2

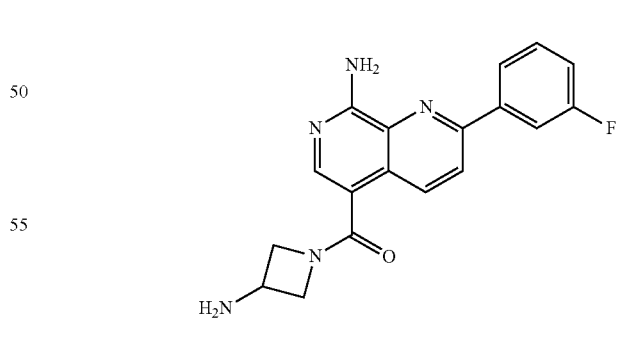

29-3

Step 3: Preparation of Compound 29-3 tert-butyl 3-[[8-amino-2-(3-fluorophenyl)-1,7-naphthyridine-5-carbonyl]amino]azetidine-1-carboxylate 29-2 (1 g, 2.29 mmol) was treated with 1 to 1 TFA and DCM, Stirred at room temperature for 1 hour until the reaction is completed. The reaction was concentrated to dryness, and Diluted with EtOAc, washed with Sat. NaHCO$_3$. The aqueous layer was extracted with EtOAc 3 times. The combined organic layers were dried and concentrated to give pale yellow solid 29-3 (69%). LC/MS (ESI+): m/z 338.4 (M+H). $^1$H NMR (400 MHz, DMSO) δ 8.78-8.60 (d, J=8.9 Hz, 1H), 8.47-8.32 (m, 2H), 8.30-8.15 (d, J=7.9 Hz, 1H), 8.11-7.95 (s, 1H), 7.79-7.61 (s, 2H), 7.63-7.52 (q, J=7.5 Hz, 1H), 7.41-7.24 (td, J=8.4, 2.4 Hz, 1H), 4.38-4.13 (t, J=8.3 Hz, 2H), 3.84-3.58 (m, 3H), 2.40-2.09 (m, 2H).

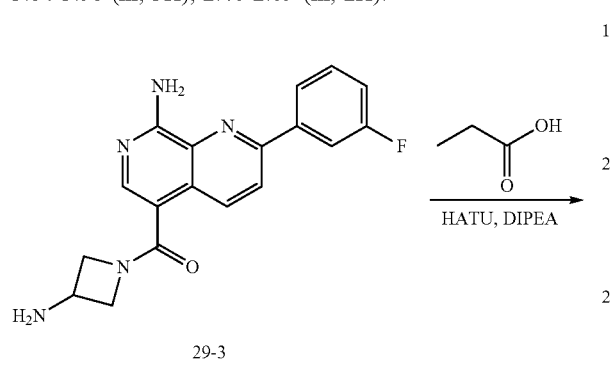

29-3

Step 4: Preparation of Compound 29

Propionic acid (0.017 mL, 0.22 mmol) in THF (1 mL) was treated with DIPEA (0.129 mL, 0.74 mmol) and HATU (87 mg, 0.22 mmol). The mixture was stirred at room temperature for 10 minutes. 3-amino azetidin-1-yl)-[8-amino-2-(3-fluorophenyl)-1,7-naphthyridin-5-yl]methanone 29-3 (50 mg, 0.15 mmol) was added, continue stirred at room temperature for 1 hour until the reaction went to completion. The reaction mixture was diluted with EtOAc, washed with 10% citric acid followed by sat. brine. The organic layer was dried and concentrated. The crude was purified with reverse phase HPLC to give pure product 29. LC/MS (ESI+): m/z 394.4 (M+H). $^1$H NMR (400 MHz, DMSO) δ 8.73-8.58 (q, J=8.9 Hz, 1H), 8.58-8.48 (m, 1H), 8.48-8.41 (d, J=6.4 Hz, 1H), 8.37-8.22 (d, J=7.9 Hz, 1H), 8.01-7.79 (s, 1H), 7.73-7.53 (q, J=7.5 Hz, 1H), 7.48-7.32 (td, J=8.3, 2.5 Hz, 1H), 4.56-4.44 (dt, J=12.1, 6.3 Hz, 1H), 4.44-4.24 (s, 2H), 4.04-3.88 (dd, J=9.6, 5.1 Hz, 2H), 2.22-1.99 (q, J=7.5 Hz, 2H), 1.10-0.87 (t, J=7.6 Hz, 3H).

Example 30

N-(1-(8-amino-2-(3-fluorophenyl)-1,7-naphthyridine-5-carbonyl)azetidin-3-yl)cyclopropanecarboxamide

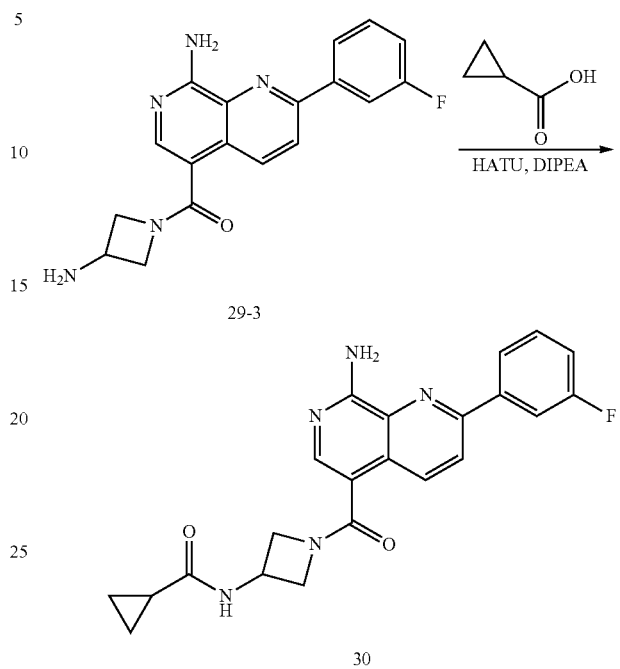

8-amino-N-(azetidin-3-yl)-2-(3-fluorophenyl)-1,7-naphthyridine-5-carboxamide 29-3 (100 mg, 0.30 mmol) in DMF (1 mL) was treated with DIPEA (0.259 mL, 1.48 mmol) and HATU (174 mg, 0.44 mmol). The reaction was stirred at room temperature for 15 minutes, and cyclopropanecarboxylic acid (25 mg, 0.30 mmol) was added, continue stirred at room temperature for 1 hour the reaction went to completion. The reaction mixture was diluted with EtOAc, washed with 10% citric acid followed by sat. brine. The organic layer was dried and concentrated. The crude was purified with reverse phase HPLC to give pure product 30. LC/MS (ESI+): m/z 406.4 (M+H). $^1$H NMR (400 MHz, DMSO) δ 8.83-8.75 (d, J=7.0 Hz, 1H), 8.75-8.66 (d, J=8.9 Hz, 1H), 8.52-8.35 (d, J=9.5 Hz, 2H), 8.29-8.17 (d, J=7.9 Hz, 1H), 8.13-8.01 (s, 1H), 7.96-7.65 (s, 2H), 7.66-7.50 (q, J=7.4 Hz, 1H), 7.44-7.21 (td, J=8.5, 2.4 Hz, 1H), 4.66-4.47 (q, J=6.7 Hz, 1H), 4.47-4.21 (s, 2H), 4.07-3.83 (s, 2H), 2.16-1.96 (s, 1H), 1.66-1.40 (p, J=6.5 Hz, 1H), 0.82-0.50 (d, J=6.1 Hz, 4H).

Example 31

N-(1-(8-amino-2-(3-fluorophenyl)-1,7-naphthyridine-5-carbonyl)azetidin-3-yl)-N-(cyclopropanecarbonyl)cyclopropanecarboxamide

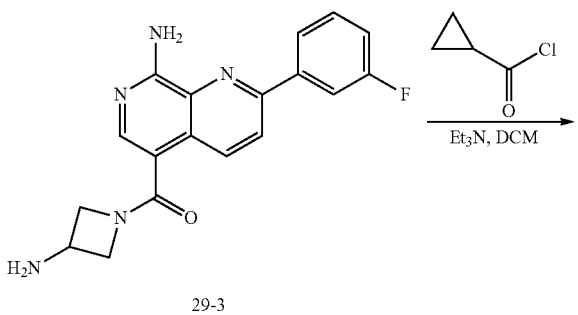

29-3

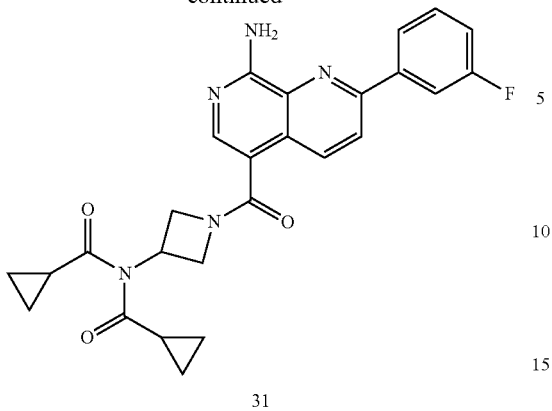

31

A mixture of 8-amino-N-(azetidin-3-yl)-2-(3-fluorophenyl)-1,7-naphthyridine-5-carboxamide 29-3 (100 mg, 0.30 mmol), cyclopropanecarbonyl chloride (0.03 mL, 0.33 mmol) and triethylamine (0.08 mL, 0.59 mmol) in DCM (1 mL) was stirred at room temperature for 2 hours and then concentrated in vacuo. The crude material was purified with reverse phase HPLC to give pure product as white solid 31.

LC/MS (ESI+): m/z 474.5 (M+H). $^1$H NMR (400 MHz, DMSO) δ 10.82-10.61 (s, 1H), 8.83-8.68 (m, 2H), 8.66-8.49 (d, J=9.0 Hz, 1H), 8.46-8.33 (m, 2H), 8.33-8.18 (d, J=7.9 Hz, 1H), 7.72-7.56 (q, J=7.5 Hz, 1H), 7.52-7.33 (td, J=8.4, 2.4 Hz, 1H), 4.64-4.49 (m, 1H), 4.49-4.27 (q, J=9.8, 9.2 Hz, 2H), 4.09-3.91 (m, 2H), 2.82-2.64 (m, 1H), 1.61-1.35 (p, J=6.4 Hz, 1H), 1.04-0.86 (d, J=6.1 Hz, 4H), 0.79-0.56 (d, J=6.6 Hz, 4H).

Example 32

N-(1-(8-amino-2-(3-fluorophenyl)-1,7-naphthyridine-5-carbonyl)azetidin-3-yl)acetamide

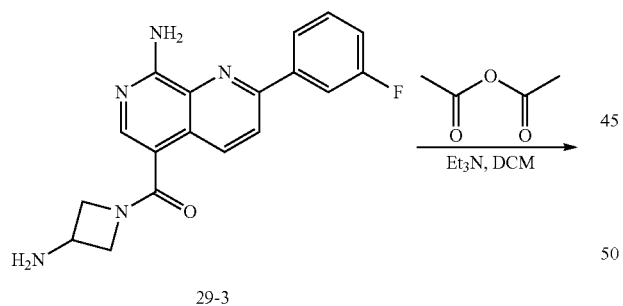

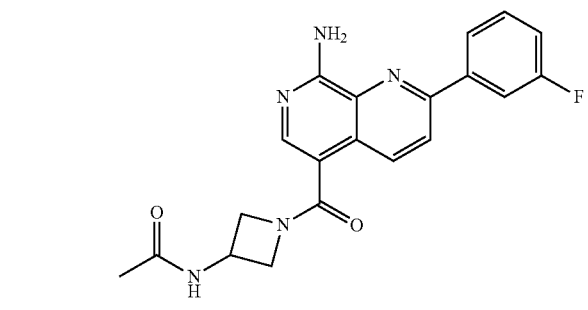

32

(3-aminoazetidin-1-yl)-[8-amino-2-(3-fluorophenyl)-1,7-naphthyridin-5-yl]methanone 29-3 (100 mg, 0.30 mmol) was suspended in DCM (1 mL), and treated with triethylamine (0.125 mL, 0.89 mmol) and acetic anhydride (0.03 mL, 0.33 mmol). The reaction mixture was stirred at room temperature for 15 minutes until the reaction went to completion. The solution was concentrated in vacuo and the crude was purified with reverse HPLC to give pure product 32. LC/MS (ESI+): m/z 380.4 (M+H). $^1$H NMR (400 MHz, DMSO) δ 8.76-8.63 (d, J=8.9 Hz, 1H), 8.63-8.48 (d, J=6.6 Hz, 1H), 8.48-8.35 (d, J=9.2 Hz, 2H), 8.31-8.20 (d, J=7.9 Hz, 1H), 8.10-7.98 (s, 1H), 7.97-7.63 (s, 2H), 7.66-7.50 (dd, J=14.5, 7.6 Hz, 1H), 7.44-7.21 (t, J=8.4 Hz, 1H), 4.54-4.44 (d, J=7.2 Hz, 1H), 4.44-4.23 (s, 2H), 4.03-3.81 (s, 2H), 1.97-1.71 (s, 3H).

Example 33

8-amino-N-cyclobutyl-2-(3-fluorophenyl)-1,7-naphthyridine-5-carboxamide

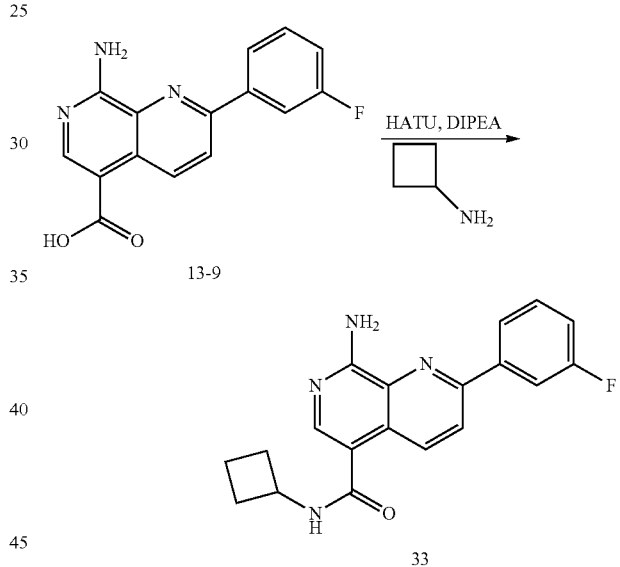

8-amino-2-(3-fluorophenyl)-1,7-naphthyridine-5-carboxylic acid 13-9 (80 mg, 0.28 mmol) in dimethylformamide was treated with DIPEA (0.15 mL, 0.85 mmol) and HATU (0.13 g, 0.34 mmol). The reaction mixture was stirred at room temperature for 10 minutes, and aminocyclobutane (0.42 mmol) was added and continue stirred for 30 minutes. The reaction mixture was diluted with EtOAc, washed with 10% citric acid followed by sat. brine. The organic layer was dried and concentrated. The crude was purified with flash column chromatography (FCC) to give 30 mg pure product 33 (32% yield). LC/MS (ESI+): m/z 337.4 (M+H). $^1$H NMR (400 MHz, DMSO) δ 8.96-8.90 (d, J=8.9 Hz, 1H), 8.60-8.52 (d, J=7.7 Hz, 1H), 8.45-8.35 (t, J=8.7 Hz, 2H), 8.27-8.19 (m, 2H), 7.89-7.62 (s, 3H), 7.62-7.53 (q, J=7.5 Hz, 1H), 7.38-7.26 (td, J=7.6, 7.1, 2.2 Hz, 1H), 4.56-4.32 (q, J=8.2 Hz, 1H), 2.36-2.16 (q, J=9.1, 8.5 Hz, 2H), 2.16-1.95 (m, 2H), 1.79-1.54 (m, 2H).

Example 34

8-amino-2-(3-fluorophenyl)-N-(1-(methylcarbamoyl)azetidin-3-yl)-1,7-naphthyridine-5-carboxamide

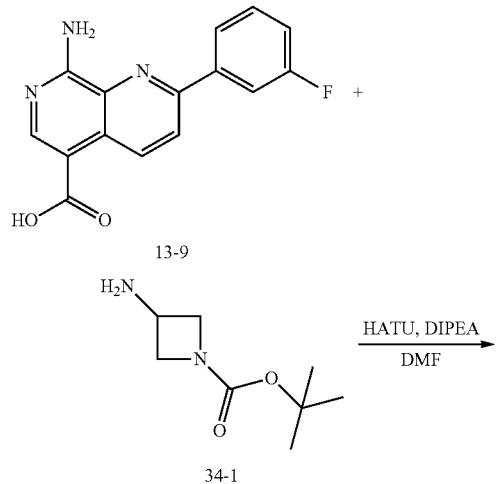

Step 1: Preparation of Compound 34-2

8-amino-2-(3-fluorophenyl)-1,7-naphthyridine-5-carboxylic acid 13-9 (200 mg, 0.71 mmol) in DMF (1 mL) was treated with DIPEA (0.37 mL, 2.1 mmol) followed by HATU (415 mg, 1.1 mmol). After stirred at room temperature for 15 minutes, tert-butyl 3-aminoazetidine-1-carboxylate (0.17 mL, 1.1 mmol) was added, continue stirred at room temperature for 10 minutes. LCMS showed major desired product. EtOAc was added to dilute the reaction. Solid was crashed out. The precipitate is the pure product 34-2. LC/MS (ESI+): m/z 438.4 (M+H).

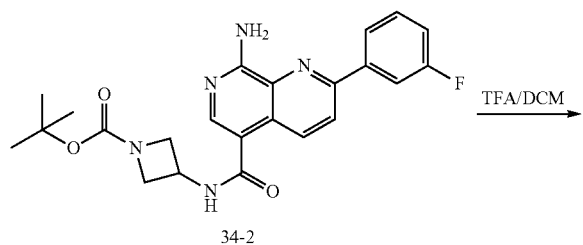

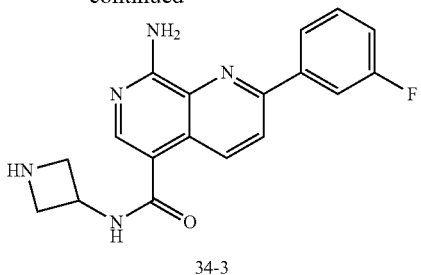

Step 2: Preparation of Compound 34-3 tert-butyl 3-[[8-amino-2-(3-fluorophenyl)-1,7-naphthyridine-5-carbonyl]amino]azetidine-1-carboxylate 34-2 was treated with 1 to 1 trifluoroacetic acid (3 mL) and methylene chloride (3 mL), and stirred at r.t. for 1 hour. The reactive mixture was concentrated to dry and washed by sat. NaHCO₃. Aqueous layer was extracted with EtOAc twice, organic layers were washed with brine, dried and concentrated to give crude product 34-3. LC/MS (ESI+): m/z 338.4 (M+H).

Step 3: Preparation of Compound 34

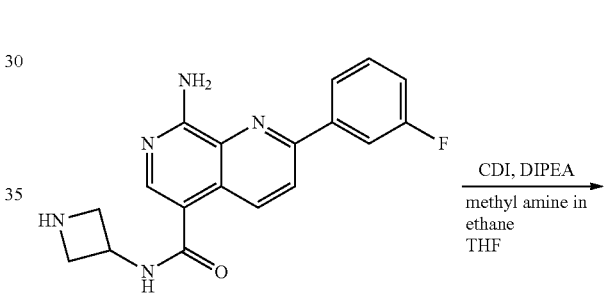

To a solution of 8-amino-N-(azetidin-3-yl)-2-(3-fluorophenyl)-1,7-naphthyridine-5-carboxamide 34-3 in DMF (1 mL), was added DIEA (0.26 mL, 1.48 mmol), n,n'-carbonyldiimidazole (74 mg, 0.44 mmol), and the mixture was stirred at r.t. for 1 hour. 0.16 mL of methylamine (2 mol/L) in THF (2 mol/L) was added, and the mixture was stirred at r.t. overnight. The reaction mixture was concentrated to dry and purified with prep HPLC to afford the product 34. LC/MS (ESI+): m/z 395.4 (M+H). ¹H NMR (400 MHz, DMSO) δ 9.04-8.95 (d, J=9.0 Hz, 1H), 8.95-8.85 (d, J=6.8 Hz, 1H), 8.46-8.37 (m, 2H), 8.37-8.31 (s, 1H), 8.31-8.18 (m, 1H), 7.87-7.64 (s, 2H), 7.63-7.52 (td, J=8.0, 6.1 Hz, 1H), 7.38-7.26 (td, J=8.5, 2.6 Hz, 1H), 4.82-4.61 (m, 1H), 4.53-4.35 (t, J=8.3 Hz, 1H), 4.21-4.12 (t, J=8.9 Hz, 1H), 4.12-4.03 (dd, J=8.7, 5.3 Hz, 1H), 3.94-3.82 (dd, J=9.8, 5.5 Hz, 1H), 2.24-1.97 (q, J=7.5 Hz, 2H), 1.08-0.85 (t, J=7.5 Hz, 3H).

Example 35

8-amino-2-(3-fluorophenyl)-N-(1-propionylazetidin-3-yl)-1,7-naphthyridine-5-carboxamide

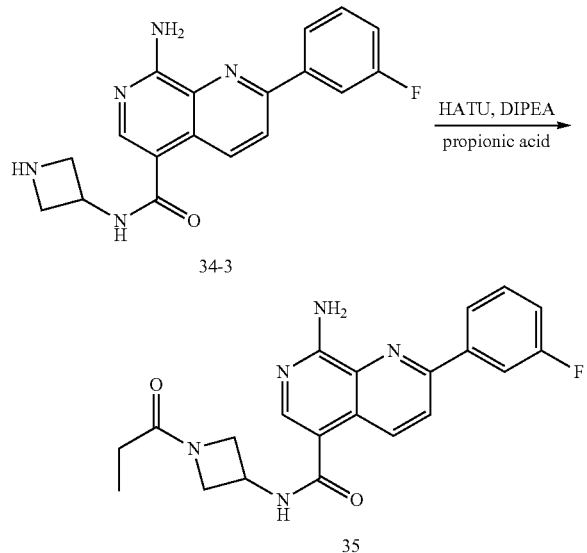

propionic acid (0.014 mL, 0.18 mmol) in DMF (1 mL) was treated with HATU (70 mg, 0.18 mmol) and DIPEA (0.13 mL, 0.74 mmol). The mixture was stirred at room temperature for 15 minutes. 8-amino-N-(azetidin-3-yl)-2-(3-fluorophenyl)-1,7-naphthyridine-5-carboxamide 34-3 (50 mg, 0.15 mmol) was added, continue stirred for 30 minutes until the reaction went to completion. The reaction mixture was diluted with EtOAc, washed with 10% citric acid followed by sat. brine. The organic layer was dried and concentrated. The crude was purified with reverse phase HPLC to give pure product 35. LC/MS (ESI+): m/z 394.4 (M+H). $^1$H NMR (400 MHz, DMSO) δ 9.03-8.85 (m, 2H), 8.47-8.36 (m, 2H), 8.36-8.29 (s, 1H), 8.28-8.18 (d, J=7.8 Hz, 1H), 8.00-7.64 (s, 2H), 7.62-7.51 (q, J=7.4 Hz, 1H), 7.43-7.24 (dd, J=9.5, 7.2 Hz, 1H), 4.79-4.62 (q, J=6.8 Hz, 1H), 4.49-4.35 (t, J=8.3 Hz, 1H), 4.23-4.12 (t, J=8.9 Hz, 1H), 4.12-4.03 (dd, J=8.6, 5.3 Hz, 1H), 3.94-3.79 (dd, J=9.8, 5.4 Hz, 1H), 2.19-1.96 (q, J=7.5 Hz, 2H), 1.07-0.88 (t, J=7.5 Hz, 3H).

Example 36

N-(1-acetylazetidin-3-yl)-8-amino-2-(3-fluorophenyl)-1,7-naphthyridine-5-carboxamide

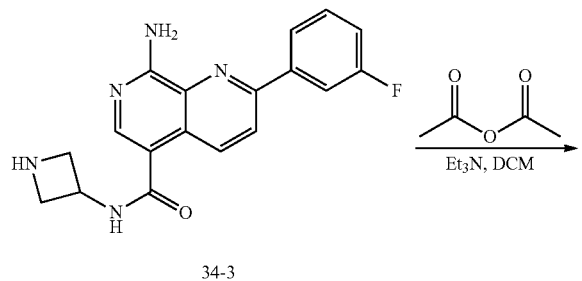

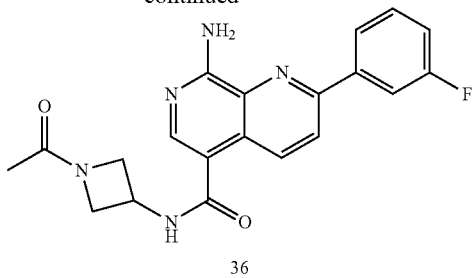

8-amino-N-(azetidin-3-yl)-2-(3-fluorophenyl)-1,7-naphthyridine-5-carboxamide 34-3 (100 mg, 0.30 mmol) was suspended in DCM (1 mL), and treated with triethylamine (0.125 mL, 0.89 mmol) and acetic anhydride (0.03 mL, 0.30 mmol). The reaction mixture was stirred at room temperature for 15 minutes until the reaction went to completion. The solution was concentrated in vacuo and the crude was purified with reverse HPLC to give pure product 36. LC/MS (ESI+): m/z 380.4 (M+H).

Example 37

8-amino-N-(1-(cyclopropanecarbonyl)azetidin-3-yl)-2-(3-fluorophenyl)-1,7-naphthyridine-5-carboxamide

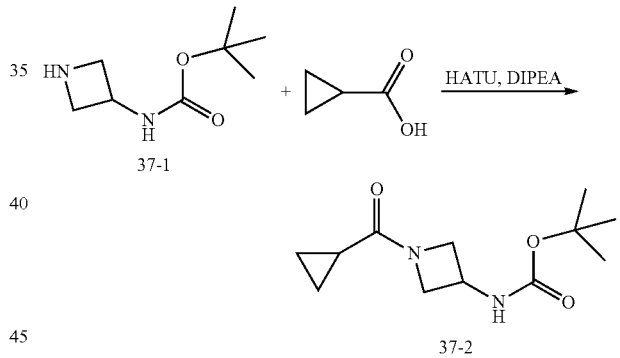

Step 1: Preparation of Compound 37-2

Cyclopropanecarboxylic acid (0.64 mL, 8 mmol) in DMF (1 mL) was treated with HATU (2.4 g, 6.4 mmol) and DIPEA (2.8 mL, 16 mmol). The mixture was stirred at r.t. for 10 minutes, and t-butyl N-(azetidin-3-yl)carbamate 37-1 (0.92 g, 5.3 mmol) was added, and the reaction mixture was stirred overnight. TLC showed the reaction completed (stained by ninhydrin spray solution). The reaction mixture was diluted with EtOAc, washed with 5% citric acid, followed by 10% NaHCO$_3$ and sat. brine. The organic layers were combined and dried, and concentrated to dryness. The crude 37-2 was used in boc removal reaction without further purification. $^1$H NMR (400 MHz, DMSO) δ 4.48-4.37 (t, J=8.2 Hz, 1H), 4.37-4.22 (t, J=6.7 Hz, 1H), 4.09-3.95 (dd, J=8.4, 5.9 Hz, 2H), 3.75-3.57 (dd, J=9.7, 5.6 Hz, 1H), 1.54-1.45 (ddd, J=7.4, 4.8, 2.7 Hz, 1H), 1.44-1.33 (s, 8H), 0.75-0.58 (m, 4H).

Step 2: Preparation of Compound 37-3

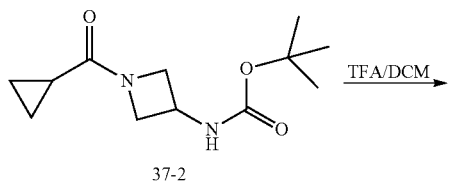

tert-butyl N-[1-(cyclopropanecarbonyl)azetidin-3-yl]carbamate 37-2 (5.1 g, 21 mmol) was treated with trifluoroacetic acid (15 mL, 194 mmol) and DCM (15 mL). The reaction was stirred at room temperature overnight. Concentrated to dryness and purified with 10% MeOH/DCM to give pure product as a white solid (2.7 g, 91%). The product 37-3 was checked with TLC using ninhydrin stain. $^1$H NMR (400 MHz, DMSO) δ 4.58-4.36 (t, J=8.2 Hz, 1H), 4.24-4.13 (dd, J=9.5, 3.7 Hz, 1H), 4.13-3.96 (m, 2H), 3.90-3.71 (dd, J=9.4, 3.3 Hz, 1H), 1.63-1.42 (m, 1H), 0.80-0.56 (m, 4H).

Step 3: Preparation of Compound 37

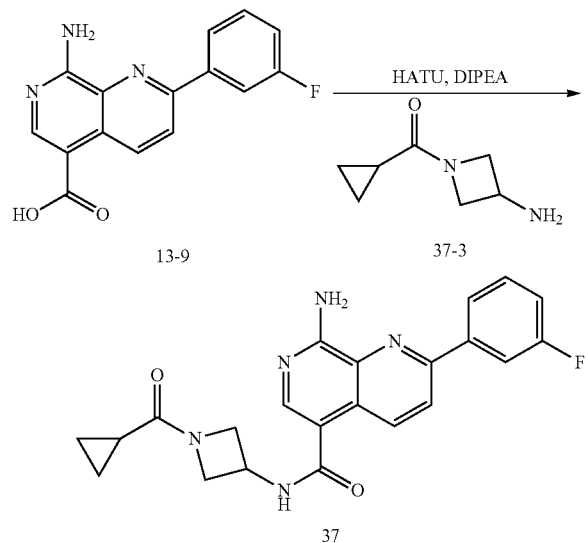

8-amino-2-(3-fluorophenyl)-1,7-naphthyridine-5-carboxylic acid 13-9 (0.8 g, 3 mmol) in DMF (5 mL) was treated with HATU (1 g, 3 mmol) and DIPEA (1.2 mL, 8 mmol). The mixture was stirred at room temperature for 15 minutes, and (3-aminoazetidin-1-yl)-cyclopropyl-methanone 37-3 (1.5 equiv., 4 mmol) was added. The reaction mixture was continue stirred at r.t. for 1 hour until the reaction went to completion. The reaction mixture was diluted with EtOAc, washed with 5% citric acid, followed by 10% NaHCO₃ and sat. brine. The organic layers were combined and dried, and concentrated to dryness. The crude was purified with FCC using 10% MeOH/EtOAc, and followed by trituration with EtOAc to obtain pure product as pale yellow solid 37. LC/MS (ESI+): m/z 406.4 (M+H). $^1$H NMR (400 MHz, DMSO) δ 9.04-8.86 (m, 2H), 7.63-7.50 (m, 1H), 8.47-8.38 (d, J=9.2 Hz, 2H), 8.38-8.30 (s, 1H), 8.30-8.18 (d, J=8.1 Hz, 1H), 7.90-7.48 (m, 3H), 7.39-7.25 (td, J=8.5, 2.6 Hz, 1H), 4.86-4.68 (m, 1H), 4.68-4.48 (t, J=8.2 Hz, 1H), 4.28-4.21 (dd, J=8.6, 5.3 Hz, 1H), 4.21-4.11 (t, J=8.9 Hz, 1H), 3.99-3.78 (dd, J=9.7, 5.5 Hz, 1H), 1.67-1.45 (m, 1H), 0.81-0.61 (dd, J=7.9, 4.7 Hz, 4H).

Example 38

8-amino-2-(3-fluorophenyl)-N-(oxetan-3-yl)-1,7-naphthyridine-5-carboxamide

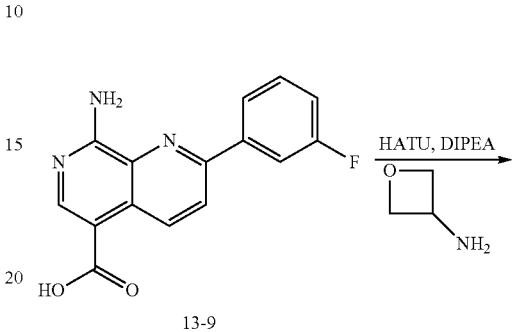

8-amino-2-(3-fluorophenyl)-1,7-naphthyridine-5-carboxylic acid 13-9 (50 mg, 0.18 mmol) in DMF (1 mL) was treated with DPIEA (0.09 mL, 0.53 mmol) and HATU (76 mg, 0.19 mmol). The mixture was stirred at r.t. for 10 minutes, and 3-aminooxetane (14 mg, 0.19 mmol) was add, stirred at r.t. for 15 minutes until the reaction went to completion. The reaction was diluted with EtOAc, and solid was crashed out. The solid was filtered off and washed with methanol and EtOAc to give pure product 38. LC/MS (ESI+): m/z 339.3 (M+H).

$^1$H NMR (400 MHz, DMSO) δ 9.01-8.90 (m, 2H), 8.46-8.37 (m, 2H), 8.37-8.30 (s, 1H), 8.29-8.17 (d, J=8.0 Hz, 1H), 7.89-7.64 (s, 2H), 7.64-7.51 (td, J=8.0, 6.2 Hz, 1H), 7.41-7.24 (td, J=8.5, 2.5 Hz, 1H), 5.12-4.91 (h, J=7.0 Hz, 1H), 4.90-4.70 (t, J=6.9 Hz, 2H), 4.70-4.52 (t, J=6.4 Hz, 2H).

Example 39

8-amino-2-(3-fluorophenyl)-N-(1-(2-methoxyacetyl)azetidin-3-yl)-1,7-naphthyridine-5-carboxamide

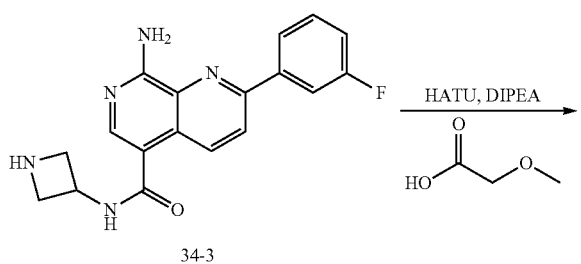

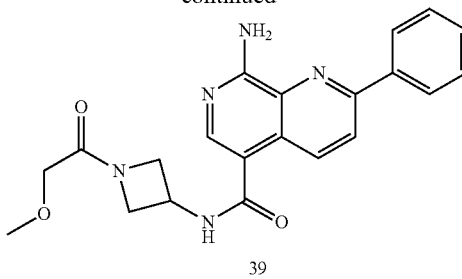

39

2-methoxyacetic acid (32 mg, 0.36 mmol) in DMF (1 mL) was treated with and treated with HATU (139 mg, 0.36 mmol) and DIPEA (0.16 mL, 0.89 mmol) The reaction mixture was stirred at room temperature for 15 minutes, 8-amino-N-(azetidin-3-yl)-2-(3-fluorophenyl)-1,7-naphthyridine-5-carboxamide 34-3 (100 mg, 0.30 mmol) was added, continue stirred for 10 minutes until the reaction went to completion. The reaction mixture was diluted with EtOAc, washed with 10% citric acid followed by sat. brine. The organic layer was dried and concentrated. The crude was purified with reverse phase HPLC to give pure product 39. LC/MS (ESI+): m/z 410.4 (M+H). $^1$H NMR (400 MHz, DMSO) δ 9.06-8.88 (m, 2H), 8.48-8.29 (m, 3H), 8.28-8.19 (m, 1H), 7.92-7.64 (s, 2H), 7.64-7.48 (td, J=8.0, 6.1 Hz, 1H), 7.41-7.23 (td, J=8.5, 2.6 Hz, 1H), 4.87-4.63 (q, J=6.7 Hz, 1H), 4.59-4.38 (t, J=8.5 Hz, 1H), 4.28-4.18 (t, J=9.0 Hz, 1H), 4.18-4.10 (dd, J=9.3, 5.4 Hz, 1H), 4.02-3.81 (m, 3H).

Example 40

8-amino-2-(3-fluorophenyl)-N-isobutyl-1,7-naphthyridine-5-carboxamide

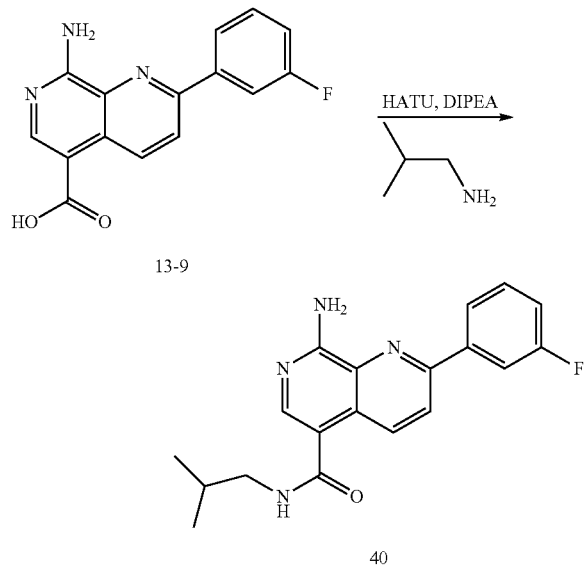

8-amino-2-(3-fluorophenyl)-1,7-naphthyridine-5-carboxylic acid 13-9 (50 mg, 0.18 mmol) in DMF (1 mL) was treated with DIPEA (0.09 mL, 0.53 mmol) and HATU (76 mg, 0.19 mmol). The mixture was stirred at r.t. for 10 minutes, and isobutylamine (0.02 mL, 0.19 mmol) was add, stirred at r.t. for 15 minutes until the reaction went to completion. The reaction was diluted with EtOAc, and solid was crashed out. The solid was filtered off and washed with methanol and EtOAc. The crude was submitted to purification to provide pure product 40. LC/MS (ESI+): m/z 339.4 (M+H).

Example 41

8-amino-N-(1-(cyclopropanecarbonyl)azetidin-3-yl)-2-(3-fluorophenyl)-N-methyl-1,7-naphthyridine-5-carboxamide

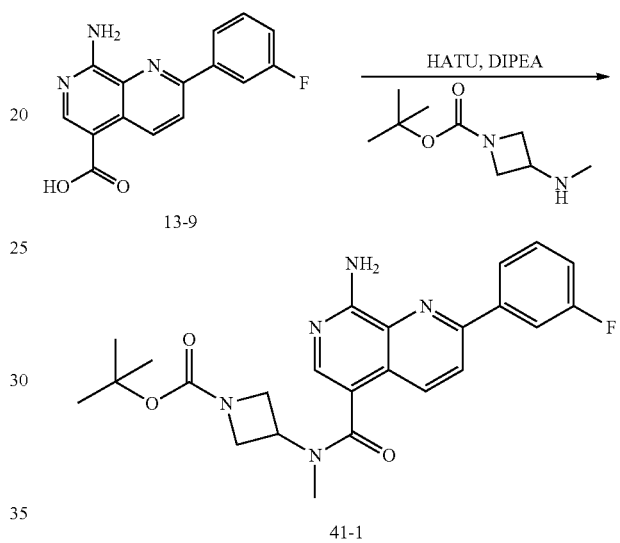

Step 1: Preparation of Compound 41-1

8-amino-2-(3-fluorophenyl)-1,7-naphthyridine-5-carboxylic acid 13-9 (150 mg, 0.53 mmol) in DMF (3 mL) was treated with HATU (242 mg, 0.64 mmol) and DIPEA (0.28 mL, 1.59 mmol). The mixture was stirred at r.t. for 10 minutes, and tert-butyl 3-(methylamino)azetidine-1-carboxylate (0.113 mL, 0.64 mmol) was added, and the reaction mixture was stirred over the weekend until the reaction went to completion. The reaction mixture was diluted with EtOAc, washed with 10% citric acid followed by sat. brine. The organic layer was dried and concentrated. The crude was purified with FCC eluting with 100% EtOAc to give pure product 41-1. LC/MS (ESI+): m/z 452.5 (M+H).

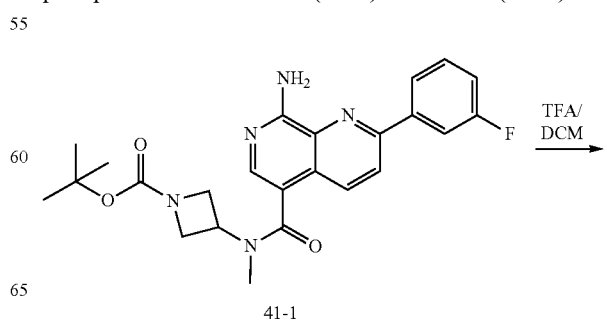

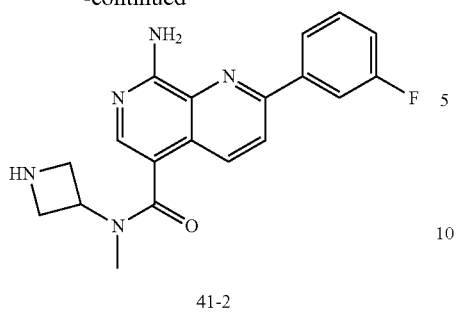

41-2

Step 2: Preparation of Compound 41-2 tert-butyl 3-[[8-amino-2-(3-fluorophenyl)-1,7-naphthyridine-5-carbonyl]amino]azetidine-1-carboxylate 41-1 (150 mg, 0.33 mmol) was treated with 1 to 1 trifluoroacetic acid (0.5 mL, 6.64 mmol) and methylene chloride (0.5 mL), and stirred at r.t. for 1 hour. The reactive mixture was concentrated to dry and washed by sat. NaHCO$_3$. Aqueous layer was extracted with EtOAc twice, organic layers were washed with brine, dried and concentrated to give crude product 41-2. LC/MS (ESI+): m/z 352.4 (M+H).

Step 3: Preparation of Compound 41

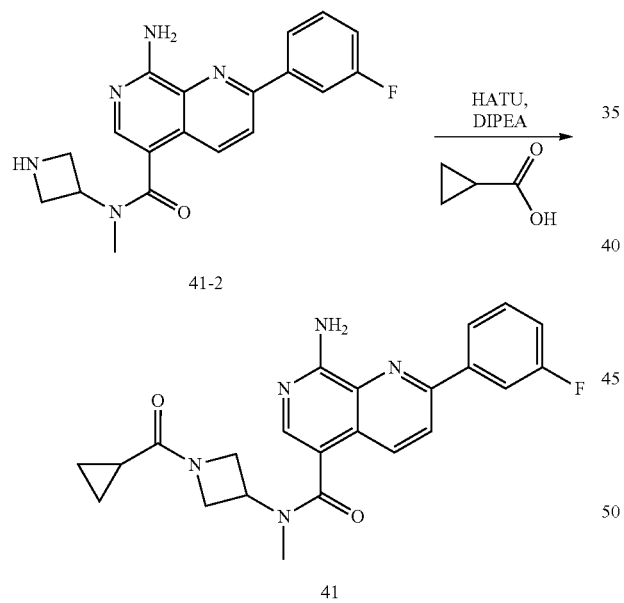

Cyclopropanecarboxylic acid (16 mg, 0.19 mmol) in DMF (1 mL) was treated with HATU (74 mg, 0.19 mmol) and DIPEA (0.08 mL, 0.47 mmol). The reaction mixture was stirred at room temperature for 15 minutes, 8-amino-N-(azetidin-3-yl)-2-(3-fluorophenyl)-N-methyl-1,7-naphthyridine-5-carboxamide 41-2 (55 mg, 0.1565 mmol) was added, continue stirred for 10 minutes until the reaction went to completion. The reaction mixture was diluted with EtOAc, washed with 10% citric acid followed by sat. brine. The organic layer was dried and concentrated. The crude was purified by reverse phase HPLC to give pure product 41. LC/MS (ESI+): m/z 420.4 (M+H). $^1$H NMR (400 MHz, DMSO) δ 9.05-8.96 (d, J=9.0 Hz, 1H), 8.96-8.90 (d, J=6.9 Hz, 1H), 8.47-8.37 (m, 2H), 8.37-8.30 (s, 1H), 8.29-8.17 (d, J=8.2 Hz, 1H), 7.92-7.64 (s, 2H), 7.63-7.49 (td, J=8.0, 6.2 Hz, 1H), 7.41-7.24 (td, J=8.5, 2.6 Hz, 1H), 4.88-4.66 (m, 1H), 4.66-4.46 (t, J=8.3 Hz, 1H), 4.29-4.21 (m, 1H), 4.20-4.09 (t, J=8.9 Hz, 1H), 4.01-3.80 (dd, J=9.9, 5.5 Hz, 1H), 2.17-2.01 (s, 3H), 1.66-1.40 (m, 1H), 0.79-0.61 (dd, J=8.2, 5.0 Hz, 4H).

Example 42

2-(3-fluorophenyl)-5-(1H-1,2,4-triazol-5-yl)-1,7-naphthyridin-8-amine

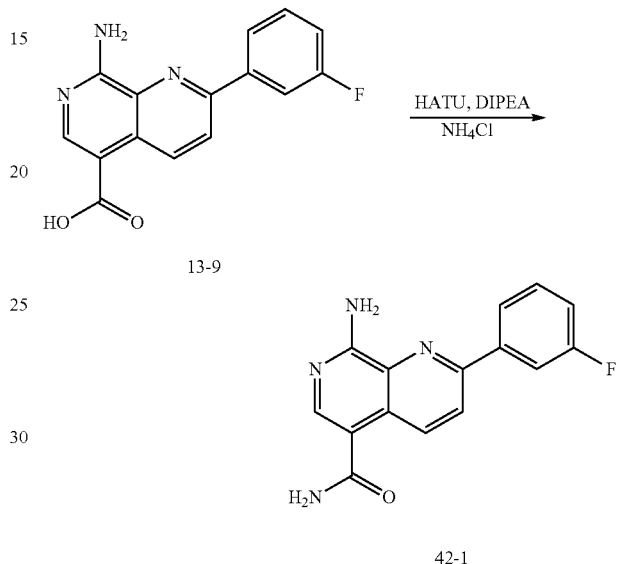

Step 1: Preparation of Compound 42-1

8-amino-2-(3-fluorophenyl)-1,7-naphthyridine-5-carboxylic acid 13-9 (100 mg, 0.3530 mmol) in DMF (1 mL) were treated with DIPEA (0.31 mL, 1.77 mmol) followed by HATU (277 mg, 0.71 mmol), stirred at r.t. for 15 minutes, ammonium chloride (76 mg, 1.412 mmol) was added and stirred for 2 hours at r.t until the reaction went to completion. The reaction mixture was diluted with EtOAc, washed with 10% citric acid followed by sat. brine. The organic layer was dried and concentrated. The crude was purified by reverse phase HPLC to give pure product 42-1. LC/MS (ESI+): m/z 283.3 (M+H). $^1$H NMR (400 MHz, DMSO) δ 9.16-9.02 (d, J=9.0 Hz, 1H), 8.43-8.37 (d, J=9.1 Hz, 2H), 8.37-8.28 (s, 1H), 8.27-8.16 (dt, J=7.8, 1.1 Hz, 1H), 7.86-7.62 (m, 2H), 7.64-7.51 (td, J=8.0, 6.1 Hz, 1H), 7.39-7.25 (td, J=8.5, 2.6 Hz, 1H).

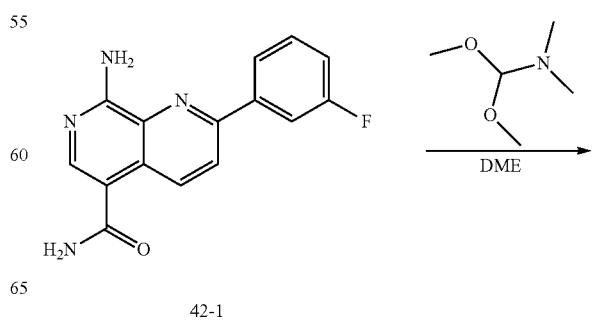

42-1

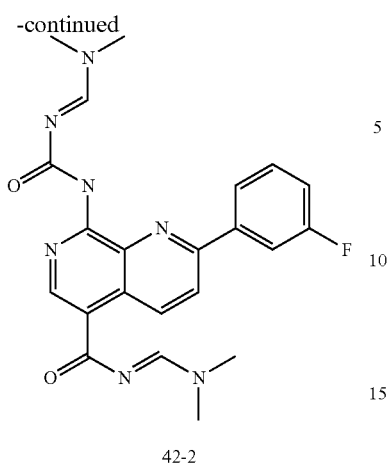

42-2

Step 2: Preparation of Compound 42-2

8-amino-2-(3-fluorophenyl)-1,7-naphthyridine-5-carboxamide 42-1 (440 mg, 0.0015 mol) in DME (6.0 mL) was treated with 1,1-Dimethoxy-N,N-dimethylmethanamine (2 mL, 0.02 mol) and heated to at 65° C. for 30 mins After cooling, the reaction mixture was concentrated and used as is in the next step. LC/MS (ESI+): m/z 436.4 (M+H).

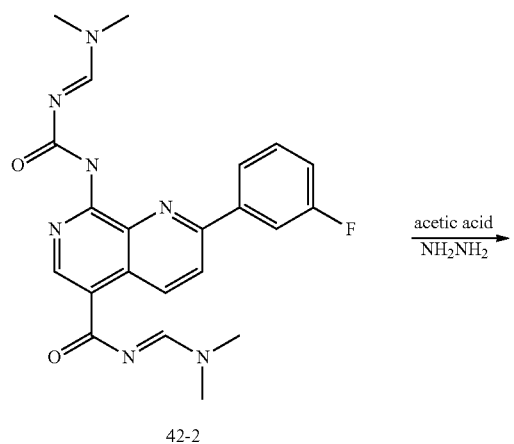

42

Step 3: Preparation of Compound 42

(E)-N-((dimethylamino)methylene)-8-((E)-3-((dimethylamino)methylene)ureido)-2-(3-fluorophenyl)-1,7-naphthyridine-5-carboxamide 42-2 (150 mg, 0.4446 mmol) was suspended in acetic acid (1.0 mL, 18 mmol), hydrazine monohydrochloride (63 mg, 0.8892 mmol) was added and the mixture was heated to 75° C. for 1 hour. The reaction mixture was cooled to r.t. and concentrated. The crude was purified by reverse phase HPLC to provide the pure triazole product 42. LC/MS (ESI+): m/z 307.3 (M+H). $^1$H NMR (400 MHz, DMSO) δ 9.50-9.41 (d, J=8.9 Hz, 1H), 8.58-8.52 (s, 1H), 8.47-8.42 (m, 2H), 8.42-8.36 (dt, J=10.9, 2.1 Hz, 1H), 8.28-8.21 (m, 1H), 7.64-7.56 (td, J=8.0, 6.1 Hz, 1H), 7.56-7.47 (s, 2H), 7.38-7.27 (td, J=8.4, 2.7 Hz, 1H).

Example 43

2-(3-fluorophenyl)-5-(1-(2-morpholinoethyl)-1H-imidazol-4-yl)-1,7-naphthyridin-8-amine

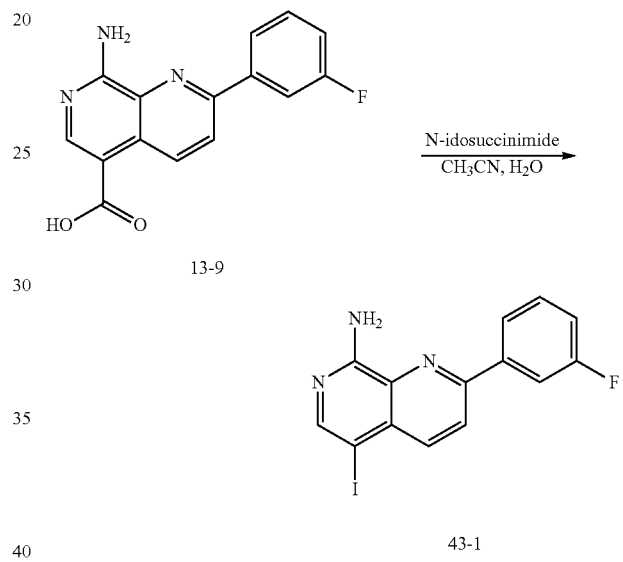

Step 1: Preparation of Compound 43-1

8-amino-2-(3-fluorophenyl)-1,7-naphthyridine-5-carboxylic acid 13-9 (300 mg, 1.059 mmol) and iodobenzene diacetate (174 mg, 0.53 mmol) were suspended in acetonitrile (1 mL) and water (0.5 mL) at 60° c. This suspension was stirred for 10 min, N-iodosuccinimide (294.7 mg, 1.27 mmol) was added, and the reaction was getting brown and gradually went dissolved, continue stirred for 30 min at 60° c. After the reaction was completed the solvent was evaporated. The crude material was purified with FCC using 50% EtOAc/hexane to provide 140 mg of pure product 43-1 as yellow solid (37% yield). LC/MS (ESI+): m/z 365.1 (M+H).

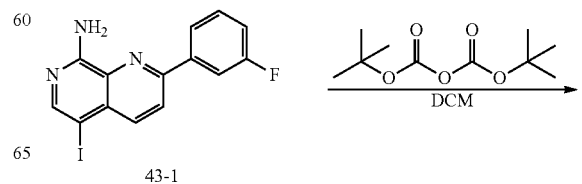

43-1

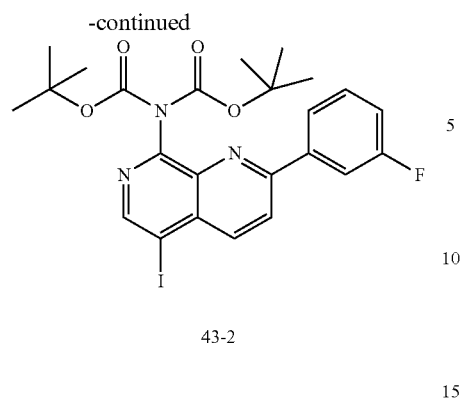

43-2

Step 2: Preparation of Compound 43-2

To a solution of 7-(3-fluorophenyl)-4-iodo-isoquinolin-1-amine 43-1 (500 mg, 1.373 mmol) in DCM (5 mL), DIPEA (0.48 mL, 2.75 mmol) was added dropwise. After the addition is completed, tert-butoxycarbonyl tert-butyl carbonate (899 mg, 4.12 mmol) was added followed by DMAP (169 mg, 1.37 mmol). The resulting solution was stirred at room temperature for overnight. The reaction mixture was concentrated and purified with FCC using 25% EtOAc/hexane to give 350 mg of pure product 43-2 as yellow solid (45% yield). LC/MS (ESI+): m/z 566.4 (M+H).

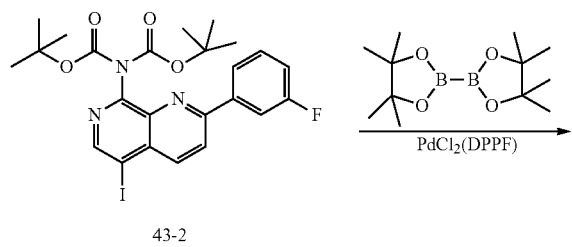

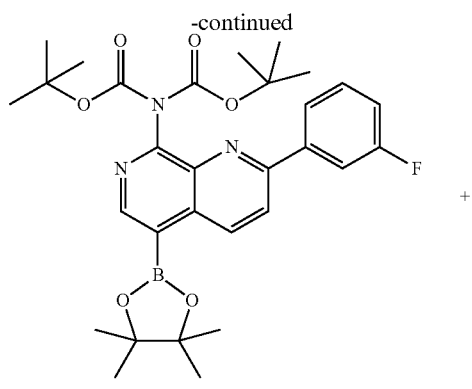

43-3

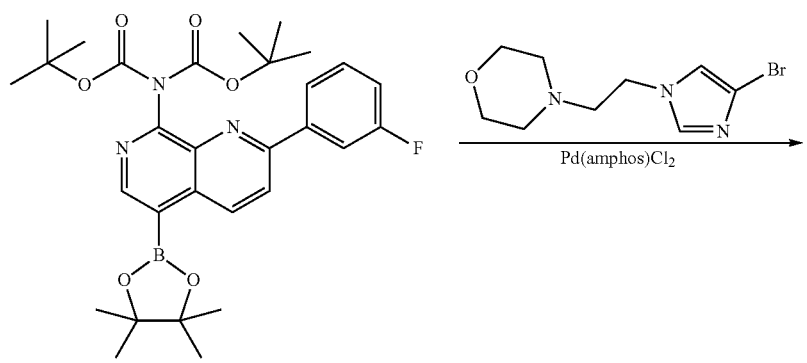

43-4

Step 3: Preparation of Compound 43-3

To a mixture of t-butyl N-tert-butoxycarbonyl-N-[2-(3-fluorophenyl)-5-iodo-1,7-naphthyridin-8-yl]carbamate 43-2 (260 mg, 0.4599 mmol), 4,4,5,5-tetramethyl-2-(4,4,5,5-tetramethyl-1,3,2-dioxaborolan-2-yl)-1,3,2-dioxaborolane (175 mg, 0.69 mmol) and potassium acetate (140 mg, 1.38 mmol,) in dioxane (1 mL) under nitrogen was added PdCl$_2$(DPPF) (34 mg, 0.05 mmol). The mixture was degased with N$_2$ for 2 minutes, sealed and heated to 90° C. for 2 hours. LCMS indicated 1 to 1 mixture of desired product 43-3 and de-iodo product 43-4. The reaction mixture was filtered through a thin layer of celite, concentrated and purified with isco using 20% EtOAc/hexane to give product 43-3 as light brown solid. LC/MS (ESI+): m/z 566.4 (M+H). LC/MS (ESI+): m/z 240.2 (M+H). De-iodo product 43-4: $^1$H NMR (400 MHz, DMSO) δ 8.39-8.29 (m, 2H), 8.27-8.22 (m, 1H), 8.23-8.18 (m, 1H), 7.88-7.84 (d, J=5.7 Hz, 1H), 7.64-7.50 (td, J=8.0, 6.1 Hz, 1H), 7.39-7.23 (tdd, J=8.5, 2.7, 0.8 Hz, 1H), 7.20-7.05 (s, 2H), 6.99-6.85 (d, J=5.6 Hz, 1H).

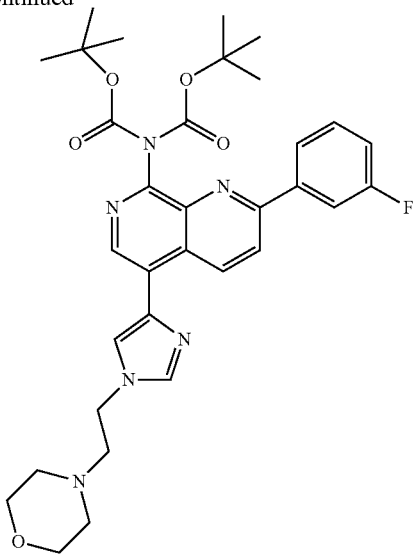

43-4

Step 4: Preparation of Compound 43-4 t-Butyl N-t-butoxycarbonyl-N-[2-(3-fluorophenyl)-5-(4,4,5,5-tetramethyl-1,3,2-dioxaborolan-2-yl)-1,7-naphthyridin-8-yl]carbamate 43-3 (130 mg, 0.2299 mmol) in DME (1 mL) was treated with 4-[2-(4-bromoimidazol-1-yl)ethyl]morpholine (120 mg, 0.4599 mmol), dichlorobis(p-dimethylamino phenyl di-t-butylphosphine) palladium(16 mg, 0.023 mmol) and 1 M potassium carbonate solution (0.69 mL, 0.69 mmol). The reaction vial was purged with nitrogen, and stirred at 100° C. for 2 hrs. LCMS showed 100% conversion to desired product. The crude was filtered through a thin layer of celite, and filtrate was washed with water and extracted with EtOAc, the organic layers were concentrated and purified with FCC using 10% MeOH/DCM to give pure product 43-4 (77% yield). LC/MS (ESI+): m/z 619.7 (M+H).

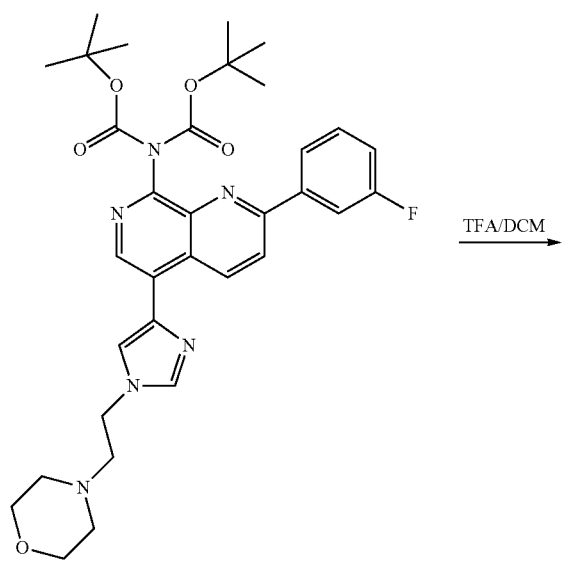

43-4

TFA/DCM

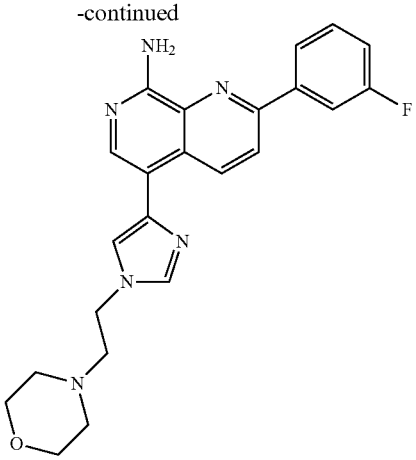

43

Step 5: Preparation of Compound 43 t-butyl N-tert-butoxycarbonyl-N-[2-(3-fluorophenyl)-5-[1-(2-morpholinoethyl)imidazol-4-yl]-1,7-naphthyridin-8-yl]carbamate 43-4 (110 mg, 0.18 mmol) was treated with trifluoroacetic acid (1 mL, 12.9 mmol) and DCM (1 mL) at room temperature for 1 hour until the reaction went to completion. The reactive mixture was concentrated to dry and washed by sat. NaHCO$_3$. Aqueous layer was extracted with EtOAc twice, organic layers were washed with brine, dried and concentrated. The crude product was purified with reverse phase HPLC to give pure product as white solid 43 (27% yield).

LC/MS (ESI+): m/z 419.5 (M+H). $^1$H NMR (400 MHz, DMSO) δ 9.21-9.06 (m, 1H), 8.43-8.30 (m, 2H), 8.30-8.17 (dt, J=7.9, 1.1 Hz, 1H), 8.16-8.01 (s, 1H), 7.91-7.73 (m, 1H), 7.67-7.47 (m, 2H), 7.39-7.25 (m, 1H), 7.23-7.07 (s, 2H), 4.27-4.03 (t, J=6.4 Hz, 2H), 3.71-3.46 (m, 4H), 2.78-2.63 (t, J=6.4 Hz, 2H), 2.48-2.43 (m, 4H).

Example 44

8-amino-N-(1-(cyclopropanecarbonyl)azetidin-3-yl)-2-(2-fluoropyridin-4-yl)-1,7-naphthyridine-5-Carboxamide

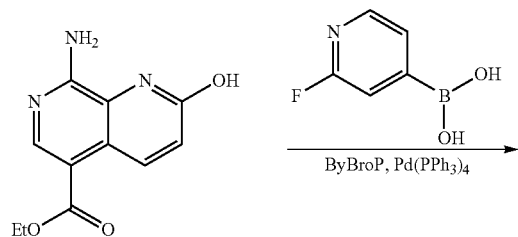

Step 1: Preparation of Compound 44-2

To a solution of D (150 mg, 0.65 mmol) in dioxane (20 mL), was added TEA (300 mg, 3.0 mol), and PyBroP (400 mg, 1.0 mmol). After the mixture was stirred at r.t. for 1 h, Pd(PPh$_3$)$_4$ (80 mg, 0.07 mmol), boronic acid 44-1 (180 mg, 1.3 mmol), K$_2$CO$_3$ (200 mg, 1.3 mmol), and H$_2$O (5 mL) was added. After the mixture was stirred at 90° C. for 3 h under N$_2$, it was extracted with EtOAc (50 mL×2), washed with sat NaCl (50 mL), dry over Na$_2$SO$_4$, and concentrated to give the crude product as brown solid. The solid was washed with EtOH (10 mL) to give the yellow solid as product: ethyl 8-amino-2-(2-fluoropyridin-4-yl)-1,7-naphthyridine-5-carboxylate 44-2 (100 mg, yield 50%). $^1$H NMR (400 MHz, CDCl$_3$) δ 9.27 (d, J=9.2 Hz, 1H), 8.67 (s, 1H), 8.56 (d, J=9.2 Hz, 1H), 8.43 (br, 1H), 8.38 (m, 3H), 8.13 (br, 1H), 4.30 (q, 2H), 1.32 (t, 3H).

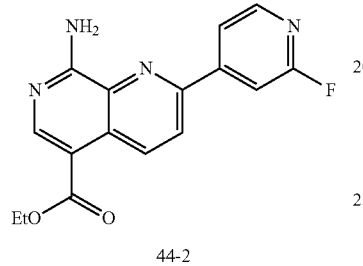

Step 2: Preparation of compound 44-3

To a solution of 44-2 (100 mg, 0.3 mmol) in a mixture of MeOH/H$_2$O (30 mL/10 mL) was added NaOH (120 mg, 3.0 mol). The mixture was stirred at r.t. o.n., adjust pH was adjust to 5-6 with HCl (aq). It was extracted with EtOAc (50 mL×2), washed with sat NaCl (50 mL), and concentrated to give the product as yellow solid (60 mg, 60%).

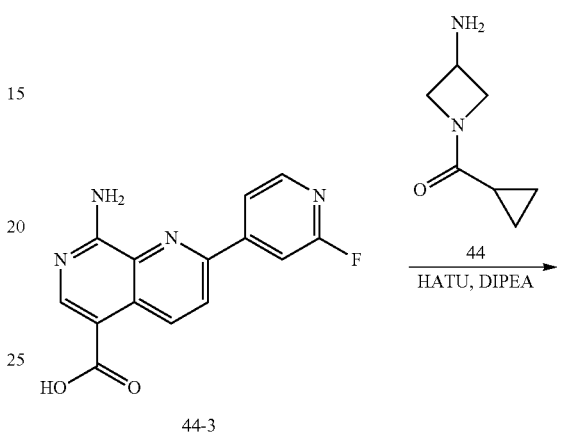

Step 3: Preparation of compound 44

To a solution of 44-3 (60 mg, 0.2 mmol), 44-4 (60 mg, 0.4 mmol) in DMF (10 mL) was added HATU (100 mg, 0.3 mmol), and DIPEA (130 mg, 1.0 mmol). After the mixture was stirred at r.t. for 3 h, water (30 mL) was added, and it was extracted with EtOAc (50 mL×2), washed with sat NaCl (50 mL), concentrated and purified by prep HPLC to give the product as yellow solid (10 mg, 10%). LCMS: (0-60, AB, 2 min), 0.942 min, MS=407.0 (M+1); $^1$H NMR (400 MHz, DMSO-d6) δ: 9.03 (d, J=10.2 Hz, 1H), 8.95 (d, J=6.8 Hz, 1H), 8.59 (d, J=8.8 Hz, 1H), 8.39-8.33 (m, 5H), 4.78-4.73 (m, 1H), 4.57-4.53 (m, 1H), 4.21-4.11 (m, 2H), 3.89-3.84 (m, 1H), 1.55-1.50 (m, 1H), 0.70-0.67 (m, 4H).

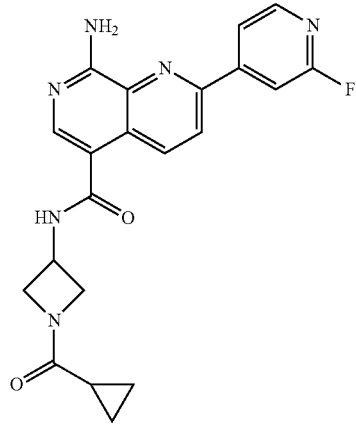

The following table summarizes methods of preparing and data measured for compounds of examples 45 to 156:

| Structure | IUPAC Name | No./ Yield/ General Method | LCMS $R_T$ (min)/ M + H+/ method | 1H NMR (ppm) |
|---|---|---|---|---|
| 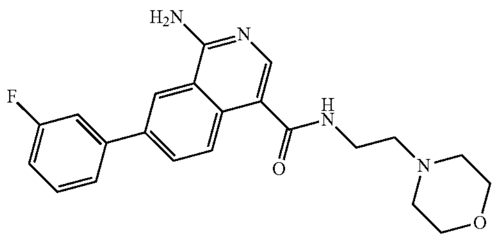 [SMILES: Nc1ncc(C(=O)NCCN2CCOCC2)c2ccc(-c3cccc(F)c3)cc12] | 1-amino-7-(3-fluorophenyl)-N-(2-morpholinoethyl)isoquinoline-4-carboxamide | 45 13.1% A | 0.959 395.0 0-60AB | 1H NMR (400 MHz, DMSO-$d_6$) δ 8.58 (d, J = 1.2 Hz, 1H), 8.45 (d, J = 8.8 Hz, 1H), 8.21 (t, J = 5.2 Hz, 1H), 8.06-8.04 (m, 2H), 7.76-7.72 (m, 2H), 7.56-7.51 (m, 2H), 7.37 (s, 1H), 7.23-7.19 (m, 3H), 3.59 (t, J = 4.4 Hz, 4H), 3.39-3.38 (m, 2H), 2.51-2.44 (m, 6H). |
| 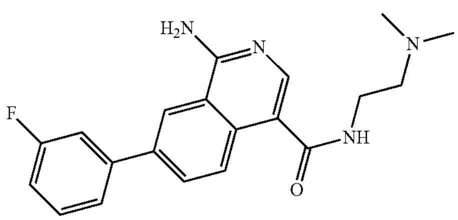 [SMILES: CN(C)CCNC(=O)c1cnc(N)c2cc(-c3cccc(F)c3)ccc12] | 1-amino-N-[2-(dimethylamino)ethyl]-7-(3-fluorophenyl)isoquinoline-4-carboxamide | 46 24.2% A | 0.956 352.9 0-60AB | 1H NMR (400 MHz, DMSO-$d_6$) δ 8.64 (s, 1H), 8.54-8.45 (m, 1H), 8.27 (s, 1H), 8.06 (s, 3H), 8.09-8.06 (m, 2H), 7.80-7.75 (m, 2H), 7.37 (s, 1H), 7.58-7.51 (m, 2H), 7.43 (s, 1H), 7.25-7.21 (m, 1H), 3.77-3.73 (m, 2H), 3.39-3.32 (m, 2H), 2.24 (s, 6H). |
| 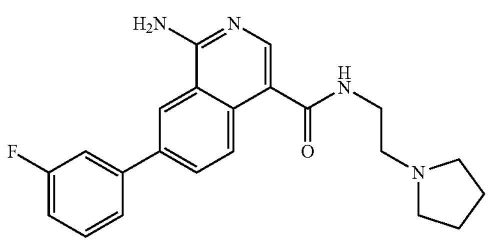 [SMILES: Nc1ncc(C(=O)NCCN2CCCC2)c2ccc(-c3cccc(F)c3)cc12] | 1-amino-7-(3-fluorophenyl)-N-(2-pyrrolidin-1-ylethyl)isoquinoline-4-carboxamide | 47 39.4% A | 0.953 379.1 0-60AB | 1H NMR (400 MHz, MeOD-$d_4$) δ 8.47-8.44 (m, 2H), 8.18 (s, 1H), 7.99 (d, J = 8.0 Hz, 1H), 7.60-7.46 (m, 3H), 7.10 (t, J = 8.4 Hz, 1H), 3.79 (t, J = 5.6 Hz, 2H), 3.48-3.42 (m, 6H), 2.10 (s, 4H). |
| 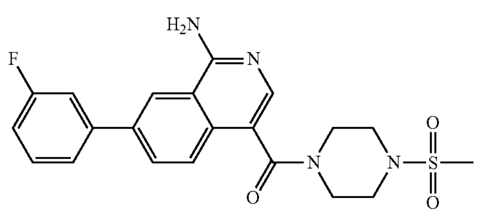 [SMILES: CS(=O)(=O)N1CCN(C(=O)c2cnc(N)c3cc(-c4cccc(F)c4)ccc23)CC1] | [1-amino-7-(3-fluorophenyl)-4-isoquinolyl]-(4-methylsulfonylpiperazin-1-yl)methanone | 48 49.7% A | 1.063 429.0 0-60AB | 1H NMR (400 MHz, MeOD-$d_4$) δ 8.72 (s, 1H), 8.15-8.13 (m, 2H), 7.85 (s, 1H), 7.80-7.74 (m, 5H), 7.61-7.55 (m, 1H), 7.26 (t, J = 8.8 Hz, 1H), 3.62-3.09 (m, 8H), 3.92 (s, 3H), 2.02-1.28 (m, 3H). |
| 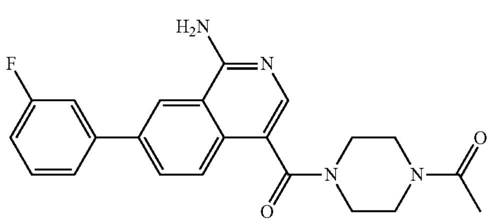 [SMILES: CC(=O)N1CCN(C(=O)c2cnc(N)c3cc(-c4cccc(F)c4)ccc23)CC1] | 1-[4-[1-amino-7-(3-fluorophenyl)isoquinoline-4-carbonyl]piperazin-1-yl]ethanone | 49 40.2% A | 1.037 393.0 0-60AB | 1H NMR (400 MHz, MeOD-$d_4$) δ 8.62 (s, 1H), 8.14 (d, J = 8.8 Hz ,1H), 8.89-8.83 (m, 2H), 7.66-7.52 (m, 3H), 7.18 (d, J = 8.0 Hz, 1H), 3.86-3.65 (m, 8H), 2.15 (s, 1H). |

| Structure | IUPAC Name | No./ Yield/ General Method | LCMS R$_T$ (min)/ M + H$^+$/ method | $^1$H NMR (ppm) |
|---|---|---|---|---|
| 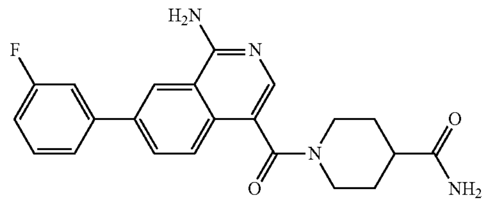 | 1-[1-amino-7-(3-fluorophenyl) isoquinoline-4-carbonyl] piperidine-4-carboxamide | 50 53% A | 1.004 393.0 0-60AB | $^1$H NMR (400 MHz, MeOD-d$_4$) δ 8.82 (s, 1H), 8.32 (d, J = 7.6 Hz, 1H), 7.91-7.84 (m, 1H), 7.69-7.50 (m, 4H), 7.17 (t, J = 8.0 Hz, 1H), 4.73 (d, J = 10.0 Hz, 1H), 3.67 (s, 1H), 3.10-3.99 (m, 2H), 2.59 (t, J = 11.2 Hz, 1H), 1.98-1.52 (m, 4H). |
| 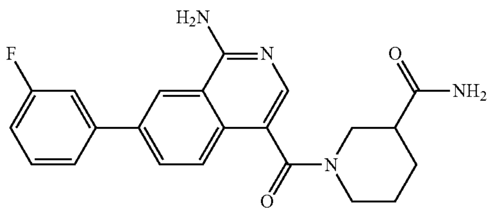 [SMILES: NC(=O)C1CCCN(C(=O)c2cnc(N)c3cc(-c4cccc(F)c4)ccc23)C1] | 1-[1-amino-7-(3-fluorophenyl) isoquinoline-4-carbonyl] piperidine-3-carboxamide | 51 33.1% A | 1.024 393.0 0-60AB | $^1$H NMR (400 MHz, MeOD-d$_4$) δ 8.81 (s, 1H), 8.30 (d, J = 8.4 Hz,1H), 7.93-7.88 (m, 1H), 7.67-7.50 (m, 4H), 7.17 (t, J = 8.4 Hz, 1H), 4.62-4.27 (m, 1H), 3.60-3.16 (m, 3H), 2.26-2.35 (m, 1H), 2.02-1.28 (m, 4H). |
| 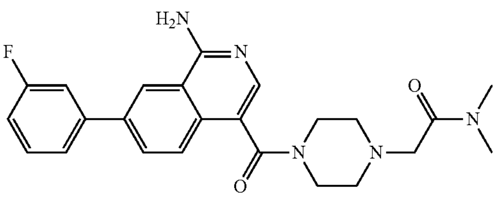 [SMILES: CN(C)C(=O)CN1CCN(C(=O)c2cnc(N)c3cc(-c4cccc(F)c4)ccc23)CC1] | 2-[4-[1-amino-7-(3-fluorophenyl) isoquinoline-4-carbonyl] piperazin-1-yl]-N,N-dimethyl-acetamide | 52 26.1% A | 0.959 436.0 0-60AB | $^1$H NMR (400 MHz, MeOD-d$_4$) δ 8.90 (s, 1H), 8.42 (s, 1H), 8.05 (s, 1H), 7.90 (s, 1H), 7.73-7.58 (m, 3H), 7.26 (t, J = 8.4 Hz, 1H), 4.44 (s, 2H), 3.67 (s, 8H), 3.07-3.04 (m, 6H). |
| 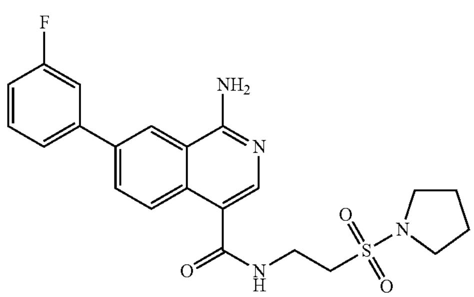 [SMILES: Nc1ncc(C(=O)NCCS(=O)(=O)N2CCCC2)c2ccc(-c3cccc(F)c3)cc12] | 1-amino-7-(3-fluorophenyl)-N-(2-pyrrolidin-1-ylsulfonylethyl) isoquinoline-4-carboxamide | 53 27.9% A | 1.130 443.0 0-60AB | $^1$NMR (400 MHz, MeOD-d$_4$) δ 8.83 (s, 1H), 8.50 (d, J = 8.8 Hz, 1H), 8.36 (d, J = 8.4 Hz, 1H), 7.92 (s, 1H), 7.71-7.56 (m, 3H), 7.24 (t, J = 8.4 Hz, 1H), 3.914 (t, J = 6.0 Hz, 2H), 3.48-3.42 (m, 6H), 2.00 (s, 4H). |
| 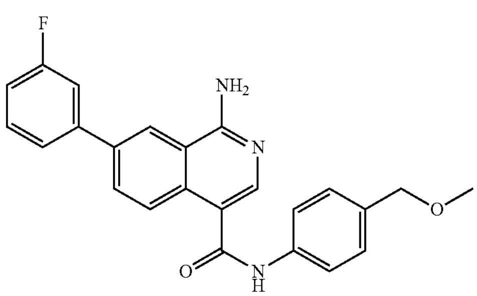 [SMILES: COCc1ccc(NC(=O)c2cnc(N)c3cc(-c4cccc(F)c4)ccc23)cc1] | 1-amino-7-(3-fluorophenyl)-N-[4-(methoxymethyl) phenyl]isoquinoline-4-carboxamide | 54 4% A | 1.202 402.0 0-60AB | $^1$H NMR (400 MHz, MeOD-d$_4$) δ 8.54 (d, J = 1.6 Hz, 1H), 8.45 (d, J = 8.8 Hz, 1H), 8.20 (s, 1H), 8.10-8.07 (m, 1H), 7.75-7.51 (m, 5H), 7.38 (d, J = 8.4 Hz, 1H), 7.18-7.14 (m, 1H), 4.48 (s, 2H), 3.41 (s, 3H). |

| Structure | IUPAC Name | No./ Yield/ General Method | LCMS $R_T$ (min)/ M + H+/ method | 1H NMR (ppm) |
|---|---|---|---|---|
| | [1-amino-7-(3-fluorophenyl)-4-isoquinolyl]-[4-(hydroxymethyl)-1-piperidyl] methanone | 55 8% A | 1.042 3380.0 0-60AB | 1H NMR (400 MHz, MeOH-d4) δ 8.63 (s, 1H), 8.14-8.07 (m, 2H), 7.77-7.69 (m, 4H), 7.60-7.54 (m, 1H), 7.30-7.23 (m, 3H), 4.49 (m, 1H), 3.55-3.45 (m, 4H), 3.06-2.84 (m, 2H), 1.84-1.39 (m, 3H), 1.23-0.98 (m, 2H). |
| 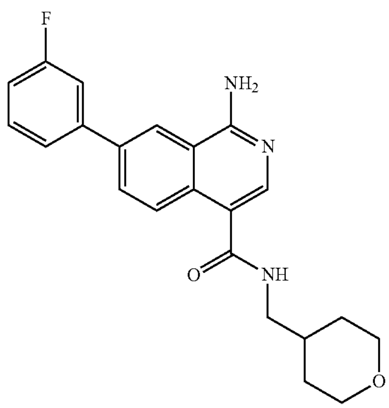 [SMILES: Nc1ncc(C(=O)NCC2CCOCC2)c2ccc(-c3cccc(F)c3)cc12] | 1-amino-7-(3-fluorophenyl)-N-(tetrahydropyran-4-ylmethyl)isoquinoline-4-carboxamide | 56 15% A | 1.093 394.9 0-60AB | 1H NMR (400 MHz, MeOH-d4) δ 8.78 (s, 1H), 8.41-8.33 (m, 2H), 7.82 (s, 1H), 7.69-7.35 (m, 3H), 7.23-7.18 (m, 1H), 4.00-3.96 (m, 1H), 3.47-3.36 (m, 4H), 1.98-1.90 (m, 1H), 1.76-1.72 (m, 2H), 1.45-1.34 (m, 2H). |
| 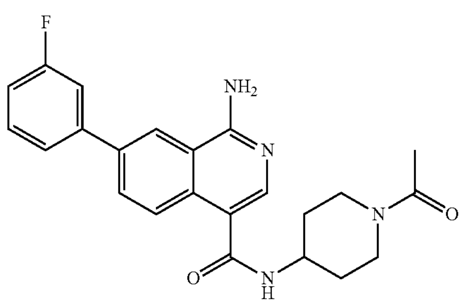 [SMILES: CC(=O)N1CCC(NC(=O)c2cnc(N)c3cc(-c4cccc(F)c4)ccc23)CC1] | N-(1-acetyl-4-piperidyl)-1-amino-7-(3-fluorophenyl) isoquinoline-4-carboxamide | 57 5% A | 1.063 407.1 0-60AB | 1H NMR (400 MHz, MeOH-d4) δ 8.53 (s, 1H), 8.35 (d, J = 8.8 Hz, 1H), 8.10 (d, J = 2.0 Hz, 2H), 7.98 (s, 1H), 7.65-7.50 (m, 3H), 7.14 (m, 1H), 4.53 (m, 1H), 4.21-4.16 (m, 1H), 3.99 (m, 1H), 3.30 (m, 1H), 2.91-2.84 (m, 1H), 2.12-1.93 (m, 5H), 1.60-1.46 (m, 2H). |
| 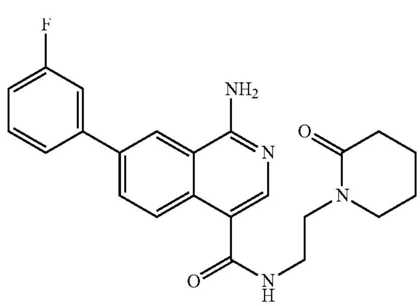 [SMILES: Nc1ncc(C(=O)NCCN2CCCCC2=O)c2ccc(-c3cccc(F)c3)cc12] | 1-amino-7-(3-fluorophenyl)-N-[2-(2-oxo-1-piperidyl) ethyl]isoquinoline-4-carboxamide | 58 9% A | 1.089 407 0-60AB | 1H NMR (400 MHz, MeOH-d4) δ 8.55 (d, J = 1.6 Hz, 1H), 8.39 (d, J = 8.2 Hz, 1H), 8.18 (s, 1H), 8.12 (m, 1H), 8.10 (s, 1H), 7.64-7.49 (m, 3H), 7.17-7.13 (m, 1H), 3.66-3.64 (m, 4H), 3.49 (t, J = 5.2 Hz, 2H), 2.35 (t, J = 5.2 Hz, 2H), 1.86-1.80 (m, 4H). |

-continued

| Structure | IUPAC Name | No./ Yield/ General Method | LCMS $R_T$ (min)/ M + H+/ method | $^1$H NMR (ppm) |
|---|---|---|---|---|
| 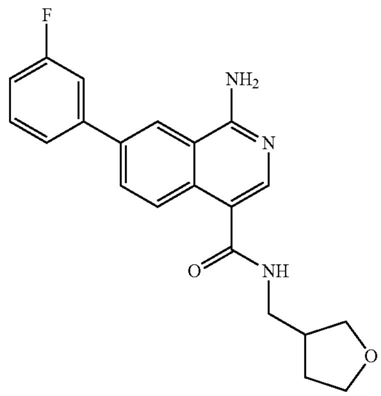 [SMILES: Nc1ncc(C(=O)NCC2CCOC2)c2ccc(-c3cccc(F)c3)cc12] | 1-amino-7-(3-fluorophenyl)-N-(tetrahydrofuran-3-ylmethyl)isoquinoline-4-carboxamide | 59 15% A | 1.069 366.0 0-60AB | $^1$H NMR (400 MHz, MeOH-d$_4$) δ 8.56 (s, 1H), 8.35 (d, J = 8.4 Hz, 1H), 8.17-8.10 (m, 2H), 7.96 (bs, 1H), 7.64-7.51 (m, 3H), 7.17-7.12 (m, 1H), 3.95-3.62 (m, 6H), 2.65-2.62 (m 1H), 2.16-2.07 (m, 1H), 1.80-1.72 (m, 1H). |
| 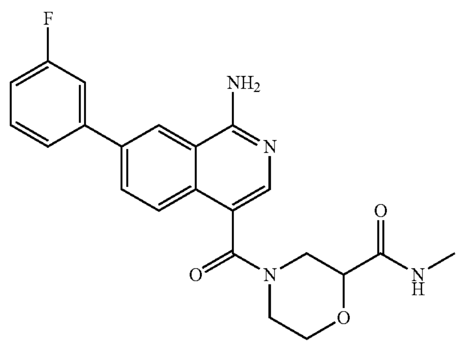 [SMILES: CNC(=O)C1CN(C(=O)c2cnc(N)c3cc(-c4cccc(F)c4)ccc23)CCO1] | 4-[1-amino-7-(3-fluorophenyl)isoquinoline-4-carbonyl]-N-methyl-morpholine-2-carboxamide | 60 12% A | 1.034 409.0 0-60AB | $^1$H NMR (400 MHz, MeOH-d$_4$) δ 8.52 (d, J = 1.6 Hz, 1H), 8.06 (m, 1H), 7.64 (bs, 2H), 7.64-7.48 (m, 3H), 7.16-7.11 (m, 1H), 4.67-4.48 (m, 1H), 4.09-3.86 (m, 4H), 3.03-2.72 (m, 5H). |
| 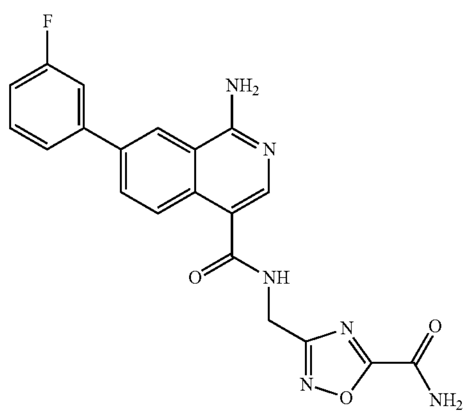 [SMILES: NC(=O)c1nc(CNC(=O)c2cnc(N)c3cc(-c4cccc(F)c4)ccc23)no1] | 3-[[[1-amino-7-(3-fluorophenyl)isoquinoline-4-carbonyl]amino]methyl]-1,2,4-oxadiazole-5-carboxamide | 61 5% A | 1.039 407.0 0-60AB | $^1$H NMR (400 MHz, DMSO-d$_6$) δ 8.99 (d, J = 5.6 Hz, 1H), 8.77-8.10 (m, 7H), 7.80-7.75 (m, 2H), 7.59-7.54 (m, 2H), 7.26-7.22 (m, 1H), 4.68 (d, J = 5.2 Hz, 2H). |
| 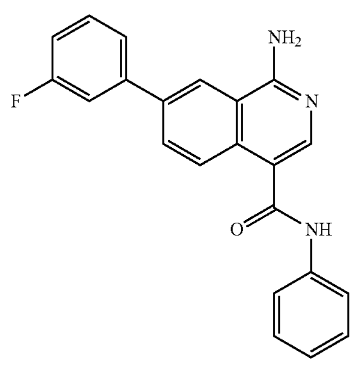 [SMILES: Nc1ncc(C(=O)Nc2ccccc2)c2ccc(-c3cccc(F)c3)cc12] | 1-amino-7-(3-fluorophenyl)-N-phenyl-isoquinoline-4-carboxamide | 62 5% A | 1.192 358.0 0-60AB | $^1$H NMR (400 MHz, MeOH-d$_4$) δ 8.82 (s, 1H), 8.56 (d, J = 8.4 Hz, 1H), 8.46 (d, J = 8.8 Hz, 1H), 8.02 (s, 1H), 7.76-7.57 (m, 5H), 7.45-7.40 (m, 2H), 7.27-7.20 (m, 2H). |

-continued

| Structure | IUPAC Name | No./ Yield/ General Method | LCMS R$_T$ (min)/ M + H$^+$/ method | $^1$H NMR (ppm) |
|---|---|---|---|---|
| 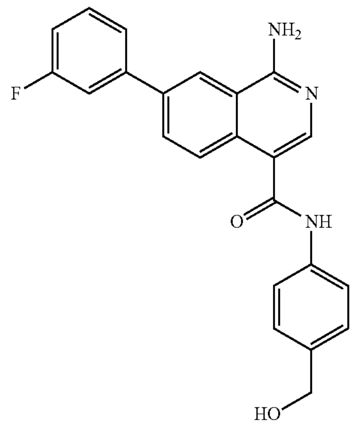 [SMILES: Nc1ncc(C(=O)Nc2ccc(CO)cc2)c2ccc(-c3cccc(F)c3)cc12] | 1-amino-7-(3-fluorophenyl)-N-[4-(hydroxymethyl)phenyl]isoquinoline-4-carboxamide | 63 3% A | 1.115 388.0 0-60AB | $^1$H NMR (400 MHz, MeOH-d$_4$) δ 8.87 (d, J = 2.0 Hz, 1H), 8.44-8.24 (m, 2H), 8.19 (s, 1H), 7.83-7.58 (m, 5H), 8.22 (s, 1H), 7.33-7.28 (m, 1H), 4.49 (s, 2H). |
| 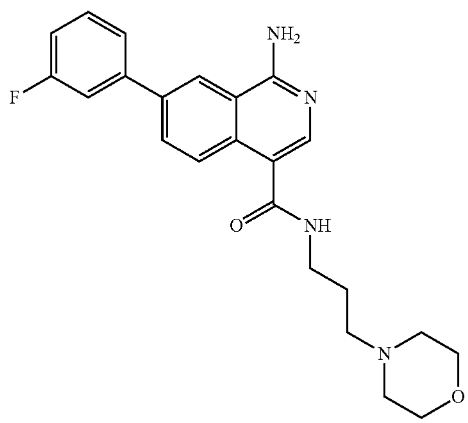 [SMILES: Nc1ncc(C(=O)NCCCN2CCOCC2)c2ccc(-c3cccc(F)c3)cc12] | 1-amino-7-(3-fluorophenyl)-N-(3-morpholinopropyl)isoquinoline-4-carboxamide | 64 8% A | 0.957 409.0 0-60AB | $^1$H NMR (400 MHz, MeOD-d$_4$) δ 8.54 (d, J = 1.6 Hz, 1H), 8.42 (d, J = 8.8 Hz, 1H), 8.29 (s, 2H), 8.10-8.07 (m, 2H), 7.67-7.51 (m, 3H), 7.18-7.14 (m, H), 3.84 (t, J = 4.4 Hz, 2H), 3.52 (t, J = 5.2 Hz, 2H), 2.97-2.91 (m, 6H), 2.06-1.99 (m, 2H). |
| 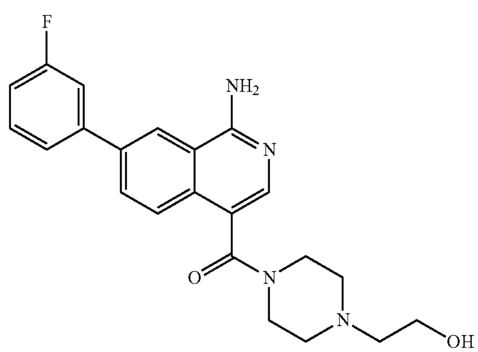 [SMILES: Nc1ncc(C(=O)N2CCN(CCO)CC2)c2ccc(-c3cccc(F)c3)cc12] | [1-amino-7-(3-fluorophenyl)-4-isoquinolyl]-[4-(2-hydroxyethyl)piperazin-1-yl]methanone | 65 13% A | 0.910 394.9 0-60AB | $^1$H NMR (400 MHz, MeOH-d$_4$) δ 8.54 (t, J = 1.6 Hz, 1H), 8.09 (m, 1H), 7.83 (m, 2H), 7.66-7.36 (m, 3H), 7.18-7.14 (m, 1H), 3.97-3.45 (m, 6H), 2.77-2.05 (m, 6H). |
| 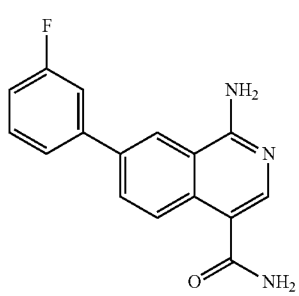 [SMILES: NC(=O)c1cnc(N)c2cc(-c3cccc(F)c3)ccc12] | 1-amino-7-(3-fluorophenyl)isoquinoline-4-carboxamide | 66 10% A | 1.010 282.0 0-60 | $^1$H NMR (400 MHz, MeOH-d$_4$) δ 8.59-8.55 (m, 2H), 8.17-8.12 (m, 2H), 7.71-7.65 (m, 2H), 7.59-7.53 (m, 2H), 7.22-7.17 (m, 1H). |

| Structure | IUPAC Name | No./ Yield/ General Method | LCMS R$_T$ (min)/ M + H$^+$/ method | $^1$H NMR (ppm) |
|---|---|---|---|---|
| 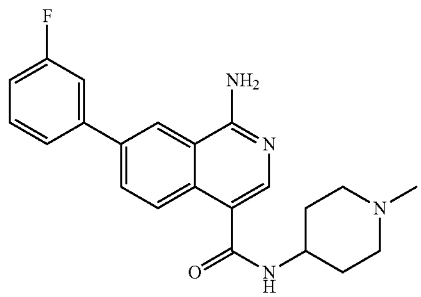 [SMILES: CN1CCC(NC(=O)c2cnc(N)c3cc(-c4cccc(F)c4)ccc23)CC1] | 1-amino-7-(3-fluorophenyl)-N-(1-methyl-4-piperidyl) isoquinoline-4-carboxamide | 67 7% A | 0.946 379.0 0-60AB | $^1$H NMR (400 MHz, MeOH-d$_4$) δ 8.37 (s, 1H), 8.36 (m, 2H), 8.06-8.02 (m, 2H), 7.64-7.48 (m, 3H), 7.16-7.10 (m, 1H), 4.22-4.16 (m, 1H), 3.53 (m, 2H), 3.20 (m, 2H), 2.86 (s, 3H), 2.30 (m, 2H), 1.97-1.82 (m, 2H). |
| 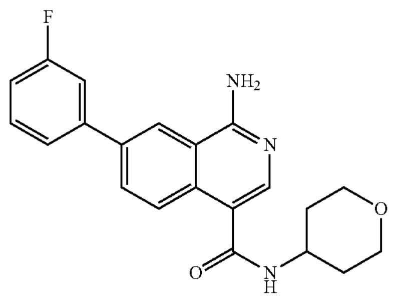 [SMILES: Nc1ncc(C(=O)NC2CCOCC2)c2ccc(-c3cccc(F)c3)cc12] | 1-amino-7-(3-fluorophenyl)-N-tetrahydropyran-4-yl-isoquinoline-4-carboxamide | 68 7% A | 1.082 366.0 0-60AB | $^1$H NMR (400 MHz, MeOH-d$_4$) δ 8.67 (s, 1H), 8.62 (d, J = 1.6 Hz, 1H), 8.44-8.07 (m, 3H), 7.75-7.69 (m, 2H), 7.62-7.56 (m, 1H), 7.25-7.20 (m, 1H), 4.20-4.14 (m, 1H), 4.03-4.00 (m, 2H), 2.00 (m, 2H), 1.74-1.64 (m, 2H). |
| 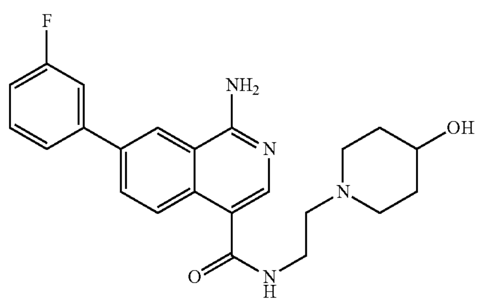 | 1-amino-7-(3-fluorophenyl)-N-[2-(4-hydroxy-1-piperidyl)ethyl] isoquinoline-4-carboxamide | 69 10% A | 0.946 409.0 0-60AB | $^1$H NMR (400 MHz, MeOH-d$_4$) δ 8.59 (d, J = 1.6 Hz, 1H), 8.47 (d, J = 8.2 Hz, 1H), 8.31 (m, 1H), 8.12-8.04 (m, 3H), 7.77-7.72 (m, 2H), 7.57-7.51 (m, 1H), 7.41 (bs, 2H), 7.24-7.19 (m, 1H), 4.71 (m, 1H), 3.55-3.43 (m, 3H), 3.00 (m, 2H), 2.75 (m, 2H), 1.80 (m, 2H), 1.52-.145 (m, 2H). |
| 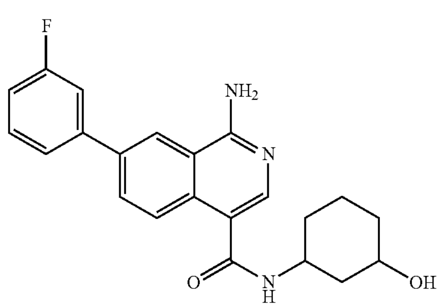 [SMILES: Nc1ncc(C(=O)NC2CCCC(O)C2)c2ccc(-c3cccc(F)c3)cc12] | 1-amino-7-(3-fluorophenyl)-N-(3-hydroxycyclohexyl) isoquinoline-4-carboxamide | 70 14% A | 1.126 380.0 0-60AB | $^1$H NMR (400 MHz, MeOH-d4) δ: 8.51 (s, 1H), 8.36 (d, J = 9.2 Hz, 1H), 8.06 (d, J = 8.8 Hz, 1H), 8.05 (s, 1H), 7.67-7.51 (m, 3H), 7.18-7.13 (m, 1H), 4.04-3.97 (m, 1H), 3.75-3.67 (m, 1H), 2.31-2.29 (m, 1H), 1.99-1.86 (m, 3H), 1.49-1.33 (m, 4H). |

-continued

| Structure | IUPAC Name | No./Yield/General Method | LCMS R$_T$ (min)/M + H$^+$/method | $^1$H NMR (ppm) |
|---|---|---|---|---|
| 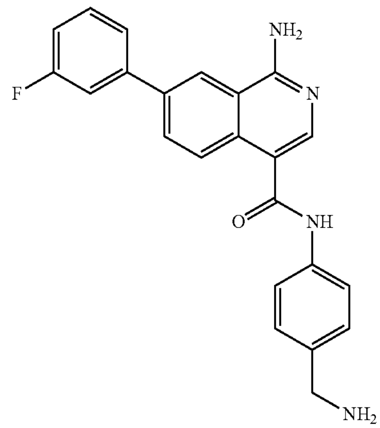 [SMILES: NCc1ccc(NC(=O)c2cnc(N)c3cc(-c4cccc(F)c4)ccc23)cc1] | 1-amino-N-[4-(aminomethyl)phenyl]-7-(3-fluorophenyl)isoquinoline-4-carboxamide | 71<br>15%<br>A | 0.991<br>370.0<br>0-60AB | $^1$H NMR (400 MHz, MeOH-d$_4$) δ 8.86 (s, 1H), 8.65 (d, J = 7.6 Hz, 1H), 8.40 (d, J = 2.0 Hz, 1H), 8.05 (s, 1H), 7.88 (d, J = 8.4 Hz, 1H), 7.73-7.52 (m, 5H), 7.27-7.23 (m, 1H), 4.16 (s, 2H). |
| 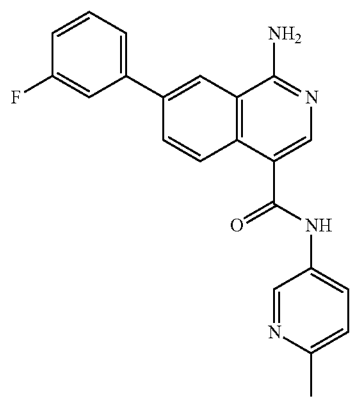 [SMILES: Cc1ccc(NC(=O)c2cnc(N)c3cc(-c4cccc(F)c4)ccc23)cn1] | 1-amino-7-(3-fluorophenyl)-N-(6-methyl-3-pyridyl)isoquinoline-4-carboxamide | 72<br>2%<br>A | 0.976<br>373.0<br>0-60AB | $^1$H NMR (400 MHz, MeOH-d$_4$) δ 9.45 (s, 1H), 8.90 (d, J = 1.6 Hz, 1H), 8.62 (d, J = 8.8 Hz, 2H), 8.41 (d, J = 1.6 Hz, 1H), 8.22 (s, 1H), 7.98 (d, J = 8.8 Hz, 1H), 7.73-7.57 (m, 3H), 7.27-7.23 (m, 1H), 2.82 (s, 3H). |
| 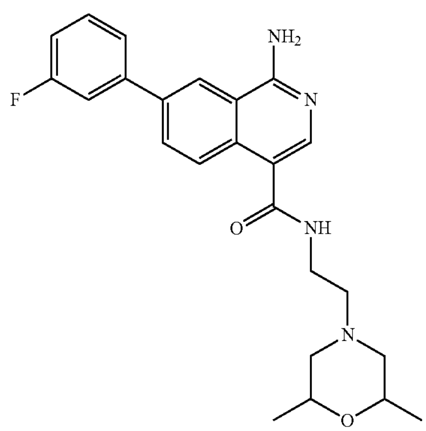 [SMILES: CC1CN(CCNC(=O)c2cnc(N)c3cc(-c4cccc(F)c4)ccc23)CC(C)O1] | 1-amino-N-[2-(2,6-dimethylmorpholin-4-yl)ethyl]-7-(3-fluorophenyl)isoquinoline-4-carboxamide | 73<br>28.6%<br>A | 1.051<br>423.1<br>0-60AB | $^1$H NMR (400 MHz, MeOD-d$_4$) δ 8.81 (s, 1H), 8.55 (d, J = 8.4 Hz, 1H), 8.34 (d, J = 8.0 Hz, 1H), 8.07 (s, 1H), 7.68-7.55 (m, 3H), 7.22 (m, 1H), 3.99-3.68 (m, 8H), 2.82 (t, 2H), 1.26 (s, 6H). |
| 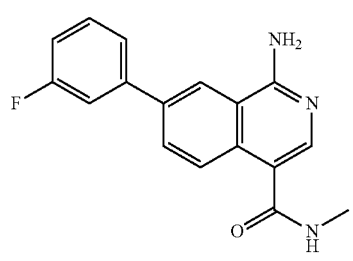 [SMILES: CNC(=O)c1cnc(N)c2cc(-c3cccc(F)c3)ccc12] | 1-amino-7-(3-fluorophenyl)-N-methyl-isoquinoline-4-carboxamide | 74<br>12%<br>A | 1.077<br>295.9<br>0-60AB | $^1$H NMR (400 MHz, DMSO-d$_6$) δ 8.56 (d, J = 1.6 Hz, 1H), 8.46 (d, J =8.8 Hz, 1H), 8.22 (m, 1H), 8.11-8.04 (m, 2H), 7.76-7.71 (m, 2H), 7.57-7.51 (m, 2H), 7.40 (bs, 2H), 7.24-7.19 (m, 2H), 2.78 (d, J = 4.4 Hz, 3H). |

-continued

| Structure | IUPAC Name | No./Yield/General Method | LCMS R$_T$ (min)/M + H$^+$/method | $^1$H NMR (ppm) |
|---|---|---|---|---|
| 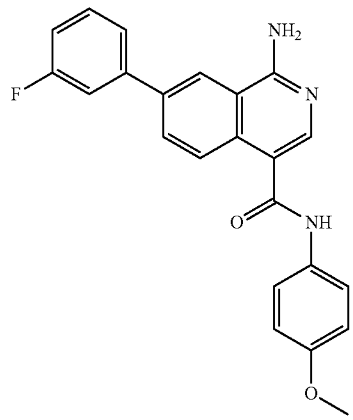 [SMILES: COc1ccc(NC(=O)c2cnc(N)c3cc(-c4cccc(F)c4)ccc23)cc1] | 1-amino-7-(3-fluorophenyl)-N-(4-methoxyphenyl) isoquinoline-4-carboxamide | 75<br>8%<br>A | 1.090<br>388.0<br>0-60AB | $^1$H NMR (400 MHz, MeOH-d$_4$) δ 8.50 (d, J = 1.6 Hz, 1H), 8.40 (d, J = 8.8 Hz, 1H), 8.16 (s, 1H), 8.12 (s, 1H), 8.04-8.01 (m, 1H), 7.67-7.60 (m, 4H), 7.52-7.46 (m, 1H), 7.15-7.10 (m, 1H), 6.89-6.87 (m, 2H), 3.73 (s, 3H). |
| 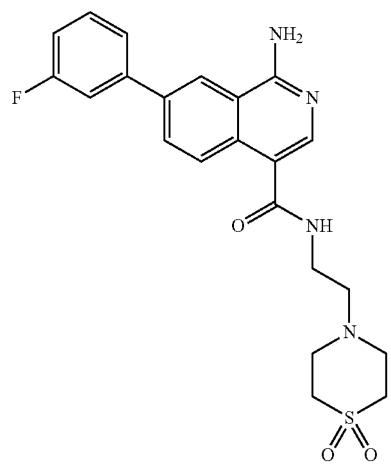 [SMILES: Nc1ncc(C(=O)NCCN2CCS(=O)(=O)CC2)c2ccc(-c3cccc(F)c3)cc12] | 1-amino-N-[2-(1,1-dioxo-1,4-thiazinan-4-yl)ethyl]-7-(3-fluorophenyl) isoquinoline-4-carboxamide | 76<br>25.0%<br>A | 1.038<br>443.0<br>0-60AB | $^1$H NMR (400 MHz, MeOD-d$_4$) δ 8.82 (s, 1H), 8.54 (d, J = 8.8 Hz, 1H), 8.36-8.33 (d, J = 6.8 Hz, 1H), 8.06 (s, 1H), 7.68-7.54 (m, 3H), 7.24-7.19 (t, 1H), 3.81 (m, 6H), 3.60-3.51 (m, 4H), 3.43 (m, 2H). |
| 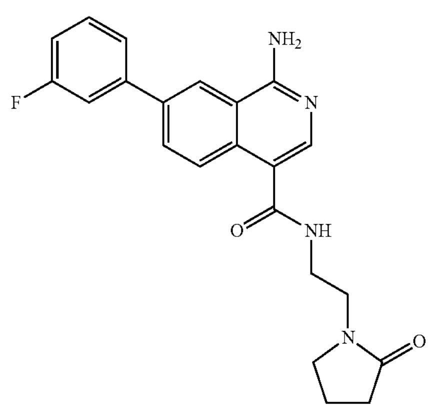 [SMILES: Nc1ncc(C(=O)NCCN2CCCC2=O)c2ccc(-c3cccc(F)c3)cc12] | 1-amino-7-(3-fluorophenyl)-N-[2-(2-oxopyrrolidin-1-yl)ethyl]isoquinoline-4-carboxamide | 77<br>17.9%<br>A | 1.089<br>392.9<br>0-60AB | $^1$H NMR (400 MHz, DMSO-d$_6$) δ 9.00 (s, 1H), 8.75 (s, 1H), 8.39 (m, 2H), 7.80-7.78 (m, 3H), 7.64-7.52 (m, 1H), 7.37-7.28 (m, 1H), 3.81 (d, J = 5.6 Hz, 1H), 3.44-3.38 (m, 6H), 2.18 (t, 2H), 1.95-1.82 (m, 2H). |
| 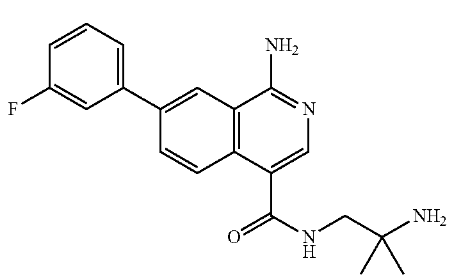 [SMILES: CC(C)(N)CNC(=O)c1cnc(N)c2cc(-c3cccc(F)c3)ccc12] | 1-amino-N-(2-amino-2-methyl-propyl)-7-(3-fluorophenyl) isoquinoline-4-carboxamide | 78<br>7%<br>A | 0.984<br>353.1<br>0-60AB | $^1$H NMR (400 MHz, MeOD-d$_4$) δ 8.56 (d, J = 1.6 Hz, 1H), 8.48 (d, J = 8.8 Hz, 1H), 8.38 (d, J = 1.6 Hz, 1H), 8.05 (s, 1H), 7.72-7.57 (m, 3H), 7.27-7.22 (m, 1H), 3.64 (s, 2H), 1.47 (s, 6H). |

-continued

| Structure | IUPAC Name | No./ Yield/ General Method | LCMS $R_T$ (min)/ M + H+/ method | $^1$H NMR (ppm) |
|---|---|---|---|---|
| 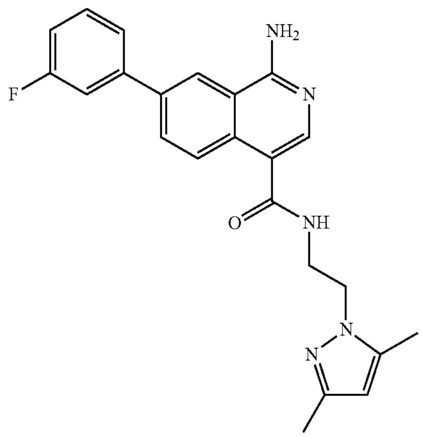 [SMILES: Cc1cc(C)n(CCNC(=O)c2cnc(N)c3cc(-c4cccc(F)c4)ccc23)n1] | 1-amino-N-[2-(3,5-dimethyl-pyrazol-1-yl)ethyl]-7-(3-fluorophenyl)isoquinoline-4-carboxamide | 79 24.9% A | 1.089 392.9 0-60AB | $^1$H NMR (400 MHz, DMSO-d$_6$) δ 9.00 (s, 1H), 8.75 (s, 1H), 8.39 (m, 2), 7.80-7.78 (m, 3H), 7.64-7.52 (m, 1H), 7.37-7.28 (m, 1H), 3.81 (d, J = 5.6 Hz, 1H), 3.44-3.38 (m, 6H), 2.18 (t, 2H), 1.95-1.82 (m, 2H). |
| 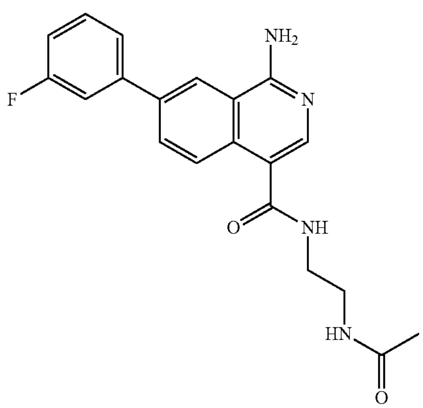 [SMILES: CC(=O)NCCNC(=O)c1cnc(N)c2cc(-c3cccc(F)c3)ccc12] | N-(2-acetamidoethyl)-1-amino-7-(3-fluorophenyl)isoquinoline-4-carboxamide | 80 5% A | 1.059 367.1 0-60AB | $^1$H NMR (400 MHz, MeOD-d$_4$) δ 8.52 (d, J = 1.6 Hz, 1H), 8.38 (d, J = 8.8 Hz, 1H), 8.17 (s, 1H), 8.09 (d, J = 1.6 Hz, 1H), 8.00 (s, 1H), 7.64-7.48 (m, 3H), 7.16-7.11 (m, 1H), 3.54-3.42 (m, 4H), 1.96 (s, 3H). |
| 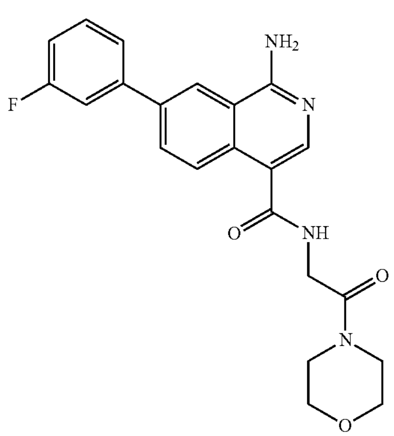 [SMILES: Nc1ncc(C(=O)NCC(=O)N2CCOCC2)c2ccc(-c3cccc(F)c3)cc12] | 1-amino-7-(3-fluorophenyl)-N-(2-morpholino-2-oxo-ethyl)isoquinoline-4-carboxamide | 81 3.5% A | 1.092 409.0 0-60AB | $^1$H NMR (400 MHz, MeOD-d$_4$) δ 8.81 (s, 1H), 8.55 (d, J = 8.8 Hz, 1H), 8.36-8.33 (m, 1H), 7.93 (s, 1H), 7.68-7.53 (m, 3H), 7.22 (m, 1H), 7.24-7.19 (m, 1H), 4.33 (s, 2H), 3.76-3.70 (m, 4H), 3.65-3.59 (m, 4H). |

-continued

| Structure | IUPAC Name | No./ Yield/ General Method | LCMS R_T (min)/ M + H+/ method | ¹H NMR (ppm) |
|---|---|---|---|---|
| 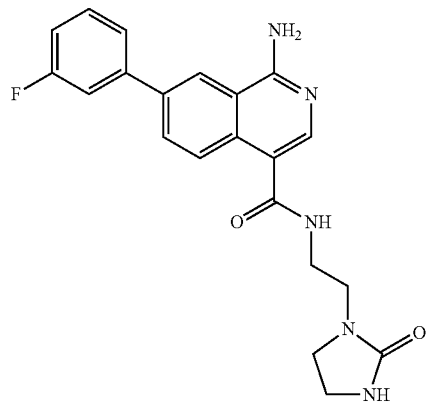 [SMILES: Nc1ncc(C(=O)NCCN2CCNC2=O)c2ccc(-c3cccc(F)c3)cc12] | 1-amino-7-(3-fluorophenyl)-N-[2-(2-oxoimidazolidin-1-yl)ethyl]isoquinoline-4-carboxamide | 82 13.4% A | 1.052 394.0 0-60AB | ¹H NMR (400 MHz, DMSO-d₆) δ 8.99 (s, 1H), 8.74 (m, 1H), 8.39-8.36 (m, 2H), 7.84-7.78 (m, 3H), 7.63-7.57 (m, 1H), 7.33-7.28 (m, 1H), 3.48-3.37 (m, 4H), 3.27-3.20 (m, 4H). |
| 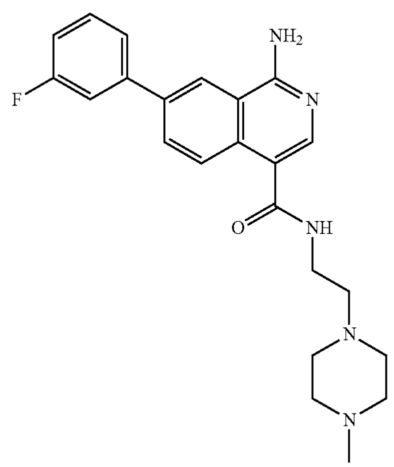 [SMILES: CN1CCN(CCNC(=O)c2cnc(N)c3cc(-c4cccc(F)c4)ccc23)CC1] | 1-amino-7-(3-fluorophenyl)-N-[2-(4-methylpiperazin-1-yl)ethyl]isoquinoline-4-carboxamide | 83 6% A | 0.992 408.1 0-60AB | ¹H NMR (400 MHz, MeOD-d₄) δ 8.53 (s, 1H), 8.42 (d, J = 8.8 Hz, 1H), 8.31 (s, 1H), 8.10-8.05 (m, 2H), 7.67-7.51 (m, 3H), 7.19-7.14 (m, 1H), 3.61 (t, J = 6.0 Hz, 2H), 2.93-2.74 (m, 9H). |
| 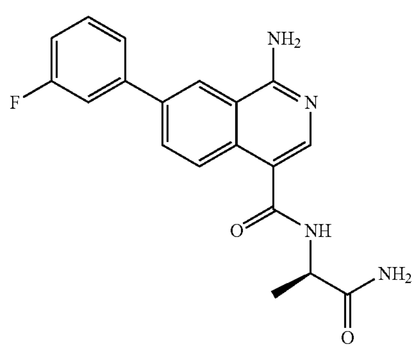 [SMILES: C[C@@H](NC(=O)c1cnc(N)c2cc(-c3cccc(F)c3)ccc12)C(N)=O] | 1-amino-N-[(1R)-2-amino-1-methyl-2-oxo-ethyl]-7-(3-fluorophenyl)isoquinoline-4-carboxamide | 84 2.8% A | 1.049 352.9 0-60AB | ¹H NMR (400 MHz, MeOD-d₄) δ 8.80 (s, 1H), 8.46 (d, J = 8.8 Hz, 1H), 8.34-8.31 (m, 1H), 7.93 (s, 1H), 7.68-7.53 (m, 3H), 7.23-7.18 (m, 1H), 4.63-4.58 (m, 1H), 1.50 (m, J = 7.2 Hz, 3H). |
| 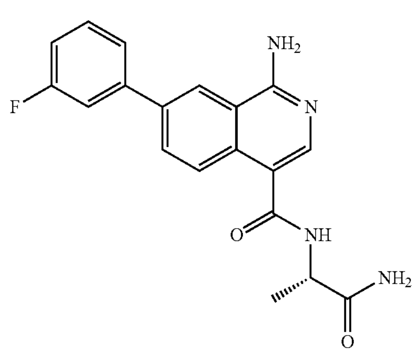 [SMILES: C[C@H](NC(=O)c1cnc(N)c2cc(-c3cccc(F)c3)ccc12)C(N)=O] | 1-amino-N-[(1S)-2-amino-1-methyl-2-oxo-ethyl]-7-(3-fluorophenyl)isoquinoline-4-carboxamide | 85 1.1% A | 1.043 353.1 0-60AB | ¹H NMR (400 MHz, MeOD-d₄) δ 8.80 (s, 1H), 8.46 (d, J = 8.4 Hz, 1H), 8.34-8.32 (m, 1H), 7.94 (s, 1H), 7.68-7.53 (m, 3H), 7.23-7.18 (m, 1H), 4.63-4.58 (m, 1H), 1.50 (m, J = 7.2 Hz, 3H). |

-continued

| Structure | IUPAC Name | No./ Yield/ General Method | LCMS R_T (min)/ M + H+/ method | $^1$H NMR (ppm) |
|---|---|---|---|---|
| 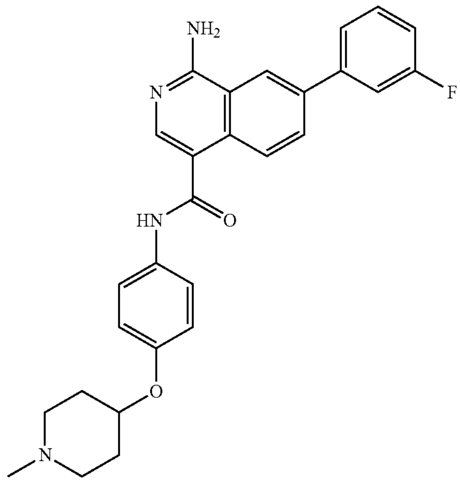 [SMILES: CN1CCC(Oc2ccc(NC(=O)c3cnc(N)c4cc(-c5cccc(F)c5)ccc34)cc2)CC1] | 1-amino-7-(3-fluorophenyl)-N-[4-[(1-methyl-4-piperidyl)oxy]phenyl]isoquinoline-4-carboxamide | 86 30% A | 1.099 471.0 0-60AB | $^1$H NMR (400 MHz, Methanol-d4) δ: 8.85 (s, 1H), 8.46 (d, J = 8.8 Hz, 1H), 8.37 (d, J = 8.8 Hz, 1H), 7.98 (s, 1H), 7.69-7.62 (m, 3H), 7.59-7.54 (m, 2H), 7.22 (t, J = 8.8 Hz, 1H), 7.09 (d, J = 9.2 Hz, 1H), 7.04 (d, J = 9.2 Hz, 1H), 4.59-4.51 (m, 1H), 3.63-3.60 (m, 1H), 3.40-3.32 (m, 2H), 3.23-3.19 (m, 1H), 2.93 (s, 3H), 2.41-2.38 (m, 1H), 2.28-2.24 (m, 1H), 2.14-2.08 (m, 1H), 1.94-1.87 (m, 1H). |
| 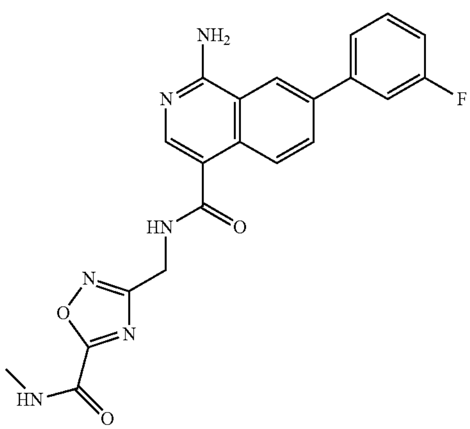 [SMILES: CNC(=O)c1nc(CNC(=O)c2cnc(N)c3cc(-c4cccc(F)c4)ccc23)no1] | 3-[[[1-amino-7-(3-fluorophenyl)isoquinoline-4-carbonyl]amino]methyl]-N-methyl-1,2,4-oxadiazole-5-carboxamide | 87 26% A | 1.049 420.9 0-60AB | $^1$H NMR (400 MHz, DMSO-d6) δ: 9.33 (d, J = 4.8 Hz, 1H), 9.04 (t, J = 5.6 Hz, 1H), 8.65 (s, 1H), 8.49 (d, J = 8.8 Hz, 1H), 8.15-8.11 (m, 3H), 7.79-7.73 (m, 4H), 7.58-7.52 (m, 1H), 7.23 (t, J = 8.0 Hz, 1H), 4.66 (d, J = 5.6 Hz, 2H), 2.78 (d, J = 4.8 Hz, 3H). |
| 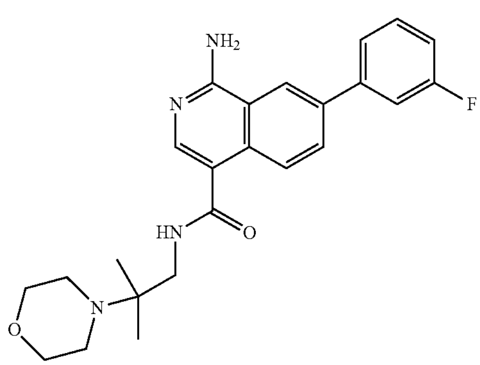 [SMILES: CC(C)(CNC(=O)c1cnc(N)c2cc(-c3cccc(F)c3)ccc12)N1CCOCC1] | 1-amino-7-(3-fluorophenyl)-N-(2-methyl-2-morpholino-propyl)isoquinoline-4-carboxamide | 88 22% A | 0.972 423.0 0-60AB | $^1$H NMR (400 MHz, DMSO-d6) δ: 10.75 (m, 1H), 9.07 (t, J = 6.4 Hz, 1H), 9.03 (s, 1H), 8.41 (s, 1H), 8.35 (s, 1H), 7.84-7.79 (m, 2H), 7.62-7.57 (m, 1H), 7.33-7.28 (m, 1H), 4.08-3.95 (m, 4H), 3.68 (d, J = 6.0 Hz, 2H), 3.54 (d, J = 6.0 Hz, 2H), 3.23-3.20 (m, 2H), 1.42 (s, 6H). |

| Structure | IUPAC Name | No./ Yield/ General Method | LCMS R_T (min)/ M + H+/ method | 1H NMR (ppm) |
|---|---|---|---|---|
| 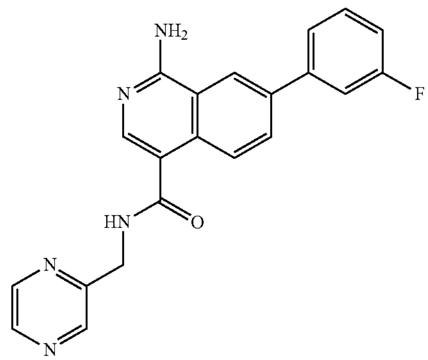 [SMILES: Nc1ncc(C(=O)NCc2cnccn2)c2ccc(-c3cccc(F)c3)cc12] | 1-amino-7-(3-fluorophenyl)-N-(pyrazin-2-ylmethyl)isoquinoline-4-carboxamide | 89 31% A | 1.078 373.9 0-60AB | 1H NMR (400 MHz, DMSO-d6) δ: 9.43 (t, J = 6.0 Hz, 1H), 9.06 (s, 1H), 8.77 (s, 1H), 8.65 (s, 1H), 8.59 (s, 1H), 8.49-8.43 (m, 2H), 8.08 (s, 1H), 7.83 (t, J = 7.2 Hz, 2H), 7.65-7.59 (m, 1H), 7.37-7.30 (m, 1H), 4.68 (d, J = 6.0 Hz, 2H). |
| 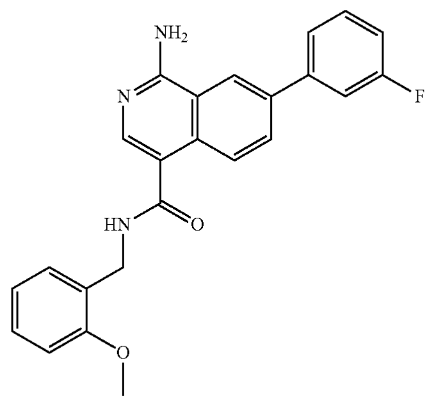 [SMILES: COc1ccccc1CNC(=O)c1cnc(N)c2cc(-c3cccc(F)c3)ccc12] | 1-amino-7-(3-fluorophenyl)-N-[(2-methoxyphenyl)methyl]isoquinoline-4-carboxamide | 90 33% A | 1.252 401.9 0-60AB | 1H NMR (400 MHz, MeOH-d4) δ: 8.83 (s, 1H), 8.42-8.35 (m, 2H), 7.80 (s, 1H), 7.71-7.56 (m, 3H), 7.39 (dd, J = 7.2 1.6 Hz, 1H), 7.33 (t, J = 8.0 Hz, 1H), 7.26-7.24 (m, 1H), 5.65 (s, 2H), 3.93 (s, 3H). |
| 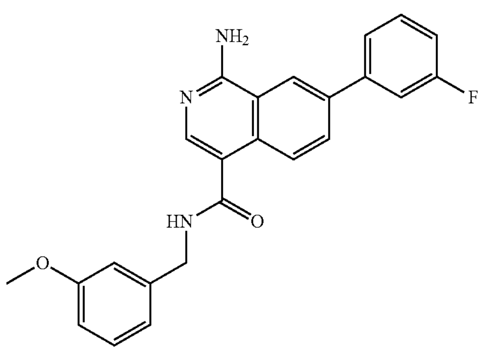 [SMILES: COc1cccc(CNC(=O)c2cnc(N)c3cc(-c4cccc(F)c4)ccc23)c1] | 1-amino-7-(3-fluorophenyl)-N-[(3-methoxyphenyl)methyl]isoquinoline-4-carboxamide | 91 34% A | 1.162 401.9 0-60AB | 1H NMR (400 MHz, DMSO-d6) δ: 8.85 (t, J = 5.6 Hz, 1H), 8.62 (s, 1H), 8.59 (d, J = 8.8 Hz, 1H), 8.19 (s, 1H), 8.09 (dd, J = 8.8 1.6 Hz, 1H), 7.79-7.75 (m, 2H), 7.60-7.54 (m, 1H), 7.44 (s, 2H), 7.29-7.22 (m, 2H), 6.96-6.94 (m, 2H), 6.83 (dd, J = 8.8 2.0 Hz, 1H), 4.48 (d, J = 6.0 Hz, 2H), 3.76 (s, 3H). |
| 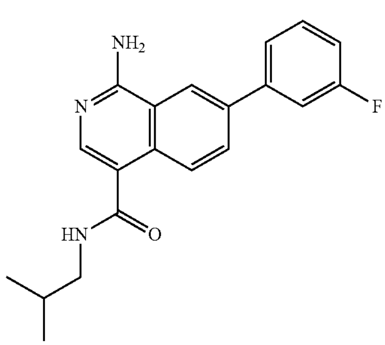 [SMILES: CC(C)CNC(=O)c1cnc(N)c2cc(-c3cccc(F)c3)ccc12] | 1-amino-7-(3-fluorophenyl)-N-isobutyl-isoquinoline-4-carboxamide | 92 42% A | 1.229 337.9 0-60AB | 1H NMR (400 MHz, MeOH-d4) δ: 8.84 (s, 1H), 8.76 (bs, 1H), 8.43-8.37 (m, 2H), 7.81 (s, 1H), 7.71-7.56 (m, 3H), 7.24 (t, J = 8.8 Hz, 1H), 3.32-3.28 (m, 2H), 2.02-1.96 (m, 1H), 1.05 (d, J = 6.4 Hz, 6H). |

| Structure | IUPAC Name | No./ Yield/ General Method | LCMS R$_T$ (min)/ M + H$^+$/ method | $^1$H NMR (ppm) |
|---|---|---|---|---|
| 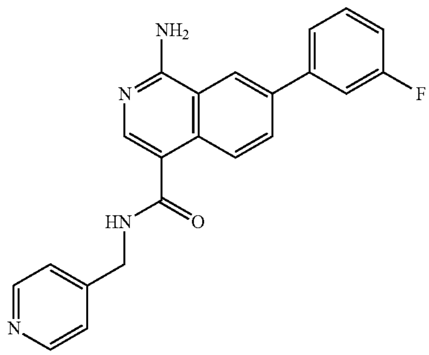 [SMILES: Nc1ncc(C(=O)NCc2ccncc2)c2ccc(-c3cccc(F)c3)cc12] | 1-amino-7-(3-fluorophenyl)-N-(4-pyridylmethyl)isoquinoline-4-carboxamide | 93 27% A | 0.950 372.9 0-60AB | $^1$H NMR (400 MHz, DMSO-d6) δ: 8.92 (t, J = 6.0 Hz, 1H), 8.60 (s, 1H), 8.52-8.45 (m, 3H), 8.23 (s, 1H), 8.06 (dd, J = 8.8 1.6 Hz, 1H), 7.74 (t, J = 8.8 Hz, 2H), 7.57-7.51 (m, 1H), 7.45 (s, 1H), 7.24 (s, 2H), 7.22-7.21 (m, 1H), 4.49 (d, J = 5.6 Hz, 2H). |
| 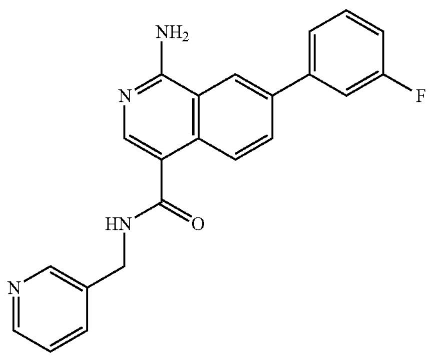 [SMILES: Nc1ncc(C(=O)NCc2cccnc2)c2ccc(-c3cccc(F)c3)cc12] | 1-amino-7-(3-fluorophenyl)-N-(3-pyridylmethyl)isoquinoline-4-carboxamide | 94 18% A | 0.976 372.9 0-60AB | $^1$H NMR (400 MHz, DMSO-d6) δ: 9.53 (t, J = 6.0 Hz, 1H), 9.04 (s, 1H), 8.91 (s, 1H), 8.78 (d, J = 4.8 Hz, 1H), 8.48-8.39 (m, 3H), 8.13 (s, 1H), 7.96-7.93 (m, 1H), 7.84-7.79 (m, 2H), 7.62-7.56 (m, 1H), 7.34-7.30 (m, 1H), 4.67 (d, J = 6.0 Hz, 2H). |
| 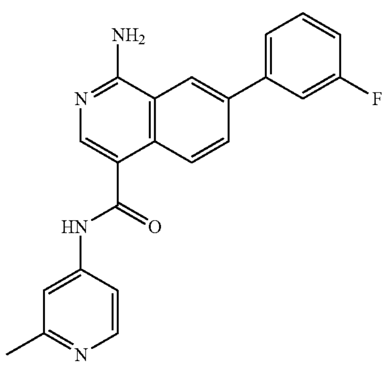 [SMILES: Cc1cc(NC(=O)c2cnc(N)c3cc(-c4cccc(F)c4)ccc23)ccn1] | 1-amino-7-(3-fluorophenyl)-N-(2-methyl-4-pyridyl)isoquinoline-4-carboxamide | 95 12% A | 1.119 372.9 0-60AB | $^1$H NMR (400 MHz, DMSO-d6) δ: 12.1 (s, 1H), 9.05 (s, 1H), 8.63 (d, J = 6.8 Hz, 1H), 8.48-8.40 (m, 3H), 8.21 (s, 1H), 8.11 (dd, J = 6.8 2.0 Hz, 1H), 7.85-7.80 (m, 2H), 7.63-7.57 (m, 1H), 7.33-7.28 (m, 1H), 2.70 (s, 3H). |
| 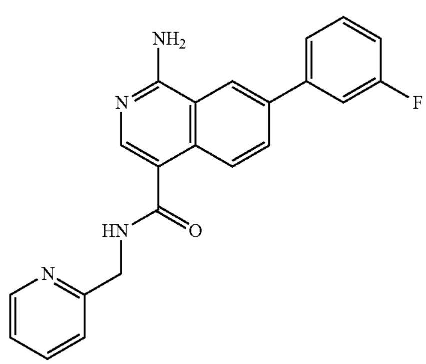 [SMILES: Nc1ncc(C(=O)NCc2ccccn2)c2ccc(-c3cccc(F)c3)cc12] | 1-amino-7-(3-fluorophenyl)-N-(2-pyridylmethyl)isoquinoline-4-carboxamide | 96 30% A | 0.977 372.9 0-60AB | $^1$H NMR (400 MHz, DMSO-d6) δ: 9.56 (t, J = 6.0 Hz, 1H), 9.05 (s, 1H), 8.73 (d, J = 5.2 Hz, 1H), 8.46 (d, J = 8.8 Hz, 1H), 8.42 (dd, J = 8.8 Hz, 1H), 8.25 (t, J = 7.6 Hz, 1H), 8.21 (s, 1H), 7.84-7.79 (m, 3H), 7.69 (t, J = 6.0 Hz, 1H), 7.62-7.56 (m, 1H), 7.34-7.28 (m, 1H), 4.77 (d, J = 5.6 Hz, 2H). |

-continued

| Structure | IUPAC Name | No./ Yield/ General Method | LCMS $R_T$ (min)/ M + H$^+$/ method | $^1$H NMR (ppm) |
|---|---|---|---|---|
| 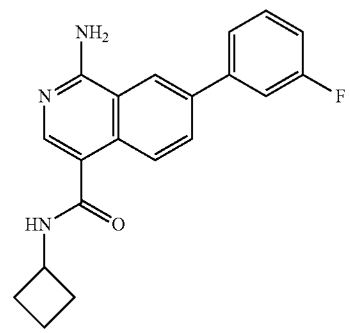 [SMILES: Nc1ncc(C(=O)NC2CCC2)c2ccc(-c3cccc(F)c3)cc12] | 1-amino-N-cyclobutyl-7-(3-fluorophenyl)isoquinoline-4-carboxamide | 97 25% A | 1.120 335.9 0-60AB | $^1$H NMR (400 MHz, DMSO-d6) δ: 8.97 (s, 1H), 8.90 (d, J = 7.2 Hz, 1H), 8.39 (s, 2H), 7.91 (s, 1H), 7.81-7.77 (m, 2H), 7.63-7.56 (m, 1H), 7.32-7.27 (m, 1H), 4.44-4.38 (m, 1H), 2.26-2.23 (m, 2H), 2.09-2.02 (m, 2H), 1.73-1.67 (m, 2H). |
| 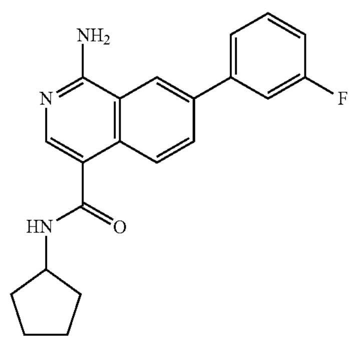 [SMILES: Nc1ncc(C(=O)NC2CCCC2)c2ccc(-c3cccc(F)c3)cc12] | 1-amino-N-cyclopentyl-7-(3-fluorophenyl)isoquinoline-4-carboxamide | 98 35% A | 1.194 349.9 0-60AB | $^1$H NMR (400 MHz, MeOH-d4) δ: 8.84 (s, 1H), 8.40-8.35 (m, 2H), 7.80 (s, 1H), 7.71-7.56 (m, 3H), 7.26-7.21 (m, 1H), 4.42-4.39 (m, 1H), 2.14-2.08 (m, 2H), 1.84-1.77 (m, 2H), 1.70-1.63 (m, 4H). |
| 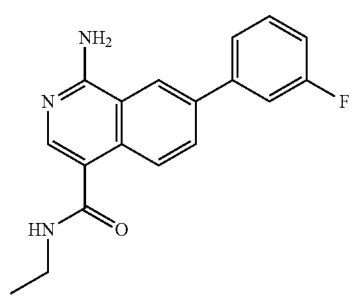 [SMILES: CCNC(=O)c1cnc(N)c2cc(-c3cccc(F)c3)ccc12] | 1-amino-N-ethyl-7-(3-fluorophenyl)isoquinoline-4-carboxamide | 99 9% A | 1.089 310.1 0-60AB | $^1$H NMR (400 MHz, DMSO-d6) δ: 8.58 (s, 1H), 8.44 (d, J = 8.8 Hz, 1H), 8.28-8.25 (m, 1H), 8.06-8.04 (m, 2H), 7.76-7.72 (m, 2H), 7.57-7.51 (m, 1H), 7.35 (bs, 2H), 7.24-7.19 (m, 1H), 3.27-3.26 (m, 2H), 1.13 (t, J = 7.2 Hz, 3H). |
| 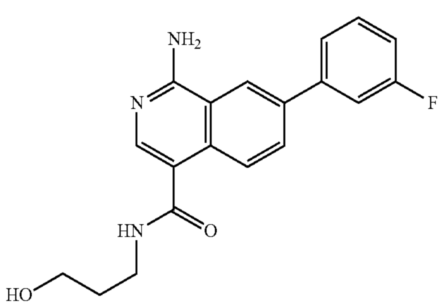 [SMILES: Nc1ncc(C(=O)NCCCO)c2ccc(-c3cccc(F)c3)cc12] | 1-amino-7-(3-fluorophenyl)-N-(3-hydroxypropyl)isoquinoline-4-carboxamide | 100 15% A | 1.094 339.9 0-60AB | $^1$N NMR (400 MHz, DMSO-d6) δ: 9.02 (s, 1H), 8.68 (t, J = 6.4 Hz, 1H), 8.40 (s, 2H), 7.90 (s, 1H), 7.84-7.78 (m, 2H), 7.62-7.56 (m, 1H), 7.31-7.27 (m, 1H), 3.49 (t, J = 6.4 Hz, 2H), 3.36-3.31 (m, 2H), 1.73-1.66 (m, 2H). |

| Structure | IUPAC Name | No./ Yield/ General Method | LCMS $R_T$ (min)/ M + H+/ method | 1H NMR (ppm) |
|---|---|---|---|---|
| 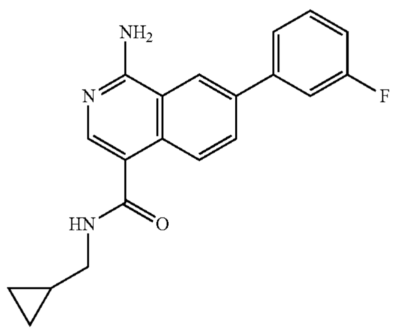 [SMILES: Nc1ncc(C(=O)NCC2CC2)c2ccc(-c3cccc(F)c3)cc12] | 1-amino-N-(cyclopropyl methyl)-7-(3-fluorophenyl) isoquinoline-4-carboxamide | 101 A 20% | 1.158 335.9 0-60AB | 1H NMR (400 MHz, MeOH-d4) δ: 8.80 (s, 1H), 8.39 (d, J = 8.8 Hz, 1H), 8.34 (dd, J = 8.8 1.6 Hz, 1H), 7.79 (s, 1H), 7.67-7.52 (m, 3H), 7.24-7.18 (m, 1H), 3.30-3.29 (m, 2H), 1.15-1.08 (m, 1H), 0.60-0.55 (m, 2H), 0.33-0.30 (m, 2H). |
| 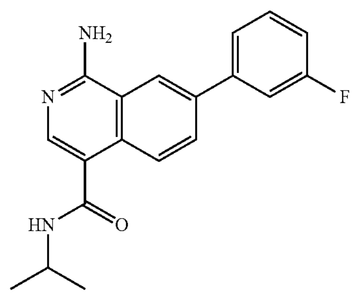 [SMILES: CC(C)NC(=O)c1cnc(N)c2cc(-c3cccc(F)c3)ccc12] | 1-amino-7-(3-fluorophenyl)-N-isopropyl-isoquinoline-4-carboxamide | 102 22% A | 1.087 324.0 0-60AB | 1H NMR (400 MHz, DMSO-d6) δ: 8.96 (s, 1H), 8.39 (d, J = 7.6 Hz, 1H), 8.38 (s, 2H), 7.86 (s, 1H), 7.81-7.77 (m, 2H), 7.62-7.56 (m, 1H), 7.32-7.27 (m, 1H), 4.13-4.05 (m, 1H), 1.18 (d, J = 6.4 Hz, 6H). |
| 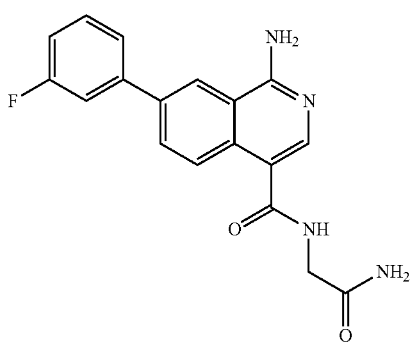 [SMILES: NC(=O)CNC(=O)c1cnc(N)c2cc(-c3cccc(F)c3)ccc12] | 1-amino-N-(2-amino-2-oxo-ethyl)-7-(3-fluorophenyl) isoquinoline-4-carboxamide | 103 10% A | 1.006 338.9 0-60AB | 1H NMR (400 MHz, DMSO-d6) δ 8.59 (s, 1H), 8.45 (d, J = 8.8 Hz, 1H), 8.42 (t, J = 6.0 Hz, 1H), 8.18 (s, 1H), 8.08-8.05 (m, 1H), 7.76-7.71 (m, 2H), 7.56-7.52 (m, 3H), 7.35 (bs, 1H), 7.23-7.19 (m, 1H), 7.01 (bs, 1H), 3.81 (d, J = 6.0 Hz, 2H). |
| 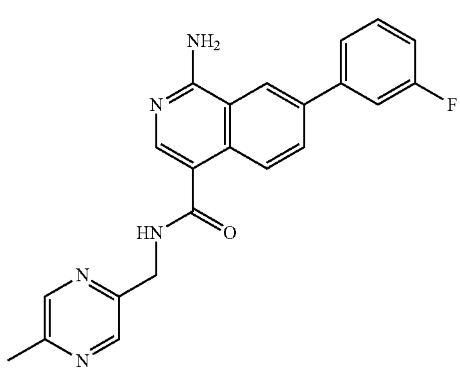 [SMILES: Cc1cnc(CNC(=O)c2cnc(N)c3cc(-c4cccc(F)c4)ccc23)cn1] | 1-amino-7-(3-fluorophenyl)-N-[(5-methylpyrazin-2-yl)methyl]isoquinoline-4-carboxamide | 104 15% A | 1.094 387.9 0-60AB | 1H NMR (400 MHz, DMSO-d6) δ: 9.06 (t, J = 6.0 Hz, 1H), 8.73 (s, 1H), 8.57 (s, 1H), 8.50 (t, J = 8.8 Hz, 2H), 8.21-8.14 (m, 2H), 8.04 (bs, 2H), 7.80-7.76 (m, 2H), 7.61-7.56 (m, 1H), 7.27 (t, J = 8.0 Hz, 1H), 4.60 (d, J = 6.0 Hz, 2H), 2.51 (s, 3H). |

| Structure | IUPAC Name | No./ Yield/ General Method | LCMS $R_T$ (min)/ M + H+/ method | 1H NMR (ppm) |
|---|---|---|---|---|
| 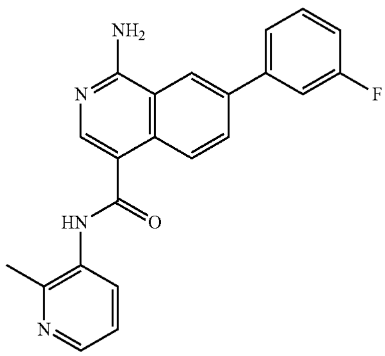 [SMILES: Cc1ncccc1NC(=O)c1cnc(N)c2cc(-c3cccc(F)c3)ccc12] | 1-amino-7-(3-fluorophenyl)-N-(2-methyl-3-pyridyl)isoquinoline-4-carboxamide | 105 14% A | 1.081 372.9 0-60AB | 1H NMR (400 MHz, MeOH-d4) δ: 8.91-8.89 (m, 2H), 8.65 (dd, J = 5.6 1.6 Hz, 1H), 8.60 (d, J = 5.6 Hz, 1H), 8.42 (d, J = 8.8 Hz, 1H), 8.27 (s, 1H), 8.04-8.00 (m, 1H), 7.73-7.57 (m, 3H), 7.28-7.23 (m, 1H), 2.86 (s, 3H). |
| 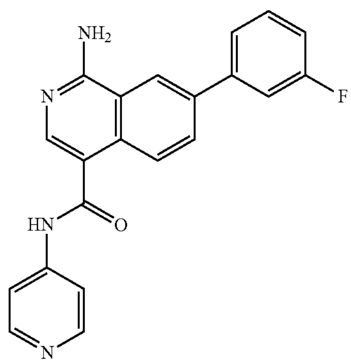 [SMILES: Nc1ncc(C(=O)Nc2ccncc2)c2ccc(-c3cccc(F)c3)cc12] | 1-amino-7-(3-fluorophenyl)-N-(4-pyridyl)isoquinoline-4-carboxamide | 106 9% A | 1.034 358.9 0-60AB | 1H NMR (400 MHz, MeOH-d4) δ: 9.62 (s, 1H), 8.88 (s, 1H), 8.78 (d, J = 8.8 Hz, 1H), 8.66 (d, J = 5.6 Hz, 1H), 8.61 (d, J = 8.8 Hz, 1H), 8.38 (d, J = 8.8 Hz, 1H), 8.23 (s, 1H), 8.16-7.12 (m, 1H), 7.71-7.57 (m, 3H), 7.23-7.21 (m, 1H). |
| 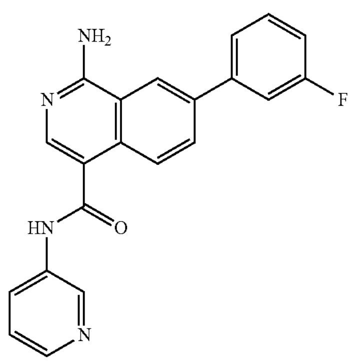 [SMILES: Nc1ncc(C(=O)Nc2cccnc2)c2ccc(-c3cccc(F)c3)cc12] | 1-amino-7-(3-fluorophenyl)-N-(3-pyridyl)isoquinoline-4-carboxamide | 107 10% A | 1.024 358.9 0-60AB | 1H NMR (400 MHz, MeOH-d4) δ: 8.87 (s, 1H), 8.72 (d, J = 6.8 Hz, 2H), 8.59 (d, J = 8.8 Hz, 1H), 8.40-8.35 (m, 3H), 8.25 (s, 1H), 7.70-7.55 (m, 3H), 7.25-7.20 (m, 1H). |
| 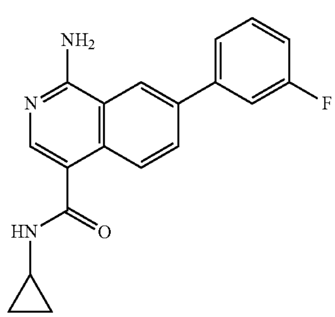 [SMILES: Nc1ncc(C(=O)NC2CC2)c2ccc(-c3cccc(F)c3)cc12] | 1-amino-N-cyclopropyl-7-(3-fluorophenyl)isoquinoline-4-carboxamide | 108 16% A | 1.164 322.1 0-60AB | 1H NMR (400 MHz, DMSO-d6) δ: 8.95 (s, 1H), 8.68 (d, J = 4.4 Hz, 1H), 8.43-8.38 (m, 2H), 7.86 (s, 1H), 7.81-7.77 (m, 2H), 7.63-7.57 (m, 1H), 7.32-7.27 (m, 1H), 2.90-2.84 (m, 1H), 0.75-0.70 (m, 2H), 0.60-0.56 (m, 2H). |

-continued

| Structure | IUPAC Name | No./ Yield/ General Method | LCMS R_T (min)/ M + H+/ method | ¹H NMR (ppm) |
|---|---|---|---|---|
| 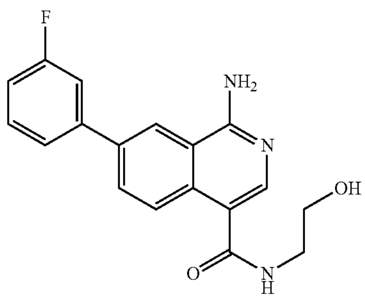 [SMILES: Nc1ncc(C(=O)NCCO)c2ccc(-c3cccc(F)c3)cc12] | 1-amino-7-(3-fluorophenyl)-N-(2-hydroxyethyl)isoquinoline-4-carboxamide | 109 7% A | 1.021 326.1 0-60AB | ¹H NMR (400 MHz, MeOH-d$_4$) δ 8.83 (s, 1H), 8.47 (d, J = 8.4 Hz, 1H), 8.38 (d, J = 8.8 Hz, 1H), 7.89 (s, 1H), 7.71-7.56 (m, 3H), 7.27-7.22 (m, 1H), 3.80 (t, J = 5.6 Hz, 2H), 3.59 (t, J = 5.6 Hz, 2H). |
| 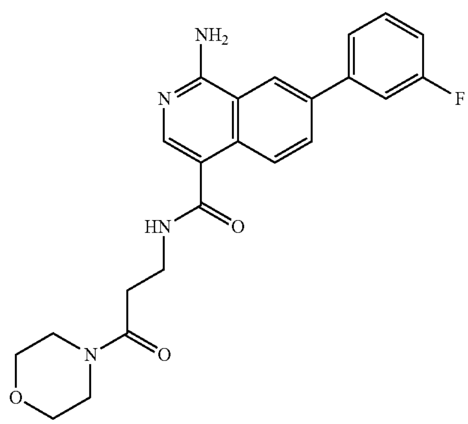 [SMILES: Nc1ncc(C(=O)NCCC(=O)N2CCOCC2)c2ccc(-c3cccc(F)c3)cc12] | 1-amino-7-(3-fluorophenyl)-N-(3-morpholino-3-oxo-propyl)isoquinoline-4-carboxamide | 110 32% A | 1.036 422.9 0-60AB | ¹H NMR (400 MHz, DMSO-d6) δ: 8.84 (s, 1H), 8.83 (bs, 1H), 8.56 (t, J = 5.6 Hz, 1H), 8.41 (d, J = 8.8 Hz, 1H), 8.30 (d, J = 8.8 Hz, 1H), 7.88 (s, 1H), 7.78-7.74 (m, 2H), 7.60-7.55 (m, 1H), 7.27 (t, J = 8.8 Hz, 1H), 3.56-3.51 (m, 10H), 2.63 (t, J = 7.2 Hz, 1H). |
| 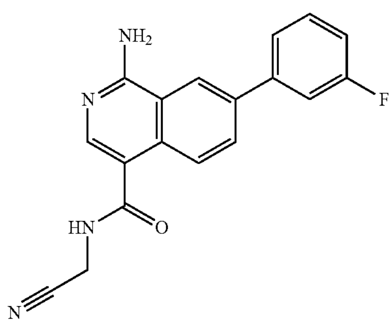 [SMILES: N#CCNC(=O)c1cnc(N)c2cc(-c3cccc(F)c3)ccc12] | 1-amino-N-(cyanomethyl)-7-(3-fluorophenyl)isoquinoline-4-carboxamide | 111 28% A | 1.065 321.1 0-60AB | ¹H NMR (400 MHz, DMSO-d6) δ: 9.21 (bs, 1H), 8.82 (s, 1H), 8.66 (bs, 1H), 8.47 (d, J =8.8 Hz, 1H), 8.31 (d, J = 8.0 Hz, 1H), 8.04 (s, 1H), 7.79-7.75 (m, 2H), 7.61-7.56 (m, 1H), 7.30-7.25 (m, 1H), 4.34 (d, J = 5.6 Hz, 2H). |
| 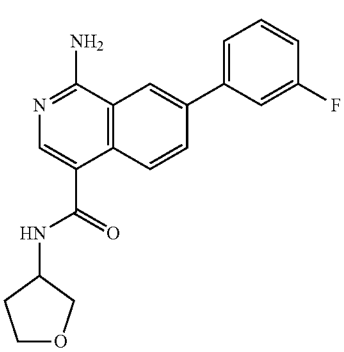 [SMILES: Nc1ncc(C(=O)NC2CCOC2)c2ccc(-c3cccc(F)c3)cc12] | 1-amino-7-(3-fluorophenyl)-N-tetrahydrofuran-3-yl-isoquinoline-4-carboxamide | 112 13% A | 1.046 351.9 0-60AB | ¹H NMR (400 MHz, DMSO-d6) δ: 8.59 (s, 1H), 8.46-8.40 (m, 2H), 8.11-8.04 (m, 3H), 7.77-7.72 (m, 2H), 7.57-7.51 (m, 1H), 7.40 (s, 2H), 7.24-7.19 (m, 1H), 4.49-4.42 (m, 1H), 3.90-3.80 (m, 2H), 3.73-3.68 (m, 1H), 3.61-6.57 (m, 1H), 2.19-2.10 (m, 1H), 1.94-1.86 (m, 1H). |

-continued

| Structure | IUPAC Name | No./ Yield/ General Method | LCMS R$_T$ (min)/ M + H$^+$/ method | $^1$H NMR (ppm) |
|---|---|---|---|---|
| 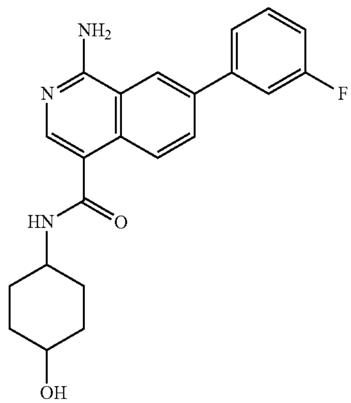 [SMILES: Nc1ncc(C(=O)NC2CCC(O)CC2)c2ccc(-c3cccc(F)c3)cc12] | 1-amino-7-(3-fluorophenyl)-N-(4-hydroxycyclohexyl)isoquinoline-4-carboxamide | 113 17% A | 1.091 354.9 0-60AB | $^1$H NMR (400 MHz, DMSO-d6) δ: 8.70 (s, 1H), 8.36 (d, J = 8.8 Hz, 1H), 8.22-8.14 (m, 2H), 8.11 (s, 1H), 7.98-7.91 (m, 2H), 7.78-7.73 (m, 2H), 7.59-7.53 (m, 1H), 7.27-7.22 (m, 1H), 4.54 (bs, 1H), 3.79-3.62 (m, 1H), 1.89-1.83 (m, 4H), 1.37-1.25 (m, 4H). |
| | 1-amino-7-(3-fluorophenyl)-N-[2-hydroxy-1-(hydroxymethyl)ethyl]isoquinoline-4-carboxamide | 114 16% A | 0.951 355.9 0-60AB | $^1$H NMR (400 MHz, DMSO-d6) δ: 8.94 (d, J = 8.8 Hz, 1H), 8.78 (s, 1H), 8.64 (s, 1H), 8.23 (s, 2H), 8.15 (dd, J = 8.8 2.0 Hz, 1H), 7.95-7.92 (m, 2H), 7.78-7.73 (m, 2H), 7.57-7.51 (m, 1H), 7.24-7.20 (m, 1H), 4.32-4.21 (m, 2H), 3.65-3.52 (m, 2H), 3.34-3.31 (m, 1H). |
| 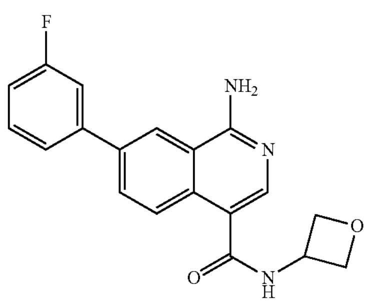 [SMILES: Nc1ncc(C(=O)NC2COC2)c2ccc(-c3cccc(F)c3)cc12] | 1-amino-7-(3-fluorophenyl)-N-(oxetan-3-yl)isoquinoline-4-carboxamide | 115 6% A | 1.113 337.9 0-60AB | $^1$H NMR (400 MHz, DMSO-d$_6$) δ 8.96 (d, J = 6.4 Hz, 1H), 8.59 (s, 1H), 8.45 (d, J = 9.2 Hz, 1H), 8.18 (s, 1H), 8.06-8.04 (m, 1H), 7.76-7.75 (m, 2H), 7.56-7.51 (m, 1H), 7.46 (bs, 2H), 7.24-7.19 (m, 1H), 5.05-5.00 (m, 1H), 4.78 (d, J = 6.4 Hz, 2H), 4.58 (d, J = 6.4 Hz, 1H). |
| 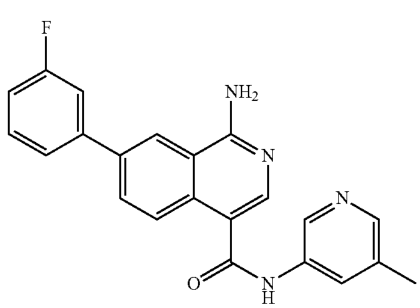 [SMILES: Cc1cncc(NC(=O)c2cnc(N)c3cc(-c4cccc(F)c4)ccc23)c1] | 1-amino-7-(3-fluorophenyl)-N-(5-methyl-3-pyridyl)isoquinoline-4-carboxamide | 116 16% A | 1.105 372.9 0-60AB | $^1$H NMR (400 MHz, MeOH-d4) δ: 8.72 (s, 1H), 8.54 (s, 1H), 8.47 (d, J = 8.8 Hz, 1H), 8.22 (s, 1H), 8.16 (s, 1H), 8.11-8.07 (m, 2H), 7.65 (d, J = 8.8 Hz, 1H), 7.60 (dd, J = 6.4 2.0 Hz, 1H), 7.58-7.49 (m, 1H), 7.16-7.11 (m, 1H), 2.40 (s, 3H). |

| Structure | IUPAC Name | No./ Yield/ General Method | LCMS $R_T$ (min)/ M + H+/ method | 1H NMR (ppm) |
|---|---|---|---|---|
| 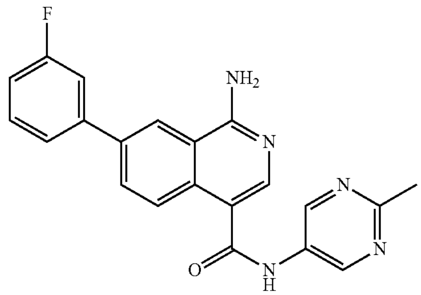 [SMILES: Cc1ncc(NC(=O)c2cnc(N)c3cc(-c4cccc(F)c4)ccc23)cn1] | 1-amino-7-(3-fluorophenyl)-N-(2-methylpyrimidin-5-yl)isoquinoline-4-carboxamide | 117 9% A | 1.150 373.9 0-60AB | 1H NMR (400 MHz, MeOH-d4) δ: 9.21 (s, 2H), 8.86 (s, 1H), 8.57 (d, J = 8.8 Hz, 1H), 8.38 (dd, J = 8.8, 1.6 Hz, 1H), 8.12 (s, 1H), 7.69-7.54 (m, 3H), 7.25-7.20 (m, 1H), 2.75 (s, 3H). |
| 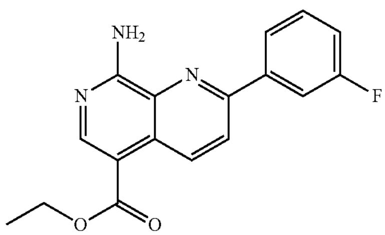 [SMILES: CCOC(=O)c1cnc(N)c2nc(-c3cccc(F)c3)ccc12] | ethyl 8-amino-2-(3-fluorophenyl)-1,7-naphthyridine-5-carboxylate | 118 | NA | 1H NMR (400 MHz, DMSO) δ 9.29-9.23 (d, J = 9.0 Hz, 1H), 8.69-8.64 (s, 1H), 8.52-8.39 (m, 2H), 8.31-8.14 (m, 2H), 8.14-7.96 (bs, 1H), 7.64-7.52 (m, 1H), 7.38-7.28 (m, 1H), 4.40-4.28 (q, J = 7.1 Hz, 2H), 1.40-1.33 (t, J = 7.1 Hz, 3H). |
| 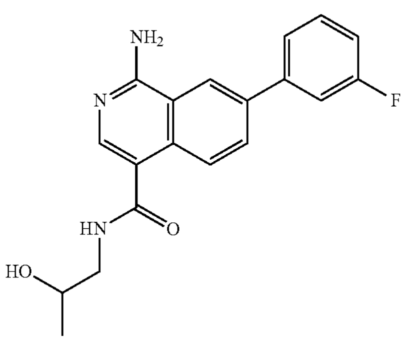 [SMILES: CC(O)CNC(=O)c1cnc(N)c2cc(-c3cccc(F)c3)ccc12] | 1-amino-7-(3-fluorophenyl)-N-(2-hydroxypropyl)isoquinoline-4-carboxamide | 119 25% A | 1.115 339.9 0-60AB | 1H NMR (400 MHz, DMSO-d6) δ: 9.00 (s, 1H), 8.68 (t, J = 6.0 Hz, 1H), 8.45-8.37 (m, 2H), 7.94 (s, 1H), 7.83-7.78 (m, 1H), 7.62-7.54 (m, 1H), 7.32-7.27 (m, 1H), 3.82-3.81 (m, 1H), 3.29-3.14 (m, 2H), 1.13-1.08 (m, 3H). |
| 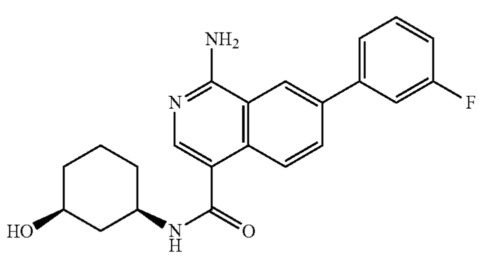 [SMILES: Nc1ncc(C(=O)N[C@@H]2CCC[C@H](O)C2)c2ccc(-c3cccc(F)c3)cc12] | 1-Amino-7-(3-fluoro-phenyl)-isoquinoline-4-carboxylic acid ((1R,3S)-3-hydroxy-cyclohexyl)-amide | 120 14% A | 1.126 380.0 0-60AB | 1H NMR (400 MHz, MeOH-d4) δ: 8.51 (s, 1H), 8.36 (d, J = 9.2 Hz, 1H), 8.06 (d, J = 8.8 Hz, 1H), 8.05 (s, 1H), 7.67-7.51 (m, 3H), 7.18-7.13 (m, 1H), 4.04-3.97 (m, 1H), 3.75-3.67 (m, 1H), 2.31-2.29 (m, 1H), 1.99-1.86 (m, 3H), 1.49-1.33 (m, 4H). |

-continued

| Structure | IUPAC Name | No./ Yield/ General Method | LCMS R_T (min)/ M + H+/ method | $^1$H NMR (ppm) |
|---|---|---|---|---|
| 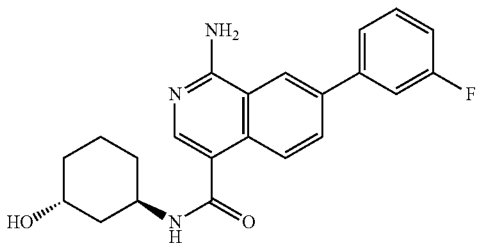 [SMILES: Nc1ncc(C(=O)N[C@@H]2CCC[C@@H](O)C2)c2ccc(-c3cccc(F)c3)cc12] | 1-Amino-7-(3-fluoro-phenyl)-isoquinoline-4-carboxylic acid ((1R,3R)-3-hydroxy-cyclohexyl)-amide | 121 18% A | 1.135 380.0 0-60AB | $^1$H NMR (400 MHz, MeOH-d4) δ: 8.48 (s, 1H), 8.30 (d, J = 9.2 Hz, 1H), 8.04 (dd, J = 8.8 2.0 Hz, 1H), 7.96 (bs, 1H), 7.64-7.47 (m, 3H), 7.15-7.10 (m, 1H), 4.39-4.34 (m, 1H), 4.13 (bs, 1H), 2.00-1.97 (m, 2H), 1.87-1.81 (m, 1H), 1.72-1.43 (m, 5H). |
| 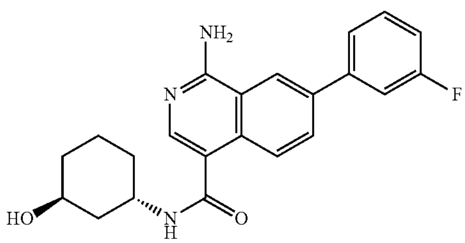 [SMILES: Nc1ncc(C(=O)N[C@H]2CCC[C@H](O)C2)c2ccc(-c3cccc(F)c3)cc12] | 1-Amino-7-(3-fluoro-phenyl)-isoquinoline-4-carboxylic acid ((1S,3S)-3-hydroxy-cyclohexyl)-amide | 122 24% A | 1.141 379.9 0-60AB | $^1$H NMR (400 MHz, MeOH-d4) δ: 8.50 (s, 1H), 8.33 (d, J = 9.2 Hz, 1H), 8.06 (dd, J = 8.8 2.0 Hz, 1H), 7.99 (s, 1H), 7.66-7.50 (m, 3H), 7.17-7.13 (m, 1H), 4.43-4.38 (m, 1H), 4.15 (bs, 1H), 2.04-2.01 (m, 2H), 1.90-1.84 (m, 1H), 1.76-1.51 (m, 5H). |
| 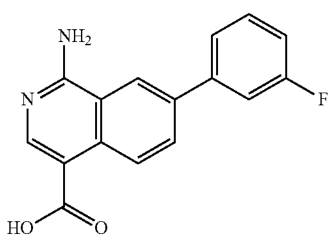 [SMILES: Nc1ncc(C(=O)O)c2ccc(-c3cccc(F)c3)cc12] | 1-amino-7-(3-fluorophenyl) isoquinoline-4-carboxylic acid | 123 23% A | 1.034 283.2 0-60AB | $^1$H NMR (400 MHz, MeOH-d4) δ: 9.25 (d, J = 8.8 Hz, 1H), 8.80 (s, 1H), 8.37-8.34 (m, 2H), 7.69-7.53 (m, 3H), 7.22-7.18 (m, 1H). |
| 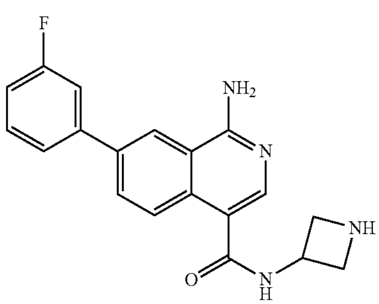 [SMILES: Nc1ncc(C(=O)NC2CNC2)c2ccc(-c3cccc(F)c3)cc12] | 1-amino-N-(azetidin-3-yl)-7-(3-fluorophenyl) isoquinoline-4-carboxamide | 124 16% E | 0.959 337.1 0-60AB | $^1$H NMR (400 MHz, DMSO-d6) δ: 8.92 (d, J = 6.8 Hz, 1H), 8.60 (s, 1H), 8.49 (d, J = 8.8 Hz, 1H), 8.22-8.17 (m, 3H), 8.07 (dd, J = 8.8 1.6 Hz, 1H), 7.76-7.72 (m, 2H), 7.57-7.52 (m, 3H), 7.25-7.20 (m, 1H), 4.83-4.77 (m, 1H), 4.07-4.02 (m, 2H), 43.97-3.93 (m, 2H). |

| Structure | IUPAC Name | No./ Yield/ General Method | LCMS R$_T$ (min)/ M + H$^+$/ method | $^1$H NMR (ppm) |
|---|---|---|---|---|
| 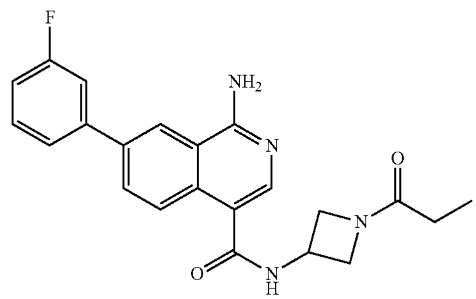 [SMILES: CCC(=O)N1CC(NC(=O)c2cnc(N)c3cc(-c4cccc(F)c4)ccc23)C1] | 1-amino-7-(3-fluorophenyl)-N-(1-propanoylazetidin-3-yl)isoquinoline-4-carboxamide | 125 10% G | 1.090 392.9 0-60AB | $^1$H NMR (400 MHz, DMSO-d6) δ: 8.55 (s, 1H), 8.42 (d, J = 8.8 Hz, 1H), 8.10 (dd, J = 8.8 1.6 Hz, 1H), 8.06 (s, 1H), 7.65-7.49 (m, 3H), 7.17-7.12 (m, 1H), 4.84-4.80 (m, 1H), 4.59 (t, J = 8.8 Hz, 1H), 4.37 (t, J = 8.8 Hz, 1H), 4.23-4.19 (m, 1H), 4.03-3.99 (m, 1H), 2.22-2.17 (m, 2H), 1.11 (t, J = 7.8 Hz, 3H). |
| | 1-amino-N-[1-(cyclopropanecarbonyl)azetidin-3-yl]-7-(3-fluorophenyl)isoquinoline-4-carboxamide | 126 9% G | 1.104 404.9 0-60AB | $^1$H NMR (400 MHz, MeOH-d4) δ: 8.59 (s, 1H), 8.45 (d, J = 8.4 Hz, 1H), 8.18-8.09 (m, 2H), 8.06 (s, 1H), 7.68-7.52 (m, 3H), 7.20-7.15 (m, 1H), 4.86-4.84 (m, 1H), 4.76 (t, J = 8.4 Hz, 1H), 4.43-4.35 (m, 2H), 4.07-4.03 (m, 1H), 1.67-1.61 (m, 1H), 0.90-0.85 (m, 4H). |
| 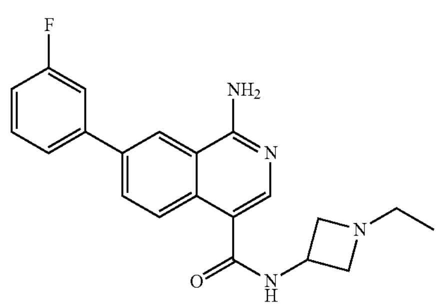 [SMILES: CCN1CC(NC(=O)c2cnc(N)c3cc(-c4cccc(F)c4)ccc23)C1] | 1-amino-N-(1-ethylazetidin-3-yl)-7-(3-fluorophenyl)isoquinoline-4-carboxamide | 127 9% E | 0.968 365.0. 0-60AB | $^1$H NMR (400 MHz, MeOH-d4) δ: 8.50-8.48 (m, 2H), 8.34 (bs, 1H), 8.14 (s, 1H), 8.04 (dd, J = 8.8 1.6 Hz, 1H), 7.63-7.48 (m, 3H), 7.16-7.11 (m, 1H), 4.81-4.77 (m, 1H), 4.48-4.43 (m, 2H), 4.31-4.26 (m, 2H), 3.35-3.33 (m, 2H), 1.24 (t, J = 7.2 Hz, 3H). |

-continued

| Structure | IUPAC Name | No./ Yield/ General Method | LCMS R$_T$ (min)/ M + H$^+$/ method | $^1$H NMR (ppm) |
|---|---|---|---|---|
| 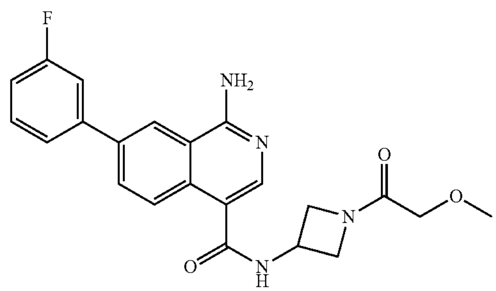 [SMILES: COCC(=O)N1CC(NC(=O)c2cnc(N)c3cc(-c4cccc(F)c4)ccc23)C1] | 1-amino-7-(3-fluorophenyl)-N-[1-(2-methoxyacetyl)azetidin-3-yl]isoquinoline-4-carboxamide | 128 8% G | 1.078 409.0 0-60AB | $^1$H NMR (400 MHz, MeOH-d4) δ: 8.57 (s, 1H), 8.45 (d, J = 8.8 Hz, 1H), 8.14-8.11 (m, 2H), 7.68-7.52 (m, 3H), 7.18-7.17 (m, 1H), 4.85-4.83 (m, 1H), 4.73-4.69 (m, 1H), 4.48-4.44 (m, 1H), 4.34-4.30 (m, 1H), 4.11-4.06 (m, 1H), 4.05 (s, 2H) 3.42 (s, 3H). |
| 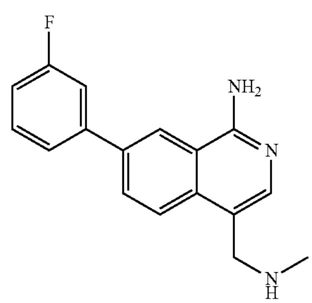 [SMILES: CNCc1cnc(N)c2cc(-c3cccc(F)c3)ccc12] | 7-(3-fluorophenyl)-4-(methylaminomethyl)isoquinolin-1-amine | 129 9% D | 0.934 282.1 0-60AB | $^1$H NMR (400 MHz, MeOH-d4) δ: 8.88 (s, 1H), 8.44 (dd, J = 8.8 1.6 Hz, 1H), 8.30 (d, J = 8.8 Hz, 1H), 7.88 (s, 1H), 7.71-7.56 (m, 3H), 7.26-7.21 (m, 1H), 4.59 (s, 2H), 2.85 (s, 3H). |
| | 1-amino-N-[1-[(cyclopropylcarbamoylamino)methyl]-2-hydroxy-ethyl]-7-(3-fluorophenyl)isoquinoline-4-carboxamide | 130 18% F | 1.053 438.0 0-60AB | $^1$H NMR (400 MHz, DMSO-d6) δ: 8.96 (d, J = 8.8 Hz, 1H), 8.79 (s, 1H), 8.66 (s, 1H), 8.22 (s, 2H), 8.17 (dd, J = 8.8 1.6 Hz, 1H), 7.93 (bs, 2H), 7.79-7.75 (m, 2H), 7.59-7.53 (m, 1H), 7.26-7.22 (m, 1H), 6.37 (s, 1H), 6.22 (bs, 1H), 4.27-4.16 (m, 2H), 3.30-3.17 (m, 4H), 2.42-2.40 (m, 1H), 0.57-0.59 (m, 2H), 0.34 (m, 2H). |

-continued

| Structure | IUPAC Name | No./ Yield/ General Method | LCMS R$_T$ (min)/ M + H$^+$/ method | $^1$H NMR (ppm) |
|---|---|---|---|---|
| 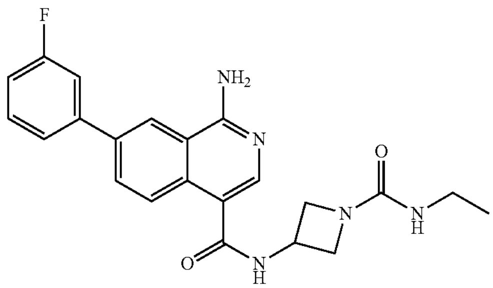 [SMILES: CCNC(=O)N1CC(NC(=O)c2cnc(N)c3cc(-c4cccc(F)c4)ccc23)C1] | 1-amino-N-[1-(ethylcarbamoyl)azetidin-3-yl]-7-(3-fluorophenyl)isoquinoline-4-carboxamide | 131 14% F | 1.098 407.9 0-60AB | $^1$H NMR (400 MHz, DMSO-d6) δ: 9.28 (d, J = 8.8 Hz, 1H), 8.62 (s, 1H), 8.41 (s, 1H), 8.11 (dd, J = 8.8 1.6 Hz, 1H), 7.78-7.73 (m, 2H), 7.62-7.52 (m, 3H), 7.25-7.20 (m, 1H), 5.96-5.87 (m, 2H), 4.36-4.30 (m, 2H), 4.04 (t, J = 6.4 Hz, 1H), 3.37-3.33 (m, 1H), 3.23-3.17 (m, 1H), 3.01-2.97 (m, 2H), 0.95 (t, J = 7.2 Hz, 3H). |
| | 1-amino-N-[1-(cyclopropylcarbamoyl)azetidin-3-yl]-7-(3-fluorophenyl)isoquinoline-4-carboxamide | 132 18% F | 1.112 420.0 0-60AB | $^1$H NMR (400 MHz, DMSO-d6) δ: 9.30 (d, J = 8.8 Hz, 1H), 8.64 (s, 1H), 8.43 (s, 1H), 8.14 (dd, J = 8.8 1.6 Hz, 1H), 7.65 (bs, 2H), 7.60-7.55 (m, 1H), 7.27-7.23 (m, 1H), 6.28 (s, 1H), 5.92-5.90 (m, 1H), 4.41-4.32 (m, 2H), 4.09 (t, J = 7.2 Hz, 1H), 3.42-3.37 (m, 1H), 3.26-3.20 (m, 1H), 2.42-2.39 (m, 1H), 0.56-0.48 (m, 2H), 0.345-0.336 (m, 2H). |
| 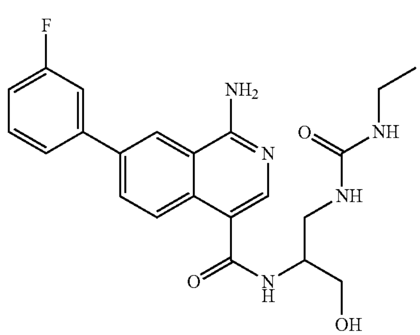 [SMILES: CCNC(=O)NCC(CO)NC(=O)c1cnc(N)c2cc(-c3cccc(F)c3)ccc12] | 1-amino-N-[1-[(ethylcarbamoyl-amino)methyl]-2-hydroxy-ethyl]-7-(3-fluorophenyl)isoquinoline-4-carboxamide | 133 20% F | 1.025 425.9 0-60AB | $^1$H NMR (400 MHz, DMSO-d6) δ: 8.95 (d, J = 8.8 Hz, 1H), 8.79 (s, 1H), 8.65 (s, 1H), 8.20 (bs, 2H), 8.16 (dd, J = 9.2 2.0 Hz, 1H), 7.92 (bs, 2H), 7.78-7.74 (m, 2H), 7.58-7.52 (m, 1H), 7.25-7.20 (m, 1H), 6.18 (bs, 1H), 6.05 (t, J = 5.2 Hz, 1H), 4.27-4.15 (m, 2H), 3.31-3.13 (m, 4H), 3.03-2.97 (m, 2H), 0.97 (t, J = 6.8 Hz, 3H). |

-continued

| Structure | IUPAC Name | No./ Yield/ General Method | LCMS $R_T$ (min)/ M + H$^+$/ method | $^1$H NMR (ppm) |
|---|---|---|---|---|
| 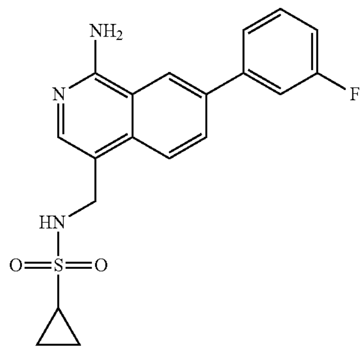 [SMILES: Nc1ncc(CNS(=O)(=O)C2CC2)c2ccc(-c3cccc(F)c3)cc12] | N-[[1-amino-7-(3-fluoro-phenyl)-4-isoquinolyl]methyl]cyclopropanesulfonamide | 134 13% D | 1.237 371.9 0-60AB | $^1$H NMR (400 MHz, DMSO-d6) δ: 9.37 (bs, 1H), 9.00 (s, 1H), 8.48-8.44 (m, 1H), 8.21 (d, J = 8.8 Hz, 1H), 7.85-7.80 (m, 2H), 7.69-7.67 (m, 2H), 7.60-7.57 (m, 1H), 7.32-7.28 (m, 1H), 4.44 (d, J = 6.0 Hz, 2H), 2.70-2.61 (m, 1H), 0.96-0.95 (m, 4H). |
| 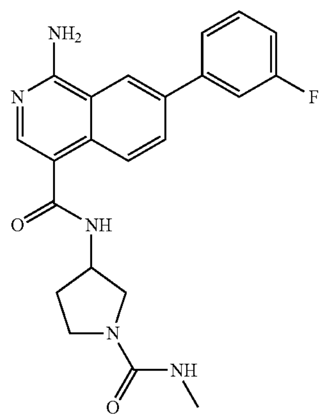 [SMILES: CNC(=O)N1CCC(NC(=O)c2cnc(N)c3cc(-c4cccc(F)c4)ccc23)C1] | 1-amino-7-(3-fluorophenyl)-N-[1-(methylcarbamoyl)pyrrolidin-3-yl]isoquinoline-4-carboxamide | 135 10% F | 0.961 407.8 10-80AB | $^1$H NMR (400 MHz, DMSO-d6) δ: 9.04 (s, 1H), 8.92 (d, J = 6.4 Hz, 1H), 8.41-8.36 (m, 2H), 7.92 (s, 1H), 7.83-7.78 (m, 2H), 7.60-7.55 (m, 1H), 7.31-7.26 (m, 1H), 4.45-4.41 (m, 1H), 3.55-3.51 (m, 1H), 3.38-3.21 (m, 3H), 2.54 (s, 3H), 2.13-2.09 (m, 1H), 1.98-1.96 (m, 1H). |
| 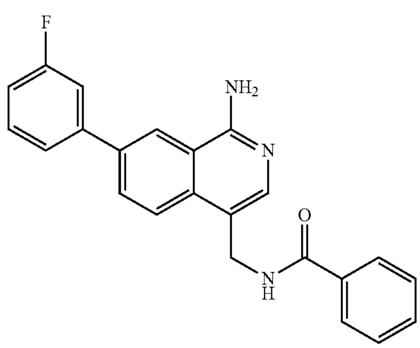 [SMILES: Nc1ncc(CNC(=O)c2ccccc2)c2ccc(-c3cccc(F)c3)cc12] | N-[[1-amino-7-(3-fluoro-phenyl)-4-isoquinolyl]methyl]benzamide | 136 10% D | 1.288 371.9 0-60AB 2 min | $^1$H NMR (400 MHz, DMSO-d6) δ: 8.85 (t, J = 5.2 Hz, 1H), 8.64, (s, 1H), 8.12-8.06 (m, 3H), 7.85-7.82 (m, 2H), 7.79-7.72 (m, 3H), 7.56-7.39 (m, 6H), 7.23-7.18 (m, 1H), 4.68 (d, J = 5.6 Hz, 2H). |
| 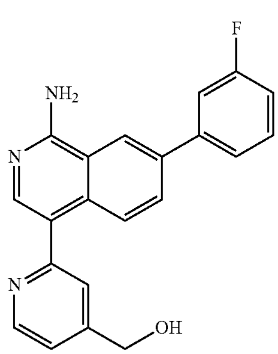 [SMILES: Nc1ncc(-c2cc(CO)ccn2)c2ccc(-c3cccc(F)c3)cc12] | [2-[1-amino-7-(3-fluoro-phenyl)-4-isoquinolyl]-4-pyridyl]methanol | 137 17% H | 1.153 345.8 0-60AB 2 min | $^1$H NMR (400 MHz, DMSO-d6) δ: 9.18 (s, 1H), 8.84 (d, J = 5.6, 1H), 8.39 (dd, J = 8.8 2.0 Hz, 1H), 8.08 (d, J = 8.8 Hz, 1H), 8.02 (s, 1H), 7.90-7.83 (m, 3H), 7.77 (d, J = 5.2 Hz, 1H), 7.62-7.58 (m, 1H), 7.34-7.29 (m, 1H), 4.78 (s, 2H). |

-continued

| Structure | IUPAC Name | No./ Yield/ General Method | LCMS $R_T$ (min)/ $M + H^+$/ method | $^1$H NMR (ppm) |
|---|---|---|---|---|
| 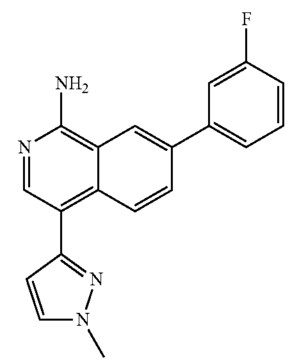 [SMILES: Cn1ccc(-c2cnc(N)c3cc(-c4cccc(F)c4)ccc23)n1] | 7-(3-fluorophenyl)-4-(1-methylpyrazol-3-yl)isoquinolin-1-amine | 138 10% H | 1.289 318.9 0-60AB 2 min | $^1$H NMR (400 MHz, MeOH-d4) δ: 8.83 (s, 1H), 8.58 (d, J = 8.8 Hz, 1H), 8.32 (dd, J = 8.8 2.0 Hz, 1H), 7.81 (s, 1H), 7.72 (s, 1H), 7.70-7.54 (m, 3H), 7.24-7.19 (m, 1H), 6.64 (s, 1H), 4.04 (s, 3H). |
| | ethyl 8-amino-2-[3-(trifluoromethoxy)phenyl]-1,7-naphthyridine-5-carboxylate | 139 K | 0.831 377.8 5-95 AB 2 min | $^1$H NMR (400 MHz, CDCl3) δ: 9.45 (d, J = 8.8 Hz, 1H), 8.77 (s, 1H), 8.11 (d, J = 8.8 Hz, 1H), 7.99-8.03 (m, 2H), 7.56 (m, 1H), 7.35 (m, 1H) 4.41 (q, 2H), 1.44 (t, J = 7.2 Hz, 3H) |
| | ethyl 8-amino-2-[3-(difluoromethoxy)phenyl]-1,7-naphthyridine-5-carboxylate | 140 K | 1.09 308.9 5-95AB 2 min | $^1$H NMR (400 MHz, CDCl$_3$) δ: 9.44 (d, J = 9.2 Hz, 1H), 8.82 (s, 1H), 8.11 (d, J = 8.8 Hz, 1H), 7.95 (m, 2H), 7.53 (m, 1H), 6.80 (s, 0.3H), 6.62 (s, 0.5H), 6.44 (s, 0.3H), 4.43 (m, 2H), 1.45 (m, 3H) |
| 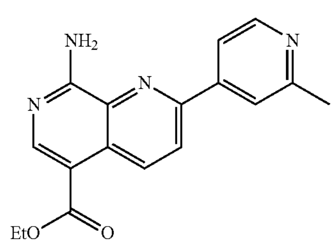 [SMILES: CCOC(=O)c1cnc(N)c2nc(-c3ccnc(C)c3)ccc12] | ethyl 8-amino-2-(2-methyl-4-pyridyl)-1,7-naphthyridine-5-carboxylate | 141 K | 0.615 308.9 5-95AB 1.5 min | $^1$H NMR (400 MHz, CDCl$_3$): δ: 9.48~9.50 (d, J = 8.0 Hz, 1H), 8.78 (s, 1H), 8.67~8.68 (d, J = 4.0 Hz, 1H), 8.16~8.16 (m, 1H), 7.87 (s, 1H), 7.80~7.81 (m, 2H), 4.39~4.45 (dd, J = 14.0 Hz, 7.2 Hz, 2H), 2.70 (s, 3H), 1.42-1.45 (t, J = 14.0 Hz, 7.2 Hz, 3H) |

-continued

| Structure | IUPAC Name | No./ Yield/ General Method | LCMS R$_T$ (min)/ M + H$^+$/ method | $^1$H NMR (ppm) |
|---|---|---|---|---|
| 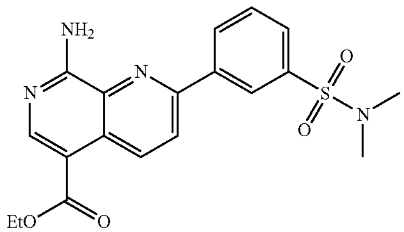 [SMILES: CCOC(=O)c1cnc(N)c2nc(-c3cccc(S(=O)(=O)N(C)C)c3)ccc12] | ethyl 8-amino-2-[3-(dimethyl-sulfamoyl)phenyl]-1,7-naphthyridine-5-carboxylate | 142 K | 0.761 400.9 5-95AB 1.5 min | δ: 9.40~9.43 (d, J = 8.8 Hz, 1H), 8.81 (s, 1H), 8.44~8.48 (d, J = 1.6 Hz, 1H), 8.29~8.31 (d, J = 4.0 Hz, 1H), 8.07~8.10 (d, J = 8.8 Hz, 1H), 7.81~7.83 (d, J = 8.0 Hz, 1H), 7.64~7.68 (m, 1H), 4.34~4.39 (q, 2H), 2.70 (s, 6H), 1.36~1.40 (t, J = 14.0 Hz, 7.2 Hz, 3H) |
| 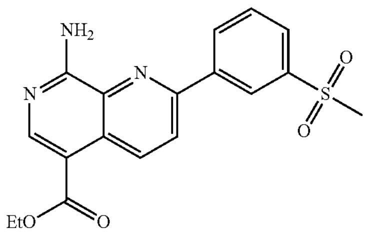 [SMILES: CCOC(=O)c1cnc(N)c2nc(-c3cccc(S(C)(=O)=O)c3)ccc12] | ethyl 8-amino-2-(3-methyl-sulfonylphenyl)-1,7-naphthyridine-5-carboxylate | 143 K | 0.713 371.9 5-95AB 2 min | $^1$H NMR (400 MHz, CDCl3) δ: 9.48 (d, J = 9.2 Hz, 1H), 8.83 (s, 1H), 8.71 (s, 1H), 8.40 (d, J = 8.4 Hz, 1H), 8.15 (d, J = 8.8 Hz, 1H), 8.05 (d, J = 8.0 Hz, 1H), 7.75 (m, 1H), 4.41 (q, 2H), 3.14 (s, 3H), 1.44 (t, J = 7.2 Hz, 3H) |
| 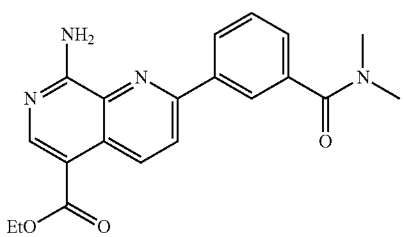 [SMILES: CCOC(=O)c1cnc(N)c2nc(-c3cccc(C(=O)N(C)C)c3)ccc12] | ethyl 8-amino-2-[3-(dimethyl-carbamoyl)phenyl]-1,7-naphthyridine-5-carboxylate | 144 K | 0.721 364.9 5-95AB 2 min | $^1$H NMR (400 MHz, CDCl3) δ: 9.35 (d, J = 9.2 Hz, 1H), 8.74 (s, 1H), 8.16 (m, 1H), 8.04-8.08 (m, 2H), 7.43-7.52 (m, 2H), 4.36 (q, 2H), 3.17 (s, 3H), 2.95 (s, 3H), 1.44 (t, J = 7.2 Hz, 3H) |
| 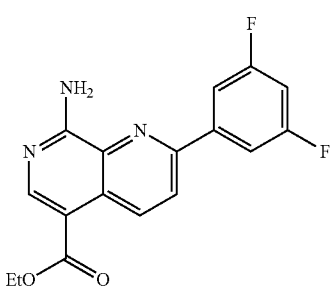 [SMILES: CCOC(=O)c1cnc(N)c2nc(-c3cc(F)cc(F)c3)ccc12] | ethyl 8-amino-2-(3,5-difluoro-phenyl)-1,7-naphthyridine-5-carboxylate | 145 K | 0.792 329.9 5-95AB 2 min | $^1$H NMR (400 MHz, CDCl3) δ: 9.46 (d, J = 9.2 Hz, 1H), 8.78 (s, 1H), 8.06 (d, J = 8.8 Hz, 1H), 7.65 (m, 2H), 6.92 (m, 1H), 4.41 (q, 2H), 1.44 (t, J = 7.2 Hz, 3H) |
| 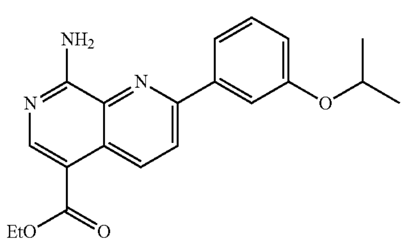 [SMILES: CCOC(=O)c1cnc(N)c2nc(-c3cccc(OC(C)C)c3)ccc12] | ethyl 8-amino-2-(3-isopropoxy-phenyl)-1,7-naphthyridine-5-carboxylate | 146 K | 5-95AB 1.5 min | $^1$H NMR (400 MHz, CDCl$_3$) δ: 9.32~9.34 (d, J = 8.8 Hz, 1H), 8.73 (s, 1H), 8.03~8.05 (d, J = 9.2 Hz, 1H), 7.61~7.63 (dd, J = 7.2 Hz, 2H), 7.37~7.41 (m, 1H), 6.96~6.98 (m, 1H), 4.64-4.71 (m, 1H), 4.40 (q, 2H), 1.42 (t, 3H) |

-continued

| Structure | IUPAC Name | No./ Yield/ General Method | LCMS R$_T$ (min)/ M + H$^+$/ method | $^1$H NMR (ppm) |
|---|---|---|---|---|
| 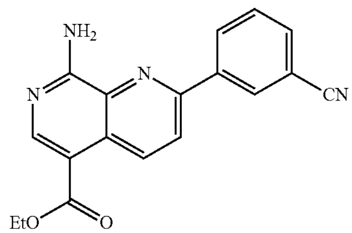 [SMILES: CCOC(=O)c1cnc(N)c2nc(-c3cccc(C#N)c3)ccc12] | ethyl 8-amino-2-(3-cyanophenyl)-1,7-naphthyridine-5-carboxylate | 147 K | 0.756 318.9 5-95AB 1.5 min | $^1$H NMR (400 MHz, CDCl$_3$) δ: 9.42 (d, J = 8.8 Hz, 1H), 8.78 (s, 1H), 8.41 (m, 1H), 8.26 (m, 1H), 8.03 (d, J = 8.8 Hz, 1H), 7.71 (m, 1H), 7.59 (m, 1H), 4.36 (q, 2H), 1.44 (t, J = 7.2 Hz, 3H) |
| 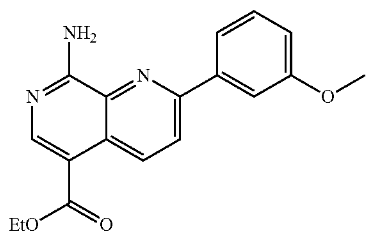 [SMILES: CCOC(=O)c1cnc(N)c2nc(-c3cccc(OC)c3)ccc12] | ethyl 8-amino-2-(3-methoxy-phenyl)-1,7-naphthyridine-5-carboxylate | 148 K | 0.765 323.9 5-95AB 1.5 min | $^1$H NMR (400 MHz, CDCl$_3$) δ: 9.32~9.34 (d, J = 8.8 Hz, 1H), 8.73 (s, 1H), 8.03~8.05 (d, J = 9.2 Hz, 1H), 7.61~7.63 (dd, J = 7.2 Hz, 2H), 7.37~7.41 (m, 1H), 6.96~6.98 (m, 1H), 4.33~4.38 (q, 2H), 3.86 (s, 3H), 1.36-1.39 (t, 3H) |
| 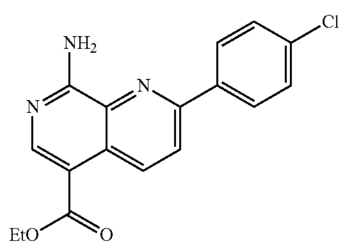 [SMILES: CCOC(=O)c1cnc(N)c2nc(-c3ccc(Cl)cc3)ccc12] | ethyl 8-amino-2-(4-chlorophenyl)-1,7-naphthyridine-5-carboxylate | 149 K | 0.81 327.9 5-95AB 1.5 min | $^1$H NMR (400 MHz, CDCl3) δ: 9.42 (d, J = 8.8 Hz, 1H), 8.81 (s, 1H), 8.08 (d, J = 8.8 Hz, 3H), 7.51 (d, J = 8.4 Hz, 2H), 4.45-4.40 (m, 2H), 1.46-1.43 (m, 3H) |
| 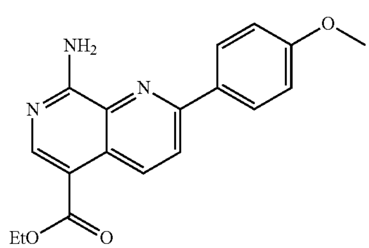 [SMILES: CCOC(=O)c1cnc(N)c2nc(-c3ccc(OC)cc3)ccc12] | ethyl 8-amino-2-(4-methoxy-phenyl)-1,7-naphthyridine-5-carboxylate | 150 K | 0.822 361.9 5-95AB 1.5 min | $^1$H NMR (400 MHz, CDCl3) δ: 9.47 (d, J = 8.8 Hz, 1H), 8.83 (s, 1H), 8.24 (d, J = 8.4 Hz, 2H), 8.13 (d, J = 8.8 Hz, 1H), 7.79 (d, J = 8.4 Hz, 1H), 4.46-4.40 (q, 2H), 1.45 (t, 3H) |
| 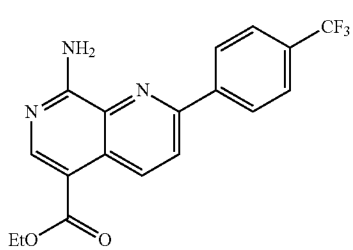 [SMILES: CCOC(=O)c1cnc(N)c2nc(-c3ccc(C(F)(F)F)cc3)ccc12] | ethyl 8-amino-2-[4-(trifluoro-methyl)phenyl]-1,7-naphthyridine-5-carboxylate | 151 K | 0.792 327.9 5-95AB 1.5 min | $^1$H NMR (400 MHz, CDCl$_3$) δ: 9.41 (s, 1H), 8.73 (s, 1H), 8.02 (s, 1H), 7.65~7.99 (m, 2H), 7.51~7.53 (m, 1H), 7.39~7.43 (m, 2H), 4.39~4.44 (q, 2H), 1.41-1.47 (t, 3H) |

-continued

| Structure | IUPAC Name | No./ Yield/ General Method | LCMS $R_T$ (min)/ M + H$^+$/ method | $^1$H NMR (ppm) |
|---|---|---|---|---|
| 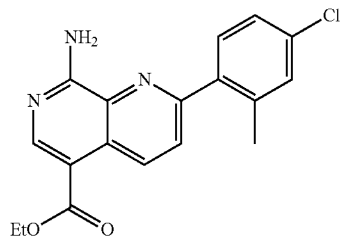 [SMILES: CCOC(=O)c1cnc(N)c2nc(-c3ccc(Cl)cc3C)ccc12] | ethyl 8-amino-2-(4-chloro-2-methyl-phenyl)-1,7-naphthyridine-5-carboxylate | 152 K | 0.815 341.9 5-95AB 1.5 min | $^1$H NMR (400 MHz, CDCl$_3$) δ: 9.24 (d, J = 8.8 Hz, 1H), 8.67 (s, 1H), 7.98 (d, J = 9.2 Hz, 1H), 7.62 (d, J = 8.0 Hz, 1H), 7.48 (m, 1H), 7.41 (m, 1H), 4.32 (q, 2H), 2.48 (s, 3H), 1.39-1.35 (t, J = 7.2 Hz, 3H) |
| 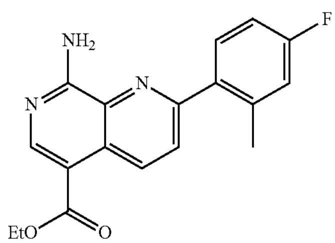 [SMILES: CCOC(=O)c1cnc(N)c2nc(-c3ccc(F)cc3C)ccc12] | ethyl 8-amino-2-(4-fluoro-2-methyl-phenyl)-1,7-naphthyridine-5-carboxylate | 153 K | 0.794 325.9 5-95AB 2 min | $^1$H NMR (400 MHz, CDCl3) δ: 9.32 (d, J = 8.8 Hz, 1H), 8.72 (s, 1H), 7.70 (d, J = 8.8 Hz, 1H), 7.43-7.40 (m, 1H), 7.00-6.94 (m, 2H), 4.38-4.33 (q, 2H), 2.38 (s, 3H), 1.39-1.35 (t, J = 7.2 Hz, 3H) |
| 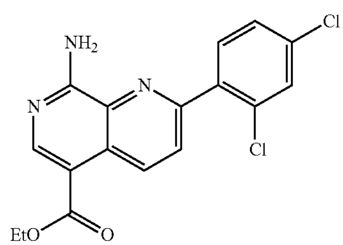 | ethyl 8-amino-2-(2,4-dichloro-phenyl)-1,7-naphthyridine-5-carboxylate | 154 K | 0.829 361.8 5-95AB 1.5 min | $^1$H NMR (400 MHz, CDCl$_3$) δ: 9.32~9.35 (d, J = 8.8 Hz, 1H), 8.76 (s, 1H), 7.91~7.94 (d, J = 9.2 Hz, 1H), 7.55~7.57 (dd, J = 8.4 Hz, 1H), 7.48~7.49 (m, 1H), 7.33~7.35 (m, 1H), 4.33~4.39 (q, 2H), 1.36-1.39 (t, 3H) |
| 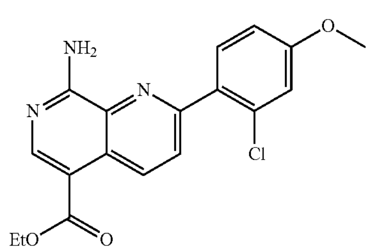 [SMILES: CCOC(=O)c1cnc(N)c2nc(-c3ccc(OC)cc3Cl)ccc12] | ethyl 8-amino-2-(2-chloro-4-methoxy-phenyl)-1,7-naphthyridine-5-carboxylate | 155 K | 0.796 357.9 5-95AB 1.5 min | $^1$H NMR (400 MHz, CDCl$_3$) δ: δ 9.27~9.29 (d, J = 8.8 Hz, 1H), 8.74 (s, 1H), 7.94~7.96 (d, J = 8.8 Hz, 1H), 7.56~7.58 (dd, J = 8.4 Hz, 1H), 6.99 (s, 1H), 6.89~6.91 (d, J = 8.4 Hz, 1H), 4.33~4.38 (q, 2H), 3.82 (s, 3H), 1.36-1.39 (t, 3H) |
| 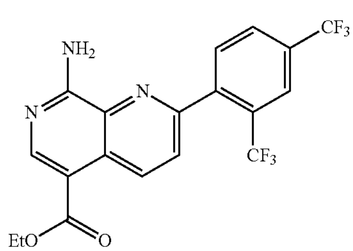 [SMILES: CCOC(=O)c1cnc(N)c2nc(-c3ccc(C(F)(F)F)cc3C(F)(F)F)ccc12] | ethyl 8-amino-2-[2,4-bis(trifluoro-methyl)phenyl]-1,7-naphthyridine-5-carboxylate | 156 K | 1.209 430.1 5-95AB 2 min | $^1$H NMR (400 MHz, CDCl$_3$) δ 9.48 (d, J = 8.8 Hz, 1H), 8.87 (s, 1H), 8.11 (s, 1H), 7.95 (m, 1H), 7.81 (d, J = 8.8 Hz, 1H), 7.75 (m, 1H), 4.43 (q, 1H), 1.36-1.39 (m, 3H) |

BIOLOGICAL EXAMPLE

MAP4K4 Inhibition Assay Protocol No. 1

The kinase activity of purified human MAP4K4 kinase domain was measured by monitoring the phosphorylation of a peptide substrate derived from moesin protein (Leu-Gly-Arg-Asp-Lys-Tyr-Lys-Thr-Leu-Arg-Gln-Ile-Arg-Gln) fluorescently labeled on the N-terminus with 5-carboxyfluorescein using the Caliper LabChip technology (Caliper Life Sciences, Hopkinton, Mass.). To determine inhibition constants (IC50), compounds were serially diluted in DMSO and added to 10 uL kinase reactions containing 1 nM purified MAP4K4 enzyme, 1 uM peptide substrate, 10 uM ATP, 10 mM $MgCl_2$, 1 mM EGTA, 50 mM Hepes pH 7.2, 1 mM DTT, 0.01% Triton X-100, and 2% DMSO. Reactions were incubated at room temperature in Perkin Elmer Proxiplates for 45 minutes and stopped by the addition of 10 uL of an EDTA-containing solution (50 mM Hepes pH 7.2, 40 mM EDTA, 0.02% Triton X-100). The fraction of phosphorylated peptide was determined as a fraction of total peptide substrate using the Caliper Lab Chip 3000 according to the manufacturer's instructions. IC50 values were determined using the four-parameter non-linear fit model.

MAP4K4 Inhibition Assay Protocol No. 2

The kinase activity of purified human MAP4K4 kinase domain was monitored using Z'-LYTE™ technology from Invitrogen to determine inhibition constants (IC50) of small molecule inhibitors. The Z'-LYTE™ biochemical assay employs a fluorescence-based, coupled-enzyme format and is based on the differential sensitivity of phosphorylated and non-phosphorylated peptides to proteolytic cleavage. In the primary reaction, the kinase transfers the gamma-phosphate of ATP to a single tyrosine, serine or threonine residue in a synthetic FRET-peptide. In the secondary reaction, a site-specific protease recognizes and cleaves non-phosphorylated FRET-peptides. Phosphorylation of FRET-peptides suppresses cleavage by the Development Reagent. Cleavage disrupts FRET between the donor (i.e., coumarin) and acceptor (i.e., fluorescein) fluorophores on the FRET-peptide, whereas uncleaved, phosphorylated FRET-peptides maintain FRET. To determine inhibition constants (IC50), compounds were serially diluted in DMSO and added to 10 uL kinase reactions containing 1 nM purified MAP4K4 enzyme, 2 uM ser/thr7 Z'-LYTE™ substrate, 10 uMATP, 50 mM Hepes (pH 7.5), 10 mM MgCl2, 1 mM EGTA, 0.01% Brij-35, and 2% DMSO. Reactions were incubated at room temperature in Corning Black 384 well plates (Corning#3573) for 60 minutes and stopped by the addition of 5 uL of Z'-LYTE™ development reagent A and incubated at room temp for 60 minutes. The plate is then analyzed on Perkin Elmer Envision by FRET mode. The high ratio of coumarin/fluorescein represents 0% phosphorylation rate while low ratio of coumarin/fluorescein represents 100% phosphorylation rate. The following equations are used to determine extent of peptide phosphorylation or inhibition:

$$\text{emission ration} = \frac{\text{coumarin emssion signal intensity(at 445 nm)}}{\text{fluorescein emission signal intensity(at 520 nm)}}$$

$$\text{percent phosphorylation} = \left\{1 - \frac{(\text{Emission Ratio} \times F100\%) - C100\%}{(C0\% - C100\%) + [\text{Emission Ratio} \times (F100\% - F0\%)]}\right\} \times 100$$

The compounds of the present invention were tested for their capacity to inhibit a MAP4K4 activity and activation as described herein. The Examples were tested in the above assay and found to have $IC_{50}$ of about 0.0005 µM to about 5 µM. Particular compounds of Formula (I) were found to have $IC_{50}$ of about 0.0005 µM to about 1 µM.

| Ex. No. | MAP4K4 IC50 (µM) Assay 1 | MAP4K4 IC50 (µM) Assay 2 |
|---|---|---|
| 1 | 0.122 | NA |
| 2 | 0.299 | NA |
| 3 | 0.0388 | NA |
| 4 | 0.0221 | NA |
| 5 | 1.2 | NA |
| 6 | 0.0414 | 0.0294 |
| 7 | 0.869 | 0.776 |
| 8 | 0.0112 | 0.015 |
| 9 | 0.0506 | NA |
| 10 | NA | 0.0287 |
| 11 | NA | 0.00873 |
| 12 | NA | 0.218 |
| 13 | 0.00129 | NA |
| 14a | 0.00256 | 0.00305 |
| 14b | 0.00419 | 0.0044 |
| 15 | NA | 0.00455 |
| 16 | NA | 0.0045 |
| 17 | NA | 0.0195 |
| 18 | NA | 0.0116 |
| 19 | NA | 0.00385 |
| 20 | NA | 0.0068 |
| 21 | NA | 0.0018 |
| 22 | NA | 0.0244 |
| 23 | NA | 0.0285 |
| 24 | NA | 0.0040 |
| 25 | NA | 0.00918 |
| 26 | NA | 0.00411 |
| 27 | NA | 0.0147 |
| 28 | NA | 0.0020 |
| 29 | NA | 0.0608 |
| 30 | NA | 0.0139 |
| 31 | NA | 0.284 |
| 32 | NA | 0.0198 |
| 33 | NA | 0.00165 |
| 34 | NA | 0.0016 |
| 35 | NA | 0.00378 |
| 36 | NA | 0.00411 |
| 37 | NA | 0.00294 |
| 38 | NA | 0.00569 |
| 39 | NA | 0.0044 |
| 40 | NA | 0.00563 |
| 41 | NA | 1.2 |
| 42 | NA | 0.00832 |
| 43 | NA | 0.00248 |
| 44 | NA | 0.00263 |
| 45 | 0.0841 | NA |
| 46 | 2.4 | NA |
| 47 | 1.6 | NA |
| 48 | 4.2 | NA |
| 49 | 2.6 | NA |
| 50 | 1.5 | NA |
| 51 | 2 | NA |
| 52 | 1.5 | NA |
| 53 | 0.388 | NA |
| 54 | 0.0175 | NA |
| 55 | 0.622 | NA |
| 56 | 0.249 | NA |
| 57 | 0.102 | NA |
| 58 | 0.146 | NA |
| 59 | 0.0999 | NA |
| 60 | 0.238 | NA |
| 61 | 0.0368 | NA |
| 62 | 0.0338 | NA |
| 63 | 0.0127 | NA |
| 64 | 0.34 | NA |
| 65 | 1.7 | NA |
| 66 | 0.0327 | NA |
| 67 | 0.651 | NA |
| 68 | 0.12 | NA |
| 69 | 0.35 | NA |
| 70 | 0.0852 | NA |

| Ex. No. | MAP4K4 IC50 (μM) Assay 1 | MAP4K4 IC50 (μM) Assay 2 |
|---|---|---|
| 74 | 0.0395 | NA |
| 75 | 0.0148 | NA |
| 76 | 0.245 | NA |
| 77 | 0.507 | NA |
| 78 | 2.4 | NA |
| 79 | 1.4 | NA |
| 80 | 0.25 | NA |
| 81 | 0.138 | NA |
| 82 | 0.148 | NA |
| 83 | 0.217 | NA |
| 84 | 0.557 | NA |
| 85 | 0.363 | NA |
| 86 | 0.0081 | NA |
| 87 | 0.0452 | NA |
| 88 | 0.95 | NA |
| 89 | 0.231 | NA |
| 90 | 0.141 | NA |
| 91 | 0.0511 | NA |
| 92 | 0.0335 | NA |
| 93 | 0.0645 | NA |
| 94 | 0.077 | NA |
| 95 | 0.0391 | NA |
| 96 | 0.179 | NA |
| 97 | 0.030 | NA |
| 98 | 0.0459 | NA |
| 99 | 0.0257 | NA |
| 100 | 0.0395 | NA |
| 101 | 0.0399 | NA |
| 102 | 0.135 | NA |
| 103 | 0.115 | NA |
| 104 | 0.0909 | NA |
| 105 | 0.0377 | NA |
| 106 | 0.0224 | NA |
| 107 | 0.0124 | NA |
| 108 | 0.0156 | NA |
| 109 | 0.0774 | NA |
| 110 | 0.403 | NA |
| 111 | 0.0441 | NA |
| 112 | 0.0731 | NA |
| 113 | 0.0565 | NA |
| 114 | 0.0386 | NA |
| 115 | 0.0454 | NA |
| 116 | 0.114 | NA |
| 117 | 0.070 | NA |
| 118 | 0.000464 | 0.000648 |
| 119 | 0.0996 | NA |
| 123 | 2.1 | NA |
| 124 | 0.40 | NA |
| 125 | 0.0503 | NA |
| 126 | 0.0357 | NA |
| 127 | 1.2 | 0.756 |
| 128 | 0.0705 | 0.0724 |
| 129 | 4.1 | 3 |
| 130 | 0.0609 | 0.0665 |
| 131 | 0.168 | 0.174 |
| 132 | 0.18 | 0.191 |
| 133 | 0.0602 | 0.0919 |
| 134 | NA | 0.155 |
| 135 | NA | 0.162 |
| 136 | NA | 0.919 |
| 137 | NA | 0.0106 |
| 138 | NA | 0.0145 |
| 139 | NA | 0.00216 |
| 140 | NA | 0.00769 |
| 141 | NA | 0.00339 |
| 142 | NA | 0.48 |
| 143 | NA | 0.0636 |
| 144 | NA | 0.0031 |
| 145 | NA | 0.00184 |
| 146 | NA | 0.0326 |
| 147 | NA | 0.00145 |
| 148 | NA | 0.00853 |
| 149 | NA | 0.0278 |
| 150 | NA | 0.0212 |
| 153 | NA | 0.00652 |
| 154 | NA | 0.382 |
| 155 | NA | 0.134 |

NA: Not Available

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

The invention claimed is:
1. A compounds of Formula (I)

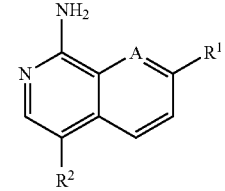

and stereoisomers, geometric isomers, tautomers, and pharmaceutically acceptable salts thereof, wherein:
A is CH or N;
$R^1$ and $R^2$ are independently selected from:
 CN;
 $C_1$-$C_{12}$-alkyl which is unsubstituted or substituted by one or more substituents selected from the group consisting of cyano, halo, hydroxy, $C_1$-$C_{12}$-alkoxy, $C_3$-$C_{12}$-cycloalkyl, —$NH_2$, —NH—$C_1$-$C_{12}$-alkyl, —NH—$C_2$-$C_{12}$-heteroaryl, —NHC(O)—$C_1$-$C_{12}$-alkyl, —NHC(O)—$C_3$-$C_{12}$-cycloalkyl, —NHC(O)—$C_6$-$C_{20}$-aryl, —NHC(O)—$C_2$-$C_{12}$-heteroaryl, —NHC(O)NH—$C_1$-$C_{12}$-alkyl, —NHC(O)NH—$C_2$-$C_{12}$-heteroaryl, —NHS(O)$_2$—$C_1$-$C_{12}$-alkyl, and —NHS(O)$_2$—$C_3$-$C_{12}$-cycloalkyl;
 $C_1$-$C_{12}$-alkoxy which is unsubstituted or substituted by halo;
 $C_3$-$C_{12}$-cycloalkyl which is unsubstituted or substituted by one or more substituents selected from the group consisting of cyano, halo, hydroxy, —$NH_2$, $C_1$-$C_{12}$-alkyl, $C_1$-$C_{12}$-alkoxy, $C_3$-$C_{12}$-cycloalkyl, $C_2$-$C_{12}$-heterocyclyl, $C_6$-$C_{20}$-aryl, and $C_2$-$C_{12}$-heteroaryl, wherein said cycloalkyl, heterocyclyl, aryl, and heteroaryl can be unsubstituted or substituted by one or more substituents selected from the group consisting of: halo, OH, CN, $NH_2$, —NH($C_1$-$C_{12}$-alkyl), —N($C_1$-$C_{12}$-alkyl)$_2$, $C_1$-$C_{12}$-alkyl, $C_1$-$C_{12}$-alkoxy, $C_1$-$C_{12}$-haloalkyl, $C_1$-$C_{12}$-hydroxyalkyl, —C(O)$C_1$-$C_{12}$-alkyl, and —C(O)NH$C_1$-$C_{12}$-alkyl;

—NHR$^a$, wherein R$^a$ is selected from the group consisting of:
- $C_3$-$C_{12}$-cycloalkyl, which is unsubstituted or substituted by one or more $C_1$-$C_{12}$-alkyl;
- —$C_2$-$C_{12}$-heterocyclyl, which is unsubstituted or substituted by one or more substituents
- —$C_1$-$C_{12}$-alkylenyl-$C_6$-$C_{20}$-aryl, wherein the aryl is unsubstituted or substituted by one or more substituents selected from the group consisting of: halo, $C_1$-$C_{12}$-alkyl and $C_2$-$C_{12}$-heterocyclyl;
- —$C_1$-$C_{12}$-alkylenyl-$C_1$-$C_{12}$-alkoxy-$C_6$-$C_{20}$-aryl, wherein the aryl is unsubstituted or substituted by halo; and
- —$C_1$-$C_{12}$-alkylenyl-$C_2$-$C_{12}$-heteroaryl, wherein the heteroaryl is unsubstituted or substituted by $C_1$-$C_{12}$-alkyl;

—C(O)—$C_2$-$C_{12}$-heterocyclyl, which is unsubstituted or substituted by one or more substituents selected from the group consisting of: $C_1$-$C_{12}$-alkyl, —$C_1$-$C_{12}$-hydroxyalkyl, —C(O)—NH$_2$, —C(O)—N(H)($C_1$-$C_{12}$-alkyl), —C(O)—N($C_1$-$C_{12}$-alkyl)$_2$, —$C_1$-$C_{12}$-alkylenyl—C(O)—N($C_1$-$C_{12}$-alkyl)$_2$, —NH—C(O)—$C_1$-$C_{12}$-alkyl, —NH—C(O)—$C_3$-$C_{12}$-cycloalkyl, and —N(C(O)—$C_3$-$C_{12}$-cycloalkyl)$_2$;

—C(O)OH;

—C(O)—$C_1$-$C_{12}$-alkoxy;

—C(O)NR$^b$R$^c$, wherein R$^b$ and R$^c$ are independently selected from the group consisting of:
H;
- —$C_1$-$C_{12}$-alkyl, which is unsubstituted or substituted by one or more substituent selected from the group consisting of:
  OH, CN, NH$_2$, —$C_3$-$C_{12}$-cycloalkyl, —C(O)—NH$_2$, —C(O)—$C_2$-$C_{12}$-heterocyclyl, —N(H)(C(O)—$C_1$-$C_{12}$-alkyl), —N(H)($C_1$-$C_{12}$-alkyl), —N($C_1$-$C_{12}$-alkyl)$_2$, —NHC(O)—NH($C_3$-$C_{12}$-cycloalkyl), —NHC(O)—NH($C_1$-$C_{12}$-alkyl);
- $C_2$-$C_{12}$-heterocyclyl, wherein the heterocyclyl is unsubstituted or substituted by one or more substituents selected from the group consisting of oxo, hydroxy and $C_1$-$C_{12}$-alkyl;
- —C(O)—$C_2$-$C_{12}$-heterocyclyl, wherein the heterocyclyl is unsubstituted or substituted by one or more substituents selected from the group consisting of oxo, hydroxy and $C_1$-$C_{12}$-alkyl;
- —SO$_2$—$C_2$-$C_{12}$-heterocyclyl;
- aryl, which is unsubstituted or substituted by one or more substituents selected from the group consisting of $C_1$-$C_{12}$-alkyl, $C_1$-$C_{12}$-alkoxy, —$C_1$-$C_{12}$-hydroxyalkyl, $C_1$-$C_{12}$-alkylenyl-$C_1$-$C_{12}$-alkoxy, $C_1$-$C_{12}$-alkylenyl-NH$_2$, and —O—$C_2$-$C_{12}$-heterocyclyl, which heterocyclyl is unsubstituted or substituted by $C_1$-$C_{12}$-alkyl; and
- $C_2$-$C_{12}$-heteroaryl, which is unsubstituted or substituted by one or more substituents selected from the group consisting of $C_1$-$C_{12}$-alkyl, $C_1$-$C_{12}$-alkoxy, —C(O)—NH$_2$, —C(O)—N(H)($C_1$-$C_{12}$-alkyl), —C(O)—N($C_1$-$C_{12}$-alkyl)$_2$, and —$C_1$-$C_{12}$-alkylenyl-C(O)—N($C_1$-$C_{12}$-alkyl)$_2$;
- —$C_3$-$C_{12}$-cycloalkyl, which is unsubstituted or substituted by one ore more hydroxy;
- —$C_2$-$C_{12}$-heterocyclyl, which is unsubstituted or substituted by one or more substituents selected from the group consisting of: $C_1$-$C_{12}$-alkyl, —SO$_2$—$C_1$-$C_{12}$-alkyl, —C(O)—$C_1$-$C_{12}$-alkyl, —C(O)—NH$_2$, —C(O)—N(H)($C_1$-$C_{12}$-alkyl), —C(O)—N($C_1$-$C_{12}$-alkyl)$_2$, —C(O)—$C_1$-$C_{12}$-alkylenyl-$C_1$-$C_{12}$-alkoxy, —$C_1$-$C_{12}$-alkylenyl-C(O)—N($C_1$-$C_{12}$-alkyl)$_2$, —C(O)—$C_3$-$C_{12}$-cycloalkyl, and —C(O)NH—$C_3$-$C_{12}$-cycloalkyl;
- $C_6$-$C_{20}$-aryl, which is unsubstituted or substituted by one or more substituents selected from the group consisting of $C_1$-$C_{12}$-alkyl, $C_1$-$C_{12}$-alkoxy, $C_1$-$C_{12}$-hydroxyalkyl, $C_1$-$C_{12}$-alkylenyl-$C_1$-$C_{12}$-alkoxy, $C_1$-$C_{12}$-alkylenyl-NH$_2$, and —O—$C_2$-$C_{12}$-heterocyclyl, which heterocyclyl is unsubstituted or substituted by $C_1$-$C_{12}$-alkyl; and,
- $C_6$-$C_{20}$-heteroaryl, which is unsubstituted or substituted by one or more substituents selected from the group consisting of $C_1$-$C_{12}$-alkyl, $C_1$-$C_{12}$-hydroxyalkyl, and —O—$C_2$-$C_{12}$-heterocyclyl which heterocyclyl is unsubstituted or substituted by $C_1$-$C_{12}$-alkyl;

—O—$C_3$-$C_{12}$-cycloalkyl, —O—$C_2$-$C_{12}$-heterocyclyl, —O—$C_6$-$C_{20}$-aryl and —O—$C_6$-$C_{20}$-heteroaryl, wherein the cycloalkyl, heterocyclyl, aryl and heteroaryl is unsubstituted or substituted by one or more substituent(s) selected from the group consisting of: halo, cyano, $C_1$-$C_{12}$-alkyl, $C_1$-$C_{12}$-alkoxy and —C(O)NH$_2$;

$C_2$-$C_{12}$-heterocyclyl, which is unsubstituted or substituted by one or more substituents selected from the group consisting of:
halo,
oxo,
—NH$_2$;
- $C_1$-$C_{12}$-alkyl, which is unsubstituted or substituted by one or more substituents selected from the group consisting of: OH, halo, $C_1$-$C_{12}$-alkoxy, —C(O)—NH—$C_1$-$C_{12}$-alkyl, and $C_2$-$C_{12}$-heteroaryl, which heteroaryl is unsubstituted or substituted by one or more substituents selected from the group consisting of: $C_1$-$C_{12}$-alkyl, $C_1$-$C_{12}$-alkylenyl-$C_1$-$C_{12}$-alkoxy and —N($C_1$-$C_{12}$-alkyl)$_2$;
- $C_1$-$C_{12}$-alkoxy;
- —C(O)—R$^d$, wherein R$^d$ is selected from the group consisting of $C_1$-$C_{12}$-alkyl, —$C_2$-$C_{12}$-heterocyclyl, —NH$_2$, —NH—$C_3$-$C_{12}$-cycloalkyl, and —O—$C_1$-$C_{12}$-alkyl;
- —N($C_1$-$C_{12}$-alkyl)$_2$;
- —N($C_1$-$C_{12}$-alkyl)C(O)—$C_1$-$C_{12}$-alkyl;
- —NH(CO)—$C_1$-$C_{12}$-alkylenyl-N($C_1$-$C_{12}$-alkyl)$_2$;
- —NH(CO)—$C_1$-$C_{12}$-alkylenyl-$C_1$-$C_{12}$-alkoxy;
- —NH(CO)O—$C_1$-$C_{12}$-alkyl;
- —NH(CO)—$C_1$-$C_{12}$-alkylenyl-N($C_1$-$C_{12}$-alkyl)-C(O)—$C_1$-$C_{12}$-alkyl;
- —NH(CO)—$C_2$-$C_{12}$-heterocyclyl, wherein the heterocyclyl is unsubstituted or substituted by one or more substituents selected from the group consisting of: oxo, $C_1$-$C_{12}$-alkyl, —C(O)—$C_1$-$C_{12}$-alkyl and —S(O)$_2$—$C_1$-$C_{12}$-alkyl;
- —NH(CO)—$C_1$-$C_{12}$-alkylenyl-$C_2$-$C_{12}$-heterocyclyl, wherein the heterocyclyl is unsubstituted or substituted by one or more substituents selected from the group consisting of oxo, $C_1$-$C_{12}$-alkyl and —C(O)—$C_1$-$C_{12}$-alkyl;
- —NH(CO)—$C_1$-$C_{12}$-alkylenyl-$C_2$-$C_{12}$-heteroaryl, wherein the heteroaryl is unsubstituted or substituted by $C_1$-$C_{12}$-alkyl; and $C_3$-$C_{12}$-cycloalkyl, $C_2$-$C_{12}$-heterocyclyl, $C_6$-$C_{20}$-aryl or $C_2$-$C_{12}$-heteroaryl which cycloalkyl, heterocycloalkyl, aryl or heteroaryl is unsubstituted or substituted by one or more substituents selected from the group consisting of: OH, $C_1$-$C_{12}$-alkyl, $C_1$-$C_{12}$-haloalkyl, $C_1$-$C_{12}$-hydroxyalkyl, $C_1$-$C_{12}$-alkylenyl —$C_1$-$C_{12}$-alkoxy, —NH—$C_1$-$C_{12}$-alkyl, —N($C_1$-$C_{12}$-alkyl)$_2$, —C(O)NH$_2$, —C(O)NH—$C_1$-$C_{12}$-alkyl, —C(O)N($C_1$-$C_{12}$-alkyl)$_2$ and —S(O)$_2$—$C_1$-$C_{12}$-alkyl;

$C_6$-$C_{20}$-aryl which is unsubstituted or substituted by one or more substituents selected from the group consisting of:

halo;
CN;
OH;
—NH$_2$;
$C_1$-$C_{12}$-alkyl, which is unsubstituted or substituted by one or more substituents selected from the group consisting of:
 halo;
 OH;
 —NH($C_1$-$C_{12}$-alkyl), wherein the alkyl is unsubstituted or substituted by OH or —N($C_1$-$C_{12}$-alkyl)$_2$, —C(O)N($C_1$-$C_{12}$-alkyl)$_2$, ($C_3$-$C_{12}$-cycloalkyl, $C_2$-$C_{12}$-heterocyclyl, which cycloalkyl or heterocyclyl is unsubstituted or substituted by $C_1$-$C_{12}$-alkyl;
 —NH($C_2$-$C_{12}$-heterocyclyl) which heterocyclyl is unsubstituted or substituted by one or more substituents selected from the group consisting of: oxo and $C_1$-$C_{12}$-alkyl;
 —N($C_1$-$C_{12}$-alkyl)($C_2$-$C_{12}$-heterocyclyl) which heterocyclyl is unsubstituted or substituted by one or more substituents selected from the group consisting of: oxo and $C_1$-$C_{12}$-alkyl;
 —N($C_1$-$C_{12}$-alkyl)($C_1$-$C_{12}$-alkylenyl-$C_1$-$C_{12}$-alkoxy);
 —N($C_1$-$C_{12}$-alkyl)-C(O)—$C_2$-$C_{12}$-heterocyclyl;
 —NH($C_3$-$C_{12}$-cycloalkyl), wherein the cycloalkyl is unsubstituted or substituted by halo, $C_1$-$C_{12}$-hydroxyalkyl;
 $C_2$-$C_{12}$-heterocyclyl which is unsubstituted or substituted by one or more substituents selected from the group consisting of:
  halo, oxo, OH, $C_1$-$C_{12}$-alkyl, $C_1$-$C_{12}$-hydroxyalkyl, $C_1$-$C_{12}$-alkoxy, $C_1$-$C_{12}$-alkylenlyl-C(O)—$C_1$-$C_{12}$-alkyl, $C_1$-$C_{12}$-alkylenyl—C(O)N($C_1$-$C_{12}$-alkyl)$_2$, —N($C_1$-$C_{12}$-alkyl)$_2$, —N($C_1$-$C_{12}$-alkyl)—C(O)—$C_1$-$C_{12}$-alkyl, —C(O)—$C_1$-$C_{12}$-alkyl, —C(O)NH$_2$, —C(O)NH($C_1$-$C_{12}$-alkyl), —C(O)NH($C_1$-$C_{12}$-haloalkyl), —C(O)NH($C_1$-$C_{12}$-hydroxyalkyl), —S(O)$_2$—$C_1$-$C_{12}$-alkyl, —S(O)$_2$—N($C_1$-$C_{12}$-alkyl)$_2$, —C(O)NH($C_2$-$C_{12}$-heterocyclyl), —C(O)N($C_1$-$C_{12}$-alkyl)$_2$, and —C(O)—$C_2$-$C_{12}$-heterocyclyl, which heterocyclyl is unsubstituted or substituted by $C_1$-$C_{12}$-alkyl, —C(O)OH, —S(O)$_2$—$C_1$-$C_{12}$-alkyl, —S(O)$_2$—N($C_1$-$C_{12}$-alkyl)$_2$, or $C_2$-$C_{12}$-heterocyclyl; and,
 —$C_1$-$C_{12}$-alkoxy which is unsubstituted or substituted by one or more substituents selected from the group consisting of: halo and $C_2$-$C_{12}$-heterocyclyl;
$C_1$-$C_{12}$-alkoxy which is unsubstituted or substituted by $C_2$-$C_{12}$-heterocyclyl;

$C_1$-$C_{12}$-haloalkoxy;
—NH—$C_1$-$C_{12}$-alkylenyl-N($C_1$-$C_{12}$-alkyl)$_2$;
—NH—$C_1$-$C_{12}$-alkylenyl-$C_2$-$C_{12}$-heterocyclyl;
—NH—$C_1$-$C_{12}$-alkylenyl-$C_6$-$C_{20}$-aryl, wherein the $C_6$-$C_{20}$-aryl is unsubstituted or substituted by halo;
—NH—$C_2$-$C_{12}$-heterocyclyl-$C_1$-$C_{12}$-alkylenyl-$C_2$-$C_{12}$-heterocyclyl;
—NHC(O)—$C_1$-$C_{12}$-alkyl, wherein the $C_1$-$C_{12}$-alkyl group is unsubstituted or substituted by one or more substituents selected from the group consisting of: halo, $C_1$-$C_{12}$-alkoxy, —N($C_1$-$C_{12}$-alkyl)$_2$, —$C_3$-$C_{12}$-cycloalkyl, and —$C_2$-$C_{12}$-heterocyclyl, wherein the heterocyclyl is unsubstituted or substituted by oxo;
—NHC(O)—$C_1$-$C_{12}$-alkoxy;
—NHC(O)—$C_3$-$C_{12}$-cycloalkyl, wherein the cycloalkyl is unsubstituted or substituted by halo;
—NHC(O)—$C_2$-$C_{12}$-heterocyclyl, wherein the heterocyclyl is unsubstituted or substituted by one or more substituents selected from the group consisting of: $C_1$-$C_{12}$-alkyl and —C(O)—$C_1$-$C_{12}$-alkyl;
—NHC(O)NH—$C_3$-$C_{12}$-cycloalkyl, wherein the cycloalkyl is unsubstituted or substituted by OH;
—NH(SO$_2$)—$C_1$-$C_{12}$-alkylenyl-$C_2$-$C_{12}$-heterocyclyl, wherein the heterocyclyl is unsubstituted or substituted by $C_1$-$C_{12}$-alkyl;
—NH(SO$_2$)—$C_2$-$C_{12}$-heterocyclyl;
—C(O)NH$_2$;
—C(O)NH—$C_1$-$C_{12}$-alkyl;
—C(O)NH—$C_1$-$C_{12}$-alkylenyl-N($C_1$-$C_{12}$-alkyl)$_2$;
—C(O)NH—$C_1$-$C_{12}$-alkylenyl-$C_2$-$C_{12}$-heterocyclyl, wherein the heterocyclyl is unsubstituted or substituted by one or more substituents selected from the group consisting of $C_1$-$C_{12}$-alkyl, —C(O)NH—$C_1$-$C_{12}$-hydroxyalkyl, and —C(O)NH—$C_3$-$C_{12}$-cycloalkyl; and $C_3$-$C_{12}$-cycloalkyl, $C_2$-$C_{12}$-heterocyclyl, $C_6$-$C_{20}$-aryl; $C_2$-$C_{12}$-heteroaryl; and —O—$C_2$-$C_{12}$-heteroaryl wherein said cycloalkyl, heterocyclyl, aryl, and heteroaryl can be unsubstituted or substituted by one or more substituents selected from the group consisting of: halo, oxo, OH, CN, NH$_2$, —NH($C_1$-$C_{12}$-alkyl), —N($C_1$-$C_{12}$-alkyl)$_2$, $C_1$-$C_{12}$-alkyl, $C_1$-$C_{12}$-alkoxy, $C_1$-$C_{12}$-haloalkyl, $C_1$-$C_{12}$-hydroxyalkyl, —C(O)$C_1$-$C_{12}$-alkyl, and —C(O)NH$C_1$-$C_{12}$-alkyl; and, —$C_2$-$C_{12}$-heteroaryl which is unsubstituted or substituted by one or more substituents selected from the group consisting of:
oxo,
halo,
—CN,
—NH$_2$
—NH—$C_1$-$C_{12}$-alkylenyl-N($C_1$-$C_{12}$-alkylenyl)$_2$,
—NH—$C_1$-$C_{12}$-alkylenyl-$C_2$-$C_{12}$-heterocyclyl;
$C_1$-$C_{12}$-alkyl, which is unsubstituted or substituted by one or more substituents selected from the group consisting of halo, —C(O)—N($C_1$-$C_{12}$-alkyl)$_2$, and —$C_2$-$C_{12}$-heterocyclyl, wherein the $C_2$-$C_{12}$-heterocyclyl is unsubstituted or substituted by $C_1$-$C_{12}$-alkyl;
—C(O)—NH$_2$,
—C(O)—N(H)($C_1$-$C_{12}$-alkyl),
—C(O)—N($C_1$-$C_{12}$-alkyl)$_2$, and
$C_3$-$C_{12}$-cycloalkyl, $C_2$-$C_{12}$-heterocyclyl, $C_6$-$C_{20}$-aryl, $C_2$-$C_{12}$-heteroaryl wherein said cycloalkyl, heterocyclyl, aryl, and heteroaryl can be unsubstituted or substituted by one or more substituents selected from the group consisting of: halo, OH, CN, $NH_2$, —$NH(C_1$-$C_{12}$-alkyl), —$N(C_1$-$C_{12}$-alkyl)$_2$, $C_1$-$C_{12}$-alkyl, $C_1$-$C_{12}$-alkoxy, $C_1$-$C_{12}$-haloalkyl, $C_1$-$C_{12}$-hydroxyalkyl, —$C(O)C_1$-$C_{12}$-alkyl, and —$C(O)NHC_1$-$C_{12}$-alkyl;

with the proviso that when A is CH, $R^1$ is selected from phenyl that is unsubstituted or substituted by halo.

2. The compound of claim 1, wherein:

A is CH or N;

$R^1$ is $C_6$-$C_{20}$-aryl, which is unsubstituted or substituted by one or more halo, CN, $C_1$-$C_{12}$-haloalkoxy, C(O)NH—$C_1$-$C_{12}$-alkyl, which is unsubstituted or substituted by one or more halo; or $C_2$-$C_{12}$-heteroaryl which is unsubstituted or substituted by one or more substituents selected from the group consisting of halo and $C_1$-$C_{12}$-alkyl;

$R^2$ is:

CN;

$C_1$-$C_{12}$-alkyl which is unsubstituted or substituted by one or more substituents selected from the group consisting of cyano, halo, hydroxy, $C_1$-$C_{12}$-alkoxy, $C_3$-$C_{12}$-cycloalkyl, —$NH_2$, —NH—$C_1$-$C_{12}$-alkyl, —NH—$C_2$-$C_{12}$-heteroaryl, —NHC(O)—$C_1$-$C_{12}$-alkyl, —NHC(O)—$C_3$-$C_{12}$-cycloalkyl, —NHC(O)—$C_6$-$C_{20}$-aryl, —NHC(O)—$C_2$-$C_{12}$-heteroaryl, —NHC(O)NH—$C_1$-$C_{12}$-alkyl, —NHC(O)NH—$C_2$-$C_{12}$-heteroaryl, —NHS(O)$_2$—$C_1$-$C_{12}$-alkyl, and —NHS(O)$_2$—$C_3$-$C_{12}$-cycloalkyl;

—C(O)—$C_2$-$C_{12}$-heterocyclyl, which is unsubstituted or substituted by one or more substituents selected from the group consisting of: $C_1$-$C_{12}$-alkyl, $C_1$-$C_{12}$-hydroxyalkyl, —C(O)—$NH_2$, —C(O)—N(H)($C_1$-$C_{12}$-alkyl), —C(O)—N($C_1$-$C_{12}$-alkyl)$_2$, —$C_1$-$C_{12}$-alkylenyl-C(O)—N($C_1$-$C_{12}$-alkyl)$_2$, —NH—C(O)—$C_1$-$C_{12}$-alkyl, —NH—C(O)—$C_3$-$C_{12}$-cycloalkyl, and —N(C(O)—$C_3$-$C_{12}$-cycloalkyl)$_2$;

—C(O)OH;

—C(O)—$C_1$-$C_{12}$-alkoxy;

—C(O)NR$^b$R$^c$, wherein R$^b$ and R$^c$ are independently selected from the group consisting of:

H;

—$C_1$-$C_{12}$-alkyl, which is unsubstituted or substituted by one or more substituent selected from the group consisting of:

OH, CN, $NH_2$, —$C_3$-$C_{12}$-cycloalkyl, —C(O)—$NH_2$, —C(O)—$C_2$-$C_{12}$-heterocyclyl, —N(H)(C(O)—$C_1$-$C_{12}$-alkyl), —N(H)($C_1$-$C_{12}$-alkyl), —N($C_1$-$C_{12}$-alkyl)$_2$, —NHC(O)—NH($C_3$-$C_{12}$-cycloalkyl), —NHC(O)—NH($C_1$-$C_{12}$-alkyl);

$C_2$-$C_{12}$-heterocyclyl, wherein the heterocyclyl is unsubstituted or substituted by one or more substituents selected from the group consisting of oxo, hydroxy and $C_1$-$C_{12}$-alkyl;

—C(O)—$C_2$-$C_{12}$-heterocyclyl, wherein the heterocyclyl is unsubstituted or substituted by one or more substituents selected from the group consisting of oxo, hydroxy and $C_1$-$C_{12}$-alkyl;

—SO$_2$—$C_2$-$C_{12}$-heterocyclyl;

$C_6$-$C_{20}$-aryl, which is unsubstituted or substituted by one or more substituents selected from the group consisting of $C_1$-$C_{12}$-alkyl, $C_1$-$C_{12}$-alkoxy, —$C_1$-$C_{12}$-hydroxyalkyl, $C_1$-$C_{12}$-alkylenyl-$C_1$-$C_{12}$-alkoxy; $C_1$-$C_{12}$-alkylenyl-$NH_2$, and —O—$C_2$-$C_{12}$-heterocyclyl, which heterocyclyl is unsubstituted or substituted by $C_1$-$C_{12}$-alkyl; and $C_2$-$C_{12}$-heteroaryl, which is unsubstituted or substituted by one or more substituents selected from the group consisting of $C_1$-$C_{12}$-alkyl, $C_1$-$C_{12}$-alkoxy, —C(O)—$NH_2$, —C(O)—N(H)($C_1$-$C_{12}$-alkyl), —C(O)—N($C_1$-$C_{12}$-alkyl)$_2$, and —$C_1$-$C_{12}$-alkylenyl-C(O)—N($C_1$-$C_{12}$-alkyl)$_2$;

—$C_3$-$C_{12}$-cycloalkyl, which is unsubstituted or substituted by one or more hydroxy;

—$C_2$-$C_{12}$-heterocyclyl, which is unsubstituted or substituted by one or more substituents selected from the group consisting of: $C_1$-$C_{12}$-alkyl, —SO$_2$—$C_1$-$C_{12}$-alkyl, —C(O)—$C_1$-$C_{12}$-alkyl, —C(O)—$NH_2$, —C(O)—N(H)($C_1$-$C_{12}$-alkyl), —C(O)—N($C_1$-$C_{12}$-alkyl)$_2$, —C(O)—$C_1$-$C_{12}$-alkylenyl-$C_1$-$C_{12}$-alkoxy, —$C_1$-$C_{12}$-alkylenyl-C(O)—N($C_1$-$C_{12}$-alkyl)$_2$, —C(O)—$C_3$-$C_{12}$-cycloalkyl, and —C(O)NH—$C_3$-$C_{12}$-cycloalkyl;

$C_6$-$C_{20}$-aryl, which is unsubstituted or substituted by one or more substituents selected from the group consisting of $C_1$-$C_{12}$-alkyl, $C_1$-$C_{12}$-alkoxy, —$C_1$-$C_{12}$-hydroxyalkyl, $C_1$-$C_{12}$-alkylenyl-$C_1$-$C_{12}$-alkoxy; $C_1$-$C_{12}$-alkylenyl-$NH_2$, and —O—$C_2$-$C_{12}$-heterocyclyl, which heterocyclyl is unsubstituted or substituted by $C_1$-$C_{12}$-alkyl; and, $C_6$-$C_{20}$-heteroaryl, which is unsubstituted or substituted by one or more substituents selected from the group consisting of $C_1$-$C_{12}$-alkyl, $C_1$-$C_{12}$-hydroxyalkyl, and —O—$C_2$-$C_{12}$-heterocyclyl which heterocyclyl is unsubstituted or substituted by $C_1$-$C_{12}$-alkyl; and, $C_2$-$C_{12}$-heteroaryl which is unsubstituted or substituted by $C_1$-$C_{12}$-alkyl, which alkyl is unsubstituted or substituted by one or more substituents selected from the group consisting of halo, —C(O)—N($C_1$-$C_{12}$-alkyl)$_2$, and —$C_2$-$C_{12}$-heterocyclyl, wherein the $C_2$-$C_{12}$-heterocyclyl is unsubstituted or substituted by $C_1$-$C_{12}$-alkyl;

with the proviso that when A is CH, $R^1$ is selected from phenyl that is unsubstituted or substituted by halo.

3. The compound of any one of claim 1, wherein:

A is CH or N;

$R^1$ is $C_6$-$C_{20}$-aryl substituted by one two or three halo;

$R^2$ is:

CN;

$C_1$-$C_{12}$-alkyl which is unsubstituted or substituted by one or more substituents selected from the group consisting of —$NH_2$, —NH—$C_1$-$C_{12}$-alkyl, —NHC(O)—$C_3$-$C_{12}$-cycloalkyl, —NHC(O)—$C_6$-$C_{20}$-aryl, and —NHS(O)$_2$—$C_3$-$C_{12}$-cycloalkyl;

—C(O)—$C_2$-$C_{12}$-heterocyclyl, which is unsubstituted or substituted by one or more substituents selected from the group consisting of: —$C_1$-$C_{12}$-hydroxyalkyl, —$C_1$-$C_{12}$-alkylenyl—C(O)—N($C_1$-$C_{12}$-alkyl)$_2$, —NH—C(O)—$C_1$-$C_{12}$-alkyl, —NH—C(O)—$C_3$-$C_{12}$-cycloalkyl, and —N(C(O)—$C_3$-$C_{12}$-cycloalkyl)$_2$;

—C(O)OH;

—C(O)—$C_1$-$C_{12}$-alkoxy;

—C(O)NR$^b$R$^c$, wherein R$^b$ and R$^c$ are independently selected from the group consisting of:

H;

—$C_1$-$C_{12}$-alkyl, which is unsubstituted or substituted by one or more substituent selected from the group consisting of:

OH, CN, $NH_2$, —$C_3$-$C_{12}$-cycloalkyl, —C(O)—$NH_2$, —C(O)—$C_2$-$C_{12}$-heterocyclyl, —N(H)(C(O)—$C_1$-$C_{12}$-alkyl), —N(H)($C_1$-$C_{12}$alkyl), —N($C_1$-$C_{12}$-alkyl)$_2$, —NHC(O)—NH($C_3$-$C_{12}$-cycloalkyl), —NHC(O)—NH($C_1$-$C_{12}$-alkyl);

$C_2$-$C_{12}$-heterocyclyl, wherein the heterocyclyl is unsubstituted or substituted by one or more substituents selected from the group consisting of oxo, hydroxy and $C_1$-$C_{12}$-alkyl;
—C(O)—$C_2$-$C_{12}$-heterocyclyl;
—$SO_2$—$C_2$-$C_{12}$-heterocyclyl;
$C_6$-$C_{20}$-aryl, which is unsubstituted or substituted by $C_1$-$C_{12}$alkoxy; and
$C_2$-$C_{12}$-heteroaryl, which is unsubstituted or substituted by one or more substituents selected from the group consisting of $C_1$-$C_{12}$-alkyl, —C(O)—$NH_2$, —C(O)—N(H)($C_1$-$C_{12}$-alkyl), and —C(O)—N($C_1$-$C_{12}$-alkyl)$_2$;
—$C_3$-$C_{12}$-cycloalkyl, which is unsubstituted or substituted by one or more hydroxy;
—$C_2$-$C_{12}$-heterocyclyl, which is unsubstituted or substituted by one or more substituents selected from the group consisting of: $C_1$-$C_{12}$-alkyl, —$SO_2$—$C_1$-$C_{12}$-alkyl, —C(O)—$C_1$-$C_{12}$-alkyl, —C(O)—$NH_2$, —C(O)—N(H)($C_1$-$C_{12}$-alkyl), —C(O)—N($C_1$-$C_{12}$-alkyl)$_2$, —C(O)—$C_1$-$C_{12}$-alkylenyl-$C_1$-$C_{12}$-alkoxy, —$C_1$-$C_{12}$-alkylenyl-C(O)—N($C_1$-$C_{12}$-alkyl)$_2$, —C(O)—$C_3$-$C_{12}$-cycloalkyl and —C(O)NH—$C_3$-$C_{12}$-cycloalkyl;
$C_6$-$C_{20}$-aryl, which is unsubstituted or substituted by one or more substituents selected from the group consisting of $C_1$-$C_{12}$-alkyl, $C_1$-$C_{12}$-alkoxy, —$C_1$-$C_{12}$-hydroxyalkyl, $C_1$-$C_{12}$-alkylenyl-$C_1$-$C_{12}$-alkoxy; $C_1$-$C_{12}$-alkylenyl-$NH_2$, and —O—$C_2$-$C_{12}$-heterocyclyl, which heterocyclyl is unsubstituted or substituted by $C_1$-$C_{12}$-alkyl; and,
$C_6$-$C_{20}$-heteroaryl, which is unsubstituted or substituted by one or more substituents selected from the group consisting of $C_1$-$C_{12}$-alkyl, which is unsubstituted or substituted by $C_2$-$C_{12}$-heterocyclyl, $C_1$-$C_{12}$-hydroxyalkyl, and —O—$C_2$-$C_{12}$-heterocyclyl which is unsubstituted or substituted by $C_1$-$C_{12}$-alkyl; and
$C_2$-$C_{12}$-heteroaryl which is unsubstituted or substituted by $C_1$-$C_{12}$-alkyl, which alkyl is unsubstituted or substituted by one or more substituents selected from the group consisting of halo, —C(O)—N($C_1$-$C_{12}$-alkyl)$_2$, and —$C_2$-$C_{12}$-heterocyclyl, wherein the heterocyclyl is unsubstituted or substituted by $C_1$-$C_{12}$-alkyl;
with the proviso that when A is CH, $R^1$ is selected from phenyl that is unsubstituted or substituted by halo.

4. The compound of any one of claims 1 wherein A is CH.
5. The compound of claim 4 wherein $R^2$ is CN.
6. The compound of claim 5, wherein it is:

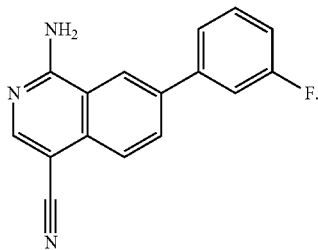 [SMILES: N#Cc1cnc(N)c2cc(-c3cccc(F)c3)ccc12]

7. The compound of claim 4 wherein $R^2$ is $C_1$-$C_{12}$-alkyl which is unsubstituted or substituted by one or more substituents selected from the group consisting of —$NH_2$, —NH—$C_1$-$C_{12}$-alkyl, —NHC(O)—$C_3$-$C_{12}$-cycloalkyl, —NHC(O)—$C_6$-$C_{20}$-aryl, and —NHS(O)$_2$—$C_3$-$C_{12}$-cycloalkyl.
8. The compound of claim 7, wherein the compound is selected from the group consisting of:

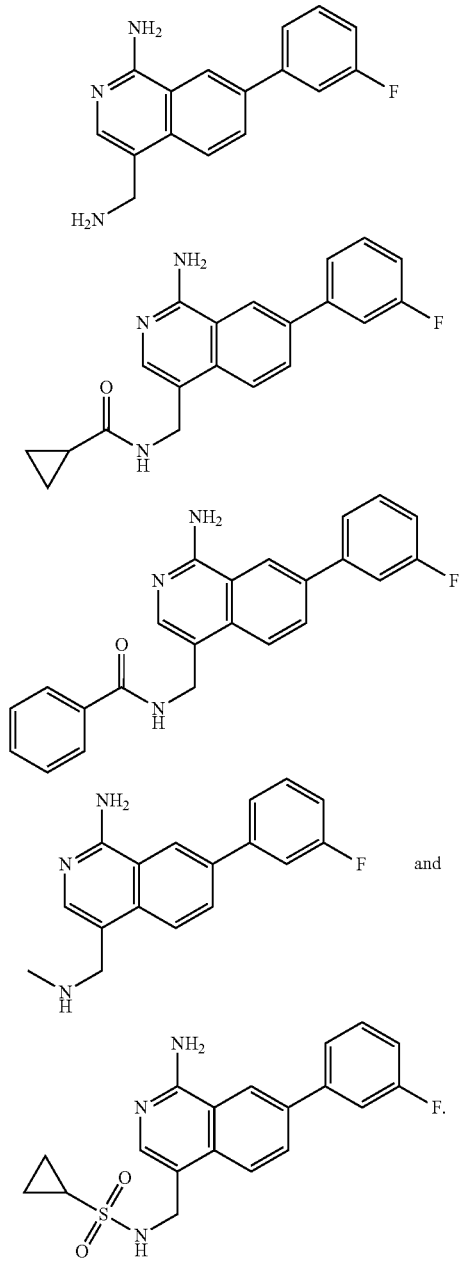

9. The compound of claim 4 wherein $R^2$ is —C(O)—$C_2$-$C_{12}$-heterocyclyl, which is unsubstituted or substituted by one or more substituents selected from the group consisting of: —$C_1$-$C_{12}$-hydroxyalkyl and —$C_1$-$C_{12}$-alkylenyl-C(O)—N($C_1$-$C_{12}$-alkyl)$_2$, —C(O)—$NH_2$ and —C(O)—N(H)($C_1$-$C_{12}$-alkyl)-.

10. The compound of claim 9, wherein the compound is selected from the group consisting of:

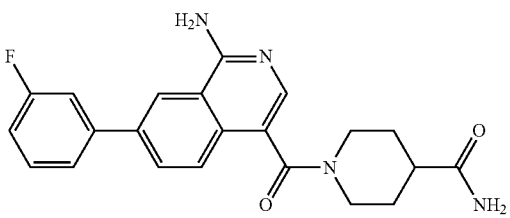

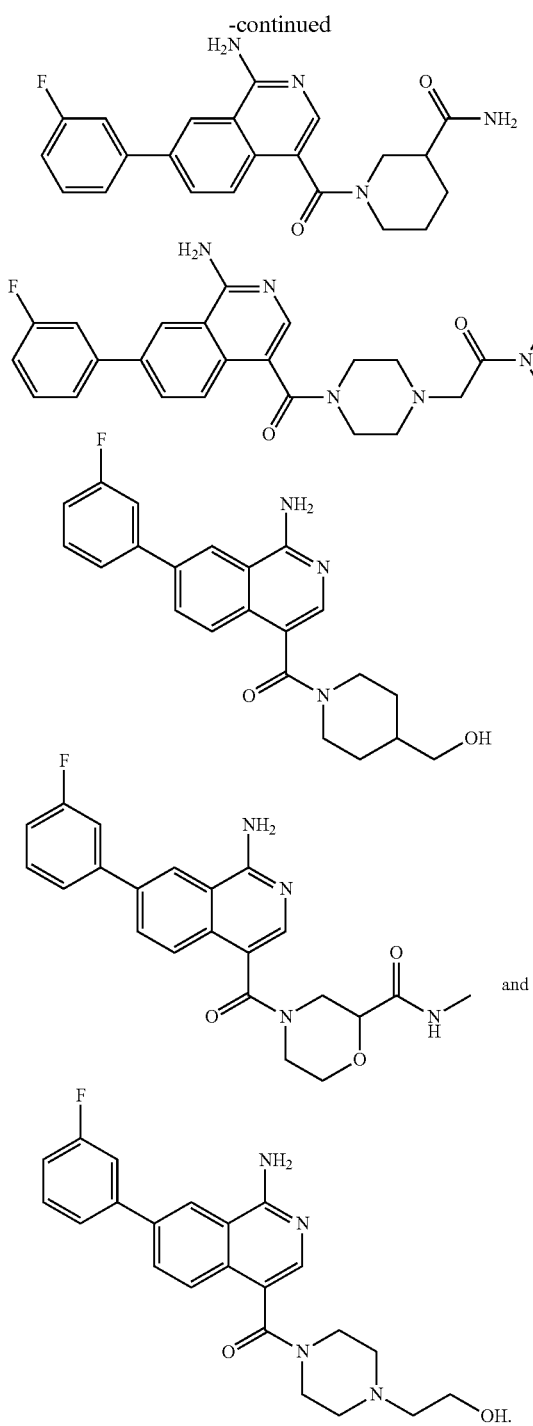

11. The compound of claim 4 wherein $R^2$ is —C(O)OH.

12. The compound of claim 11, wherein the compound is:

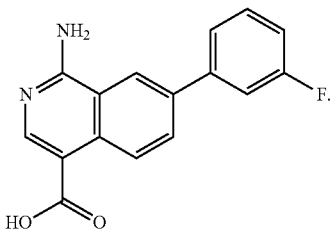 [SMILES: Nc1ncc(C(=O)O)c2ccc(-c3cccc(F)c3)cc12]

13. The compound of claim 4 wherein $R^2$ is —C(O)NR$^b$R$^c$, wherein R$^b$ and R$^c$ are independently selected from the group consisting of:

H;

—$C_1$-$C_{12}$-alkyl, which is unsubstituted or substituted by one or more substituent selected from the group consisting of:

OH, CN, NH$_2$, —$C_3$-$C_{12}$-cycloalkyl, —C(O)—NH$_2$, —C(O)—$C_2$-$C_{12}$-heterocyclyl, —N(H)(C(O)—$C_1$-$C_{12}$-alkyl), —N(H)($C_1$-$C_{12}$-alkyl), —N($C_1$-$C_{12}$-alkyl)$_2$, —NHC(O)—NH($C_3$-$C_{12}$-cycloalkyl), —NHC(O)—NH($C_1$-$C_{12}$-alkyl);

$C_2$-$C_{12}$-heterocyclyl, wherein the heterocyclyl is unsubstituted or substituted by one or more substituents selected from the group consisting of oxo, hydroxy and $C_1$-$C_{12}$-alkyl;

—C(O)—$C_2$-$C_{12}$-heterocyclyl;

—SO$_2$—$C_2$-$C_{12}$-heterocyclyl;

$C_6$-$C_{20}$-aryl, which is unsubstituted or substituted by $C_1$-$C_{12}$-alkoxy; and $C_2$-$C_{12}$-heteroaryl, which is unsubstituted or substituted by one or more substituents selected from the group consisting of $C_1$-$C_{12}$-alkyl, —C(O)—NH$_2$, —C(O)—N(H)($C_1$-$C_{12}$-alkyl), and —C(O)—N($C_1$-$C_{12}$-alkyl)$_2$;

—$C_3$-$C_{12}$-cycloalkyl, which is unsubstituted or substituted by or more hydroxy;

—$C_2$-$C_{12}$-heterocyclyl, which is unsubstituted or substituted by one or more substituents selected from the group consisting of: oxo, hydroxy, $C_1$-$C_{12}$-alkyl, —SO$_2$—$C_1$-$C_{12}$-alkyl, —C(O)—$C_1$-$C_{12}$-alkyl, —C(O)—NH$_2$, —C(O)—N(H)($C_1$-$C_{12}$-alkyl), —C(O)—N($C_1$-$C_{12}$-alkyl)$_2$, —C(O)—$C_1$-$C_{12}$-alkylenyl-$C_1$-$C_{12}$-alkoxy, —$C_1$-$C_{12}$-alkylenyl-C(O)—N($C_1$-$C_{12}$-alkyl)$_2$, —C(O)—$C_3$-$C_{12}$-cycloalkyl, and —C(O)NH—$C_3$-$C_{12}$-cycloalkyl;

$C_6$-$C_{20}$-aryl, which is unsubstituted or substituted by one or more substituents selected from the group consisting of $C_1$-$C_{12}$-alkyl, $C_1$-$C_{12}$-alkoxy, —$C_1$-$C_{12}$-hydroxyalkyl, $C_1$-$C_{12}$-alkylenyl-$C_1$-$C_{12}$-alkoxy, $C_1$-$C_{12}$-alkylenyl-NH$_2$, and —O—$C_2$-$C_{12}$-heterocyclyl, which heterocyclyl is unsubstituted or substituted by $C_1$-$C_{12}$-alkyl; and $C_6$-$C_{20}$-heteroaryl, which is unsubstituted or substituted by one or more substituents selected from the group consisting of $C_1$-$C_{12}$-alkyl, which is unsubstituted or substituted by $C_2$-$C_{12}$-heterocyclyl, $C_1$-$C_{12}$-hydroxyalkyl, and —O—$C_2$-$C_{12}$-heterocyclyl which is unsubstituted or substituted by $C_1$-$C_{12}$-alkyl.

14. The compound of claim 13, wherein the compound is selected from the group consisting of:

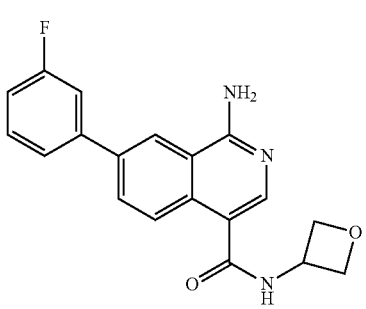

225
-continued
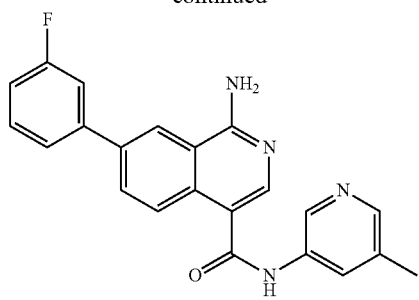
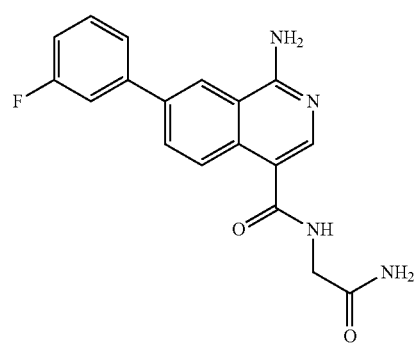
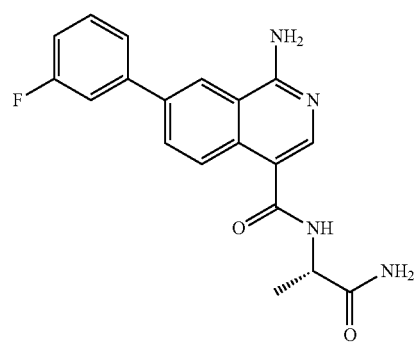
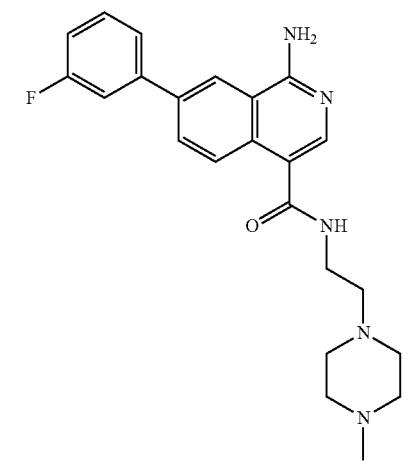
226
-continued
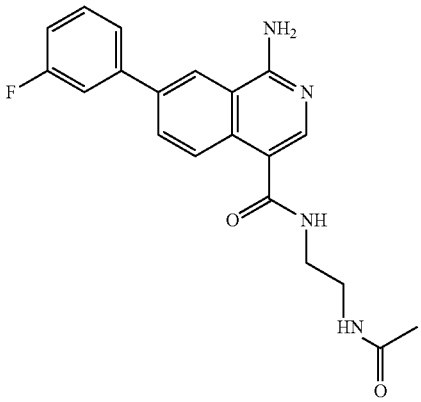
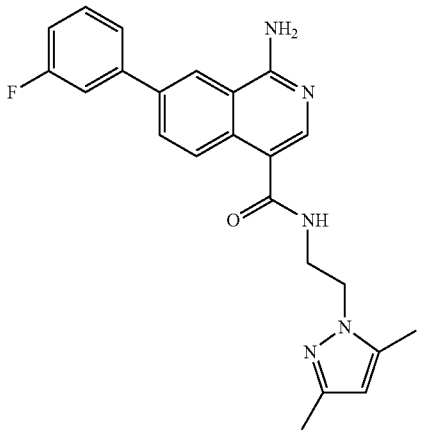
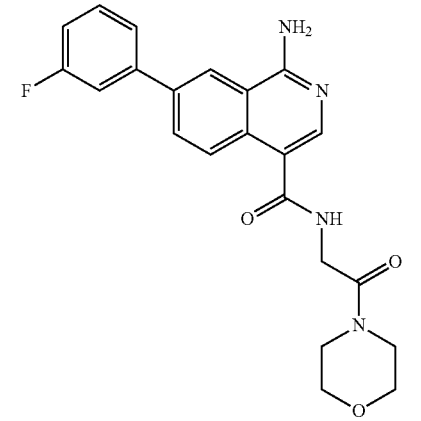
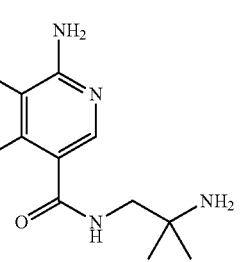

227
-continued
228
-continued
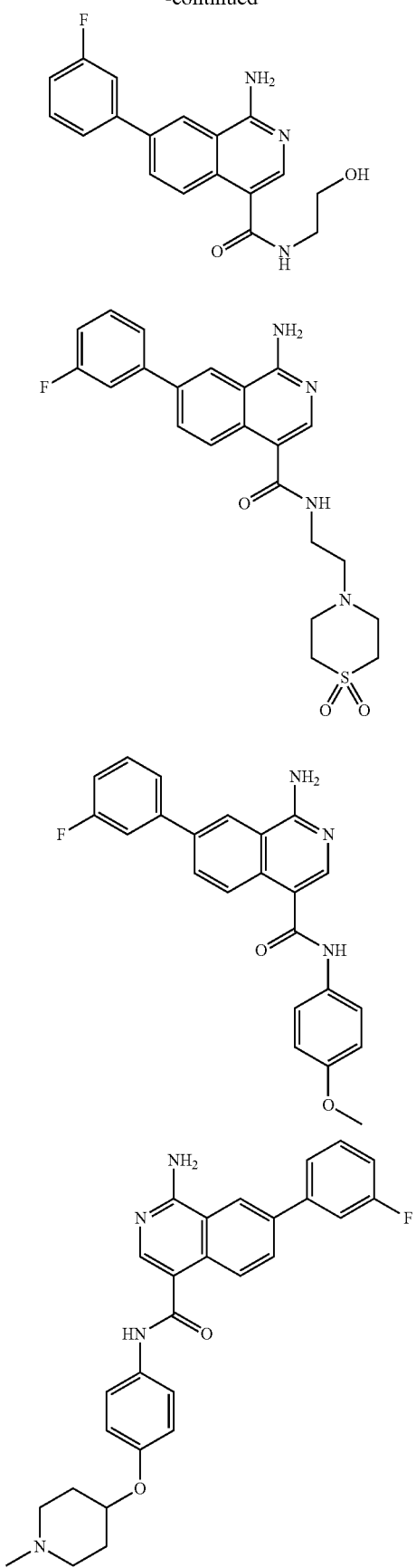
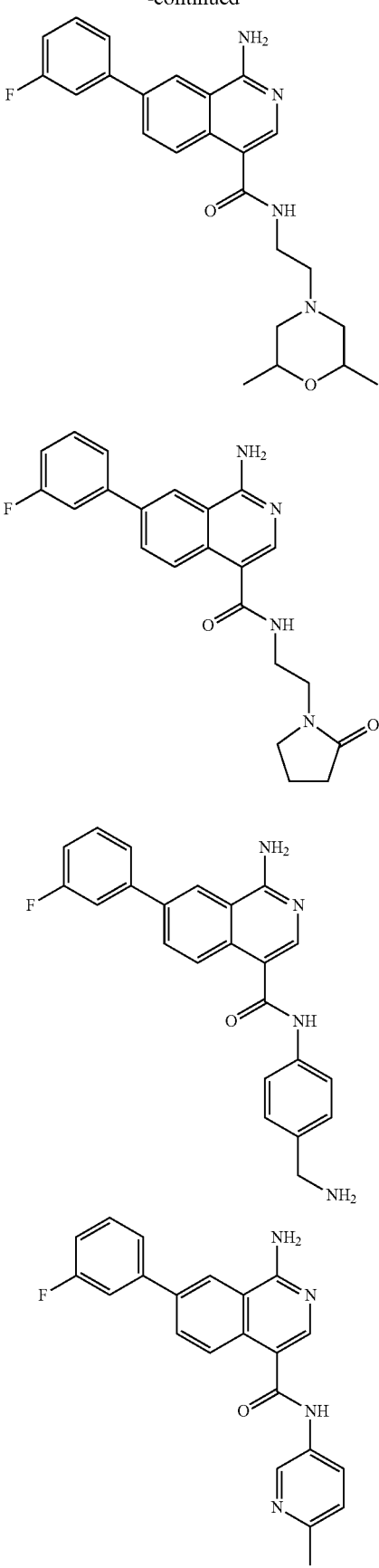

229
-continued
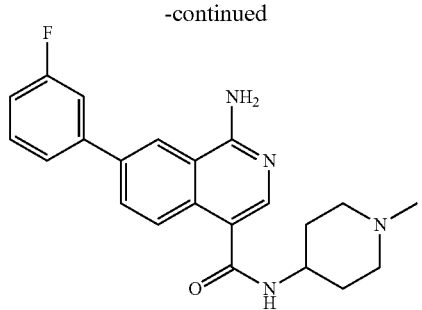
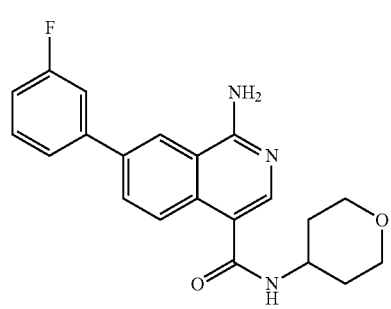
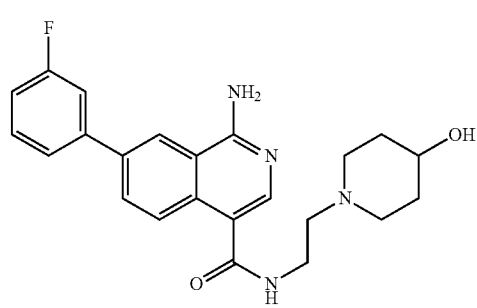
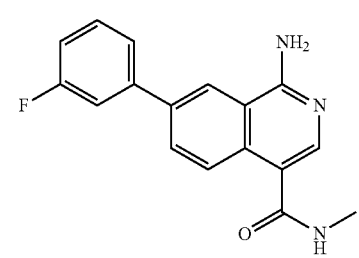
230
-continued
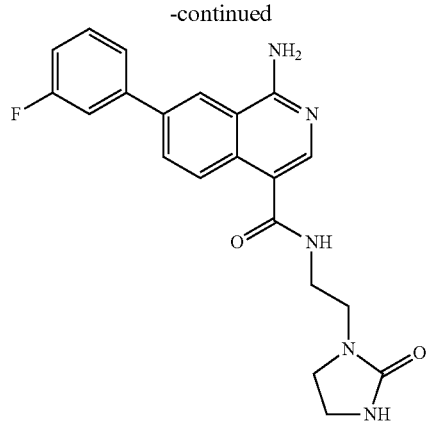
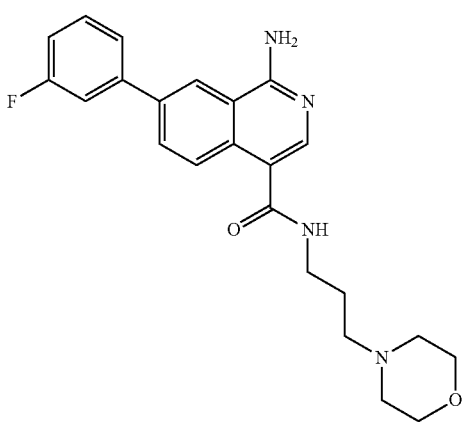
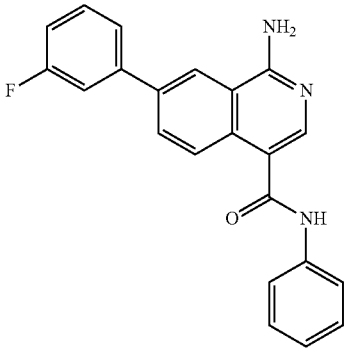
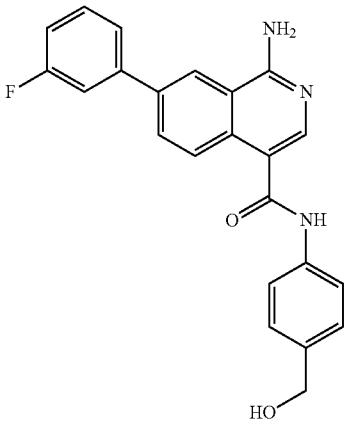

231
-continued
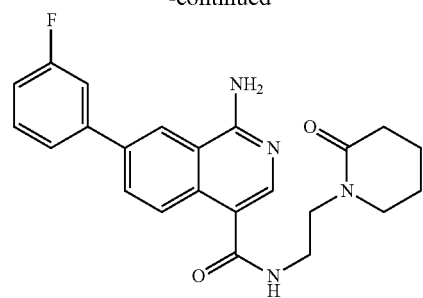
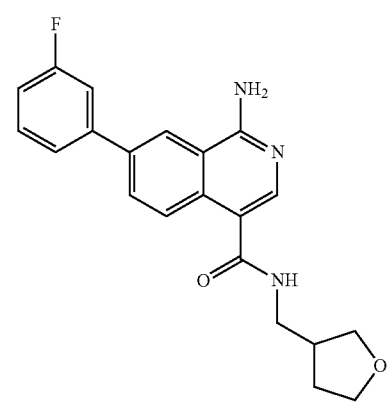
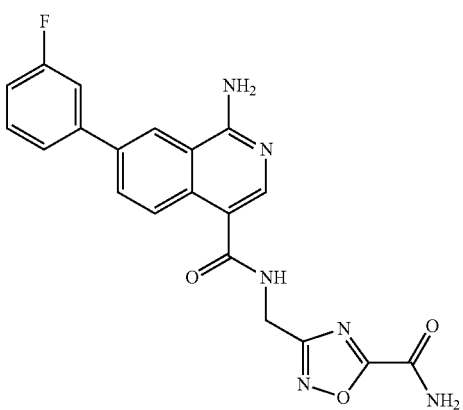
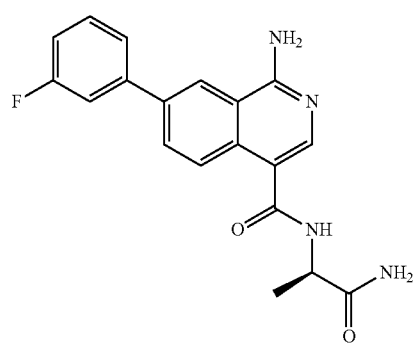
232
-continued
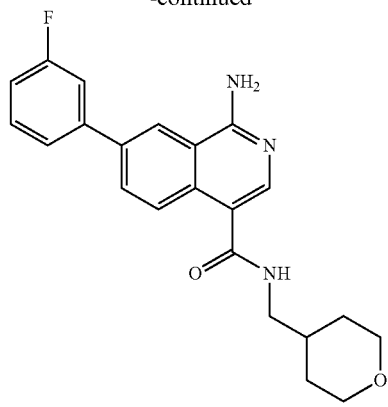
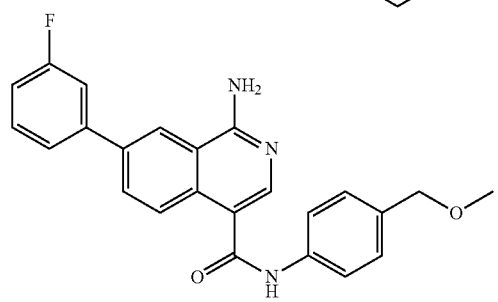
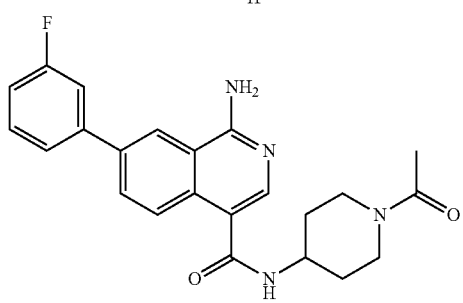
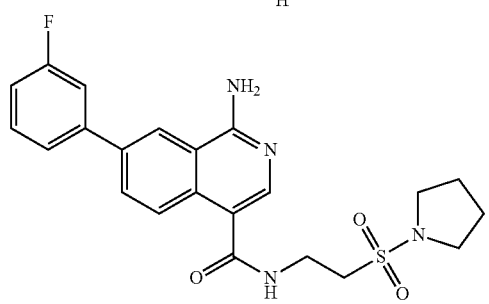
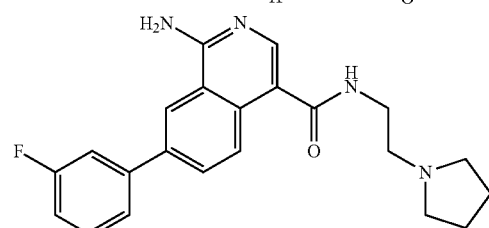
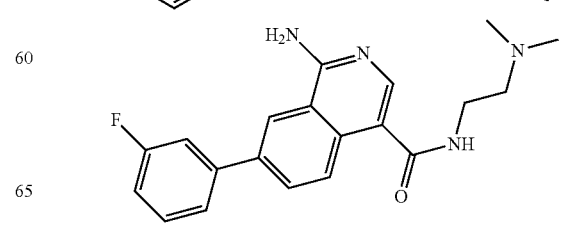

233
-continued
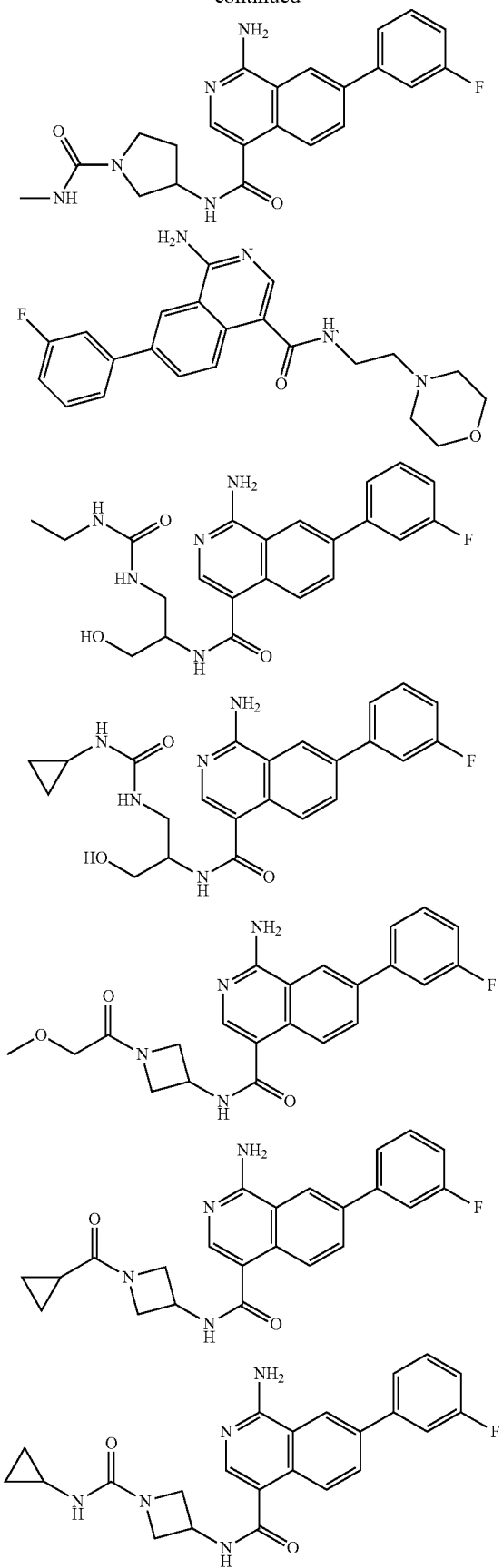
234
-continued
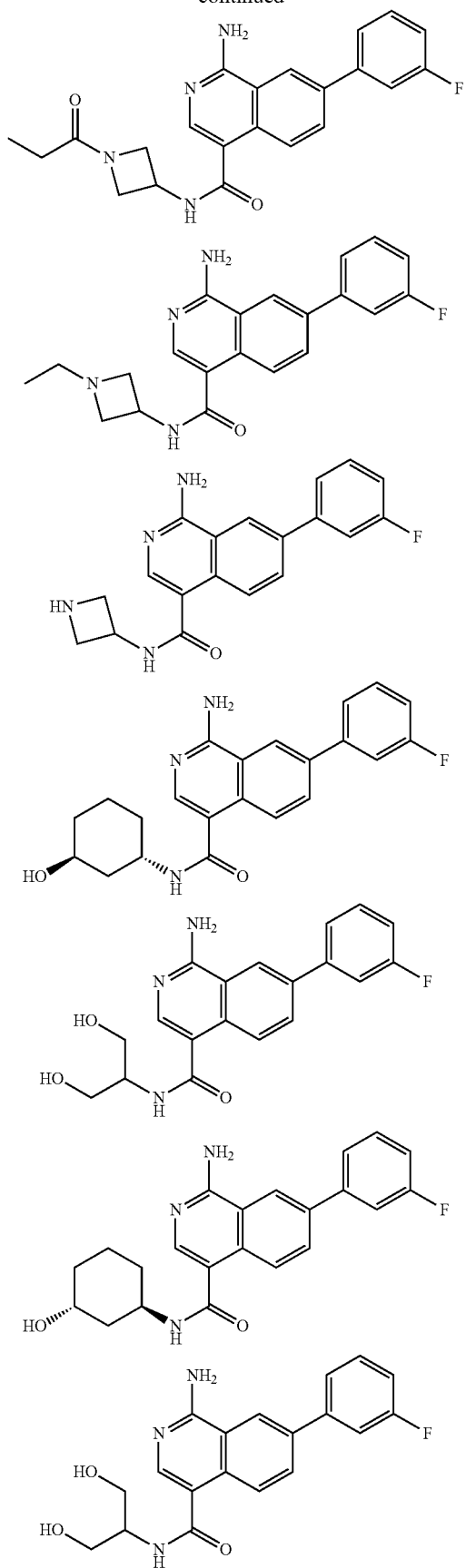

235
-continued
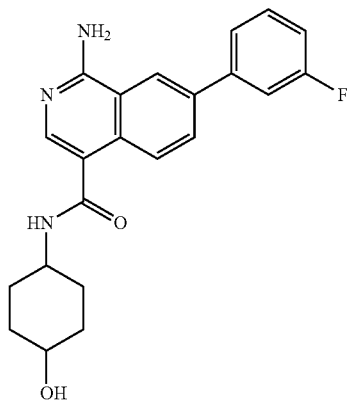
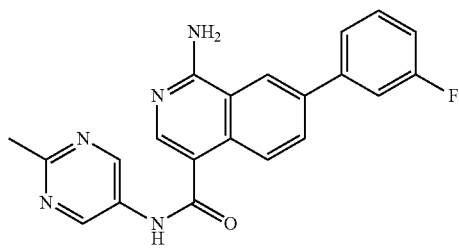
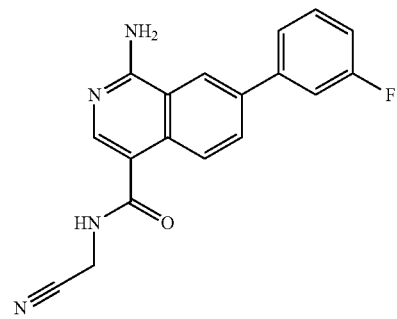
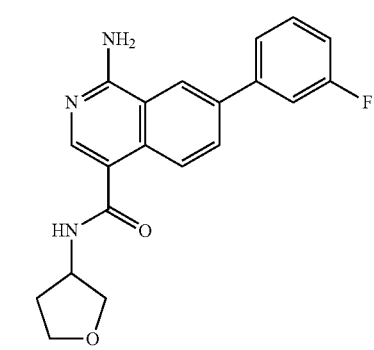
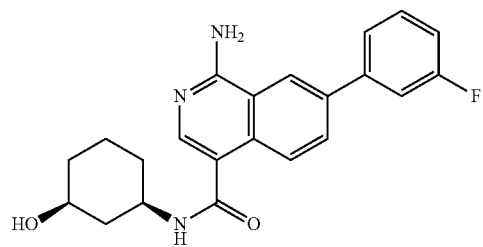
236
-continued
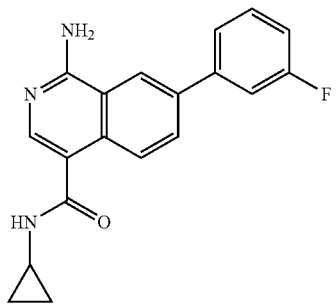
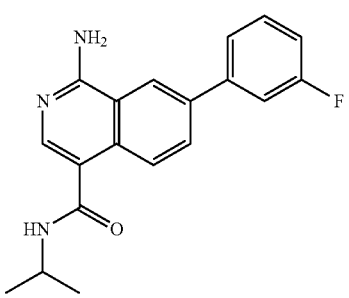
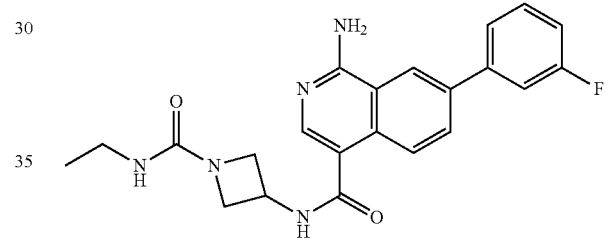
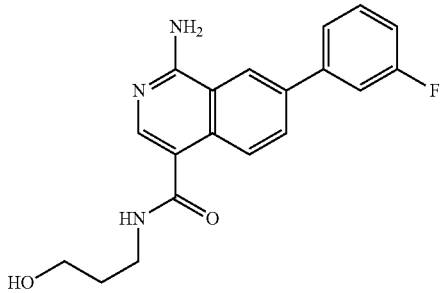
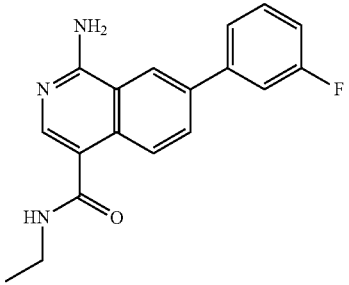

237
-continued
238
-continued
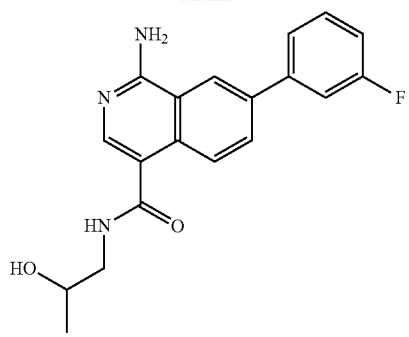
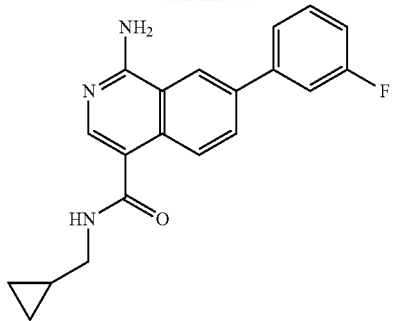

239
-continued

240
-continued

241
-continued
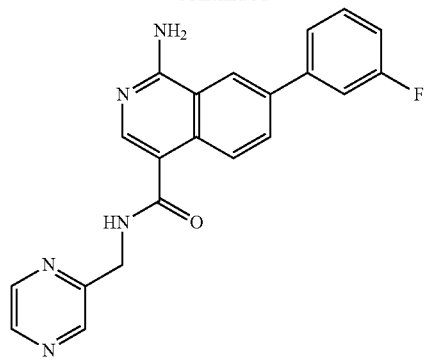
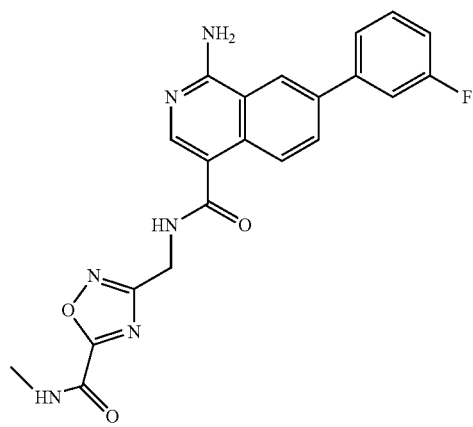
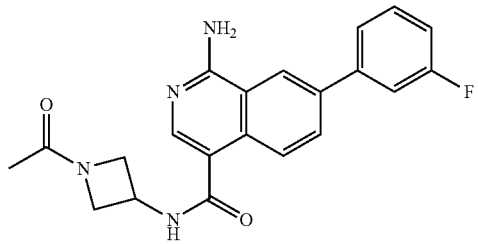
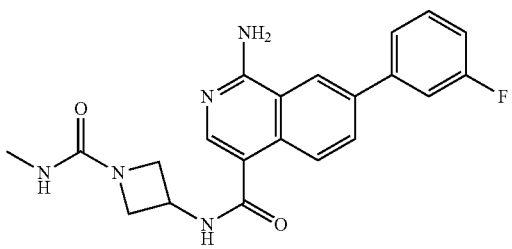
242
-continued
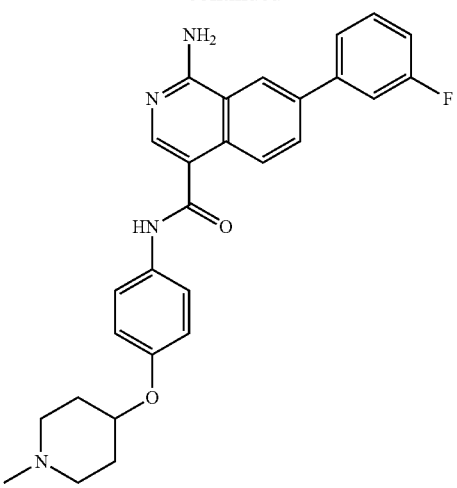
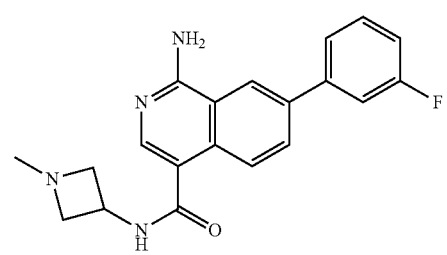
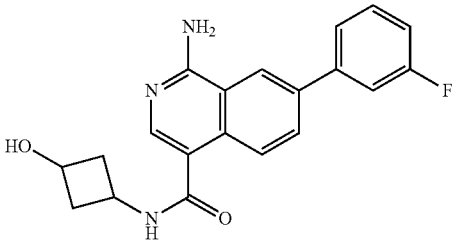
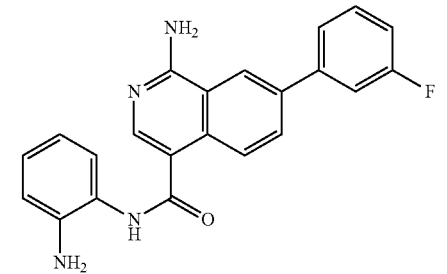
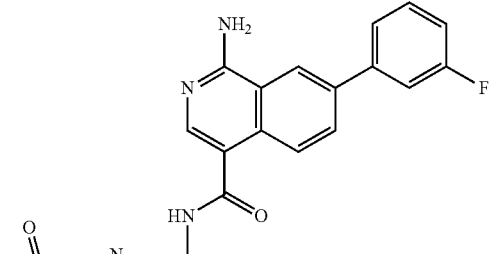

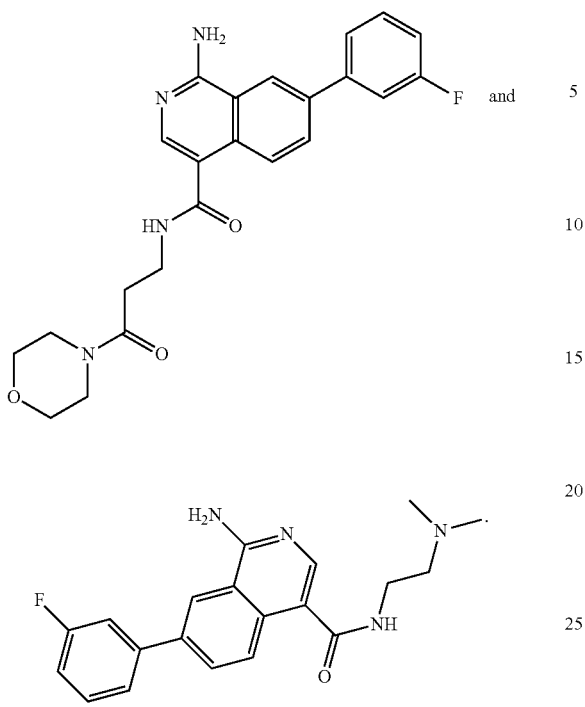

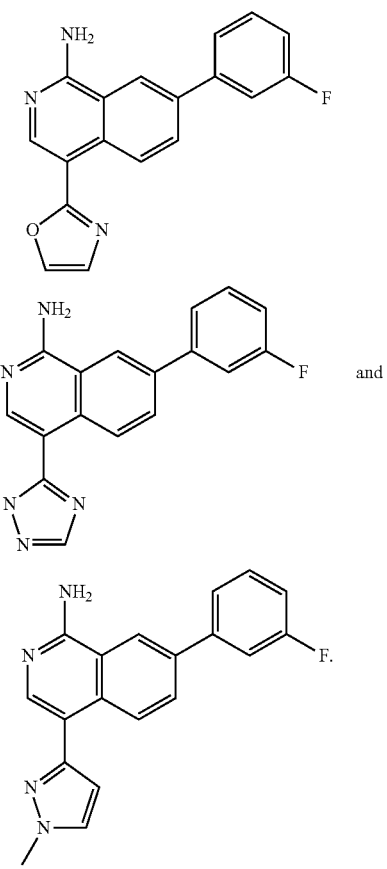

15. The compound of claim 4 wherein $R^2$ is —$C_2$-$C_{12}$-heteroaryl which is unsubstituted or substituted by $C_1$-$C_{12}$-alkyl, which alkyl is unsubstituted or substituted by one or more substituents selected from the group consisting of halo, —C(O)—N($C_1$-$C_{12}$-alkyl)$_2$, and —$C_2$-$C_{12}$-heterocyclyl, wherein the heterocyclyl is unsubstituted or substituted by $C_1$-$C_{12}$-alkyl.

16. The compound of claim 15, wherein they are selected from the group consisting of:

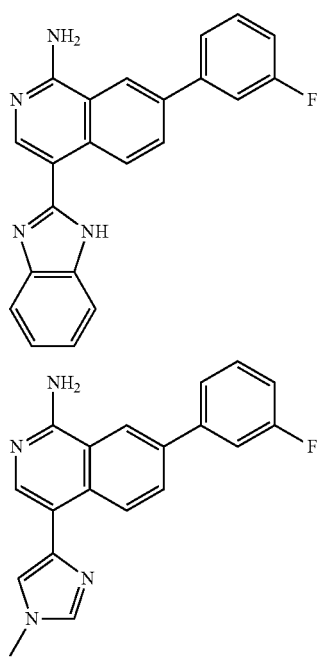

17. The compound of claim 2 wherein A is N.

18. The compound of claim 17, wherein $R^2$ is $C_6$-$C_{20}$-heteroaryl, which is unsubstituted or substituted by one or more —$C_1$-$C_{12}$-alkyl, which is unsubstituted or substituted by $C_2$-$C_{12}$-heterocyclyl.

19. The compound of claim 18, wherein the compound is selected from the group consisting of:

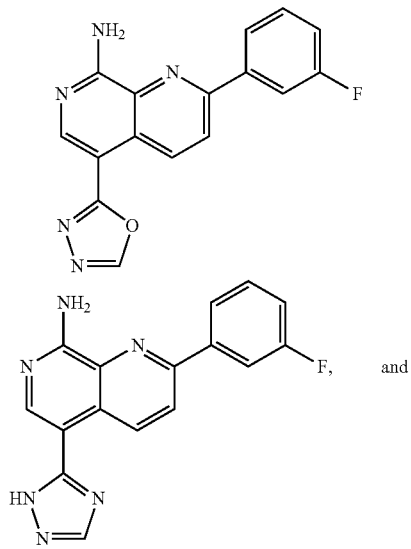

20. The compound of claim 17, wherein R² is —C(O)—C₁-C₁₂-alkoxy.

21. The compound of claim 20, selected from:

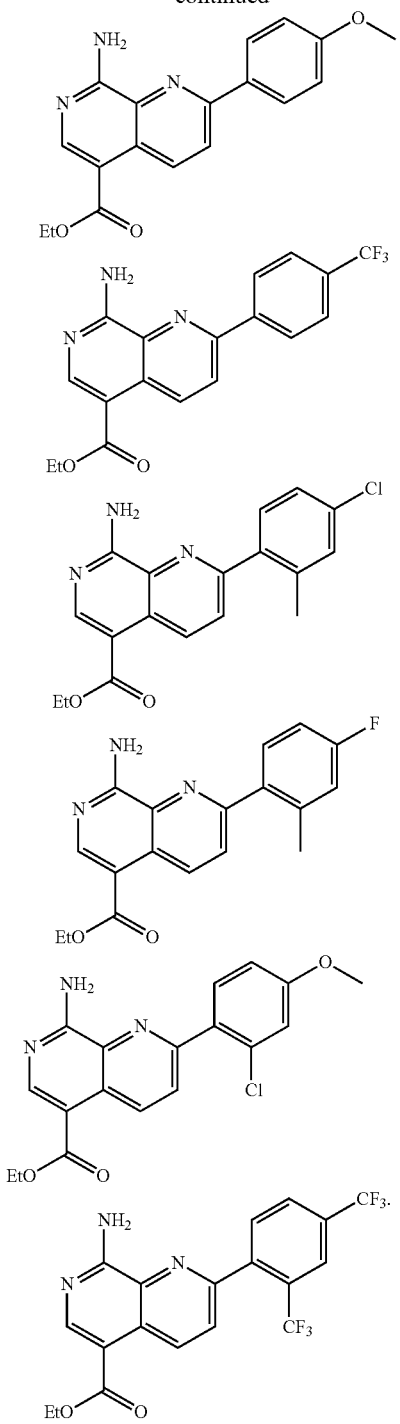

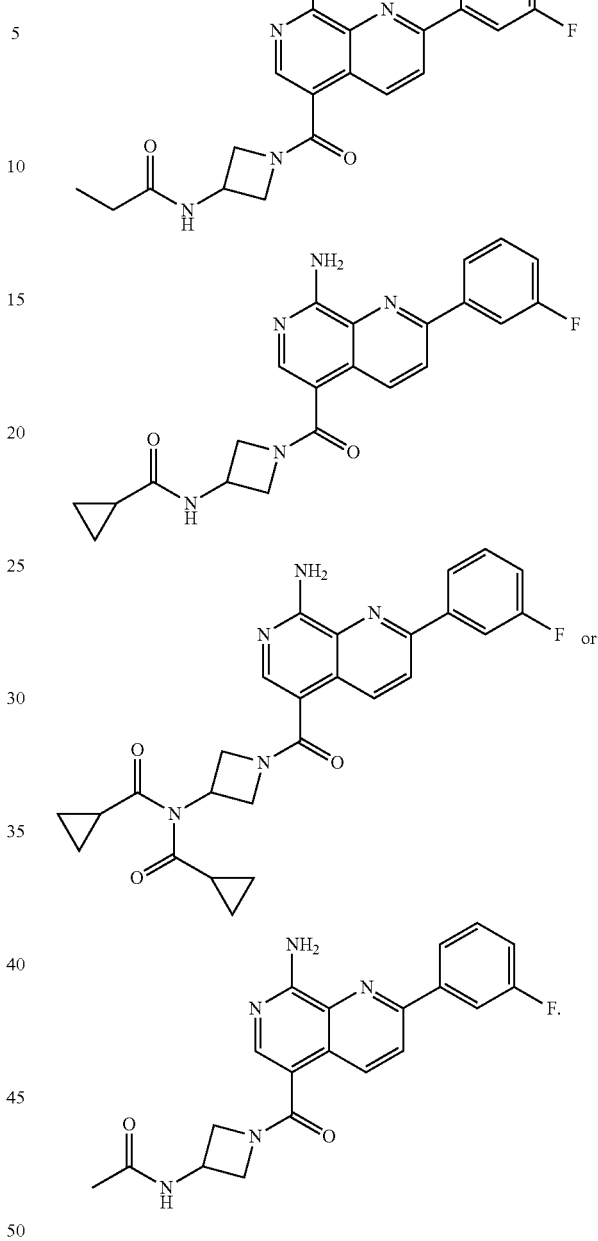

22. The compound of claim 17, wherein $R^2$ is —C(O)—$C_2$-$C_{12}$-heterocyclyl, which is unsubstituted or substituted by one or more substituents selected from the group consisting of: $C_1$-$C_{12}$-alkyl, —$C_1$-$C_{12}$-hydroxyalkyl, —C(O)—$NH_2$, —C(O)—N(H)($C_1$-$C_{12}$-alkyl), —C(O)—N($C_1$-$C_{12}$-alkyl)$_2$, —$C_1$-$C_{12}$-alkylenyl-C(O)—N($C_1$-$C_{12}$-alkyl)$_2$, —NH—C(O)—$C_1$-$C_{12}$-alkyl, —NH—C(O)—$C_3$-$C_{12}$-cycloalkyl, and —N(C(O)—$C_3$-$C_{12}$-cycloalkyl)$_2$.

23. The compound of claim 22, wherein the compound is selected from:

24. The compound of claim 17, wherein $R^2$ is —C(O) $NR^bR^c$, wherein $R^b$ and $R^c$ are independently selected from the group consisting of:

H;

$C_1$-$C_{12}$-alkyl;

—$C_3$-$C_{12}$-cycloalkyl, which is unsubstituted or substituted by one or more hydroxy, and —$C_2$-$C_{12}$-heterocyclyl, which is unsubstituted or substituted by:

—C(O)—N(H)($C_1$-$C_{12}$-alkyl);

—C(O)—$C_1$-$C_{12}$-alkylenyl-$C_1$-$C_{12}$-alkoxy;

$C_1$-$C_{12}$-alkyl which is unsubstituted;

—(CO)—$C_1$-$C_{12}$-alkyl, which alkyl is unsubstituted;

—(CO)—$C_3$-$C_{12}$-cycloalkyl;

—S(O)$_2$—$C_1$-$C_{12}$-alkyl, which alkyl is unsubstituted.

25. The compound of claim 24, selected from:
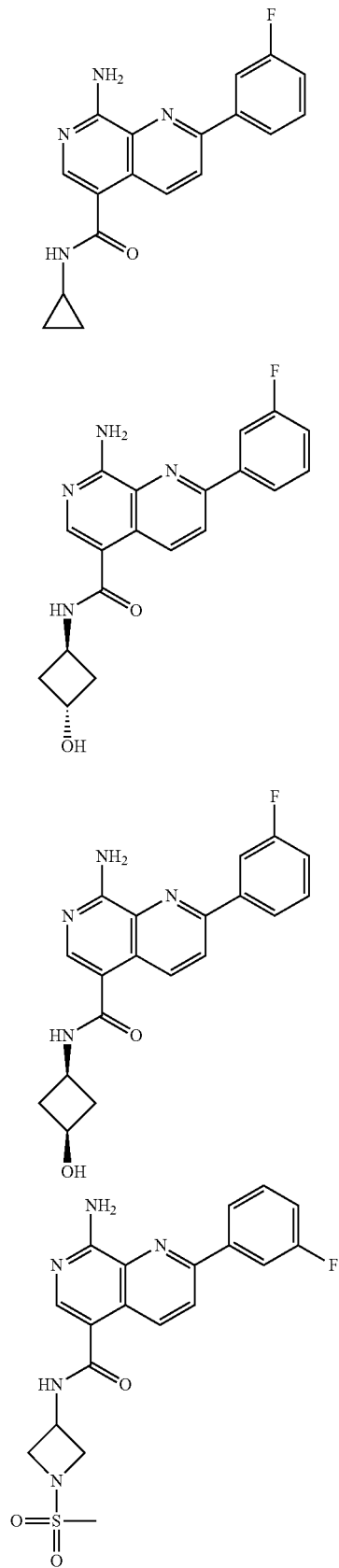
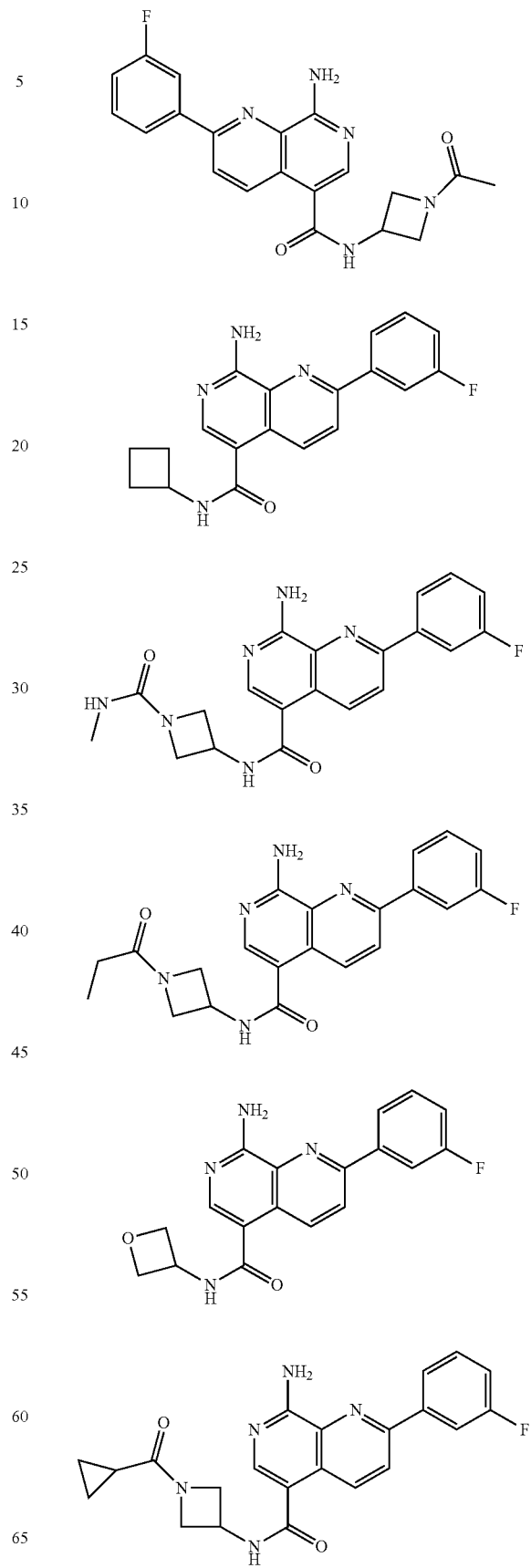

-continued

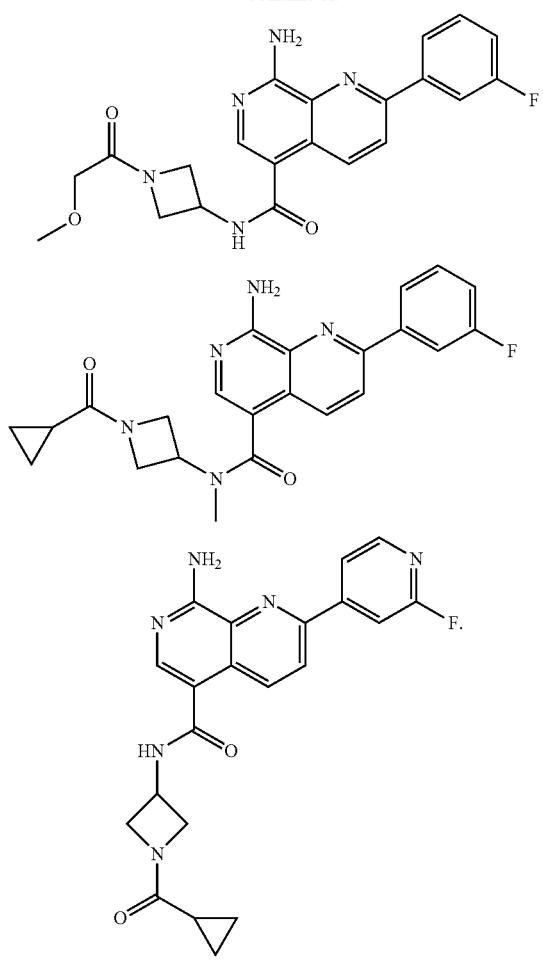

26. The compound of any one of claims 1, wherein R¹ is phenyl substituted by halo.
27. The compound of claim 26, wherein R¹ is phenyl meta-substituted by halo.
28. The compound of claim 27, wherein halo is F.
29. The compound of claim 1 having the Formula (I-c):

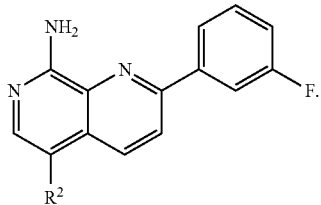

I-c

30. The compound of claim 1 having the Formula (I-d):

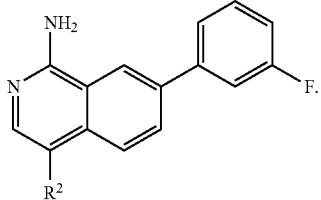

I-d

31. A pharmaceutical composition comprising a compound in accordance with any one of claim 1 and a therapeutically inert carrier.
32. A method for the treatment of cancer which method comprises administering an effective amount of a compound as defined in claim 1 to a subject having said cancer.

* * * * *